(12) United States Patent
Hadida-Ruah et al.

(10) Patent No.: US 9,090,619 B2
(45) Date of Patent: Jul. 28, 2015

(54) MODULATORS OF ATP-BINDING CASSETTE TRANSPORTERS

(71) Applicant: Vertex Pharmaceuticals Incorporated, Boston, MA (US)

(72) Inventors: Sara Hadida-Ruah, La Jolla, CA (US); Anna Hazlewood, San Diego, CA (US); Peter Grootenhuis, San Diego, CA (US); Fredrick Van Goor, San Diego, CA (US); Ashvani Singh, San Diego, CA (US); Jinglan Zhou, San Diego, CA (US); Jason McCartney, Cardiff by the Sea, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/446,870

(22) Filed: Jul. 30, 2014

(65) Prior Publication Data
US 2014/0343315 A1 Nov. 20, 2014

Related U.S. Application Data

(60) Division of application No. 11/841,646, filed on Aug. 20, 2007, now Pat. No. 8,829,204, which is a continuation of application No. 11/165,818, filed on Jun. 24, 2005, now Pat. No. 7,495,103.

(60) Provisional application No. 60/582,676, filed on Jun. 24, 2004, provisional application No. 60/630,127, filed on Nov. 22, 2004, provisional application No. 60/635,674, filed on Dec. 13, 2004, provisional application No. 60/658,219, filed on Mar. 3, 2005, provisional application No. 60/661,311, filed on Mar. 11, 2005.

(51) Int. Cl.
| | |
|---|---|
| *C07C 209/00* | (2006.01) |
| *C07C 211/17* | (2006.01) |
| *C07C 215/28* | (2006.01) |
| *C07D 471/10* | (2006.01) |
| *C07C 215/76* | (2006.01) |
| *C07D 209/08* | (2006.01) |
| *C07D 209/14* | (2006.01) |
| *C07D 209/18* | (2006.01) |
| *C07D 209/42* | (2006.01) |
| *C07D 209/94* | (2006.01) |
| *C07D 213/20* | (2006.01) |
| *C07D 213/73* | (2006.01) |
| *C07D 215/227* | (2006.01) |
| *C07D 215/38* | (2006.01) |
| *C07D 215/56* | (2006.01) |
| *C07D 217/06* | (2006.01) |

(Continued)

(52) U.S. Cl.
CPC ............ *C07D 471/10* (2013.01); *A61K 8/4926* (2013.01); *A61K 31/136* (2013.01); *A61K 31/265* (2013.01); *A61K 31/352* (2013.01); *A61K 31/404* (2013.01); *A61K 31/4045* (2013.01); *A61K 31/47* (2013.01); *A61K 31/4709* (2013.01); *A61K 31/4747* (2013.01); *A61K 31/55* (2013.01); *A61K 45/06* (2013.01); *C07C 209/00* (2013.01); *C07C 211/17* (2013.01); *C07C 215/28* (2013.01); *C07C 215/76* (2013.01); *C07C 215/78* (2013.01); *C07C 217/84* (2013.01); *C07C 219/34* (2013.01); *C07D 209/08* (2013.01); *C07D 209/12* (2013.01); *C07D 209/14* (2013.01); *C07D 209/18* (2013.01); *C07D 209/20* (2013.01); *C07D 209/42* (2013.01); *C07D 209/94* (2013.01); *C07D 213/20* (2013.01); *C07D 213/73* (2013.01); *C07D 215/227* (2013.01); *C07D 215/233* (2013.01); *C07D 215/38* (2013.01); *C07D 215/56* (2013.01); *C07D 217/06* (2013.01); *C07D 223/16* (2013.01); *C07D 265/36* (2013.01); *C07D 279/16* (2013.01); *C07D 311/58* (2013.01); *C07D 401/12* (2013.01); *C07D 401/14* (2013.01); *C07D 405/12* (2013.01); *C07D 409/12* (2013.01); *C07D 413/12* (2013.01); *C07D 417/12* (2013.01); *G01N 33/48728* (2013.01); *G01N 33/5035* (2013.01); *G01N 33/566* (2013.01); *G01N 33/6872* (2013.01); *G01N 2333/705* (2013.01)

(58) Field of Classification Search
CPC .... C07C 209/00; C07C 211/17; C07C 215/28
See application file for complete search history.

(56) References Cited

U.S. PATENT DOCUMENTS

| | | | |
|---|---|---|---|
| 3,443,940 | A | 5/1969 | Bloom et al. |
| 3,524,858 | A | 8/1970 | Kaminsky et al. |

(Continued)

FOREIGN PATENT DOCUMENTS

| | | |
|---|---|---|
| CA | 2065106 A1 | 10/1992 |
| CN | 1473827 A | 2/2004 |

(Continued)

OTHER PUBLICATIONS

Heilbron, Isidor M., et al., "The Intermolecular Condensation of Acetylmethylanthranilic Acid by Means of Phosphorus Pentachloride and the Formation of a Complex isoCyanine Dye," J. Chem. Soc., 1928, pp. 934-941, XP008056964.

(Continued)

*Primary Examiner* — Samantha Shterengarts
(74) *Attorney, Agent, or Firm* — Honigman Miller Schwartz and Cohn LLP; Christopher C. Forbes; Jonathan P. O'Brien

(57) ABSTRACT

The present invention relates to modulators of ATP-Binding Cassette ("ABC") transporters or fragments thereof, including Cystic Fibrosis Transmembrane Conductance Regulator, compositions thereof, and methods therewith. The present invention also relates to methods of treating ABC transporter mediated diseases using such modulators.

10 Claims, No Drawings

(51) Int. Cl.
| | | |
|---|---|---|
| C07D 223/16 | (2006.01) | |
| C07D 265/36 | (2006.01) | |
| C07D 279/16 | (2006.01) | |
| C07D 311/58 | (2006.01) | |
| C07D 401/12 | (2006.01) | |
| C07D 401/14 | (2006.01) | |
| C07D 405/12 | (2006.01) | |
| C07D 409/12 | (2006.01) | |
| C07D 413/12 | (2006.01) | |
| C07D 417/12 | (2006.01) | |
| C07D 215/233 | (2006.01) | |
| A61K 8/49 | (2006.01) | |
| A61K 31/47 | (2006.01) | |
| A61K 31/4709 | (2006.01) | |
| A61K 45/06 | (2006.01) | |
| C07C 215/78 | (2006.01) | |
| C07C 217/84 | (2006.01) | |
| C07D 209/12 | (2006.01) | |
| C07D 209/20 | (2006.01) | |
| A61K 31/136 | (2006.01) | |
| A61K 31/265 | (2006.01) | |
| A61K 31/352 | (2006.01) | |
| A61K 31/404 | (2006.01) | |
| A61K 31/4045 | (2006.01) | |
| A61K 31/4747 | (2006.01) | |
| A61K 31/55 | (2006.01) | |
| C07C 219/34 | (2006.01) | |
| G01N 33/566 | (2006.01) | |
| G01N 33/487 | (2006.01) | |
| G01N 33/50 | (2006.01) | |
| G01N 33/68 | (2006.01) | |

(56) References Cited

U.S. PATENT DOCUMENTS

| | | | |
|---|---|---|---|
| 3,698,292 A | 10/1972 | Koester | |
| 3,812,094 A | 5/1974 | MacLeay et al. | |
| 3,992,540 A | 11/1976 | Clémence et al. | |
| 4,107,310 A | 8/1978 | Allais et al. | |
| 4,110,355 A | 8/1978 | Bloom et al. | |
| 4,284,629 A | 8/1981 | Grohe et al. | |
| 4,312,870 A | 1/1982 | Yokoyama | |
| 4,450,166 A | 5/1984 | Clémence et al. | |
| 4,450,167 A | 5/1984 | Le Martret et al. | |
| 4,638,067 A | 1/1987 | Culbertson et al. | |
| 4,777,252 A | 10/1988 | Slusarchyk et al. | |
| 4,786,644 A | 11/1988 | Glamkowski et al. | |
| 4,845,105 A | 7/1989 | Clémence et al. | |
| 4,908,366 A | 3/1990 | Schriewer et al. | |
| 4,956,465 A | 9/1990 | Schriewer et al. | |
| 5,026,711 A | 6/1991 | Mendes et al. | |
| 5,175,151 A | 12/1992 | Afonso et al. | |
| 5,180,400 A | 1/1993 | Baudry et al. | |
| 5,254,135 A | 10/1993 | Lang et al. | |
| 5,322,847 A | 6/1994 | Marfat et al. | |
| 5,352,690 A | 10/1994 | Sofia | |
| 5,364,414 A | 11/1994 | Lang et al. | |
| 5,378,694 A | 1/1995 | Afonso et al. | |
| 5,380,713 A | 1/1995 | Balasubramanian et al. | |
| 5,412,104 A | 5/1995 | Afonso et al. | |
| 5,491,139 A | 2/1996 | Demuth, Jr. et al. | |
| 5,527,763 A | 6/1996 | Miyazaki et al. | |
| 5,536,727 A | 7/1996 | Witzel et al. | |
| 5,573,868 A | 11/1996 | Umemoto et al. | |
| 5,610,162 A | 3/1997 | Witzel et al. | |
| 5,663,179 A | 9/1997 | Dumaitre et al. | |
| 5,708,000 A | 1/1998 | Charvet-Faury et al. | |
| 5,728,691 A | 3/1998 | Corpi Constantino | |
| 5,744,471 A | 4/1998 | Bare et al. | |
| 5,750,754 A | 5/1998 | Mills | |
| 5,753,666 A | 5/1998 | Beasley et al. | |
| 5,804,588 A | 9/1998 | Dyke et al. | |
| 5,807,869 A | 9/1998 | Furuya et al. | |
| 5,811,553 A | 9/1998 | Farina et al. | |
| 5,834,485 A | 11/1998 | Dyke et al. | |
| 5,840,745 A | 11/1998 | Buzzetti et al. | |
| 5,874,424 A | 2/1999 | Batchelor et al. | |
| 5,891,878 A | 4/1999 | Beasley et al. | |
| 5,892,114 A | 4/1999 | Goldmann et al. | |
| 6,069,151 A | 5/2000 | Dyke et al. | |
| 6,133,265 A | 10/2000 | Blum et al. | |
| 6,215,016 B1 | 4/2001 | Kawai et al. | |
| 6,218,393 B1 | 4/2001 | Ryder et al. | |
| 6,258,822 B1 | 7/2001 | Geyer et al. | |
| 6,362,340 B1 | 3/2002 | Dang | |
| 6,395,750 B1 | 5/2002 | Hedlund et al. | |
| 6,413,956 B1 | 7/2002 | Albaugh et al. | |
| 6,429,207 B1 | 8/2002 | Van Wagenen et al. | |
| 6,444,617 B1 | 9/2002 | Takaishi et al. | |
| 6,448,254 B1 | 9/2002 | Lubisch et al. | |
| 6,515,001 B2 | 2/2003 | Saxena et al. | |
| 6,544,987 B2 | 4/2003 | Guo et al. | |
| 6,720,344 B2 | 4/2004 | Kerwin et al. | |
| 6,723,850 B1 | 4/2004 | Guarna et al. | |
| 6,790,858 B2 | 9/2004 | Strehlke et al. | |
| 6,849,648 B2 | 2/2005 | Bunker et al. | |
| 6,878,713 B2 | 4/2005 | De Souza et al. | |
| 6,930,131 B2 | 8/2005 | Sabatucci et al. | |
| 6,974,806 B2 | 12/2005 | Terashita et al. | |
| 6,977,001 B2 | 12/2005 | Sauter et al. | |
| 7,037,913 B2 | 5/2006 | Wang et al. | |
| 7,084,156 B2 | 8/2006 | DeVita et al. | |
| 7,105,535 B2 | 9/2006 | Berta et al. | |
| 7,112,594 B2 | 9/2006 | Ushio et al. | |
| 7,179,839 B2 | 2/2007 | Strobel et al. | |
| 2003/0195191 A1 | 10/2003 | Burton et al. | |
| 2003/0195201 A1 | 10/2003 | Bo et al. | |
| 2004/0033959 A1 | 2/2004 | Chen et al. | |
| 2004/0043983 A1 | 3/2004 | Li | |
| 2004/0082798 A1 | 4/2004 | Alonso-Alija et al. | |
| 2005/0187300 A1 | 8/2005 | Bajji et al. | |
| 2005/0222199 A1 | 10/2005 | Hayman et al. | |
| 2006/0148806 A1 | 7/2006 | Watanuki et al. | |
| 2006/0178516 A1 | 8/2006 | Johnstone et al. | |
| 2008/0071095 A1 | 3/2008 | Hadida-Ruah et al. | |

FOREIGN PATENT DOCUMENTS

| | | |
|---|---|---|
| DE | 2050966 A1 | 4/1971 |
| DE | 2407744 A1 | 8/1974 |
| DE | 2415763 A1 | 10/1974 |
| DE | 3827253 A1 | 3/1989 |
| DE | 279887 A1 | 6/1990 |
| DE | 3903799 A1 | 8/1990 |
| DE | 4017516 A1 | 12/1991 |
| DE | 19601142 A1 | 1/1997 |
| DE | 19532235 A1 | 3/1997 |
| EP | 0308702 A2 | 3/1989 |
| EP | 0332033 A2 | 9/1989 |
| EP | 0332930 A2 | 9/1989 |
| EP | 0343398 A2 | 11/1989 |
| EP | 0363585 A1 | 4/1990 |
| EP | 0472091 B1 | 11/1994 |
| EP | 0705835 A1 | 4/1996 |
| EP | 1227084 B1 | 7/2002 |
| EP | 1224172 B1 | 4/2007 |
| FR | 960299 A | 4/1950 |
| FR | 2002888 A1 | 10/1969 |
| FR | 2324304 A | 4/1977 |
| FR | 2340092 A2 | 9/1977 |
| FR | 2537140 A1 | 6/1984 |
| GB | 2372986 A | 9/2002 |
| JP | 1988116431 A | 11/1989 |
| JP | 1989168920 A | 2/1991 |
| JP | 1992171521 A | 3/1994 |
| JP | 1993184185 A | 2/1995 |
| JP | 1993231760 A | 3/1995 |
| JP | 1994278180 A | 7/1995 |
| JP | 1995132761 A | 11/1996 |

(56) References Cited

FOREIGN PATENT DOCUMENTS

| JP | 1996164798 A | 3/1997 |
|---|---|---|
| JP | 200016982 A | 1/2000 |
| JP | 2000256358 A | 9/2000 |
| JP | 2001233859 A | 8/2001 |
| JP | 2002212179 A | 7/2002 |
| JP | 2002322054 A | 11/2002 |
| JP | 2002322154 A | 11/2002 |
| JP | 200312667 A | 1/2003 |
| JP | 2003238413 A | 8/2003 |
| WO | 9214714 A1 | 9/1992 |
| WO | 9218093 A1 | 10/1992 |
| WO | 9218483 A1 | 10/1992 |
| WO | 9414797 A1 | 7/1994 |
| WO | 9511244 A1 | 4/1995 |
| WO | 9615099 A1 | 5/1996 |
| WO | 9723462 A1 | 7/1997 |
| WO | 9730999 A1 | 8/1997 |
| WO | 9826127 A1 | 6/1998 |
| WO | 9831226 A1 | 7/1998 |
| WO | 9905096 A2 | 2/1999 |
| WO | 9932436 A1 | 7/1999 |
| WO | 0134570 A1 | 5/2001 |
| WO | 0140217 A1 | 6/2001 |
| WO | 01/87806 | 11/2001 |
| WO | 0203938 A1 | 1/2002 |
| WO | 02078693 A2 | 10/2002 |
| WO | 02094809 A1 | 11/2002 |
| WO | 2004039783 A1 | 5/2004 |
| WO | 2004048314 A1 | 6/2004 |
| WO | 2004105779 A2 | 12/2004 |
| WO | 2005035514 A2 | 4/2005 |
| WO | 2007067559 A2 | 6/2007 |

OTHER PUBLICATIONS

Brown, R.K., et al., JACS, "Derivatives of Indole, 6-Amino-3-indoleacetic Acid," 1955, vol. 77, No. 14, pp. 3839-3842.
Hester, J.B., et al., "Enzyme Inhibitory Activity of 3-(2-Aminobutyl)indole Derivatives," J. Med. Chem., 1964, vol. 7, No. 3, pp. 274-279.
Kaminsky, Daniel, et al., "Quinolone Antibacterial Agents. Oxolinic Acid and Related Compounds," J. Med. Chem., 1968, vol. 11, No. 1, pp. 160-163, XP002358488.
Haynes, R.K., et al., "Amine Oxidation and the Chemistry of Quinone Imines. Part I, 3-Methoxy-4-t-butylaniline," J. Chem. Soc, Perkins Trans., 1972, vol. 1, pp. 396-408.
Grohe, Klaus, et al., "Synthese von 1-amino-4-chinolon-3-carbonsäuren," Liebigs Annalen Der Chemie, 1987, vol. 10, pp. 871-879, XP008057198.
Irie, Kazuhiro, et al., "Synthesis of 6-Substituted Indolactams by Microbial Conversion," Tetrahedron, 1995, vol. 51, No. 22, pp. 6255-6266.
Imanishi, T., et al., "Evidence that a Hybrid Molecule of Norfloxacin and Biphenylacetic Acid is a Potent Antagonist at the GABA-A Receptor," Neuropharmacology, 1996, vol. 35, No. 9/10, pp. 1271-1277, XP002358486.
Ito, Y., et al., "Inhibition of GABA-A Receptor Chloride Channel by Quinolones and Norfloxacin-Biphenylacetic Acid Hybrid Compounds," Neuropharmacology, 1996, vol. 35, No. 9/10, pp. 1263-1269, XP002358485.
Showalter, H.D. Hollis, et al., "Concise Syntheses of the Novel 1H-Pyrrolo[3,2-g]quinazoline Ring System and its [2,3-f] Angular Isomer," J. Org. Chem., 1996, vol. 61, No. 3, pp. 1155-1158.
Hennequin, Laurent F., et al., "Design and Structure-Activity Relationship of a New Class of Potent VEGF Receptor Tyrosine Kinase Inhibitors," J. Med. Chem., 1999, vol. 42, No. 26, pp. 5369-5389.
Srivastava, Sanjay K., et al., "Quinolones: Novel Probes in Antifilarial Chemotheraphy," J. Med. Chem., 2000, vol. 43, No. 11, pp. 2275-2279.
Van Es, Theodorus, et al., "N,1-Dialkyl-7-(alkylamino)-4-(alkylimino)-1,4-dihydroquinoline-3-carboxamides and their 4-oxo derivatives: Synthesis and properties," S. Afr. J. Chem., 2001, vol. 54, pp. 102-117, XP002358484.
Nosova, E.V., et al., "Synthesis of new fluorinated derivatives of Quinolinecarboxylic acids," Chem. of Heter. Compounds, 2002, vol. 38, No. 8, pp. 922-928.
Van Es, T., et al., "1-alkyl-1,4-dihydro-4-iminoquinoline-3-carboxylic acids: Synthesis, Structure, and Properties," S. Afr. J. Chem., 2002, vol. 55, pp. 13-33.
Ma, Tonghui, et al., "High-affinity Activators of Cystic Fibrosis Transmembrane Conductance Regulator (CFTR) Chloride Conductance Identified by High-Throughput Screening," J. Biol. Chem., Amer. Soc. for Biochem. and Mol. Biol., 2002, vol. 277, No. 40, pp. 37235-37241, XP002276764.
Dhar, T.G. Murali, et al., "2-Cyanoindole-based Inhibitors of Inosine Monophosphate Dehydrogenase: Synthesis and Initial Structure-Activity Relationships," Bioorg. Med. Chem. Lett., 2003, vol. 13, No. 20, pp. 3557-3560.
Perez-Guille, B., et al., "Pharmacokinetics of a cephalone (CQ-M-EPCA) in rats after oral, intraduodenal and intravenous administration," International J. of Pharm., 2004, vol. 282, No. 1-2, pp. 87-94.
Kurata, Hitoshi, et al., "A novel class of apical sodium-dependent bile acid transporter inhibitors: the amphiphilic 4-oxo-1-phenyl-1,4-dihydroquinoline derivatives," Bioorg. Med. Chem. Lett., 2004, vol. 14, pp. 1183-1186, XP002358487.
International Search Report for PCT/US2005/022768, dated Jul. 25, 2006, 12 pages.
Sen, A.B., et al., "Synthesis of Substituted Dinitrophenyl Ketones, and Phenylacetic Acids. Part I.," J. of the Indian Chemical Society, 1947, vol. 24, pp. 268-270.
Sen, A.B., et al., "Synthesis of Substituted Dinitro Phenylketones and Phenylacetic Acids, Part III.," J. of the Indian Chemical Society, 1948, vol. 25, pp. 282-284.
Sen, A.B., et al., "Synthesis of Substituted Dinitrophenyl Ketones and Phenylacetic Acids. Part IV.," J. of the Indian Chemical Society, 1948, vol. 25, No. 8, pp. 403-404.
Brown, R.K., et al., "6-Aminoindole," J. Am. Chem. Soc., 1954, vol. 76, No. 20, pp. 5149-5150.
Johnson, Herbert E., et al., "Reactions of Indole. IV. The Synthesis of Some Aminoindoles," J. Org. Chem., 1963, vol. 28, No. 10, pp. 2794-2797.
Database Registry CAS, Columbus, OH, Accession No. RN174311-74-1, entered STN: Mar. 19, 1996, 2 pages.
Database Registry CAS, Columbus, OH, Accession No. RN625115-91-5, entered STN: Dec. 9, 2003, 3 pages.
Database Registry CAS, Columbus, OH, Accession No. RN849644-14-0, entered STN: Nov. 2, 2004.
Database WPI Week 200145, Thomson Scientific, London, GB, AN 2001-425173, XP002715039.
Mashkovsky, M.D., "Medicaments," 2001, vol. 1, p. 11.
Tzetis, Maria, et al., "CFTR gene mutations—including three novel nucleotide substitutions—and haplotype background in patients with asthma, disseminated bronchiectasis and chronic obstructive pulmonary disease," Hum. Genet., 2001, vol. 108, pp. 216-221.
Noone, Peadar G., et al., Review "'CFTR-opathies': disease phenotypes associated with cycstic fibrosis transmembrane regulator gene mutations," Pulmonary Research and Treatment Center, Department of Medicine, university of North Carolina, Respiratory Research, 2001, vol. 2, No. 6, pp. 1-5.
Kapranov, N.I., et al., "Cystic fibrosis: Achievements and challenges at the present stage," Medical Genetics, 2004, vol. 3, No. 9, pp. 398-412.

MODULATORS OF ATP-BINDING CASSETTE TRANSPORTERS

CROSS-REFERENCE TO RELATED APPLICATIONS

The present application is a division of U.S. Ser. No. 11/841,646, filed Aug. 20, 2007, which is a continuation of U.S. Ser. No. 11/165,818, filed Jun. 24, 2005 (now U.S. Pat. No. 7,495,103, issued Feb. 24, 2009), which claims priority under 35 U.S.C. §119 to U.S. Provisional Application No. 60/582,676, filed Jun. 24, 2004 and entitled "MODULATORS OF ATP-BINDING CASSETTE TRANSPORTERS", U.S. Provisional Application No. 60/630,127, filed Nov. 22, 2004 and entitled "MODULATORS OF ATP-BINDING CASSETTE TRANSPORTERS", U.S. Provisional Application No. 60/635,674, filed Dec. 13, 2004 and entitled "MODULATORS OF ATP-BINDING CASSETTE TRANSPORTERS", U.S. Provisional Application No. 60/658,219, filed Mar. 3, 2005 and entitled "MODULATORS OF ATP-BINDING CASSETTE TRANSPORTERS", and U.S. Provisional Application No. 60/661,311, filed Mar. 11, 2005 and entitled "MODULATORS OF ATP-BINDING CASSETTE TRANSPORTERS", the entire contents of each of the above application being incorporated herein by reference.

TECHNICAL FIELD OF THE INVENTION

The present invention relates to modulators of ATP-Binding Cassette ("ABC") transporters or fragments thereof, including cystic fibrosis transmembrane conductance regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to α1-antitrypsin; non Piz variants), hereditary hemochromatosis, hoagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyctransferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to α1-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to PAPP and presenilins), Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS)

and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E. coli* (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula I:

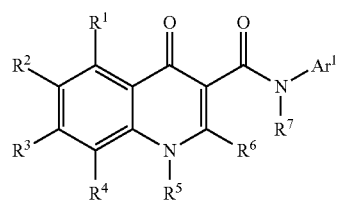

or a pharmaceutically acceptable salt thereof, wherein $R^1$, $R^2$, $R^3$, $R^4$, $R^5$, $R^6$, $R^7$, and $Ar^1$ are described generally and in classes and subclasses below.

These compounds and pharmaceutically acceptable compositions are useful for treating or lessening the severity of a variety of diseases, disorders, or conditions, including, but not limited to, cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

DETAILED DESCRIPTION OF THE INVENTION

I. General Description of Compounds of the Invention

The present invention relates to compounds of formula I useful as modulators of ABC transporter activity:

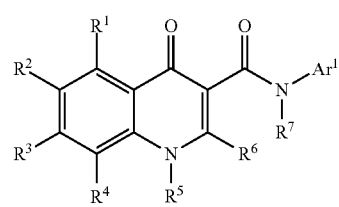

or a pharmaceutically acceptable salt thereof, wherein:

$Ar^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein $Ar^1$ has m substituents, each independently selected from —$WR^W$;

W is a bond or is an optionally substituted $C_1$-$C_6$ alkylidene chain wherein up to two methylene units of W are optionally and independently replaced by —CO—, —CS—, —COCO—, —CONR'—, —CONR'NR'—, —$CO_2$—, —OCO—, —$NR'CO_2$—, —O—, —NR'CONR'—, —OCONR'—, —NR'NR', —NR'NR'CO—, —NR'CO—, —S—, —SO, —$SO_2$—, —NR'—, —$SO_2NR'$—, $NR'SO_2$—, or —$NR'SO_2NR'$—;

$R^W$ is independently R', halo, $NO_2$, CN, $CF_3$, or $OCF_3$;

m is 0-5;

each of $R^1$, $R^2$, $R^3$, $R^4$, and $R^5$ is independently —X—$R^X$;

X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

$R^X$ is independently R', halo, NO$_2$, CN, CF$_3$, or OCF$_3$;

$R^6$ is hydrogen, CF$_3$, —OR', —SR', or an optionally substituted $C_{1-6}$ aliphatic group;

$R^7$ is hydrogen or a $C_{1-6}$ aliphatic group optionally substituted with —X—$R^X$;

R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain other embodiments, compounds of formula I are provided:

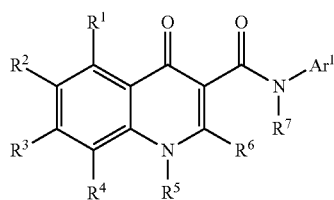

I or a pharmaceutically acceptable salt thereof, wherein:

$Ar^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein $Ar^1$ has m substituents each independently selected from —$WR^W$;

W is a bond or is an optionally substituted $C_1$-$C_6$ alkylidene chain wherein up to two methylene units of W are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, —NR'SO$_2$NR'—;

$R^W$ is independently R', halo, NO$_2$, CN, CF$_3$, or OCF$_3$;

m is 0-5;

each of $R^1$, $R^2$, $R^3$, $R^4$, and $R^5$ is independently —X—$R^X$;

X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

$R^X$ is independently R', halo, NO$_2$, CN, CF$_3$, or OCF$_3$;

$R^6$ is hydrogen, CF$_3$, —OR', —SR', or an optionally substituted C1-C8 aliphatic group;

$R^7$ is hydrogen or a C1-C6 aliphatic group optionally substituted with —X—$R^X$;

R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

provided that:

i) when $R^1$, $R^2$, $R^3$, $R^4$, $R^5$, $R^6$ and $R^7$ are hydrogen, then $Ar^1$ is not phenyl, 2-methoxyphenyl, 4-methoxyphenyl, 2-methylphenyl, 2,6-dichlorophenyl, 2,4-dichlorophenyl, 2-bromophenyl, 4-bromophenyl, 4-hydroxyphenyl, 2,4-dinitrophenyl, 3,5-dicarboxylic acid phenyl, 2,4-dimethylphenyl, 2,6-dimethylphenyl, 2-ethylphenyl, 3-nitro-4-methylphenyl, 3-carboxylic-acid phenyl, 2-fluorophenyl, 3-fluorophenyl, 3-trifluoromethylphenyl, 3-ethoxyphenyl, 4-chlorophenyl, 3-methoxyphenyl, 4-dimethylaminophenyl, 3,4-dimethylphenyl, 2-ethylphenyl, or 4-ethoxycarbonylphenyl;

ii) when $R^1$, $R^2$, $R^3$, $R^5$, $R^6$ and $R^7$ are hydrogen, and $R^4$ is methoxy, then $Ar^1$ is not 2-fluorophenyl or 3-fluorophenyl;

iii) when $R^1$, $R^3$, $R^4$, $R^5$, $R^6$ and $R^7$ are hydrogen, $R^2$ is 1,2,3,4-tetrahydroisoquinolin-1-yl-sulfonyl, then $Ar^1$ is not 3-trifluoromethylphenyl;

iv) when $R^1$, $R^2$, $R^3$, $R^4$, $R^5$ and $R^7$ are hydrogen, $R^6$ is methyl, then $Ar^1$ is not phenyl;

v) when $R^1$, $R^4$, $R^5$, $R^6$ and $R^7$ are hydrogen, $R^2$ and $R^3$, taken together, are methylenedioxy, then $Ar^1$ is not 4-chlorophenyl, 4-bromophenyl, 4-nitrophenyl, 4-carboethoxyphenyl, 6-ethoxy-benzothiazol-2-yl, 6-carboethoxy-benzothiazol-2-yl, 6-halo-benzothiazol-2-yl, 6-nitro-benzothiazol-2-yl, or 6-thiocyano-benzothiazol-2-yl.

vi) when $R^1$, $R^4$, $R^5$, $R^6$ and $R^7$ are hydrogen, $R^2$ and $R^3$, taken together, are methylenedioxy, then $Ar^1$ is not 4-substituted phenyl wherein said substituent is —SO$_2$NHR$^{xx}$, wherein R$^{xx}$ is 2-pyridinyl, 4-methyl-2-pyrimidinyl, 3,4-dimethyl-5-isoxazolyl;

vii) when $R^1$, $R^2$, $R^3$, $R^4$, $R^5$, $R^6$, and $R^7$ are hydrogen, then $Ar^1$ is not thiazol-2-yl, 1H-1,2,4-triazol-3-yl, or 1H-1,3,4-triazol-2-yl;

viii) when $R^1$, $R^2$, $R^3$, $R^5$, $R^6$, and $R^7$ are hydrogen, and $R^4$ is CF$_3$, OMe, chloro, SCF$_3$, or OCF$_3$, then $Ar^1$ is not 5-methyl-1,2-oxazol-3-yl, thiazol-2-yl, 4-fluorophenyl, pyrimidin-2-yl, 1-methyl-1,2-(1H)-pyrazol-5-yl, pyridine-2-yl, phenyl, N-methyl-imidazol-2-yl, imidazol-2-yl, 5-methyl-imidazol-2-yl, 1,3-oxazol-2-yl, or 1,3,5-(1H)-triazol-2-yl;

ix) when $R^1$, $R^2$, $R^3$, $R^4$, $R^5$, $R^6$, and $R^7$ each is hydrogen, then $Ar^1$ is not pyrimidin-2-yl, 4,6-dimethyl-pyrimidin-2-yl, 4-methoxy-6-methyl-1,3,5-triazin-2-yl; 5-bromo-pyridin-2-yl, pyridin-2-yl, or 3,5-dichloro-pyridin-2-yl;

x) when $R^1$, $R^2$, $R^3$, $R^4$, $R^5$ and $R^7$ each is hydrogen, $R^6$ is hydroxy, then $Ar^1$ is not 2,6-dichloro-4-aminosulfonyl-phenyl;

xi) when $R^2$ or $R^3$ is an optionally substituted N-piperazyl, N-piperidyl, or N-morpholinyl, then $Ar^1$ is not an optionally substituted ring selected from thiazol-2-yl, pyridyl, phenyl, thiadiazolyl, benzothiazol-2-yl, or indazolyl;

9 xii) when R² is optionally substituted cyclohexylamino, then Ar¹ is not optionally substituted phenyl, pyridyl, or thiadiazolyl;

xiii) Ar¹ is not optionally substituted tetrazolyl;

xiv) when R², R⁴, R⁵, R⁶, and R⁷ each is hydrogen, and R¹ and R³ both are simultaneously CF₃, chloro, methyl, or methoxy, then Ar¹ is not 4,5-dihydro-1,3-thiazol-2-yl, thiazol-2-yl, or [3,5-bis(trifluoromethyl)-1H-pyrazol-1-yl]phenyl;

xv) when R¹, R⁴, R⁵, R⁶, and R⁷ each is hydrogen, and Ar¹ is thiazol-2-yl, then neither R² nor R³ is isopropyl, chloro, or CF₃;

xvi) when Ar¹ is 4-methoxyphenyl, 4-trifluoromethylphenyl, 2-fluorophenyl, phenyl, or 3-chlorophenyl, then:
  a) when R¹, R², R⁴, R⁵, R⁶, and R⁷ each is hydrogen, then R³ is not methoxy; or
  b) when R¹, R³, R⁴, R⁵, R⁶, and R⁷ each is hydrogen, then R² is not chloro; or
  c) when R¹, R², R³, R⁵, R⁶, and R⁷ each is hydrogen, then R⁴ is not methoxy; or
  d) when R¹, R³, R⁴, R⁶, and R⁷ each is hydrogen, and R⁵ is ethyl, then R² is not chloro;
  e) when R¹, R², R⁴, R⁵, R⁶, and R⁷ each is hydrogen, then R³ is not chloro;

xvi) when R¹, R³, R⁴, R⁵, R⁶, and R⁷ each is hydrogen, and R² is CF₃ or OCF₃, then Ar¹ is not [3,5-bis(trifluoromethyl)-1H-pyrazol-1-yl]phenyl;

xvii) when R¹, R², R⁴, R⁵, R⁶, and R⁷ each is hydrogen, and R³ is hydrogen or CF₃, then Ar1 is not a phenyl substituted with —OCH₂CH₂Ph, —OCH₂CH₂(2-trifluoromethyl-phenyl), —OCH₂CH₂-(6,7-dimethoxy-1,2,3,4-tetrahydroisoquinolin-2-yl), or substituted 1H-pyrazol-3-yl; and xviii) the following two compounds are excluded:

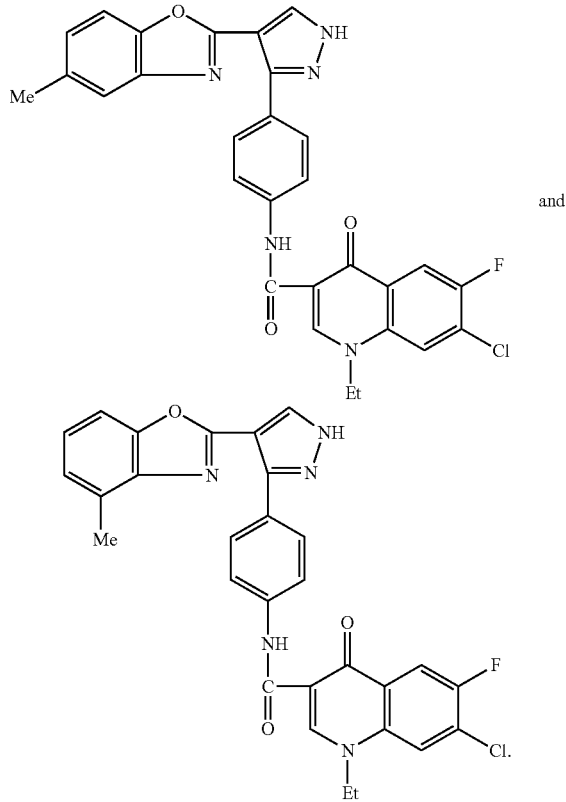

and

10

2. Compounds and Definitions

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic or tricyclic $C_8$-$C_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl" as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —$CHF_2$, —$CH_2F$, —$CF_3$, —$CF_2$—, or perhaloalkyl, such as, —$CF_2CF_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halo; —$R^°$; —$OR^°$; —$SR^°$; 1,2-methylene-dioxy; 1,2-ethylenedioxy; phenyl (Ph) optionally substituted with $R^°$; —O(Ph) optionally substituted with $R^°$; —$(CH_2)_{1-2}$(Ph), optionally substituted with $R^°$; —CH=CH(Ph), optionally substituted with $R^°$; —$NO_2$; —CN; —$N(R^°)_2$; —$NR^°C(O)R^°$; —$NR^°C(O)N(R^°)_2$; —$NR^°CO_2R^°$; —$NR^°NR^°C(O)R^°$; —$NR^°NR^°C(O)N(R^°)_2$; —$NR^°NR^°CO_2R^°$; —$C(O)C(O)R^°$; —$C(O)CH_2C(O)R^°$; —$CO_2R^°$; —$C(O)R^°$; —$C(O)N(R^°)_2$; —$OC(O)N(R^°)_2$; —$S(O)_2R^°$; —$SO_2N(R^°)_2$; —$S(O)R^°$; —$NR^°SO_2N(R^°)_2$; —$NR^°SO_2R^°$; —C(=S)$N(R^°)_2$; —C(=NH)—$N(R^°)_2$; or —$(CH_2)_{0-2}NHC(O)R^°$ wherein each independent occurrence of $R^°$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^°$, on the same substituent or different substituents, taken together with the atom(s) to which each $R^°$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^°$ are selected from $NH_2$, $NH(C_{1-4}$aliphatic), $N(C_{1-4}$aliphatic)$_2$, halo, $C_{1-4}$aliphatic, OH, O($C_{1-4}$aliphatic), $NO_2$, CN, $CO_2H$, $CO_2(C_{1-4}$aliphatic), O(halo$C_{1-4}$ aliphatic), or halo$C_{1-4}$aliphatic, wherein each of the foregoing $C_{1-4}$aliphatic groups of $R^°$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$aliphatic), $N(C_{1-4}$aliphatic)$_2$, halo, $C_{1-4}$ aliphatic, OH, O($C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —C(=S)$N(R^+)_2$, —C(=NH)—$N(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of $R^+$ are selected from $NH_2$, $NH(C_{1-4}$aliphatic), $N(C_{1-4}$aliphatic)$_2$, halo, $C_{1-4}$ aliphatic, OH, O($C_{1-4}$ aliphatic), $NO_2$, CN, $CO_2H$, $CO_2(C_{1-4}$aliphatic), O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

As detailed above, in some embodiments, two independent occurrences of $R^o$ (or $R^+$, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

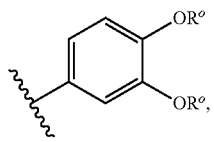

these two occurrences of $R^o$ are taken together with the oxygen atoms to which they are bound to form a fused 6-membered oxygen containing ring:

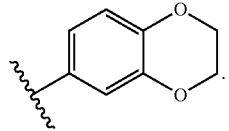

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

A substituent bond in, e.g., a bicyclic ring system, as shown below, means that the substituent can be attached to any substitutable ring atom on either ring of the bicyclic ring system:

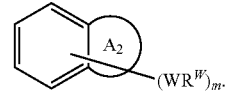

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. E.g., when $R^5$ in compounds of formula I is hydrogen, compounds of formula I may exist as tautomers:

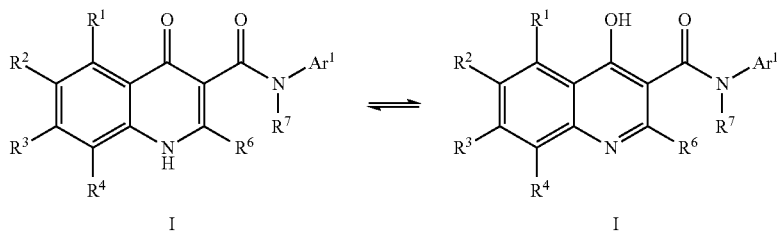

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds

In some embodiments of the present invention, $Ar^1$ is selected from:

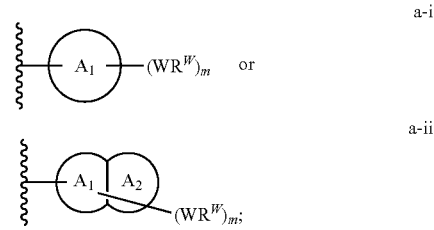

wherein ring $A_1$ 5-6 membered aromatic monocyclic ring having 0-4 heteroatoms independently selected from nitrogen, oxygen, or sulfur; or $A_1$ and $A_2$, together, is an 8-14 aromatic, bicyclic or tricyclic aryl ring, wherein each ring contains 0-4 heteroatoms independently selected from nitrogen, oxygen, or sulfur.

In some embodiments, $A_1$ is an optionally substituted 6 membered aromatic ring having 0-4 heteroatoms, wherein said heteroatom is nitrogen. In some embodiments, $A_1$ is an optionally substituted phenyl. Or, $A_1$ is an optionally substituted pyridyl, pyrimidinyl, pyrazinyl or triazinyl. Or, $A_1$ is an optionally substituted pyrazinyl or triazinyl. Or, $A_1$ is an optionally substituted pyridyl.

In some embodiments, $A_1$ is an optionally substituted 5-membered aromatic ring having 0-3 heteroatoms, wherein said heteroatom is nitrogen, oxygen, or sulfur. In some embodiments, $A_1$ is an optionally substituted 5-membered aromatic ring having 1-2 nitrogen atoms. In one embodiment, $A_1$ is an optionally substituted 5-membered aromatic ring other than thiazolyl.

In some embodiments, $A_2$ is an optionally substituted 6 membered aromatic ring having 0-4 heteroatoms, wherein said heteroatom is nitrogen. In some embodiments, $A_2$ is an optionally substituted phenyl. Or, $A_2$ is an optionally substituted pyridyl, pyrimidinyl, pyrazinyl, or triazinyl.

In some embodiments, $A_2$ is an optionally substituted 5-membered aromatic ring having 0-3 heteroatoms, wherein said heteroatom is nitrogen, oxygen, or sulfur. In some embodiments, $A_2$ is an optionally substituted 5-membered aromatic ring having 1-2 nitrogen atoms. In certain embodiments, $A_2$ is an optionally substituted pyrrolyl.

In some embodiments, $A_2$ is an optionally substituted 5-7 membered saturated or unsaturated heterocyclic ring having 1-3 heteroatoms independently selected from nitrogen, sulfur, or oxygen. Exemplary such rings include piperidyl, piperazyl, morpholinyl, thiomorpholinyl, pyrrolidinyl, tetrahydrofuranyl, etc.

In some embodiments, $A_2$ is an optionally substituted 5-10 membered saturated or unsaturated carbocyclic ring. In one embodiment, $A_2$ is an optionally substituted 5-10 membered saturated carbocyclic ring. Exemplary such rings include cyclohexyl, cyclopentyl, etc.

In some embodiments, ring $A_2$ is selected from:

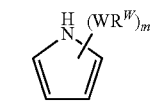

i

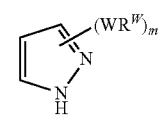

ii

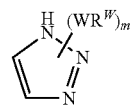

iii

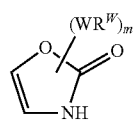

iv

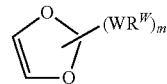

v

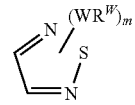

vi

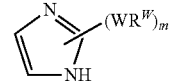

vii

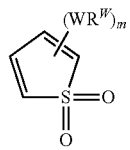

viii

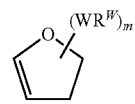

ix

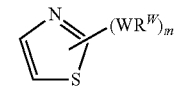

x

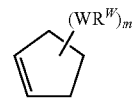

xi

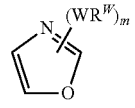

xii

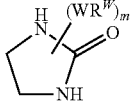

xiii

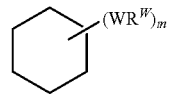

xiv

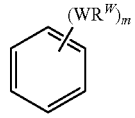

xv

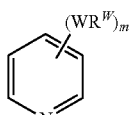

xvi

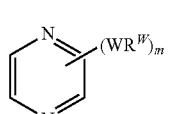

xvii

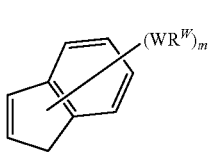

xviii

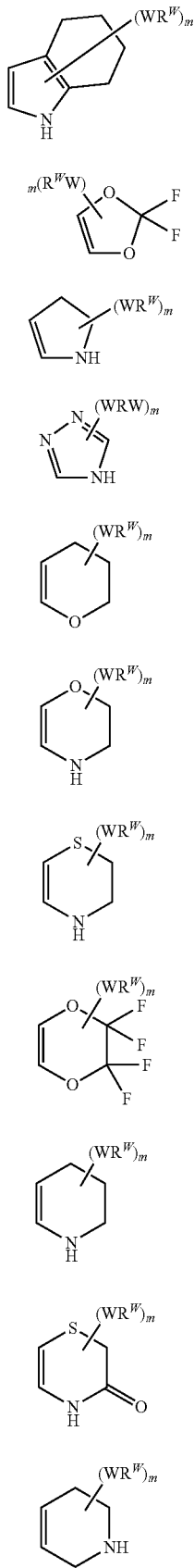

wherein ring $A_2$ is fused to ring $A_1$ through two adjacent ring atoms.

In other embodiments, W is a bond or is an optionally substituted $C_{1-6}$ alkylidene chain wherein one or two methylene units are optionally and independently replaced by O, NR', S, SO, $SO_2$, or COO, CO, $SO_2$NR', NR'$SO_2$, C(O)NR', NR'C(O), OC(O), OC(O)NR', and $R^W$ is R' or halo. In still other embodiments, each occurrence of $WR^W$ is independently —C1-C3 alkyl, C1-C3 perhaloalkyl, —O(C1-C3alkyl), —$CF_3$, —$OCF_3$, —$SCF_3$, —F, —Cl, —Br, or —COOR', —COR', —O(CH$_2$)$_2$N(R')(R'), —O(CH$_2$)N(R') (R'), —CON(R')(R'), —(CH$_2$)$_2$OR', —(CH$_2$)OR', optionally substituted monocyclic or bicyclic aromatic ring, optionally substituted arylsulfone, optionally substituted 5-membered heteroaryl ring, —N(R')(R'), —(CH$_2$)$_2$N(R')R'), or —(CH$_2$) N(R')(R').

In some embodiments, m is 0. Or, m is 1. Or, m is 2. In some embodiments, m is 3. In yet other embodiments, m is 4.

In one embodiment, $R^5$ is X—$R^X$. In some embodiments $R^5$ is hydrogen. Or, $R^5$ is an optionally substituted $C_{1-8}$ aliphatic group. In some embodiments, $R^5$ is optionally substituted $C_{1-4}$ aliphatic. Or, $R^5$ is benzyl.

In some embodiments $R^6$ is hydrogen. Or, $R^6$ is an optionally substituted $C_{1-8}$ aliphatic group. In some embodiments, $R^6$ is optionally substituted $C_{1-4}$ aliphatic. In certain other embodiments, $R^6$ is —(O—$C_{1-4}$ aliphatic) or —(S—$C_{1-4}$ aliphatic). Preferably, $R^6$ is —OMe or —SMe. In certain other embodiments, $R_6$ is $CF_3$.

In one embodiment of the present invention, $R^1$, $R^2$, $R^3$, and $R^4$ are simultaneously hydrogen. In another embodiment, $R^6$ and $R^7$ are both simultaneously hydrogen.

In another embodiment of the present invention, $R^1$, $R^2$, $R^3$, $R^4$, and $R^5$ are simultaneously hydrogen. In another embodiment of the present invention, $R^1$, $R^2$, $R^3$, $R^4$, $R^5$ and $R^6$ are simultaneously hydrogen.

In another embodiment of the present invention, $R^2$ is X—$R^X$, wherein X is —$SO_2$NR'—, and $R^X$ is R'; i.e., $R^2$ is —$SO_2$N(R')$_2$. In one embodiment, the two R' therein taken together form an optionally substituted 5-7 membered ring with 0-3 additional heteroatoms selected from nitrogen, oxygen, or sulfur. Or, $R^1$, $R^3$, $R^4$, $R^5$ and $R^6$ are simultaneously hydrogen, and $R^2$ is $SO_2N(R')_2$.

In some embodiments, X is a bond or is an optionally substituted $C_{1-6}$ alkylidene chain wherein one or two nonadjacent methylene units are optionally and independently replaced by O, NR', S, $SO_2$, or COO, CO, and $R^X$ is R' or halo. In still other embodiments, each occurrence of $XR^X$ is independently —$C_{1-3}$alkyl, —O($C_{1-3}$alkyl), —$CF_3$, —$OCF_3$, —SCF₃, —F, —Cl, —Br, OH, —COOR', —COR', —O(CH₂)₂N(R')(R'), —O(CH₂)N(R')(R'), —CON(R')(R'), —(CH₂)₂OR', —(CH₂)OR', optionally substituted phenyl, —N(R')(R'), —(CH₂)₂N(R')(R'), or —(CH₂)N(R')(R').

In some embodiments, $R^7$ is hydrogen. In certain other embodiment, $R^7$ is $C_{1-4}$ straight or branched aliphatic.

In some embodiments, $R^W$ is selected from halo, cyano, CF₃, CHF₂, OCHF₂, Me, Et, CH(Me)₂, CHMeEt, n-propyl, t-butyl, OMe, OEt, OPh, O-fluorophenyl, O-difluorophenyl, O-methoxyphenyl, O-tolyl, O-benzyl, SMe, SCF₃, SCHF₂, SEt, CH₂CN, NH₂, NHMe, N(Me)₂, NHEt, N(Et)₂, C(O)CH₃, C(O)Ph, C(O)NH₂, SPh, SO₂— (amino-pyridyl), SO₂NH₂, SO₂Ph, SO₂NHPh, SO₂—N-morpholino, SO₂—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2yl, furan-2-yl, 4-methyl-4H-[1,2,4]triazol-3-yl, 3-(4'-chlorophenyl)-[1,2,4]oxadiazol-5-yl, NHC(O)Me, NHC(O)Et, NHC(O)Ph, NHSO₂Me, 2-indolyl, 5-indolyl, —CH₂CH₂OH, —OCF₃O—(2,3-dimethylphenyl), 5-methylfuryl, —SO₂—N-piperidyl, 2-tolyl, 3-tolyl, 4-tolyl, O-butyl, NHCO₂C(Me)₃, CO₂C(Me)₃, isopropenyl, n-butyl, O-(2,4-dichlorophenyl), NHSO₂PhMe, O-(3-chloro-5-trifluoromethyl-2-pyridyl), phenylhydroxymethyl, 2,5-dimethylpyrrolyl, NHCOCH₂C(Me)₃, O-(2-tert-butyl)phenyl, 2,3-dimethylphenyl, 3,4-dimethylphenyl, 4-hydroxymethyl phenyl, 4-dimethylaminophenyl, 2-trifluoromethylphenyl, 3-trifluoromethylphenyl, 4-trifluoromethylphenyl, 4-cyanomethylphenyl, 4-isobutylphenyl, 3-pyridyl, 4-pyridyl, 4-isopropylphenyl, 3-isopropylphenyl, 2-methoxyphenyl, 3-methoxyphenyl, 4-methoxyphenyl, 3,4-methylenedioxyphenyl, 2-ethoxyphenyl, 3-ethoxyphenyl, 4-ethoxyphenyl, 2-methylthiophenyl, 4-methylthiophenyl, 2,4-dimethoxyphenyl, 2,5-dimethoxyphenyl, 2,6-dimethoxyphenyl, 3,4-dimethoxyphenyl, 5-chloro-2-methoxyphenyl, 2-OCF₃-phenyl, 3-trifluoromethoxy-phenyl, 4-trifluoromethoxyphenyl, 2-phenoxyphenyl, 4-phenoxyphenyl, 2-fluoro-3-methoxyphenyl, 2,4-dimethoxy-5-pyrimidyl, 5-isopropyl-2-methoxyphenyl, 2-fluorophenyl, 3-fluorophenyl, 4-fluorophenyl, 3-cyanophenyl, 3-chlorophenyl, 4-chlorophenyl, 2,3-difluorophenyl, 2,4-difluorophenyl, 2,5-difluorophenyl, 3,4-difluorophenyl, 3,5-difluorophenyl, 3-chloro-4-fluoro-phenyl, 3,5-dichlorophenyl, 2,5-dichlorophenyl, 2,3-dichlorophenyl, 3,4-dichlorophenyl, 2,4-dichlorophenyl, 3-methoxycarbonylphenyl, 4-methoxycarbonyl phenyl, 3-isopropyloxycarbonylphenyl, 3-acetamidophenyl, 4-fluoro-3-methylphenyl, 4-methanesulfinyl-phenyl, 4-methanesulfonyl-phenyl, 4-N-(2-N,N-dimethylaminoethyl)carbamoylphenyl, 5-acetyl-2-thienyl, 2-benzothienyl, 3-benzothienyl, furan-3-yl, 4-methyl-2-thienyl, 5-cyano-2-thienyl, N'-phenylcarbonyl-N-piperazinyl, —NHCO₂Et, —NHCO₂Me, N-pyrrolidinyl, —NHSO₂(CH₂)₂N-piperidine, —NHSO₂(CH₂)₂N-morpholine, —NHSO₂(CH₂)₂N(Me)₂, COCH₂N(Me)COCH₂NHMe, —CO₂Et, O-propyl, —CH₂CH₂NHCO₂C(Me)₃, hydroxy, aminomethyl, pentyl, adamantyl, cyclopentyl, ethoxyethyl, C(Me)₂CH₂OH, C(Me)₂CO₂Et, —CHOHMe, CH₂CO₂Et, —C(Me)₂CH₂NHCO₂C(Me)₃, O(CH₂)₂OEt, O(CH₂)₂OH, CO₂Me, hydroxymethyl, 1-methyl-1-cyclohexyl, 1-methyl-1-cyclooctyl, 1-methyl-1-cycloheptyl, C(Et)₂C(Me)₃, C(Et)₃, CONHCH₂CH(Me)₂, 2-aminomethyl-phenyl, ethenyl, 1-piperidinylcarbonyl, ethynyl, cyclohexyl, 4-methylpiperidinyl, —OCO₂Me, —C(Me)₂CH₂NHCO₂CH₂CH(Me)₂, —C(Me)₂CH₂NHCO₂CH₂CH₃, —C(Me)₂CH₂NHCO₂Et, —C(Me)₂CH₂NHCO₂Me, —C(Me)₂CH₂NHCO₂CH₂C(Me)₃, —CH₂NHCOCF₃, —CH₂NHCO₂C(Me)₃, —C(Me)₂CH₂NHCO₂(CH₂)₃CH₃, C(Me)₂CH₂NHCO₂(CH₂)₂OMe, C(OH)(CF₃)₂, —C(Me)₂CH₂NHCO₂CH₂-tetrahydrofurane-3-yl, C(Me)₂CH₂—O—(CH₂)₂OMe, or 3-ethyl-2,6-dioxopiperidin-3-yl.

In one embodiment, R' is hydrogen.

In one embodiment, R' is a C1-C8 aliphatic group, optionally substituted with up to 3 substituents selected from halo, CN, CF₃, CHF₂, OCF₃, or OCHF₂, wherein up to two methylene units of said C1-C8 aliphatic is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, CF₃, CHF₂, OCF₃, OCHF₂, or C1-C6 alkyl, wherein up to two methylene units of said C1-C6 alkyl is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, CF₃, CHF₂, OCF₃, OCHF₂, or C1-C6 alkyl, wherein up to two methylene units of said C1-C6 alkyl is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, CF₃, CHF₂, OCF₃, OCHF₂, or C1-C6 alkyl, wherein up to two methylene units of said C1-C6 alkyl is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

According to one embodiment, the present invention provides compounds of formula IIA or formula IIB:

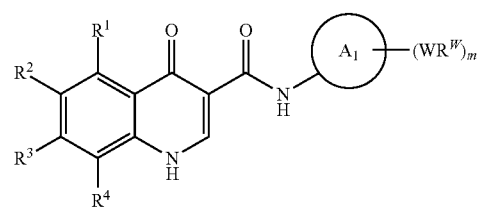

-continued

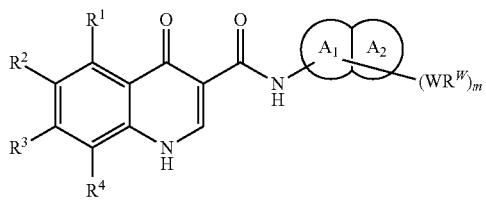
IIB

According to another embodiment, the present invention provides compounds of formula IIIA, formula IIIB, formula IIIC, formula IIID, or formula IIIE:

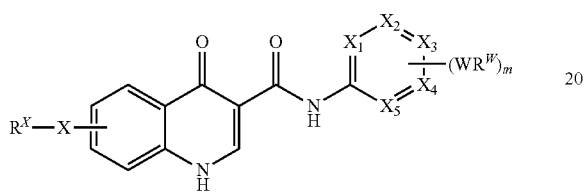
IIIA

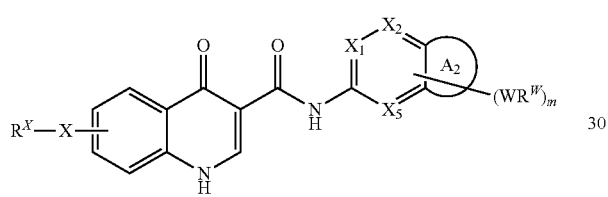
IIIB

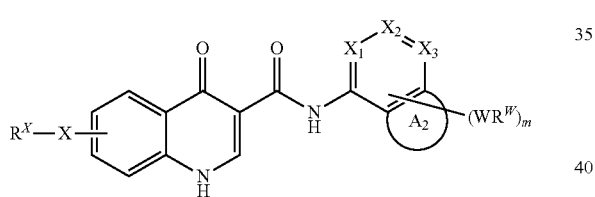
IIIC

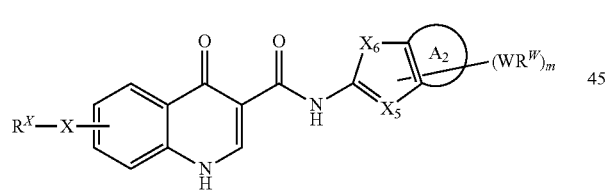
IIID

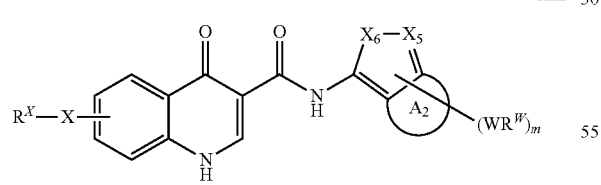
IIIE wherein each of $X_1$, $X_2$, $X_3$, $X_4$, and $X_5$ is independently selected from CH or N; and $X_6$ is O, S, or NR'.

In one embodiment, compounds of formula IIIA, formula IIIB, formula IIIC, formula IIID, or formula IIIE have y occurrences of substituent $X—R^X$, wherein y is 0-4. Or, y is 1. Or, y is 2.

In some embodiments of formula IIIA, $X_1$, $X_2$, $X_3$, $X_4$, and $X_5$ taken together with $WR^W$ and m is optionally substituted phenyl.

In some embodiments of formula IIIA, $X_1$, $X_2$, $X_3$, $X_4$, and $X_5$ taken together is an optionally substituted ring selected from:

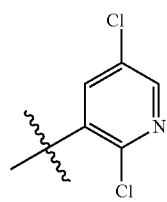
a-i

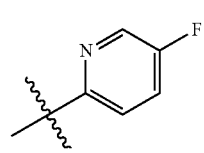
a-ii

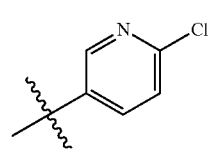
a-iii

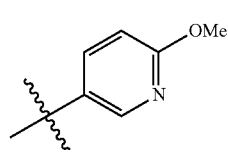
a-iv

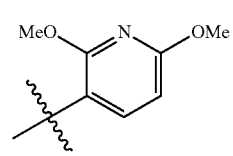
a-v

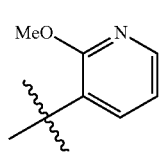
a-vi

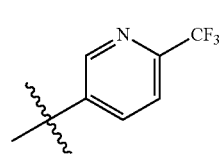
a-vii

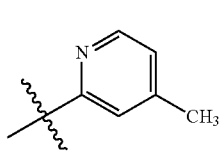
a-viii

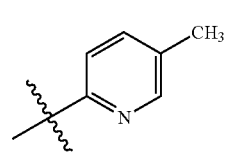
a-ix

| | |
|---|---|
| 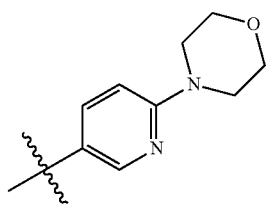 | a-x |
| 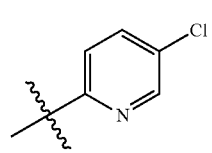 | a-xi |
| 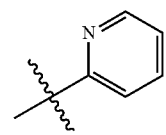 | a-xii |
| 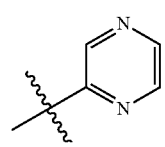 | a-xiii |
| 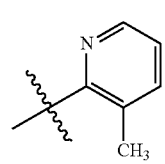 | a-xiv |
| 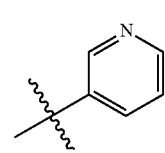 | a-xv |
| 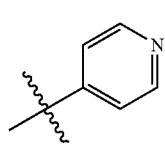 | a-xvi |
| 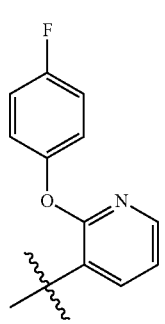 | a-xvii |
| 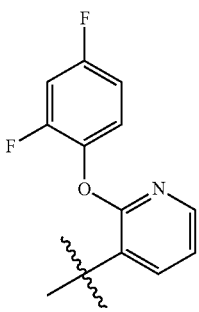 | a-xviii |
| 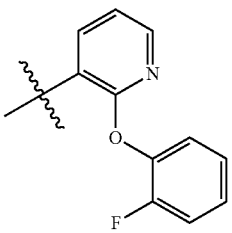 | a-xix |
| 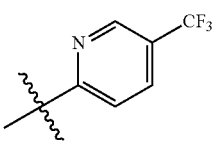 | a-xx |
| 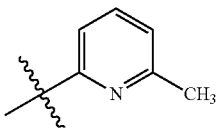 | a-xxi |
| 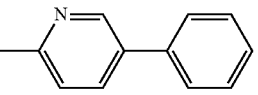 | a-xxii |
| 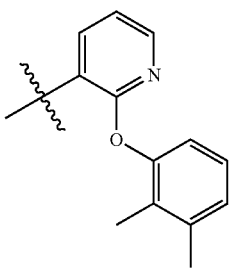 | a-xxiii |
| 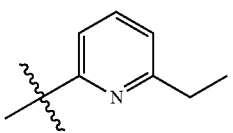 | a-xxiv |
| 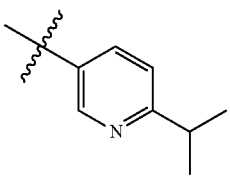 | a-xxv |

In some embodiments of formula IIIB, formula IIIC, formula IIID, or formula IIIE, $X_1$, $X_2$, $X_3$, $X_4$, $X_5$, or $X_6$, taken together with ring $A_2$ is an optionally substituted ring selected from:
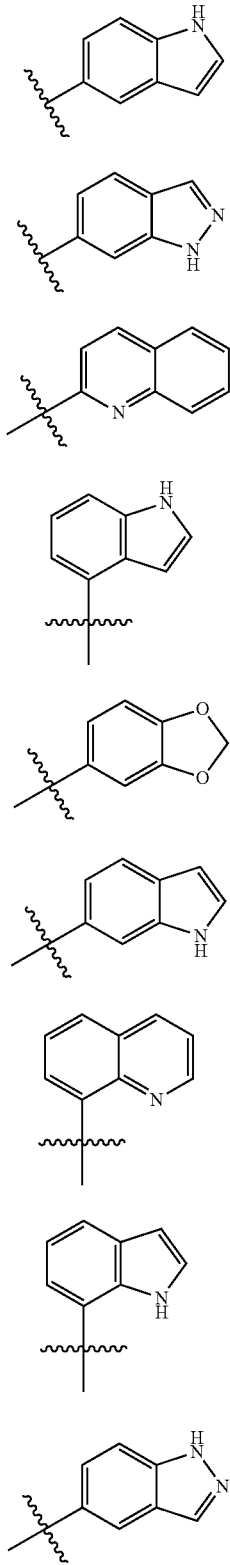
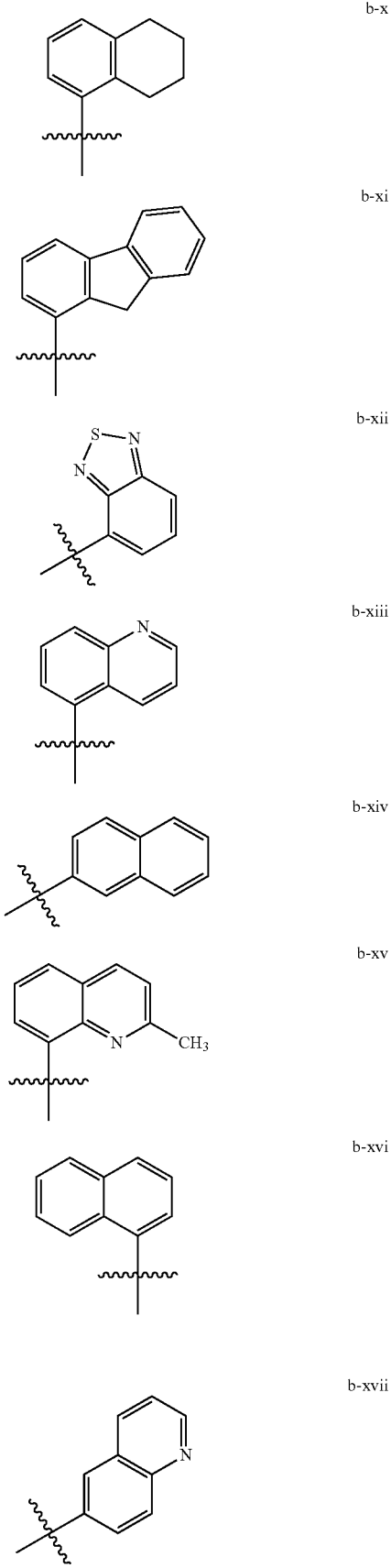

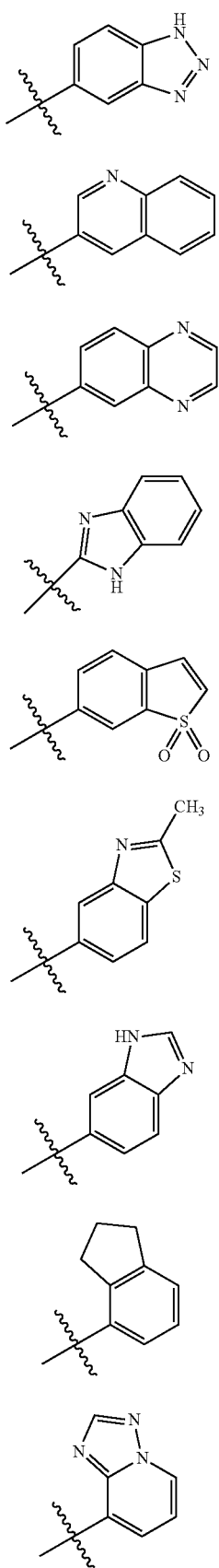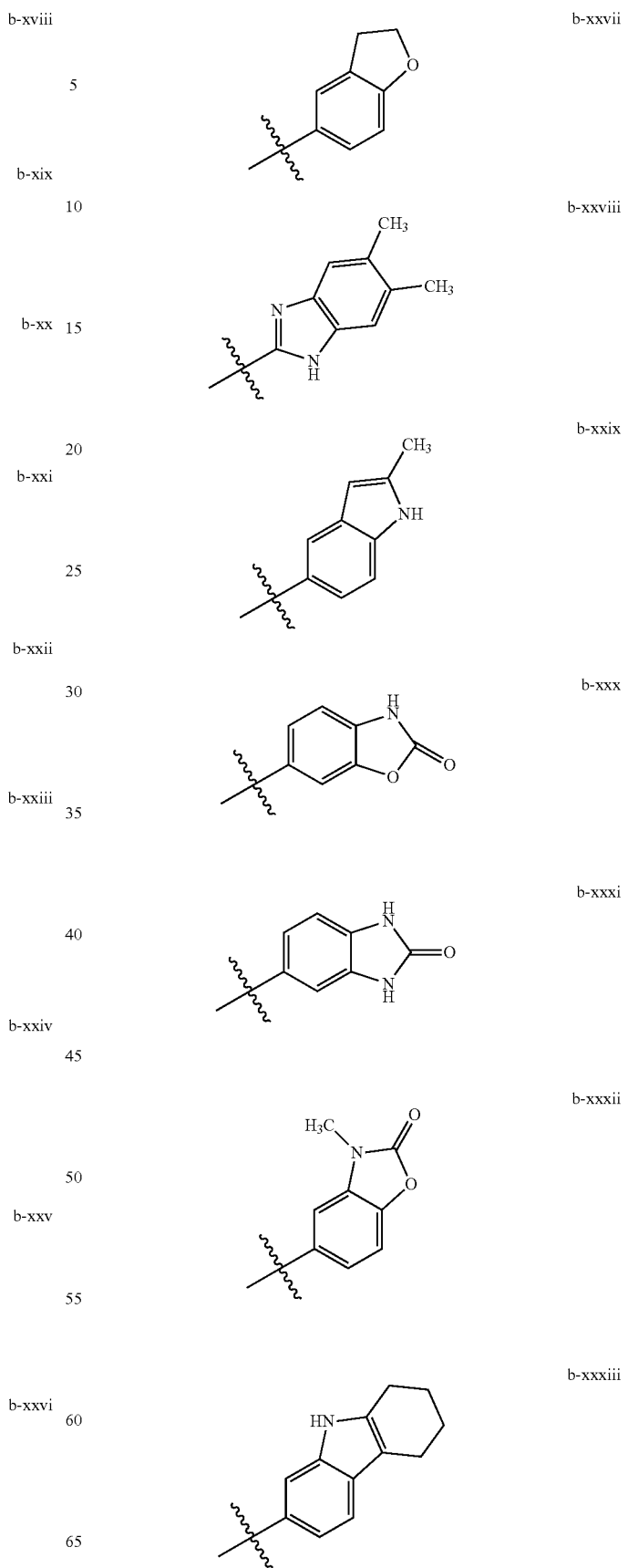

-continued b-xxxiv b-xxxv b-xxxvi b-xxxvii b-xxxviii bxxxix b-xL

-continued b-xLi b-xLii b-xLiii b-xLiv b-xLv b-xLvi b-xLvii b-xLviii b-xLix
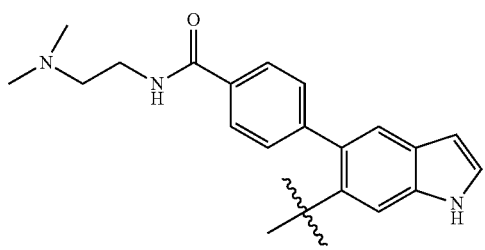
b-L
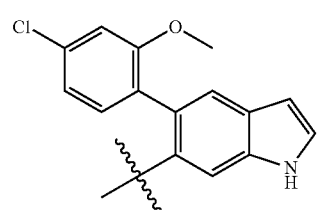
b-Li
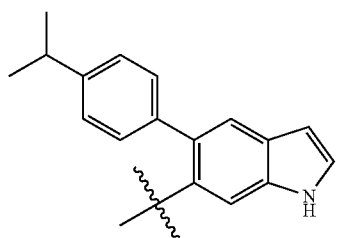
b-Lii
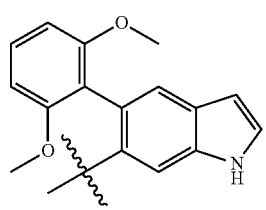
b-Liii
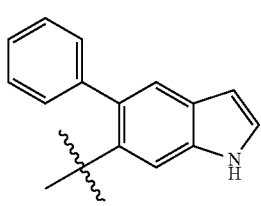
b-Liv
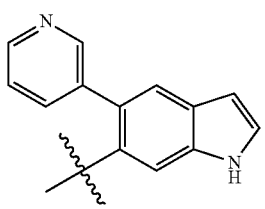
b-Lv
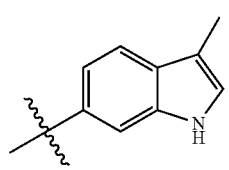
b-Lvi
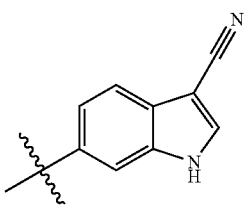
b-Lvii
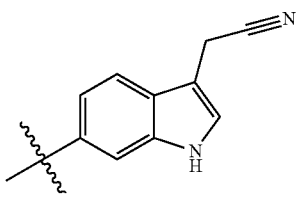
b-Lviii
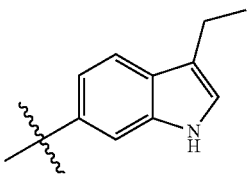
b-Lix
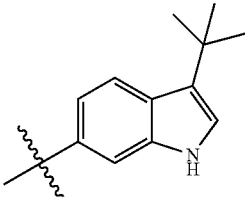
b-Lx
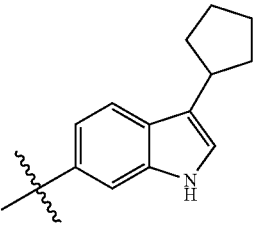
b-Lxi
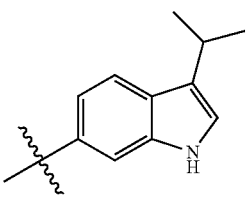
b-Lxii
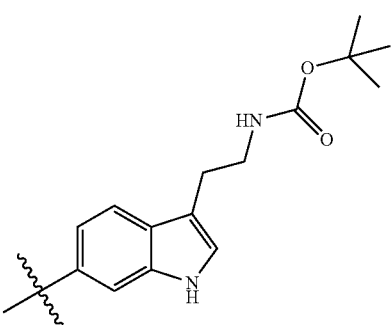

-continued
b-Lxiii
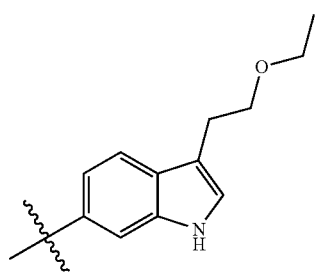
b-Lxiv
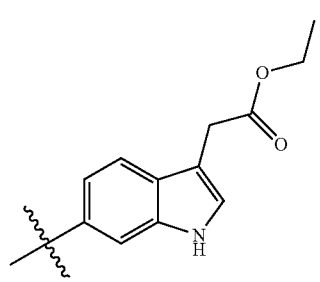
b-Lxv
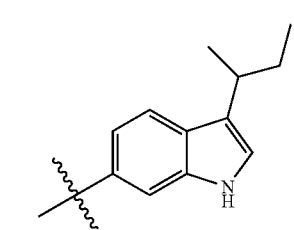
b-Lxvi
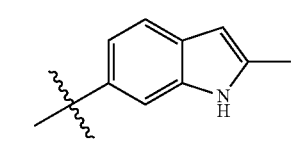
b-Lxvii
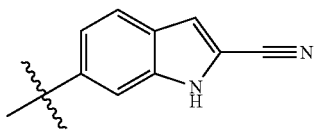
b-Lxviii
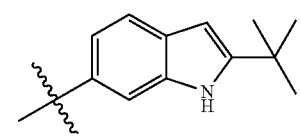
b-Lxix
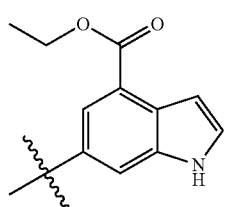
-continued
b-Lxx
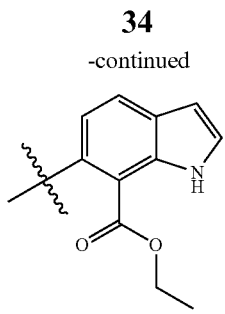
b-Lxxi
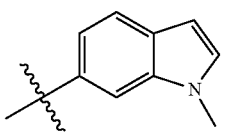
b-Lxxii
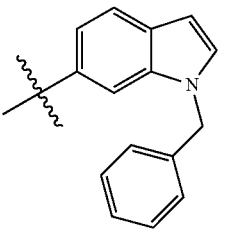
b-Lxxiii
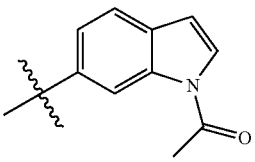
b-Lxxiv
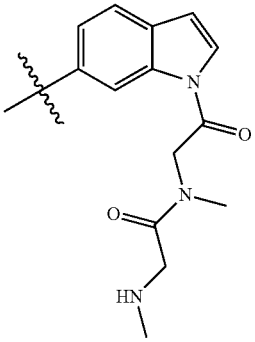
b-Lxxv
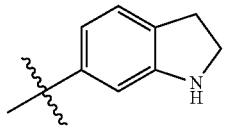
b-Lxxvi
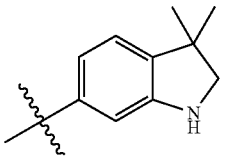
b-Lxxvii
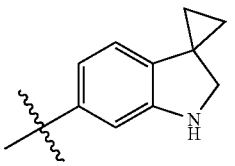

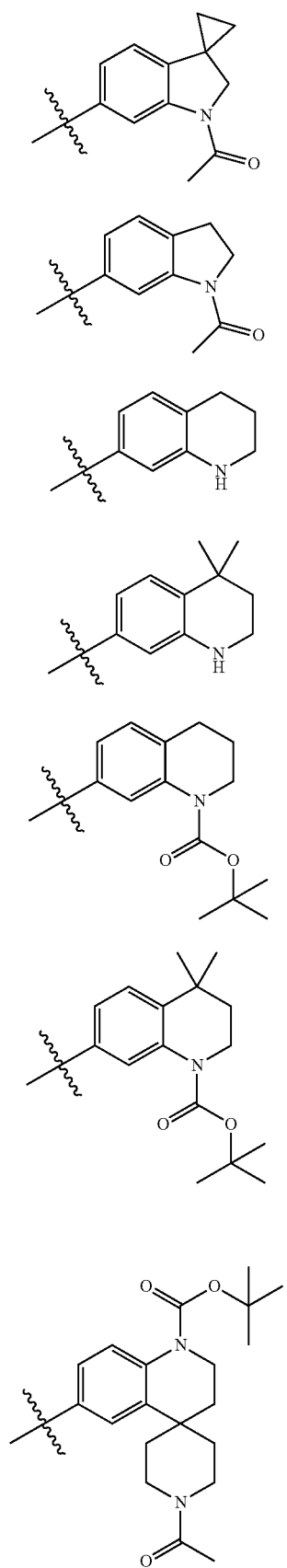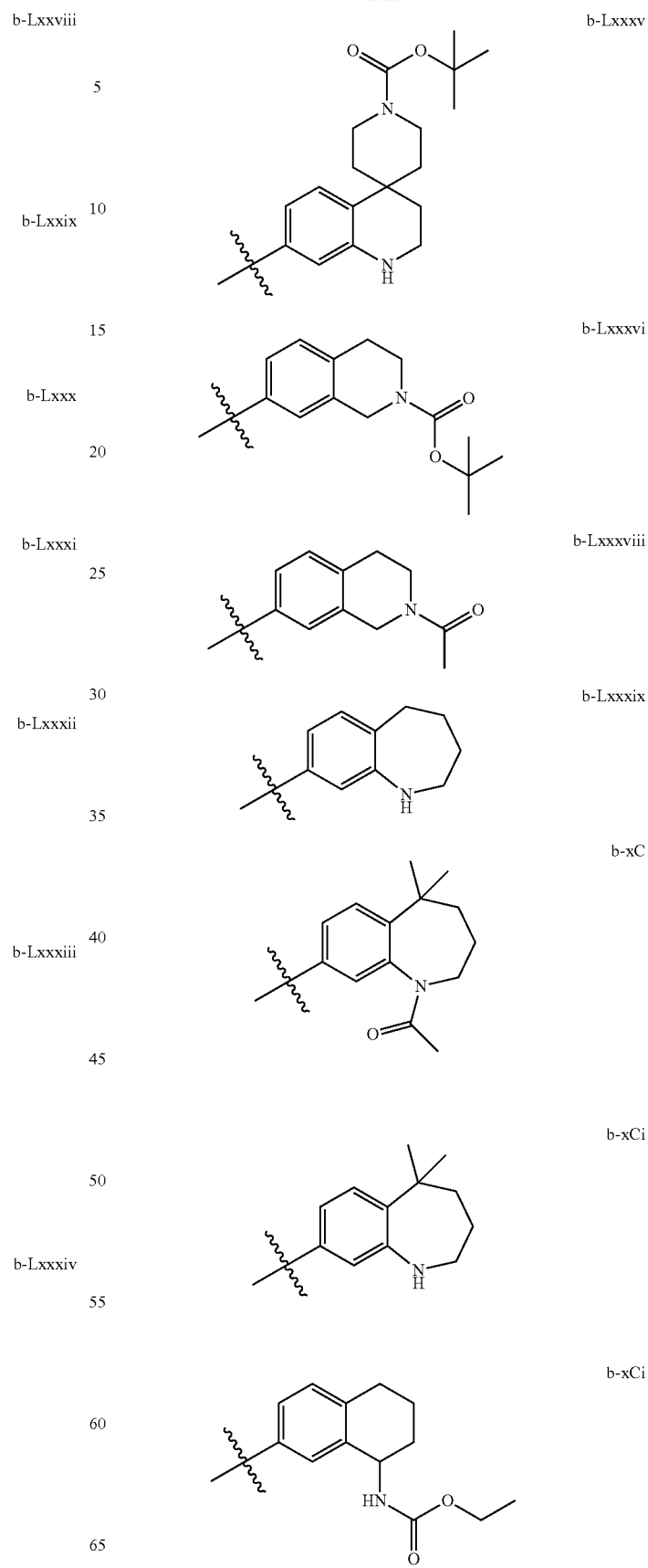

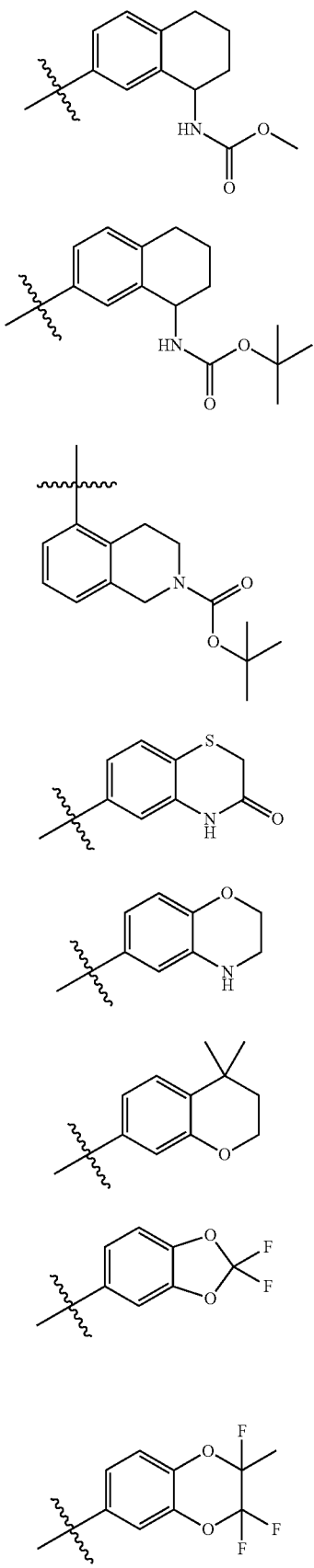

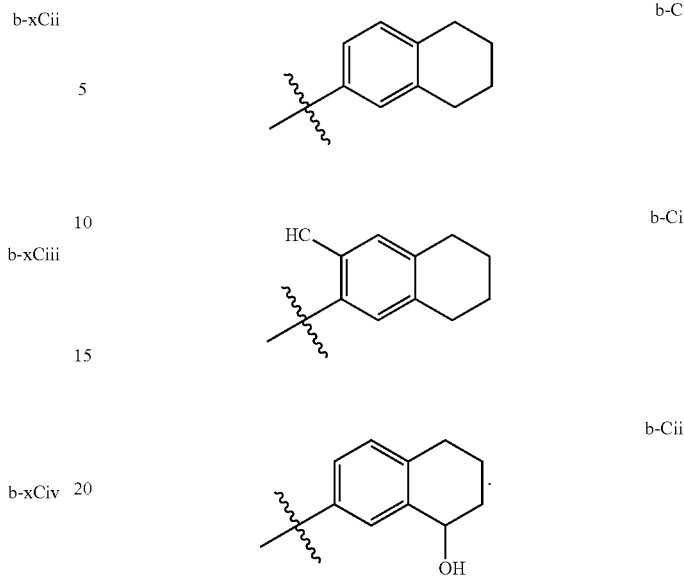

In some embodiments, $R^W$ is selected from halo, cyano, $CF_3$, $CHF_2$, $OCHF_2$, Me, Et, $CH(Me)_2$, CHMeEt, n-propyl, t-butyl, OMe, OEt, OPh, O-fluorophenyl, O-difluorophenyl, O-methoxyphenyl, O-tolyl, O-benzyl, SMe, $SCF_3$, $SCHF_2$, SEt, $CH_2CN$, $NH_2$, NHMe, $N(Me)_2$, NHEt, $N(Et)_2$, C(O)$CH_3$, C(O)Ph, C(O)$NH_2$, SPh, $SO_2$-(amino-pyridyl), $SO_2NH_2$, $SO_2Ph$, $SO_2NHPh$, $SO_2$—N-morpholino, $SO_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2yl, furan-2-yl, 4-methyl-4H-[1,2,4]triazol-3-yl, 3-(4'-chlorophenyl)-[1,2,4]oxadiazol-5-yl, NHC(O)Me, NHC(O)Et, NHC(O)Ph, or $NHSO_2Me$ In some embodiments, X and $R^X$, taken together, is Me, Et, halo, CN, $CF_3$, OH, OMe, OEt, $SO_2N(Me)$(fluorophenyl), $SO_2$-(4-methyl-piperidin-1-yl), or $SO_2$—N-pyrrolidinyl.

According to another embodiment, the present invention provides compounds of formula IVA, formula IVB, or formula IVC:

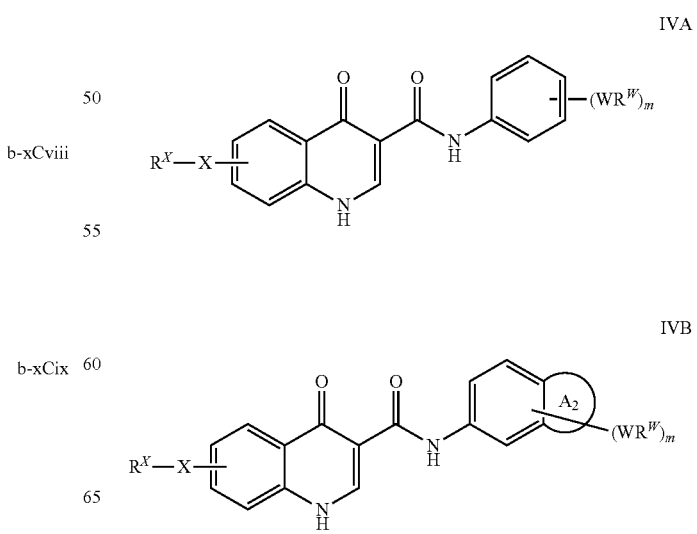

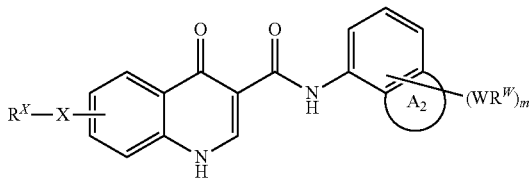

IVC

In one embodiment compounds of formula IVA, formula IVB, and formula IVC have y occurrences of substituent X—$R^X$, wherein y is 0-4. Or, y is 1. Or, y is 2.

In one embodiment, the present invention provides compounds of formula IVA, formula IVB, and formula IVC, wherein X is a bond and $R^X$ is hydrogen.

In one embodiment, the present invention provides compounds of formula formula IVB, and formula IVC, wherein ring $A_2$ is an optionally substituted, saturated, unsaturated, or aromatic seven membered ring with 0-3 heteroatoms selected from O, S, or N. Exemplary rings include azepanyl, 5,5-dimethyl azepanyl, etc.

In one embodiment, the present invention provides compounds of formula IVB and IVC, wherein ring $A_2$ is an optionally substituted, saturated, unsaturated, or aromatic six membered ring with 0-3 heteroatoms selected from O, S, or N. Exemplary rings include piperidinyl, 4,4-dimethylpiperidinyl, etc.

In one embodiment, the present invention provides compounds of formula IVB and IVC, wherein ring $A_2$ is an optionally substituted, saturated, unsaturated, or aromatic five membered ring with 0-3 heteroatoms selected from O, S, or N.

In one embodiment, the present invention provides compounds of formula IVB and IVC, wherein ring $A_2$ is an optionally substituted five membered ring with one nitrogen atom, e.g., pyrrolyl or pyrrolidinyl.

According to one embodiment of formula IVA, the following compound of formula VA-1 is provided:

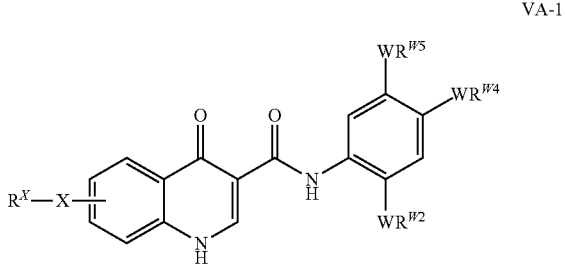

VA-1 wherein each of $WR^{W2}$ and $WR^{W4}$ is independently selected from hydrogen, CN, $CF_3$, halo, C1-C6 straight or branched alkyl, 3-12 membered cycloaliphatic, phenyl, C5-C10 heteroaryl or C3-C7 heterocyclic, wherein said heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, CN, —COOR', —COR', —O($CH_2$)$_2$N(R')(R'), —O($CH_2$)N(R')(R'), —CON(R')(R'), —($CH_2$)$_2$OR', —($CH_2$)OR', $CH_2$CN, optionally substituted phenyl or phenoxy, —N(R')(R'), —NR'C(O)OR', —NR'C(O)R', —($CH_2$)$_2$N(R')(R'), or —($CH_2$)N(R')(R'); and $WR^{W5}$ is selected from hydrogen, —OH, $NH_2$, CN, $CHF_2$, NHR', N(R')$_2$, —NHC(O)R', —NHC(O)OR', $NHSO_2R'$, —OR', $CH_2$OH, $CH_2$N(R')$_2$, C(O)OR', $SO_2$NHR', $SO_2$N(R')$_2$, or $CH_2$NHC(O)OR'. Or, $WR^{W4}$ and $WR^{W5}$ taken together form a 5-7 membered ring containing 0-3 three heteroatoms selected from N, O, or S, wherein said ring is optionally substituted with up to three $WR^W$ substituents.

In one embodiment, compounds of formula VA-1 have y occurrences of X—$R^X$, wherein y is 0-4. In one embodiment, y is 0.

In one embodiment, the present invention provides compounds of formula VA-1, wherein X is a bond and $R^X$ is hydrogen.

In one embodiment, the present invention provides compounds of formula VA-1, wherein:
each of $WR^{W2}$ and $WR^{W4}$ is independently selected from hydrogen, CN, $CF_3$, halo, C1-C6 straight or branched alkyl, 3-12 membered cycloaliphatic, or phenyl, wherein said $WR^{W2}$ and $WR^{W4}$ is independently and optionally substituted with up to three substituents selected from —OR', —$CF_3$, —$OCF_3$, —$SCF_3$, halo, —COOR', —COR', —O($CH_2$)$_2$N(R')(R'), —O($CH_2$)N(R')(R'), —CON(R')(R'), —($CH_2$)$_2$OR', —($CH_2$)OR', optionally substituted phenyl, —N(R')(R'), —NC(O)OR', —NC(O)R', —($CH_2$)$_2$N(R')(R'), or —($CH_2$)N(R')(R'); and
$WR^{W5}$ is selected from hydrogen, —OH, $NH_2$, CN, NHR', N(R')$_2$, —NHC(O)R', —NHC(O)OR', $NHSO_2R'$, —OR', $CH_2$OH, C(O)OR', $SO_2$NHR', or $CH_2$NHC(O)O—(R').

In one embodiment, the present invention provides compounds of formula VA-1, wherein:
$WR^{W2}$ is a pheny ring optionally substituted with up to three substituents selected from —OR', —$CF_3$, —$OCF_3$, SR', S(O)R', $SO_2R'$, —$SCF_3$, halo, CN, —COOR', —COR', —O($CH_2$)$_2$N(R')(R'), —O($CH_2$)N(R')(R'), —CON(R')(R'), —($CH_2$)$_2$OR', —($CH_2$)OR', $CH_2$CN, optionally substituted phenyl or phenoxy, —N(R')(R'), —NR'C(O)OR', —NR'C(O)R', —($CH_2$)$_2$N(R')(R'), or —($CH_2$)N(R')(R');
$WR^{W4}$ is C1-C6 straight or branched alkyl; and
$WR^{W5}$ is OH.

In one embodiment, each of $WR^{W2}$ and $WR^{W4}$ is independently selected from $CF_3$ or halo. In one embodiment, each of $WR^{W2}$ and $WR^{W4}$ is independently selected from optionally substituted hydrogen, C1-C6 straight or branched alkyl. In certain embodiments, each of $WR^{W2}$ and $WR^{W4}$ is independently selected from optionally substituted n-propyl, isopropyl, n-butyl, sec-butyl, t-butyl, 1,1-dimethyl-2-hydroxyethyl, 1,1-dimethyl-2-(ethoxycarbonyl)-ethyl, 1,1-dimethyl-3-(t-butoxycarbonyl-amino) propyl, or n-pentyl.

In one embodiment, each of $WR^{W2}$ and $WR^{W4}$ is independently selected from optionally substituted 3-12 membered cycloaliphatic. Exemplary embodiments of such cycloaliphatic include cyclopentyl, cyclohexyl, cycloheptyl, norbornyl, adamantyl, [2.2.2.]bicyclo-octyl, [2.3.1.]bicyclo-octyl, or [3.3.1]bicyclo-nonyl.

In certain embodiments $WR^{W2}$ is hydrogen and $WR^{W4}$ is C1-C6 straight or branched alkyl. In certain embodiments, $WR^{W4}$ is selected from methyl, ethyl, propyl, n-butyl, sec-butyl, or t-butyl.

In certain embodiments $WR^{W4}$ is hydrogen and $WR^{W2}$ is C1-C6 straight or branched alkyl. In certain embodiments, $WR^{W2}$ is selected from methyl, ethyl, propyl, n-butyl, sec-butyl, t-butyl, or n-pentyl.

In certain embodiments each of $WR^{W2}$ and $WR^{W4}$ is C1-C6 straight or branched alkyl. In certain embodiments, each of $WR^{W2}$ and $WR^{W4}$ is selected from methyl, ethyl, propyl, n-butyl, sec-butyl, t-butyl, or pentyl.

In one embodiment, WR$^{VS}$ is selected from hydrogen, CHF$_2$, NH$_2$, CN, NHR', N(R')$_2$, CH$_2$N(R')$_2$, —NHC(O)R', —NHC(O)OR', —OR', C(O)OR', or SO$_2$NHR'. Or, WR$^{VS}$ is —OR', e.g., OH.

In certain embodiments, WR$^{VS}$ is selected from hydrogen, NH$_2$, CN, CHF$_2$, NH(C1-C6 alkyl), N(C1-C6 alkyl)$_2$, —NHC(O)(C1-C6 alkyl), —CH$_2$NHC(O)O(C1-C6 alkyl), —NHC(O)O(C1-C6 alkyl), —OH, —O(C1-C6 alkyl), C(O)O(C1-C6 alkyl), CH$_2$O(C1-C6 alkyl), or SO$_2$NH$_2$. In another embodiment, WR$^{VS}$ is selected from —OH, OMe, NH$_2$, —NHMe, —N(Me)$_2$, —CH$_2$NH$_2$, CH$_2$OH, NHC(O)OMe, NHC(O)OEt, CN, CHF$_2$, —CH$_2$NHC(O)O(t-butyl), —O-(ethoxyethyl), —O-(hydroxyethyl), —C(O)OMe, or —SO$_2$NH$_2$.

In one embodiment, compound of formula VA-1 has one, preferably more, or more preferably all, of the following features:

i) WR$^{W2}$ is hydrogen;
ii) WR$^{W4}$ is C1-C6 straight or branched alkyl or monocyclic or bicyclic aliphatic; and
iii) WR$^{W5}$ is selected from hydrogen, CN, CHF$_2$, NH$_2$, NH(C1-C6 alkyl), N(C1-C6 alkyl)$_2$, —NHC(O)(C1-C6 alkyl), —NHC(O)O(C1-C6 alkyl), —CH$_2$C(O)O(C1-C6 alkyl), —OH, —O(C1-C6 alkyl), C(O)O(C1-C6 alkyl), or SO$_2$NH$_2$.

In one embodiment, compound of formula VA-1 has one, preferably more, or more preferably all, of the following features:

i) WR$^{W2}$ is halo, C1-C6 alkyl, CF$_3$, CN, or phenyl optionally substituted with up to 3 substituents selected from C1-C4 alkyl, —O(C1-C4 alkyl), or halo;
ii) WR$^{W4}$ is CF$_3$, halo, C1-C6 alkyl, or C6-C10 cycloaliphatic; and
iii) WR$^{W5}$ is OH, NH$_2$, NH(C1-C6 alkyl), or N(C1-C6 alkyl).

In one embodiment, X—R$^X$ is at the 6-position of the quinolinyl ring. In certain embodiments, X—R$^X$ taken together is C1-C6 alkyl, —O—(C1-C6 alkyl), or halo.

In one embodiment, X—R$^X$ is at the 5-position of the quinolinyl ring. In certain embodiments, X—R$^X$ taken together is —OH.

In another embodiment, the present invention provides compounds of formula VA-1, wherein WR$^{W4}$ and WR$^{W5}$ taken together form a 5-7 membered ring containing 0-3 three heteroatoms selected from N, O, or S, wherein said ring is optionally substituted with up to three WR$^W$ substituents.

In certain embodiments, WR$^{W4}$ and WR$^{W5}$ taken together form an optionally substituted 5-7 membered saturated, unsaturated, or aromatic ring containing 0 heteroatoms. In other embodiments, WR$^{W4}$ and WR$^{W5}$ taken together form an optionally substituted 5-7 membered ring containing 1-3 heteroatoms selected from N, O, or S. In certain other embodiments, WR$^{W4}$ and WR$^{W5}$ taken together form an optionally substituted saturated, unsaturated, or aromatic 5-7 membered ring containing 1 nitrogen heteroatom. In certain other embodiments, WR$^{W4}$ and WR$^{W5}$ taken together form an optionally substituted 5-7 membered ring containing 1 oxygen heteroatom.

In another embodiment, the present invention provides compounds of formula V-A-2:

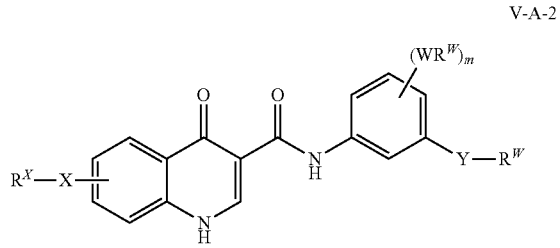

V-A-2 wherein:
Y is CH$_2$, C(O)O, C(O), or S(O)$_2$;
m is 0-4; and
X, R$^X$, W, and R$^W$ are as defined above.

In one embodiment, compounds of formula VA-2 have y occurrences of X—R$^X$, wherein y is 0-4. In one embodiment, y is 0. Or, y is 1. Or, y is 2.

In one embodiment, Y is C(O). In another embodiment, Y is C(O)O. Or, Y is S(O)$_2$. Or, Y is CH$_2$.

In one embodiment, m is 1 or 2. Or, m is 1. Or, m is 0.

In one embodiment, W is a bond.

In another embodiment, R$^W$ is C1-C6 aliphatic, halo, CF$_3$, or phenyl optionally substituted with C1-C6 alkyl, halo, cyano, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl. Exemplary embodiments of WR$^W$ include methyl, ethyl, propyl, tert-butyl, or 2-ethoxyphenyl.

In another embodiment, R$^W$ in Y—R$^W$ is C1-C6 aliphatic optionally substituted with N(R")$_2$, wherein R" is hydrogen, C1-C6 alkyl, or two R" taken together form a 5-7 membered heterocyclic ring with up to 2 additional heteroatoms selected from O, S, or NR'. Exemplary such heterocyclic rings include pyrrolidinyl, piperidyl, morpholinyl, or thiomorpholinyl.

In another embodiment, the present invention provides compounds of formula V-A-3:

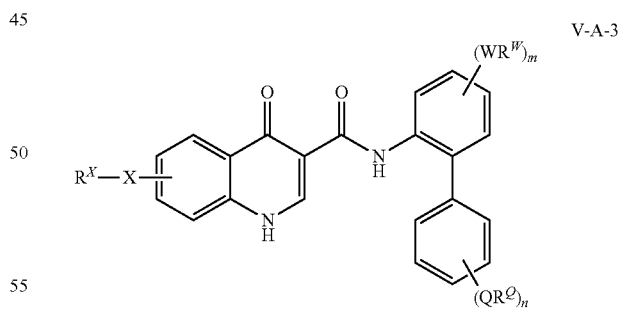

V-A-3 wherein:
Q is W;
R$^Q$ is R$^W$;
m is 0-4;
n is 0-4; and
X, R$^X$, W, and R$^W$ are as defined above.

In one embodiment, compounds of formula VA-3 have y occurrences of X—R$^X$, wherein y is 0-4. In one embodiment, y is 0. Or, y is 1. Or, y is 2.

In one embodiment, n is 0-2.

In another embodiment, m is 0-2. In one embodiment, m is 0. In one embodiment, m is 1. Or, m is 2.

In one embodiment, QR$^Q$ taken together is halo, CF$_3$, OCF$_3$, CN, C1-C6 aliphatic, O—C1-C6 aliphatic, O-phenyl, NH(C1-C6 aliphatic), or N(C1-C6 aliphatic)$_2$, wherein said aliphatic and phenyl are optionally substituted with up to three substituents selected from C1-C6 alkyl, O—C1-C6 alkyl, halo, cyano, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, SOR', SO$_2$R', —SO$_2$NR'—, NR'SO$_2$—, or —NR'SO$_2$NR'—. In another embodiment, R' above is C1-C4 alkyl.

Exemplary QR$^Q$ include methyl, isopropyl, sec-butyl, hydroxymethyl, CF$_3$, NMe$_2$, CN, CH$_2$CN, fluoro, chloro, OEt, OMe, SMe, OCF$_3$, OPh, C(O)OMe, C(O)O-iPr, S(O)Me, NHC(O)Me, or S(O)$_2$Me.

In another embodiment, the present invention provides compounds of formula V-A-4:

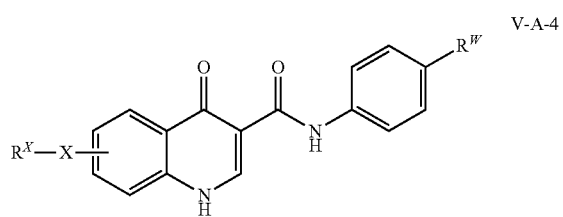

V-A-4 wherein X, R$^X$, and R$^W$ are as defined above.

In one embodiment, compounds of formula VA-4 have y occurrences of X—R$^X$, wherein y is 0-4. In one embodiment, y is 0. Or, y is 1. Or, y is 2.

In one embodiment, R$^W$ is C1-C12 aliphatic, C5-C10 cycloaliphatic, or C5-C7 heterocyclic ring, wherein said aliphatic, cycloaliphatic, or heterocyclic ring is optionally substituted with up to three substituents selected from C1-C6 alkyl, halo, cyano, oxo, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

Exemplary R$^W$ includes methyl, ethyl, n-propyl, isopropyl, n-butyl, sec-butyl, t-butyl, n-pentyl, vinyl, cyanomethyl, hydroxymethyl, hydroxyethyl, hydroxybutyl, cyclohexyl, adamantyl, or —C(CH$_3$)$_2$—NHC(O)O-T, wherein T is C1-C4 alkyl, methoxyethyl, or tetrahydrofuranylmethyl.

In another embodiment, the present invention provides compounds of formula V-A-5:

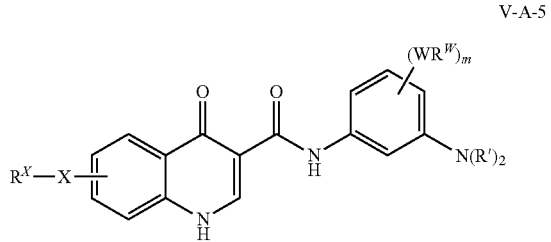

V-A-5 wherein:
m is 0-4; and
X, R$^X$, W, R$^W$, and R' are as defined above.

In one embodiment, compounds of formula VA-5 have y occurrences of X—R$^X$, wherein y is 0-4. In one embodiment, y is 0. Or, y is 1. Or, y is 2.

In one embodiment, m is 0-2. Or, m is 1. Or, m is 2.

In another embodiment, both R' are hydrogen. Or, one R' is hydrogen and the other R' is C1-C4 alkyl, e.g., methyl. Or, both R' are C1-C4 alkyl, e.g., methyl.

In another embodiment, m is 1 or 2, and R$^W$ is halo, CF$_3$, CN, C1-C6 aliphatic, O—C1-C6 aliphatic, or phenyl, wherein said aliphatic and phenyl are optionally substituted with up to three substituents selected from C1-C6 alkyl, O—C1-C6 alkyl, halo, cyano, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

Exemplary embodiments of R$^W$ include chloro, CF$_3$, OCF$_3$, methyl, ethyl, n-propyl, isopropyl, n-butyl, t-butyl, methoxy, ethoxy, propyloxy, or 2-ethoxyphenyl.

In another embodiment, the present invention provides compounds of formula V-A-6:

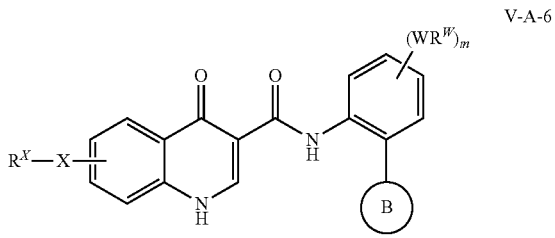

V-A-6 wherein:
ring B is a 5-7 membered monocyclic or bicyclic, heterocyclic or heteroaryl ring optionally substituted with up to n occurrences of -Q-R$^Q$, wherein n is 0-4, and Q and R$^Q$ are as defined above; and
Q, R$^Q$, X, R$^X$, W, and R$^W$ are as defined above.

In one embodiment, compounds of formula VA-6 have y occurrences of X—R$^X$, wherein y is 0-4. In one embodiment, y is 0. Or, y is 1. Or, y is 2.

In one embodiment, m is 0-2. Or, m is 0. Or m is 1.

In one embodiment, n is 0-2. Or, n is 0. Or, n is 1.

In another embodiment, ring B is a 5-7 membered monocyclic, heterocyclic ring having up to 2 heteroatoms selected from O, S, or N, optionally substituted with up to n occurrences of -Q-R$^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring B is a 5-6 membered monocyclic, heteroaryl ring having up to 2 heteroatoms selected from O, S, or N, optionally substituted with up to n occurrences of -Q-R$^Q$. Exemplary such rings include benzimidazol-2-yl, 5-methyl-furan-2-yl, 2,5-dimethyl-pyrrol-1-yl, pyridine-4-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl.

In another embodiment, the present invention provides compounds of formula V-B-1:

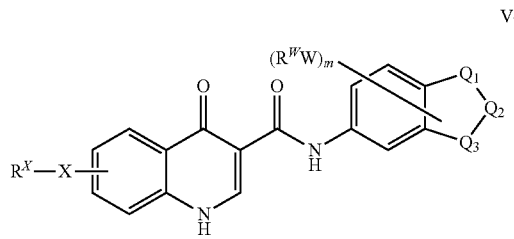

V-B-1 wherein:
one of $Q_1$ and $Q_3$ is $N(WR^W)$ and the other of $Q_1$ and $Q_3$ is selected from O, S, or $N(WR^W)$;
$Q_2$ is $C(O)$, $CH_2$—$C(O)$, $C(O)$—$CH_2$, $CH_2$, $CH_2$—$CH_2$, $CF_2$, or $CF_2$—$CF_2$;
m is 0-3; and
X, W, $R^X$, and $R^W$ are as defined above.

In one embodiment, compounds of formula V-B-1 have y occurrences of X—$R^X$, wherein y is 0-4. In one embodiment, y is 0. Or, y is 1. Or, y is 2.

In one embodiment, $Q_3$ is $N(WR^W)$; exemplary $WR^W$ include hydrogen, C1-C6 aliphatic, C(O)C1-C6 aliphatic, or C(O)OC1-C6 aliphatic.

In another embodiment, $Q_3$ is $N(WR^W)$, $Q_2$ is C(O), $CH_2$, $CH_2$—$CH_2$, and $Q_1$ is 0.

In another embodiment, the present invention provides compounds of formula V-B-2:

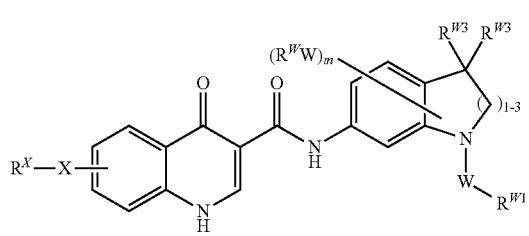

V-B-2 wherein:
$R^{W1}$ is hydrogen or C1-C6 aliphatic;
each of $R^{W3}$ is hydrogen or C1-C6 aliphatic; or
both $R^{W3}$ taken together form a C3-C6 cycloalkyl or heterocyclic ring having up to two heteroatoms selected from O, S, or NR', wherein said ring is optionally substituted with up to two $WR^W$ substituents;
m is 0-4; and
X, $R^X$, W, and $R^W$ are as defined above.

In one embodiment, compounds of formula V-B-2 have y occurrences of X—$R^X$, wherein y is 0-4. In one embodiment, y is 0. Or, y is 1. Or, y is 2.

In one embodiment, each $R^{W3}$ is hydrogen, C1-C6 aliphatic, C(O)C1-C6 aliphatic, or C(O)OC1-C6 aliphatic.

In another embodiment, each $R^{W3}$ is hydrogen, C1-C4 alkyl. Or, both $R^{W3}$ taken together form a C3-C6 cycloaliphatic ring or 5-7 membered heterocyclic ring having up to two heteroatoms selected from O, S, or N, wherein said cycloaliphatic or heterocyclic ring is optionally substituted with up to three substitutents selected from $WR^{W1}$. Exemplary such rings include cyclopropyl, cyclopentyl, optionally substituted piperidyl, etc.

In another embodiment, the present invention provides compounds of formula V-B-3:

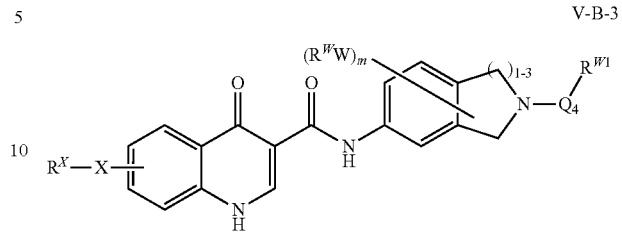

V-B-3 wherein:
$Q_4$ is a bond, C(O), C(O)O, or $S(O)_2$;
$R^{W1}$ is hydrogen or C1-C6 aliphatic;
m is 0-4; and
X, W, $R^W$, and $R^X$ are as defined above.

In one embodiment, compounds of formula V-B-3 have y occurrences of X—$R^X$, wherein y is 0-4. In one embodiment, y is 0.

In one embodiment, $Q_4$ is C(O). Or $Q_4$ is C(O)O. In another embodiment, $R^{W1}$ is C1-C6 alkyl. Exemplary $R^{W1}$ include methyl, ethyl, or t-butyl.

In another embodiment, the present invention provides compounds of formula V-B-4:

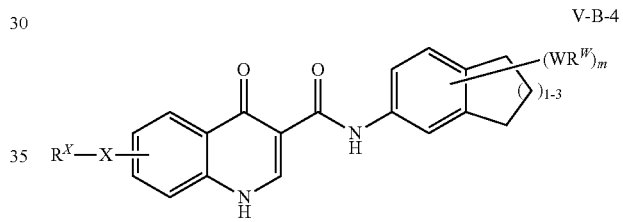

V-B-4 wherein:
m is 0-4; and
X, $R^X$, W, and $R^W$ are as defined above.

In one embodiment, compounds of formula V-B-4 have y occurrences of X—$R^X$, wherein y is 0-4. In one embodiment, y is 0. Or, y is 1. Or, y is 2.

In one embodiment, m is 0-2. Or, m is 0. Or, m is 1.

In another embodiment, said cycloaliphatic ring is a 5-membered ring. Or, said ring is a six-membered ring.

In another embodiment, the present invention provides compounds of formula V-B-5:

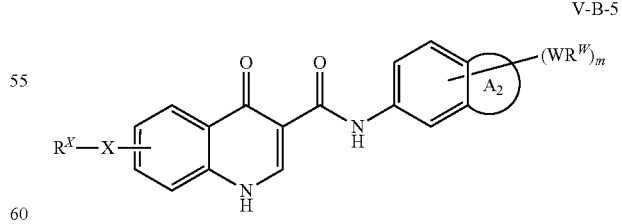

V-B-5 wherein:
ring $A_2$ is a phenyl or a 5-6 membered heteroaryl ring, wherein ring $A_2$ and the phenyl ring fused thereto together have up 4 substituents independently selected from $WR^W$;
m is 0-4; and
X, W, $R^W$ and $R^X$ are as defined above.

In one embodiment, compounds of formula V-B-5 have y occurrences of X—R$^X$, wherein y is 0-4. In one embodiment, y is 0. Or, y is 1. Or, y is 2.

In one embodiment, ring A$_2$ is an optionally substituted 5-membered ring selected from pyrrolyl, furanyl, thienyl, pyrazolyl, imidazolyl, thiazolyl, oxazolyl, thiadiazolyl, oxadiazolyl, or triazolyl.

In one embodiment, ring A$_2$ is an optionally substituted 5-membered ring selected from pyrrolyl, pyrazolyl, thiadiazolyl, imidazolyl, oxazolyl, or triazolyl. Exemplary such rings include:

aa 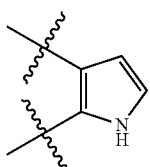

bb 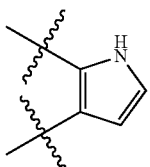

cc 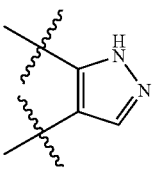

dd 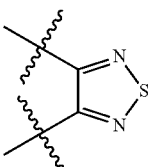

ee 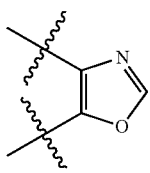

ff 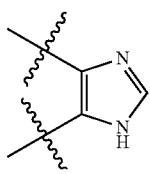

gg 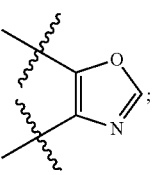

wherein said ring is optionally substituted as set forth above.

In another embodiment, ring A$_2$ is an optionally substituted 6-membered ring. Exemplary such rings include pyridyl, pyrazinyl, pyrimidinyl, or triazinyl. In another embodiment, said ring is an optionally substituted pyridyl.

In one embodiment, ring A$_2$ is phenyl.

In another embodiment, ring A$_2$ is pyrrolyl, pyrazolyl, pyridyl, or thiadiazolyl.

Exemplary R$^W$ in formula V-B-5 includes a bond, C(O), C(O)O or C1-C6 alkylene.

Exemplary R$^W$ in formula V-B-5 include cyano, halo, C1-C6 aliphatic, C3-C6 cycloaliphatic, aryl, 5-7 membered heterocyclic ring having up to two heteroatoms selected from O, S, or N, wherein said aliphatic, phenyl, and heterocyclic are independently and optionally substituted with up to three substituents selected from C1-C6 alkyl, O—C1-C6 alkyl, halo, cyano, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In one embodiment, the present invention provides compounds of formula V-B-5-a:

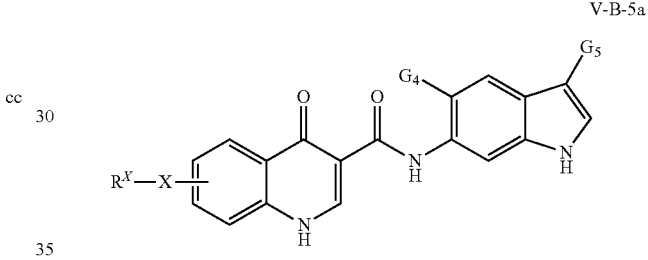

V-B-5a wherein:

G$_4$ is hydrogen, halo, CN, CF$_3$, CHF$_2$, CH$_2$F, optionally substituted C1-C6 aliphatic, aryl-C1-C6 alkyl, or a phenyl, wherein G$_4$ is optionally substituted with up to 4 WR$^W$ substituents; wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—;

G$_5$ is hydrogen or an optionally substituted C1-C6 aliphatic;

wherein said indole ring system is further optionally substituted with up to 3 substituents independently selected from WR$^W$.

In one embodiment, compounds of formula V-B-5-a have y occurrences of X—R$^X$, wherein y is 0-4. In one embodiment, y is 0. Or, y is 1. Or, y is 2.

In one embodiment, G$_4$ is hydrogen. Or, G$_5$ is hydrogen.

In another embodiment, G$_4$ is hydrogen, and G$_5$ is C1-C6 aliphatic, wherein said aliphatic is optionally substituted with C1-C6 alkyl, halo, cyano, or CF$_3$, and wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, G$_4$ is hydrogen, and G$_5$ is cyano, methyl, ethyl, propyl, isopropyl, butyl, sec-butyl, t-butyl, cyanomethyl, methoxyethyl, CH$_2$C(O)OMe, (CH$_2$)$_2$NHC(O)O-tert-butyl, or cyclopentyl.

In another embodiment, G$_5$ is hydrogen, and G$_4$ is halo, C1-C6 aliphatic or phenyl, wherein said aliphatic or phenyl is optionally substituted with C1-C6 alkyl, halo, cyano, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, G$_5$ is hydrogen, and G$_4$ is halo, CF$_3$, ethoxycarbonyl, t-butyl, 2-methoxyphenyl, 2-ethoxyphenyl, (4-C(O)NH(CH$_2$)$_2$—NMe$_2$)-phenyl, 2-methoxy-4-chloro-phenyl, pyridine-3-yl, 4-isopropylphenyl, 2,6-dimethoxyphenyl, sec-butylaminocarbonyl, ethyl, t-butyl, or piperidin-1-ylcarbonyl.

In another embodiment, G$_4$ and G$_5$ are both hydrogen, and the nitrogen ring atom of said indole ring is substituted with C1-C6 aliphatic, C(O)(C1-C6 aliphatic), or benzyl, wherein said aliphatic or benzyl is optionally substituted with C1-C6 alkyl, halo, cyano, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, G$_4$ and G$_5$ are both hydrogen, and the nitrogen ring atom of said indole ring is substituted with acyl, benzyl, C(O)CH$_2$N(Me)C(O)CH$_2$NHMe, or ethoxycarbonyl.

In another embodiment, the present invention provides compounds of formula I':

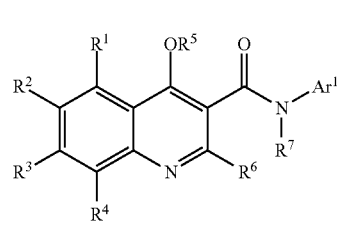

or pharmaceutically acceptable salts thereof, wherein R$^1$, R$^2$, R$^3$, R$^4$, R$^5$, R$^6$, R$^7$, and Ar$^1$ is as defined above for compounds of formula I'.

In one embodiment, each of R$^1$, R$^2$, R$^3$, R$^4$, R$^5$, R$^6$, R$^7$, and Ar$^1$ in compounds of formula I' is independently as defined above for any of the embodiments of compounds of formula I.

Representative compounds of the present invention are set forth below in Table 1 below.

TABLE 1

| Cmpd No. | Name |
|---|---|
| 1 | N-[5-(5-chloro-2-methoxy-phenyl)-1H-indol-6-yl]-4-oxo-1H-quinoline-3-carboxamide |
| 2 | N-(3-methoxy-4-tert-butyl-phenyl)-4-oxo-1H-quinoline-3-carboxamide |
| 3 | N-[2-(2-methoxyphenoxy)-5-(trifluoromethyl)phenyl]-4-oxo-1H-quinoline-3-carboxamide |
| 4 | N-(2-morpholinophenyl)-4-oxo-1H-quinoline-3-carboxamide |
| 5 | N-[4-(2-hydroxy-1,1-dimethyl-ethyl)phenyl]-4-oxo-1H-quinoline-3-carboxamide |
| 6 | N-[3-(hydroxymethyl)-4-tert-butyl-phenyl]-4-oxo-1H-quinoline-3-carboxamide |
| 7 | N-(4-benzoylamino-2,5-diethoxy-phenyl)-4-oxo-1H-quinoline-3-carboxamide |
| 8 | N-(3-amino-4-ethyl-phenyl)-4-oxo-1H-quinoline-3-carboxamide |
| 9 | 4-oxo-N-(3-sulfamoylphenyl)-1H-quinoline-3-carboxamide |
| 10 | 1,4-dihydro-N-(2,3,4,5-tetrahydro-1H-benzo[b]azepin-8-yl)-4-oxoquinoline-3-carboxamide |
| 11 | 4-oxo-N-[2-[2-(trifluoromethyl)phenyl]phenyl]-1H-quinoline-3-carboxamide |
| 12 | N-[2-(4-dimethylaminophenyl)phenyl]-4-oxo-1H-quinoline-3-carboxamide |
| 13 | N-(3-cyano-4-tert-butyl-phenyl)-4-oxo-1H-quinoline-3-carboxamide |
| 14 | [5-[(4-oxo-1H-quinolin-3-yl)carbonylamino]-2-tert-butyl-phenyl]aminoformic acid methyl ester |
| 15 | N-(2-methoxy-3-pyridyl)-4-oxo-1H-quinoline-3-carboxamide |
| 16 | 4-oxo-N-(2-propylphenyl)-1H-quinoline-3-carboxamide |
| 17 | N-(5-amino-2-propoxy-phenyl)-4-oxo-1H-quinoline-3-carboxamide |
| 18 | N-(9H-fluoren-1-yl)-4-oxo-1H-quinoline-3-carboxamide |
| 19 | 4-oxo-N-(2-quinolyl)-1H-quinoline-3-carboxamide |
| 20 | N-[2-(2-methylphenoxy)phenyl]-4-oxo-1H-quinoline-3-carboxamide |
| 21 | 4-oxo-N-[4-(2-pyridylsulfamoyl)phenyl]-1H-quinoline-3-carboxamide |
| 22 | 4-Oxo-1,4-dihydro-quinoline-3-carboxylic acid N-(1',2'-dihydrospiro[cyclopropane-1,3'-[3H]indol]-6'-yl)-amide |
| 23 | N-[2-(2-ethoxyphenyl)-5-hydroxy-4-tert-butyl-phenyl]-4-oxo-1H-quinoline-3-carboxamide |
| 24 | 4-oxo-N-(3-pyrrolidin-1-ylsulfonylphenyl)-1H-quinoline-3-carboxamide |
| 25 | N-[2-(3-acetylaminophenyl)phenyl]-4-oxo-1H-quinoline-3-carboxamide |
| 26 | 4-oxo-N-[2-(1-piperidyl)phenyl]-1H-quinoline-3-carboxamide |
| 27 | N-[1-[2-[methyl-(2-methylaminoacetyl)-amino]acetyl]-1H-indol-6-yl]-4-oxo-1H-quinoline-3-carboxamide |
| 28 | [2-methyl-2-[4-[(4-oxo-1H-quinolin-3-yl)carbonylamino]phenyl]-propyl]aminoformic acid 2-methoxyethyl ester |
| 29 | 1-isopropyl-4-oxo-N-phenyl-1H-quinoline-3-carboxamide |
| 30 | [2-isopropyl-5-[(4-oxo-1H-quinolin-3-yl)carbonylamino]phenyl]aminoformic acid methyl ester |
| 31 | 4-oxo-N-(p-tolyl)-1H-quinoline-3-carboxamide |
| 32 | N-(5-chloro-1H-indol-6-yl)-4-oxo-1H-quinoline-3-carboxamide |
| 33 | N-(1H-indol-6-yl)-4-oxo-1H-quinoline-3-carboxamide |
| 34 | N-[4-(1,1-diethylpropyl)-2-fluoro-5-hydroxy-phenyl]-4-hydroxy-quinoline-3-carboxamide |
| 35 | 1,4-dihydro-N-(2,3,4,5-tetrahydro-5,5-dimethyl-1H-benzo[b]azepin-8-yl)-4-oxoquinoline-3-carboxamide |
| 36 | N-(2-isopropylphenyl)-4-oxo-1H-quinoline-3-carboxamide |
| 37 | N-(1H-indol-7-yl)-4-oxo-1H-quinoline-3-carboxamide |
| 38 | N-[2-(1H-indol-2-yl)phenyl]-4-oxo-1H-quinoline-3-carboxamide |

TABLE 1-continued

| Cmpd No. | Name |
|---|---|
| 39 | [3-[(2,4-dimethoxy-3-quinolyl)carbonylamino]-4-tert-butyl-phenyl]aminoformic acid tert-butyl ester |
| 40 | N-[2-(2-hydroxyethyl)phenyl]-4-oxo-1H-quinoline-3-carboxamide |
| 41 | N-(5-amino-2-propyl-phenyl)-4-oxo-1H-quinoline-3-carboxamide |
| 42 | N-[2-[[3-chloro-5-(trifluoromethyl)-2-pyridyl]oxy]phenyl]-4-oxo-1H-quinoline-3-carboxamide |
| 43 | N-[2-(3-ethoxyphenyl)-5-hydroxy-4-tert-butyl-phenyl]-4-oxo-1H-quinoline-3-carboxamide |
| 44 | N-(2-methylbenzothiazol-5-yl)-4-oxo-1H-quinoline-3-carboxamide |
| 45 | N-(2-cyano-3-fluoro-phenyl)-4-oxo-1H-quinoline-3-carboxamide |
| 46 | N-[3-chloro-5-(2-morpholinoethylsulfonylamino)phenyl]-4-oxo-1H-quinoline-3-carboxamide |
| 47 | N-[4-isopropyl-2-(trifluoromethyl)phenyl]-4-oxo-1H-quinoline-3-carboxamide |
| 48 | N-(5-chloro-2-fluoro-phenyl)-4-oxo-1H-quinoline-3-carboxamide |
| 49 | N-[2-(2,6-dimethoxyphenyl)phenyl]-4-oxo-1H-quinoline-3-carboxamide |
| 50 | 4-oxo-N-(2,4,6-trimethylphenyl)-1H-quinoline-3-carboxamide |
| 51 | 6-[(4-methyl-1-piperidyl)sulfonyl]-4-oxo-N-(5-tert-butyl-1H-indol-6-yl)-1H-quinoline-3-carboxamide |
| 52 | N-[2-(m-tolyl)phenyl]-4-oxo-1H-quinoline-3-carboxamide |
| 53 | 4-oxo-N-(4-pyridyl)-1H-quinoline-3-carboxamide |
| 54 | 4-oxo-N-(8-thia-7,9-diazabicyclo[4.3.0]nona-2,4,6,9-tetraen-5-yl)-1H-quinoline-3-carboxamide |
| 55 | N-(3-amino-2-methoxy-5-tert-butyl-phenyl)-4-oxo-1H-quinoline-3-carboxamide |
| 56 | 1,4-dihydro-N-(1,2,3,4-tetrahydro-6-hydroxynaphthalen-7-yl)-4-oxoquinoline-3-carboxamide |
| 57 | N-[4-(3-ethyl-2,6-dioxo-3-piperidyl)phenyl]-4-oxo-1H-quinoline-3-carboxamide |
| 58 | N-[3-amino-4-(trifluoromethoxy)phenyl]-4-oxo-1H-quinoline-3-carboxamide |
| 59 | N-[2-(5-isopropyl-2-methoxy-phenyl)phenyl]-4-oxo-1H-quinoline-3-carboxamide |
| 60 | [4-isopropyl-3-[(4-oxo-1H-quinolin-3-yl)carbonylamino]phenyl]aminoformic acid tert-butyl ester |
| 61 | N-(2,3-dimethylphenyl)-4-oxo-1H-quinoline-3-carboxamide |
| 62 | 4-oxo-N-[3-(trifluoromethoxy)phenyl]-1H-quinoline-3-carboxamide |
| 63 | N-[2-(2,4-difluorophenyl)phenyl]-4-oxo-1H-quinoline-3-carboxamide |
| 64 | 4-oxo-N-(2-oxo-1,3-dihydrobenzoimidazol-5-yl)-1H-quinoline-3-carboxamide |
| 65 | 4-oxo-N-[5-(3-pyridyl)-1H-indol-6-yl]-1H-quinoline-3-carboxamide |
| 66 | N-(2,2-difluorobenzo[1,3]dioxol-5-yl)-4-oxo-1H-quinoline-3-carboxamide |
| 67 | 6-ethyl-4-hydroxy-N-(1H-indol-6-yl)quinoline-3-carboxamide |
| 68 | 3-[2-[(4-oxo-1H-quinolin-3-yl)carbonylamino]phenyl]benzoic acid methyl ester |
| 69 | N-(3-amino-4-isopropyl-phenyl)-4-oxo-1H-quinoline-3-carboxamide |
| 70 | 4-oxo-N-[2-(4-pyridyl)phenyl]-1H-quinoline-3-carboxamide |
| 71 | 3-[2-[(4-oxo-1H-quinolin-3-yl)carbonylamino]phenyl]benzoic acid isopropyl ester |
| 72 | N-(2-ethylphenyl)-4-oxo-1H-quinoline-3-carboxamide |
| 73 | 4-oxo-N-(2-phenyl-3H-benzoimidazol-5-yl)-1H-quinoline-3-carboxamide |
| 74 | 4-oxo-N-[5-(trifluoromethyl)-2-pyridyl]-1H-quinoline-3-carboxamide |
| 75 | 4-oxo-N-(3-quinolyl)-1H-quinoline-3-carboxamide |
| 76 | N-[2-(3,4-difluorophenyl)phenyl]-4-oxo-1H-quinoline-3-carboxamide |
| 77 | N-(5-fluoro-1H-indol-6-yl)-4-oxo-1H-quinoline-3-carboxamide |
| 78 | 4-oxo-N-(2-sulfamoylphenyl)-1H-quinoline-3-carboxamide |
| 79 | N-[2-(4-fluoro-3-methyl-phenyl)phenyl]-4-oxo-1H-quinoline-3-carboxamide |
| 80 | N-(2-methoxyphenyl)-4-oxo-1H-quinoline-3-carboxamide |
| 81 | 4-oxo-N-(3-propionylaminophenyl)-1H-quinoline-3-carboxamide |
| 82 | N-(4-diethylamino-2-methyl-phenyl)-4-oxo-1H-quinoline-3-carboxamide |
| 83 | N-[2-(3-cyanophenyl)phenyl]-4-oxo-1H-quinoline-3-carboxamide |
| 84 | N-(4-methyl-2-pyridyl)-4-oxo-1H-quinoline-3-carboxamide |
| 85 | N-[2-(3,4-dichlorophenyl)phenyl]-4-oxo-1H-quinoline-3-carboxamide |
| 86 | N-[4-[2-(aminomethyl)phenyl]phenyl]-4-oxo-1H-quinoline-3-carboxamide |
| 87 | 4-oxo-N-(3-phenoxyphenyl)-1H-quinoline-3-carboxamide |
| 88 | [2-methyl-2-[4-[(4-oxo-1H-quinolin-3-yl)carbonylamino]phenyl]-propyl]aminoformic acid tert-butyl ester |
| 89 | N-(2-cyano-5-methyl-phenyl)-4-oxo-1H-quinoline-3-carboxamide |
| 90 | 4-oxo-N-(2-tert-butylphenyl)-1H-quinoline-3-carboxamide |
| 91 | N-(3-chloro-2,6-diethyl-phenyl)-4-oxo-1H-quinoline-3-carboxamide |
| 92 | N-[2-fluoro-5-hydroxy-4-(1-methylcyclohexyl)-phenyl]-4-oxo-1H-quinoline-3-carboxamide |
| 93 | N-[2-(5-cyano-2-thienyl)phenyl]-4-oxo-1H-quinoline-3-carboxamide |
| 94 | N-(5-amino-2-methyl-phenyl)-4-oxo-1H-quinoline-3-carboxamide |
| 95 | N-(2-cyanophenyl)-4-oxo-1H-quinoline-3-carboxamide |
| 96 | N-[3-(cyanomethyl)-1H-indol-6-yl]-4-oxo-1H-quinoline-3-carboxamide |
| 97 | N-[2-(2,4-dimethoxypyrimidin-5-yl)phenyl]-4-oxo-1H-quinoline-3-carboxamide |
| 98 | N-(5-dimethylamino-2-propyl-phenyl)-4-oxo-1H-quinoline-3-carboxamide |
| 99 | 4-oxo-N-(4-pentylphenyl)-1H-quinoline-3-carboxamide |
| 100 | N-(1H-indol-4-yl)-4-oxo-1H-quinoline-3-carboxamide |
| 101 | N-(5-amino-2-isopropyl-phenyl)-4-oxo-1H-quinoline-3-carboxamide |
| 102 | N-[2-[3-(4-chlorophenyl)-1,2,4-oxadiazol-5-yl]phenyl]-4-oxo-1H-quinoline-3-carboxamide |
| 103 | 6-fluoro-N-(5-hydroxy-2,4-ditert-butyl-phenyl)-4-oxo-1H-quinoline-3-carboxamide |
| 104 | N-(2-methyl-1H-indol-6-yl)-4-oxo-1H-quinoline-3-carboxamide |
| 105 | 1,4-dihydro-N-(3,4-dihydro-2H-benzo[b][1,4]oxazin-6-yl)-4-oxoquinoline-3-carboxamide |
| 106 | N-(2-cyano-4,5-dimethoxy-phenyl)-4-oxo-1H-quinoline-3-carboxamide |
| 107 | 7-[(4-oxo-1H-quinolin-3-yl)carbonylamino]-1,2,3,4-tetrahydroisoquinoline-2-carboxylic acid tert-butyl ester |
| 108 | 4,4-dimethyl-7-[(4-oxo-1H-quinolin-3-yl)carbonylamino]-1,2,3,4-tetrahydroquinoline-1-carboxylic acid tert-butyl ester |
| 109 | N-(1-acetyl-2,3,4,5-tetrahydro-5,5-dimethyl-1H-benzo[b]azepin-8-yl)-1,4-dihydro-4-oxoquinoline-3-carboxamide |

TABLE 1-continued

| Cmpd No. | Name |
|---|---|
| 110 | N-[4-(cyanomethyl)phenyl]-4-oxo-1H-quinoline-3-carboxamide |
| 111 | 4-oxo-N-[2-(trifluoromethyl)phenyl]-1H-quinoline-3-carboxamide |
| 112 | 6-ethoxy-4-hydroxy-N-(1H-indol-6-yl)quinoline-3-carboxamide |
| 113 | N-(3-methyl-1H-indol-6-yl)-4-oxo-1H-quinoline-3-carboxamide |
| 114 | [4-(2-ethoxyphenyl)-3-[(4-oxo-1H-quinolin-3-yl)carbonylamino]phenyl]aminoformic acid tert-butyl ester |
| 115 | N-[2-(2-furyl)phenyl]-4-oxo-1H-quinoline-3-carboxamide |
| 116 | 5-hydroxy-N-(1H-indol-6-yl)-4-oxo-1H-quinoline-3-carboxamide |
| 117 | N-(3-dimethylamino-4-isopropyl-phenyl)-4-oxo-1H-quinoline-3-carboxamide |
| 118 | N-[2-(1H-indol-5-yl)phenyl]-4-oxo-1H-quinoline-3-carboxamide |
| 119 | [2-methyl-2-[4-[(4-oxo-1H-quinolin-3-yl)carbonylamino]phenyl-propyl]aminoformic acid ethyl ester |
| 120 | N-(2-methoxy-5-methyl-phenyl)-4-oxo-1H-quinoline-3-carboxamide |
| 121 | N-(3,4-dichlorophenyl)-4-oxo-1H-quinoline-3-carboxamide |
| 122 | N-(3,4-dimethoxyphenyl)-4-oxo-1H-quinoline-3-carboxamide |
| 123 | N-[2-(3-furyl)phenyl]-4-oxo-1H-quinoline-3-carboxamide |
| 124 | 6-fluoro-4-oxo-N-(5-tert-butyl-1H-indol-6-yl)-1H-quinoline-3-carboxamide |
| 125 | N-(6-ethyl-2-pyridyl)-4-oxo-1H-quinoline-3-carboxamide |
| 126 | N-[3-hydroxy-4-[2-(2-methoxyethoxy)-1,1-dimethyl-ethyl]-phenyl]-4-oxo-1H-quinoline-3-carboxamide |
| 127 | [5-[(4-oxo-1H-quinolin-3-yl)carbonylamino]-2-tert-butyl-phenyl]aminoformic acid ethyl ester |
| 128 | 1,6-dimethyl-4-oxo-N-(2-phenylphenyl)-1H-quinoline-3-carboxamide |
| 129 | [2-ethyl-5-[(4-oxo-1H-quinolin-3-yl)carbonylamino]phenyl]aminoformic acid methyl ester |
| 130 | 4-hydroxy-N-(1H-indol-6-yl)-5,7-bis(trifluoromethyl)quinoline-3-carboxamide |
| 131 | N-(3-amino-5-chloro-phenyl)-4-oxo-1H-quinoline-3-carboxamide |
| 132 | N-(5-acetylamino-2-ethoxy-phenyl)-4-oxo-1H-quinoline-3-carboxamide |
| 133 | N-[3-chloro-5-[2-(1-piperidyl)ethylsulfonylamino]phenyl]-4-oxo-1H-quinoline-3-carboxamide |
| 134 | N-[2-(4-methylsulfinylphenyl)phenyl]-4-oxo-1H-quinoline-3-carboxamide |
| 135 | N-(2-benzo[1,3]dioxol-5-ylphenyl)-4-oxo-1H-quinoline-3-carboxamide |
| 136 | N-(2-hydroxy-3,5-ditert-butyl-phenyl)-4-oxo-1H-quinoline-3-carboxamide |
| 137 | 6-[(4-fluorophenyl)-methyl-sulfamoyl]-N-(5-hydroxy-2,4-ditert-butyl-phenyl)-4-oxo-1H-quinoline-3-carboxamide |
| 138 | N-[2-(3,5-difluorophenyl)phenyl]-4-oxo-1H-quinoline-3-carboxamide |
| 139 | N-[2-(2,4-dichlorophenyl)phenyl]-4-oxo-1H-quinoline-3-carboxamide |
| 140 | N-(4-cyclohexylphenyl)-4-oxo-1H-quinoline-3-carboxamide |
| 141 | [2-methyl-5-[(4-oxo-1H-quinolin-3-yl)carbonylamino]phenyl]aminoformic acid ethyl ester |
| 142 | 4-oxo-N-(2-sec-butylphenyl)-1H-quinoline-3-carboxamide |
| 143 | N-(2-fluoro-5-hydroxy-4-tert-butyl-phenyl)-4-oxo-1H-quinoline-3-carboxamide |
| 144 | N-(3-hydroxyphenyl)-4-oxo-1H-quinoline-3-carboxamide |
| 145 | 6-[(4-oxo-1H-quinolin-3-yl)carbonylamino]-1H-indole-4-carboxylic acid ethyl ester |
| 146 | 4-oxo-N-(1,7,9-triazabicyclo[4.3.0]nona-2,4,6,8-tetraen-5-yl)-1H-quinoline-3-carboxamide |
| 147 | N-[2-(4-fluorophenoxy)-3-pyridyl]-4-oxo-1H-quinoline-3-carboxamide |
| 148 | 4-oxo-N-[5-(1-piperidylcarbonyl)-1H-indol-6-yl]-1H-quinoline-3-carboxamide |
| 149 | N-(3-acetylamino-4-ethyl-phenyl)-4-oxo-1H-quinoline-3-carboxamide |
| 150 | 4-oxo-N-[4-[2,2,2-trifluoro-1-hydroxy-1-(trifluoromethyl)ethyl]phenyl]-1H-quinoline-3-carboxamide |
| 151 | N-[2-(4-methyl-2-thienyl)phenyl]-4-oxo-1H-quinoline-3-carboxamide |
| 152 | 4-oxo-N-(2-oxo-3H-benzooxazol-6-yl)-1H-quinoline-3-carboxamide |
| 153 | N-[4-(1,1-diethyl-2,2-dimethyl-propyl)-2-fluoro-5-hydroxy-phenyl]-4-hydroxy-quinoline-3-carboxamide |
| 154 | N-[3,5-bis(trifluoromethyl)phenyl]-4-oxo-1H-quinoline-3-carboxamide |
| 155 | 4-oxo-N-(2-pyridyl)-1H-quinoline-3-carboxamide |
| 156 | 4-oxo-N-[2-[2-(trifluoromethoxy)phenyl]phenyl]-1H-quinoline-3-carboxamide |
| 157 | N-(2-ethyl-5-methylamino-phenyl)-4-oxo-1H-quinoline-3-carboxamide |
| 158 | 4-oxo-N-(5-phenyl-1H-indol-6-yl)-1H-quinoline-3-carboxamide |
| 159 | [7-[(4-oxo-1H-quinolin-3-yl)carbonylamino]tetralin-1-yl]aminoformic acid methyl ester |
| 160 | N-(3-amino-4-propyl-phenyl)-4-oxo-1H-quinoline-3-carboxamide |
| 161 | N-[3-(2-ethoxyethoxy)-4-tert-butyl-phenyl]-4-oxo-1H-quinoline-3-carboxamide |
| 162 | N-(6-methoxy-3-pyridyl)-4-oxo-1H-quinoline-3-carboxamide |
| 163 | N-[5-(aminomethyl)-2-(2-ethoxyphenyl)-phenyl]-4-oxo-1H-quinoline-3-carboxamide |
| 164 | 4-oxo-N-[3-(trifluoromethyl)phenyl]-1H-quinoline-3-carboxamide |
| 165 | 4-oxo-N-(4-sulfamoylphenyl)-1H-quinoline-3-carboxamide |
| 166 | 4-[2-[(4-oxo-1H-quinolin-3-yl)carbonylamino]phenyl]benzoic acid methyl ester |
| 167 | N-(3-amino-4-methyl-phenyl)-4-oxo-1H-quinoline-3-carboxamide |
| 168 | 4-oxo-N-(3-pyridyl)-1H-quinoline-3-carboxamide |
| 169 | N-(1-methyl-1H-indol-6-yl)-4-oxo-1H-quinoline-3-carboxamide |
| 170 | N-(5-chloro-2-pyridyl)-4-oxo-1H-quinoline-3-carboxamide |
| 171 | N-[2-(2,3-dichlorophenyl)phenyl]-4-oxo-1H-quinoline-3-carboxamide |
| 172 | N-(2-(benzo[b]thiophen-2-yl)phenyl)-1,4-dihydro-4-oxoquinoline-3-carboxamide |
| 173 | N-(6-methyl-2-pyridyl)-4-oxo-1H-quinoline-3-carboxamide |
| 174 | N-[2-(5-acetyl-2-thienyl)phenyl]-4-oxo-1H-quinoline-3-carboxamide |
| 175 | 4-Oxo-1,4-dihydro-quinoline-3-carboxylic acid N-(1'-Acetyl-1',2'-dihydrospiro[cyclopropane-1,3'-3H-indol]-6'-yl)-amide |
| 176 | 4-oxo-N-[4-(trifluoromethoxy)phenyl]-1H-quinoline-3-carboxamide |
| 177 | N-(2-butoxyphenyl)-4-oxo-1H-quinoline-3-carboxamide |
| 178 | 4-oxo-N-[2-(2-tert-butylphenoxy)phenyl]-1H-quinoline-3-carboxamide |
| 179 | N-(3-carbamoylphenyl)-4-oxo-1H-quinoline-3-carboxamide |

TABLE 1-continued

| Cmpd No. | Name |
|---|---|
| 180 | N-(2-ethyl-6-methyl-phenyl)-4-oxo-1H-quinoline-3-carboxamide |
| 181 | 4-oxo-N-[2-(p-tolyl)phenyl]-1H-quinoline-3-carboxamide |
| 182 | N-[2-(4-fluorophenyl)phenyl]-4-oxo-1H-quinoline-3-carboxamide |
| 183 | 7-[(4-oxo-1H-quinolin-3-yl)carbonylamino]-1,2,3,4-tetrahydroquinoline-1-carboxylic acid tert-butyl ester |
| 184 | N-(1H-indol-6-yl)-4-oxo-2-(trifluoromethyl)-1H-quinoline-3-carboxamide |
| 185 | N-(3-morpholinosulfonylphenyl)-4-oxo-1H-quinoline-3-carboxamide |
| 186 | N-(3-cyclopentyl-1H-indol-6-yl)-4-oxo-1H-quinoline-3-carboxamide |
| 187 | N-(1-acetyl-1H-indol-6-yl)-4-oxo-1H-quinoline-3-carboxamide |
| 188 | 6-[(4-oxo-1H-quinolin-3-yl)carbonylamino]-1H-indole-5-carboxylic acid ethyl ester |
| 189 | N-(4-benzyloxyphenyl)-4-oxo-1H-quinoline-3-carboxamide |
| 190 | N-[2-(3-chloro-4-fluoro-phenyl)phenyl]-4-oxo-1H-quinoline-3-carboxamide |
| 191 | 4-oxo-N-(5-quinolyl)-1H-quinoline-3-carboxamide |
| 192 | N-(3-methyl-2-pyridyl)-4-oxo-1H-quinoline-3-carboxamide |
| 193 | N-(2,6-dimethoxy-3-pyridyl)-4-oxo-1H-quinoline-3-carboxamide |
| 194 | N-(4-cyanophenyl)-4-oxo-1H-quinoline-3-carboxamide |
| 195 | N-(5-methyl-2-pyridyl)-4-oxo-1H-quinoline-3-carboxamide |
| 196 | N-[5-(3,3-dimethylbutanoylamino)-2-tert-butyl-phenyl]-4-oxo-1H-quinoline-3-carboxamide |
| 197 | 4-oxo-N-[6-(trifluoromethyl)-3-pyridyl]-1H-quinoline-3-carboxamide |
| 198 | N-(4-fluorophenyl)-4-oxo-1H-quinoline-3-carboxamide |
| 199 | N-[2-(o-tolyl)phenyl]-4-oxo-1H-quinoline-3-carboxamide |
| 200 | 1,4-dihydro-N-(1,2,3,4-tetrahydro-1-hydroxynaphthalen-7-yl)-4-oxoquinoline-3-carboxamide |
| 201 | N-(2-cyano-3-methyl-phenyl)-4-oxo-1H-quinoline-3-carboxamide |
| 202 | N-[2-(5-chloro-2-methoxy-phenyl)phenyl]-4-oxo-1H-quinoline-3-carboxamide |
| 203 | N-(1-benzyl-1H-indol-6-yl)-4-oxo-1H-quinoline-3-carboxamide |
| 204 | N-(4,4-dimethylchroman-7-yl)-4-oxo-1H-quinoline-3-carboxamide |
| 205 | N-[2-(4-methoxyphenoxy)-5-(trifluoromethyl)phenyl]-4-oxo-1H-quinoline-3-carboxamide |
| 206 | N-[2-(2,3-dimethylphenoxy)-3-pyridyl]-4-oxo-1H-quinoline-3-carboxamide |
| 207 | 2-[6-[(4-oxo-1H-quinolin-3-yl)carbonylamino]-1H-indol-3-yl]acetic acid ethyl ester |
| 208 | N-[4-(2-adamantyl)-5-hydroxy-2-methyl-phenyl]-4-oxo-1H-quinoline-3-carboxamide |
| 209 | N-[4-(hydroxymethyl)phenyl]-4-oxo-1H-quinoline-3-carboxamide |
| 210 | 2,4-dimethoxy-N-(2-phenylphenyl)-quinoline-3-carboxamide |
| 211 | N-(2-methoxy-5-tert-butyl-phenyl)-4-oxo-1H-quinoline-3-carboxamide |
| 212 | N-[3-(3-methyl-5-oxo-1,4-dihydropyrazol-1-yl)phenyl]-4-oxo-1H-quinoline-3-carboxamide |
| 213 | N-[2-(2,5-dichlorophenyl)phenyl]-4-oxo-1H-quinoline-3-carboxamide |
| 214 | N-(3-methylsulfonylaminophenyl)-4-oxo-1H-quinoline-3-carboxamide |
| 215 | 4-oxo-N-phenyl-1H-quinoline-3-carboxamide |
| 216 | N-(3H-benzoimidazol-2-yl)-4-oxo-1H-quinoline-3-carboxamide |
| 217 | N-(1H-indazol-5-yl)-4-oxo-1H-quinoline-3-carboxamide |
| 218 | 6-fluoro-N-[2-fluoro-5-hydroxy-4-(1-methylcyclohexyl)-phenyl]-4-oxo-1H-quinoline-3-carboxamide |
| 219 | 4-oxo-N-pyrazin-2-yl-1H-quinoline-3-carboxamide |
| 220 | N-(2,3-dihydroxy-4,6-ditert-butyl-phenyl)-4-oxo-1H-quinoline-3-carboxamide |
| 221 | [5-[(4-oxo-1H-quinolin-3-yl)carbonylamino]-2-propyl-phenyl]aminoformic acid methyl ester |
| 222 | N-(3-chloro-2-cyano-phenyl)-4-oxo-1H-quinoline-3-carboxamide |
| 223 | N-[2-(4-methylsulfanylphenyl)phenyl]-4-oxo-1H-quinoline-3-carboxamide |
| 224 | 4-oxo-N-[4-[2-[(2,2,2-trifluoroacetyl)aminomethyl]phenyl]phenyl]-1H-quinoline-3-carboxamide |
| 225 | [2-isopropyl-5-[(4-oxo-1H-quinolin-3-yl)carbonylamino]phenyl]aminoformic acid ethyl ester |
| 226 | 4-oxo-N-(4-propylphenyl)-1H-quinoline-3-carboxamide |
| 227 | N-[2-(3H-benzoimidazol-2-yl)phenyl]-4-oxo-1H-quinoline-3-carboxamide |
| 228 | N-[2-(hydroxy-phenyl-methyl)phenyl]-4-oxo-1H-quinoline-3-carboxamide |
| 229 | N-(2-methylsulfanylphenyl)-4-oxo-1H-quinoline-3-carboxamide |
| 230 | N-(2-methyl-1H-indol-5-yl)-4-oxo-1H-quinoline-3-carboxamide |
| 231 | 3-[4-hydroxy-2-[(4-oxo-1H-quinolin-3-yl)carbonylamino]-5-tert-butyl-phenyl]benzoic acid methyl ester |
| 232 | N-(5-acetylamino-2-propyl-phenyl)-4-oxo-1H-quinoline-3-carboxamide |
| 233 | N-(1-acetylindolin-6-yl)-4-oxo-1H-quinoline-3-carboxamide |
| 234 | 4-oxo-N-[5-(trifluoromethyl)-1H-indol-6-yl]-1H-quinoline-3-carboxamide |
| 235 | N-(6-isopropyl-3-pyridyl)-4-oxo-1H-quinoline-3-carboxamide |
| 236 | 4-oxo-N-[4-(trifluoromethyl)phenyl]-1H-quinoline-3-carboxamide |
| 237 | N-[5-(2-methoxyphenyl)-1H-indol-6-yl]-4-oxo-1H-quinoline-3-carboxamide |
| 238 | 7'-[(4-oxo-1H-quinolin-3-ylcarbonyl)amino]-spiro[piperidine-4,4'(1'H)-quinoline], 2',3'-dihydro-carboxylic acid tert-butyl ester |
| 239 | [4-isopropyl-3-[(4-oxo-1H-quinolin-3-yl)carbonylamino]phenyl]aminoformic acid methyl ester |
| 240 | N-(2-benzyloxyphenyl)-4-oxo-1H-quinoline-3-carboxamide |
| 241 | 4-oxo-N-(8-quinolyl)-1H-quinoline-3-carboxamide |
| 242 | N-(5-amino-2,4-dichloro-phenyl)-4-oxo-1H-quinoline-3-carboxamide |
| 243 | N-(5-acetylamino-2-isopropyl-phenyl)-4-oxo-1H-quinoline-3-carboxamide |
| 244 | 4-oxo-N-(6,7,8,9-tetrahydro-5H-carbazol-2-yl)-1H-quinoline-3-carboxamide |
| 245 | N-[2-(2,4-dichlorophenoxy)phenyl]-4-oxo-1H-quinoline-3-carboxamide |
| 246 | N-(3,4-dimethylphenyl)-4-oxo-1H-quinoline-3-carboxamide |
| 247 | 4-oxo-N-[2-(2-phenoxyphenyl)phenyl]-1H-quinoline-3-carboxamide |
| 248 | N-(3-acetylamino-4-methyl-phenyl)-4-oxo-1H-quinoline-3-carboxamide |
| 249 | [4-ethyl-3-[(4-oxo-1H-quinolin-3-yl)carbonylamino]phenyl]aminoformic acid methyl ester |
| 250 | N-(5-acetylamino-2-methoxy-phenyl)-4-oxo-1H-quinoline-3-carboxamide |
| 251 | [2-methyl-2-[4-[(4-oxo-1H-quinolin-3-yl)carbonylamino]phenyl]-propyl]aminoformic acid isobutyl ester |

TABLE 1-continued

| Cmpd No. | Name |
|---|---|
| 252 | N-(2-benzoylphenyl)-4-oxo-1H-quinoline-3-carboxamide |
| 253 | 4-oxo-N-[2-[3-(trifluoromethoxy)phenyl]phenyl]-1H-quinoline-3-carboxamide |
| 254 | 6-fluoro-N-(5-fluoro-1H-indol-6-yl)-4-oxo-1H-quinoline-3-carboxamide |
| 255 | N-(5-hydroxy-2,4-ditert-butyl-phenyl)-4-oxo-6-pyrrolidin-1-ylsulfonyl-1H-quinoline-3-carboxamide |
| 256 | N-(1H-benzotriazol-5-yl)-4-oxo-1H-quinoline-3-carboxamide |
| 257 | N-(4-fluoro-3-methyl-phenyl)-4-oxo-1H-quinoline-3-carboxamide |
| 258 | N-indolin-6-yl-4-oxo-1H-quinoline-3-carboxamide |
| 259 | 4-oxo-N-(3-sec-butyl-1H-indol-6-yl)-1H-quinoline-3-carboxamide |
| 260 | N-(5-amino-2-tert-butyl-phenyl)-4-oxo-1H-quinoline-3-carboxamide |
| 261 | N-[2-(3,4-dimethylphenyl)phenyl]-4-oxo-1H-quinoline-3-carboxamide |
| 262 | 1,4-dihydro-N-(3,4-dihydro-3-oxo-2H-benzo[b][1,4]thiazin-6-yl)-4-oxoquinoline-3-carboxamide |
| 263 | N-(4-bromo-2-ethyl-phenyl)-4-oxo-1H-quinoline-3-carboxamide |
| 264 | N-(2,5-diethoxyphenyl)-4-oxo-1H-quinoline-3-carboxamide |
| 265 | N-(2-benzylphenyl)-4-oxo-1H-quinoline-3-carboxamide |
| 266 | N-[5-hydroxy-4-tert-butyl-2-(trifluoromethyl)phenyl]-4-oxo-1H-quinoline-3-carboxamide |
| 267 | 4-oxo-N-(4-phenoxyphenyl)-1H-quinoline-3-carboxamide |
| 268 | 4-oxo-N-(3-sulfamoyl-4-tert-butyl-phenyl)-1H-quinoline-3-carboxamide |
| 269 | [4-isopropyl-3-[(4-oxo-1H-quinolin-3-yl)carbonylamino]phenyl]aminoformic acid ethyl ester |
| 270 | N-(2-cyano-1H-indol-6-yl)-4-oxo-1H-quinoline-3-carboxamide |
| 271 | N-(3-amino-4-tert-butyl-phenyl)-4-oxo-1H-quinoline-3-carboxamide |
| 272 | N-[3-(2-morpholinoethylsulfonylamino)-5-(trifluoromethyl)phenyl]-4-oxo-1H-quinoline-3-carboxamide |
| 273 | [7-[(4-oxo-1H-quinolin-3-yl)carbonylamino]tetralin-1-yl]aminoformic acid tert-butyl ester |
| 274 | 4-oxo-6-pyrrolidin-1-ylsulfonyl-N-(5-tert-butyl-1H-indol-6-yl)-1H-quinoline-3-carboxamide |
| 275 | 4-benzyloxy-N-(3-hydroxy-4-tert-butyl-phenyl)-quinoline-3-carboxamide |
| 276 | N-(4-morpholinosulfonylphenyl)-4-oxo-1H-quinoline-3-carboxamide |
| 277 | N-[2-(3-fluorophenyl)phenyl]-4-oxo-1H-quinoline-3-carboxamide |
| 278 | 4-oxo-N-[2-[3-(trifluoromethyl)phenyl]phenyl]-1H-quinoline-3-carboxamide |
| 279 | N-[2-(2-methylsulfanylphenyl)phenyl]-4-oxo-1H-quinoline-3-carboxamide |
| 280 | 4-oxo-N-(6-quinolyl)-1H-quinoline-3-carboxamide |
| 281 | N-(2,4-dimethylphenyl)-4-oxo-1H-quinoline-3-carboxamide |
| 282 | N-(5-amino-2-ethyl-phenyl)-4-oxo-1H-quinoline-3-carboxamide |
| 283 | N-[2-(3-methoxyphenyl)phenyl]-4-oxo-1H-quinoline-3-carboxamide |
| 284 | N-(1H-indazol-6-yl)-4-oxo-1H-quinoline-3-carboxamide |
| 285 | N-[2-(2,3-difluorophenyl)phenyl]-4-oxo-1H-quinoline-3-carboxamide |
| 286 | 1,4-dihydro-N-(1,2,3,4-tetrahydronaphthalen-5-yl)-4-oxoquinoline-3-carboxamide |
| 287 | N-[2-fluoro-5-hydroxy-4-(1-methylcyclohexyl)-phenyl]-5-hydroxy-4-oxo-1H-quinoline-3-carboxamide |
| 288 | N-(5-fluoro-2-methoxycarbonyloxy-3-tert-butyl-phenyl)-4-oxo-1H-quinoline-3-carboxamide |
| 289 | N-(2-fluoro-4-methyl-phenyl)-4-oxo-1H-quinoline-3-carboxamide |
| 290 | N-[2-(3-isopropylphenyl)phenyl]-4-oxo-1H-quinoline-3-carboxamide |
| 291 | N-(2-chloro-5-hydroxy-4-tert-butyl-phenyl)-4-oxo-1H-quinoline-3-carboxamide |
| 292 | N-(5-chloro-2-phenoxy-phenyl)-4-oxo-1H-quinoline-3-carboxamide |
| 293 | 4-oxo-N-[2-(1H-pyrrol-1-yl)phenyl]-1H-quinoline-3-carboxamide |
| 294 | N-(1H-indol-5-yl)-4-oxo-1H-quinoline-3-carboxamide |
| 295 | 4-oxo-N-(2-pyrrolidin-1-ylphenyl)-1H-quinoline-3-carboxamide |
| 296 | 2,4-dimethoxy-N-(2-tert-butylphenyl)-quinoline-3-carboxamide |
| 297 | N-[2-(2,5-dimethyl-1H-pyrrol-1-yl)phenyl]-4-oxo-1H-quinoline-3-carboxamide |
| 298 | [2-ethyl-5-[(4-oxo-1H-quinolin-3-yl)carbonylamino]phenyl]aminoformic acid ethyl ester |
| 299 | 4-oxo-N-(1,2,3,4-tetrahydroquinolin-7-yl)-1H-quinoline-3-carboxamide |
| 300 | N-(4,4-dimethyl-1,2,3,4-tetrahydroquinolin-7-yl)-4-oxo-1H-quinoline-3-carboxamide |
| 301 | N-[4-(4-methyl-4H-1,2,4-triazol-3-yl)phenyl]-4-oxo-1H-quinoline-3-carboxamide |
| 302 | N-[2-[4-(hydroxymethyl)phenyl]phenyl]-4-oxo-1H-quinoline-3-carboxamide |
| 303 | N-(2-acetyl-1,2,3,4-tetrahydroisoquinolin-7-yl)-4-oxo-1H-quinoline-3-carboxamide |
| 304 | [4-(2-ethoxyphenyl)-3-[(4-oxo-1H-quinolin-3-yl)carbonylamino]phenylmethyl]aminoformic acid tert-butyl ester |
| 305 | N-[2-(4-methoxyphenyl)phenyl]-4-oxo-1H-quinoline-3-carboxamide |
| 306 | N-[2-(3-ethoxyphenyl)phenyl]-4-oxo-1H-quinoline-3-carboxamide |
| 307 | N-[2-(3-chlorophenyl)phenyl]-4-oxo-1H-quinoline-3-carboxamide |
| 308 | N-[2-(cyanomethyl)phenyl]-4-oxo-1H-quinoline-3-carboxamide |
| 309 | N-(3-isoquinolyl)-4-oxo-1H-quinoline-3-carboxamide |
| 310 | 4-oxo-N-(4-sec-butylphenyl)-1H-quinoline-3-carboxamide |
| 311 | N-[2-(5-methyl-2-furyl)phenyl]-4-oxo-1H-quinoline-3-carboxamide |
| 312 | N-[2-(2,4-dimethoxyphenyl)phenyl]-4-oxo-1H-quinoline-3-carboxamide |
| 313 | N-[2-(2-fluorophenyl)phenyl]-4-oxo-1H-quinoline-3-carboxamide |
| 314 | N-(2-ethyl-6-isopropyl-phenyl)-4-oxo-1H-quinoline-3-carboxamide |
| 315 | N-(2,6-dimethylphenyl)-4-oxo-1H-quinoline-3-carboxamide |
| 316 | N-(5-acetylamino-2-tert-butyl-phenyl)-4-oxo-1H-quinoline-3-carboxamide |
| 317 | N-(2,6-dichlorophenyl)-4-oxo-1H-quinoline-3-carboxamide |
| 318 | 4-oxo-N-[3-[2-(1-piperidyl)ethylsulfonylamino]-5-(trifluoromethyl)phenyl]-1H-quinoline-3-carboxamide |
| 319 | 6-fluoro-N-(2-fluoro-5-hydroxy-4-tert-butyl-phenyl)-4-oxo-1H-quinoline-3-carboxamide |
| 320 | 4-oxo-N-(2-tert-butyl-1H-indol-6-yl)-1H-quinoline-3-carboxamide |
| 321 | N-[2-(4-benzoylpiperazin-1-yl)phenyl]-4-oxo-1H-quinoline-3-carboxamide |
| 322 | N-(2-ethyl-6-sec-butyl-phenyl)-4-oxo-1H-quinoline-3-carboxamide |
| 323 | [2-methyl-2-[4-[(4-oxo-1H-quinolin-3-yl)carbonylamino]phenyl]-propyl]aminoformic acid methyl ester |

TABLE 1-continued

| Cmpd No. | Name |
|---|---|
| 324 | N-(4-butylphenyl)-4-oxo-1H-quinoline-3-carboxamide |
| 325 | N-(2,6-diethylphenyl)-4-oxo-1H-quinoline-3-carboxamide |
| 326 | N-[2-(4-methylsulfonylphenyl)phenyl]-4-oxo-1H-quinoline-3-carboxamide |
| 327 | N-[5-(2-ethoxyphenyl)-1H-indol-6-yl]-4-oxo-1H-quinoline-3-carboxamide |
| 328 | N-(3-acetylphenyl)-4-oxo-1H-quinoline-3-carboxamide |
| 329 | N-[2-(o-tolyl)benzooxazol-5-yl]-4-oxo-1H-quinoline-3-carboxamide |
| 330 | N-(2-chlorophenyl)-4-oxo-1H-quinoline-3-carboxamide |
| 331 | N-(2-carbamoylphenyl)-4-oxo-1H-quinoline-3-carboxamide |
| 332 | N-(4-ethynylphenyl)-4-oxo-1H-quinoline-3-carboxamide |
| 333 | N-[2-[4-(cyanomethyl)phenyl]phenyl]-4-oxo-1H-quinoline-3-carboxamide |
| 334 | 7'-[(4-oxo-1H-quinolin-3-ylcarbonyl)amino]-spiro[piperidine-4,4'(1'H)-1-acetyl-quinoline], 2',3'-dihydro-carboxylic acid tert-butyl ester |
| 335 | N-(2-carbamoyl-5-methyl-phenyl)-4-oxo-1H-quinoline-3-carboxamide |
| 336 | N-(2-butylphenyl)-4-oxo-1H-quinoline-3-carboxamide |
| 337 | N-(5-hydroxy-2,4-ditert-butyl-phenyl)-N-methyl-4-oxo-1H-quinoline-3-carboxamide |
| 338 | N-(3-methyl-1H-indol-4-yl)-4-oxo-1H-quinoline-3-carboxamide |
| 339 | N-(3-cyano-1H-indol-6-yl)-4-oxo-1H-quinoline-3-carboxamide |
| 340 | N-(3-methylsulfonylamino-4-propyl-phenyl)-4-oxo-1H-quinoline-3-carboxamide |
| 341 | [2-methyl-2-[4-[(4-oxo-1H-quinolin-3-yl)carbonylamino]phenyl]-propyl]aminoformic acid neopentyl ester |
| 342 | N-[5-(4-isopropylphenyl)-1H-indol-6-yl]-4-oxo-1H-quinoline-3-carboxamide |
| 343 | N-[5-(isobutylcarbamoyl)-1H-indol-6-yl]-4-oxo-1H-quinoline-3-carboxamide |
| 344 | N-[2-(2-ethoxyphenyl)phenyl]-4-oxo-1H-quinoline-3-carboxamide |
| 345 | 6-fluoro-4-hydroxy-N-(1H-indol-6-yl)quinoline-3-carboxamide |
| 346 | 4-oxo-N-phenyl-7-(trifluoromethyl)-1H-quinoline-3-carboxamide |
| 347 | N-[5-[4-(2-dimethylaminoethylcarbamoyl)phenyl]-1H-indol-6-yl]-4-oxo-1H-quinoline-3-carboxamide |
| 348 | N-[2-(4-ethoxyphenyl)phenyl]-4-oxo-1H-quinoline-3-carboxamide |
| 349 | 4-oxo-N-(2-phenylsulfonylphenyl)-1H-quinoline-3-carboxamide |
| 350 | N-(1-naphthyl)-4-oxo-1H-quinoline-3-carboxamide |
| 351 | N-(5-ethyl-1H-indol-6-yl)-4-oxo-1H-quinoline-3-carboxamide |
| 352 | 2-[6-[(4-oxo-1H-quinolin-3-yl)carbonylamino]-1H-indol-3-yl]ethylaminoformic acid tert-butyl ester |
| 353 | [3-[(4-oxo-1H-quinolin-3-yl)carbonylamino]-4-tert-butyl-phenyl]aminoformic acid tert-butyl ester |
| 354 | N-[2-[(cyclohexyl-methyl-amino)methyl]phenyl]-4-oxo-1H-quinoline-3-carboxamide |
| 355 | N-[2-(2-methoxyphenyl)phenyl]-4-oxo-1H-quinoline-3-carboxamide |
| 356 | N-(5-methylamino-2-propyl-phenyl)-4-oxo-1H-quinoline-3-carboxamide |
| 357 | N-(3-isopropyl-1H-indol-6-yl)-4-oxo-1H-quinoline-3-carboxamide |
| 358 | 6-chloro-4-hydroxy-N-(1H-indol-6-yl)quinoline-3-carboxamide |
| 359 | N-[3-(2-dimethylaminoethylsulfonylamino)-5-(trifluoromethyl)phenyl]-4-oxo-1H-quinoline-3-carboxamide |
| 360 | N-[4-(difluoromethoxy)phenyl]-4-oxo-1H-quinoline-3-carboxamide |
| 361 | N-[2-(2,5-dimethoxyphenyl)phenyl]-4-oxo-1H-quinoline-3-carboxamide |
| 362 | N-(2-chloro-4-tert-butyl-phenyl)-4-oxo-1H-quinoline-3-carboxamide |
| 363 | N-[2-(2-fluoro-3-methoxy-phenyl)phenyl]-4-oxo-1H-quinoline-3-carboxamide |
| 364 | N-(2-methyl-8-quinolyl)-4-oxo-1H-quinoline-3-carboxamide |
| 365 | N-(2-acetylphenyl)-4-oxo-1H-quinoline-3-carboxamide |
| 366 | 4-oxo-N-[2-[4-(trifluoromethyl)phenyl]phenyl]-1H-quinoline-3-carboxamide |
| 367 | N-[2-(3,5-dichlorophenyl)phenyl]-4-oxo-1H-quinoline-3-carboxamide |
| 368 | N-(3-amino-4-propoxy-phenyl)-4-oxo-1H-quinoline-3-carboxamide |
| 369 | N-(2,4-dichloro-6-cyano-phenyl)-4-oxo-1H-quinoline-3-carboxamide |
| 370 | N-(3-chlorophenyl)-4-oxo-1H-quinoline-3-carboxamide |
| 371 | 4-oxo-N-[2-(trifluoromethylsulfanyl)phenyl]-1H-quinoline-3-carboxamide |
| 372 | N-[2-(4-methyl-1-piperidyl)phenyl]-4-oxo-1H-quinoline-3-carboxamide |
| 373 | N-indan-4-yl-4-oxo-1H-quinoline-3-carboxamide |
| 374 | 4-hydroxy-N-(1H-indol-6-yl)-2-methylsulfanyl-quinoline-3-carboxamide |
| 375 | 1,4-dihydro-N-(1,2,3,4-tetrahydronaphthalen-6-yl)-4-oxoquinoline-3-carboxamide |
| 376 | 4-oxo-N-(2-phenylbenzooxazol-5-yl)-1H-quinoline-3-carboxamide |
| 377 | 6,8-difluoro-4-hydroxy-N-(1H-indol-6-yl)quinoline-3-carboxamide |
| 378 | N-(3-amino-4-methoxy-phenyl)-4-oxo-1H-quinoline-3-carboxamide |
| 379 | N-[3-acetylamino-5-(trifluoromethyl)phenyl]-4-oxo-1H-quinoline-3-carboxamide |
| 380 | N-(2-ethoxyphenyl)-4-oxo-1H-quinoline-3-carboxamide |
| 381 | 4-oxo-N-(5-tert-butyl-1H-indol-6-yl)-1H-quinoline-3-carboxamide |
| 382 | [5-[(4-oxo-1H-quinolin-3-yl)carbonylamino]-2-propyl-phenyl]aminoformic acid ethyl ester |
| 383 | N-(3-ethyl-1H-indol-6-yl)-4-oxo-1H-quinoline-3-carboxamide |
| 384 | N-[2-(2,5-difluorophenyl)phenyl]-4-oxo-1H-quinoline-3-carboxamide |
| 385 | N-[2-(2,4-difluorophenoxy)-3-pyridyl]-4-oxo-1H-quinoline-3-carboxamide |
| 386 | N-(3,3-dimethylindolin-6-yl)-4-oxo-1H-quinoline-3-carboxamide |
| 387 | N-[2-methyl-3-(trifluoromethyl)phenyl]-4-oxo-1H-quinoline-3-carboxamide |
| 388 | 4-oxo-N-[2-[4-(trifluoromethoxy)phenyl]phenyl]-1H-quinoline-3-carboxamide |
| 389 | N-(3-benzylphenyl)-4-oxo-1H-quinoline-3-carboxamide |
| 390 | N-[3-(aminomethyl)-4-tert-butyl-phenyl]-4-oxo-1H-quinoline-3-carboxamide |
| 391 | N-[2-(4-isobutylphenyl)phenyl]-4-oxo-1H-quinoline-3-carboxamide |
| 392 | N-(6-chloro-3-pyridyl)-4-oxo-1H-quinoline-3-carboxamide |
| 393 | N-[5-amino-2-(2-ethoxyphenyl)-phenyl]-4-oxo-1H-quinoline-3-carboxamide |
| 394 | 1,6-dimethyl-4-oxo-N-phenyl-1H-quinoline-3-carboxamide |
| 395 | N-[4-(1-adamantyl)-2-fluoro-5-hydroxy-phenyl]-4-hydroxy-quinoline-3-carboxamide |

TABLE 1-continued

| Cmpd No. | Name |
|---|---|
| 396 | [2-methyl-2-[4-[(4-oxo-1H-quinolin-3-yl)carbonylamino]phenyl]-propyl]aminoformic acid tetrahydrofuran-3-ylmethyl ester |
| 397 | 4-oxo-N-(4-phenylphenyl)-1H-quinoline-3-carboxamide |
| 398 | 4-oxo-N-[2-(p-tolylsulfonylamino)phenyl]-1H-quinoline-3-carboxamide |
| 399 | N-(2-isopropyl-5-methylamino-phenyl)-4-oxo-1H-quinoline-3-carboxamide |
| 400 | N-(6-morpholino-3-pyridyl)-4-oxo-1H-quinoline-3-carboxamide |
| 401 | N-[2-(2,3-dimethylphenyl)phenyl]-4-oxo-1H-quinoline-3-carboxamide |
| 402 | 4-oxo-N-(5-phenyl-2-pyridyl)-1H-quinoline-3-carboxamide |
| 403 | N-[2-fluoro-5-hydroxy-4-(1-methylcyclooctyl)-phenyl]-4-hydroxy-quinoline-3-carboxamide |
| 404 | N-[5-(2,6-dimethoxyphenyl)-1H-indol-6-yl]-4-oxo-1H-quinoline-3-carboxamide |
| 405 | N-(4-chlorophenyl)-4-oxo-1H-quinoline-3-carboxamide |
| 406 | 6-[(4-fluorophenyl)-methyl-sulfamoyl]-4-oxo-N-(5-tert-butyl-1H-indol-6-yl)-1H-quinoline-3-carboxamide |
| 407 | N-(2-fluoro-5-hydroxy-4-tert-butyl-phenyl)-5-hydroxy-4-oxo-1H-quinoline-3-carboxamide |
| 408 | N-(3-methoxyphenyl)-4-oxo-1H-quinoline-3-carboxamide |
| 409 | N-(5-dimethylamino-2-ethyl-phenyl)-4-oxo-1H-quinoline-3-carboxamide |
| 410 | 4-oxo-N-[2-(4-phenoxyphenyl)phenyl]-1H-quinoline-3-carboxamide |
| 411 | 7-chloro-4-oxo-N-phenyl-1H-quinoline-3-carboxamide |
| 412 | 6-[(4-oxo-1H-quinolin-3-yl)carbonylamino]-1H-indole-7-carboxylic acid ethyl ester |
| 413 | 4-oxo-N-(2-phenoxyphenyl)-1H-quinoline-3-carboxamide |
| 414 | N-(3H-benzoimidazol-5-yl)-4-oxo-1H-quinoline-3-carboxamide |
| 415 | N-(3-hydroxy-4-tert-butyl-phenyl)-4-methoxy-quinoline-3-carboxamide |
| 416 | [2-methyl-2-[4-[(4-oxo-1H-quinolin-3-yl)carbonylamino]phenyl]-propyl]aminoformic acid propyl ester |
| 417 | N-(2-(benzo[b]thiophen-3-yl)phenyl)-1,4-dihydro-4-oxoquinoline-3-carboxamide |
| 418 | N-(3-dimethylaminophenyl)-4-oxo-1H-quinoline-3-carboxamide |
| 419 | N-(3-acetylaminophenyl)-4-oxo-1H-quinoline-3-carboxamide |
| 420 | 2-methyl-2-[4-[(4-oxo-1H-quinolin-3-yl)carbonylamino]phenyl]-propanoic acid ethyl ester |
| 421 | N-[5-methoxy-4-tert-butyl-2-(trifluoromethyl)phenyl]-4-oxo-1H-quinoline-3-carboxamide |
| 422 | N-(5,6-dimethyl-3H-benzoimidazol-2-yl)-4-oxo-1H-quinoline-3-carboxamide |
| 423 | N-[3-(2-ethoxyethyl)-1H-indol-6-yl]-4-oxo-1H-quinoline-3-carboxamide |
| 424 | N-[2-(4-chlorophenyl)phenyl]-4-oxo-1H-quinoline-3-carboxamide |
| 425 | N-(4-isopropylphenyl)-4-oxo-1H-quinoline-3-carboxamide |
| 426 | N-(4-chloro-5-hydroxy-2-tert-butyl-phenyl)-4-oxo-1H-quinoline-3-carboxamide |
| 427 | 5-[(4-oxo-1H-quinolin-3-yl)carbonylamino]-1,2,3,4-tetrahydroisoquinoline-2-carboxylic acid tert-butyl ester |
| 428 | N-(3-hydroxy-4-tert-butyl-phenyl)-4-oxo-1H-quinoline-3-carboxamide |
| 429 | N-[3-amino-5-(trifluoromethyl)phenyl]-4-oxo-1H-quinoline-3-carboxamide |
| 430 | N-(2-isopropyl-6-methyl-phenyl)-4-oxo-1H-quinoline-3-carboxamide |
| 431 | N-(3-aminophenyl)-4-oxo-1H-quinoline-3-carboxamide |
| 432 | N-[2-(4-isopropylphenyl)phenyl]-4-oxo-1H-quinoline-3-carboxamide |
| 433 | N-(5-hydroxy-2,4-ditert-butyl-phenyl)-4-oxo-1H-quinoline-3-carboxamide |
| 434 | N-(2,5-dimethylphenyl)-4-oxo-1H-quinoline-3-carboxamide |
| 435 | N-[2-(2-fluorophenoxy)-3-pyridyl]-4-oxo-1H-quinoline-3-carboxamide |
| 436 | N-[2-(3,4-dimethoxyphenyl)phenyl]-4-oxo-1H-quinoline-3-carboxamide |
| 437 | N-benzo[1,3]dioxol-5-yl-4-oxo-1H-quinoline-3-carboxamide |
| 438 | N-[5-(difluoromethyl)-2,4-ditert-butyl-phenyl]-4-oxo-1H-quinoline-3-carboxamide |
| 439 | N-(4-methoxyphenyl)-4-oxo-1H-quinoline-3-carboxamide |
| 440 | N-(2,2,3,3-tetrafluoro-2,3-dihydrobenzo[b][1,4]dioxin-6-yl)-1,4-dihydro-4-oxoquinoline-3-carboxamide |
| 441 | N-[3-methylsulfonylamino-5-(trifluoromethyl)phenyl]-4-oxo-1H-quinoline-3-carboxamide |
| 442 | 4-oxo-N-[3-(1-piperidylsulfonyl)phenyl]-1H-quinoline-3-carboxamide |
| 443 | 4-oxo-N-quinoxalin-6-yl-1H-quinoline-3-carboxamide |
| 444 | 5-[(4-oxo-1H-quinolin-3-yl)carbonylamino]-2-tert-butyl-benzoic acid methyl ester |
| 445 | N-(2-isopropenylphenyl)-4-oxo-1H-quinoline-3-carboxamide |
| 446 | N-(1,1-dioxobenzothiophen-6-yl)-4-oxo-1H-quinoline-3-carboxamide |
| 447 | N-(3-cyanophenyl)-4-oxo-1H-quinoline-3-carboxamide |
| 448 | 4-oxo-N-(4-tert-butylphenyl)-1H-quinoline-3-carboxamide |
| 449 | N-(m-tolyl)-4-oxo-1H-quinoline-3-carboxamide |
| 450 | N-[4-(1-hydroxyethyl)phenyl]-4-oxo-1H-quinoline-3-carboxamide |
| 451 | N-(4-cyano-2-ethyl-phenyl)-4-oxo-1H-quinoline-3-carboxamide |
| 452 | 4-oxo-N-(4-vinylphenyl)-1H-quinoline-3-carboxamide |
| 453 | N-(3-amino-4-chloro-phenyl)-4-oxo-1H-quinoline-3-carboxamide |
| 454 | N-(2-methyl-5-phenyl-phenyl)-4-oxo-1H-quinoline-3-carboxamide |
| 455 | N-[4-(1-adamantyl)phenyl]-4-oxo-1H-quinoline-3-carboxamide |
| 456 | 4-oxo-N-[3-(trifluoromethylsulfanyl)phenyl]-1H-quinoline-3-carboxamide |
| 457 | N-(4-morpholinophenyl)-4-oxo-1H-quinoline-3-carboxamide |
| 458 | N-[3-(2-hydroxyethoxy)-4-tert-butyl-phenyl]-4-oxo-1H-quinoline-3-carboxamide |
| 459 | N-(o-tolyl)-4-oxo-1H-quinoline-3-carboxamide |
| 460 | [2-methyl-2-[4-[(4-oxo-1H-quinolin-3-yl)carbonylamino]phenyl]-propyl]aminoformic acid butyl ester |
| 461 | 4-oxo-N-(2-phenylphenyl)-1H-quinoline-3-carboxamide |
| 462 | N-(3-dimethylamino-4-propyl-phenyl)-4-oxo-1H-quinoline-3-carboxamide |
| 463 | N-(4-ethylphenyl)-4-oxo-1H-quinoline-3-carboxamide |
| 464 | 5-hydroxy-N-(5-hydroxy-2,4-ditert-butyl-phenyl)-4-oxo-1H-quinoline-3-carboxamide |
| 465 | [5-[(4-oxo-1H-quinolin-3-yl)carbonylamino]-2-tert-butyl-phenylmethyl]aminoformic acid tert-butyl ester |

TABLE 1-continued

| Cmpd No. | Name |
|---|---|
| 466 | N-(2,6-diisopropylphenyl)-4-oxo-1H-quinoline-3-carboxamide |
| 467 | N-(2,3-dihydrobenzofuran-5-yl)-4-oxo-1H-quinoline-3-carboxamide |
| 468 | 1-methyl-4-oxo-N-phenyl-1H-quinoline-3-carboxamide |
| 469 | 4-oxo-N-(2-phenylphenyl)-7-(trifluoromethyl)-1H-quinoline-3-carboxamide |
| 470 | 4-oxo-N-(4-phenylsulfanylphenyl)-1H-quinoline-3-carboxamide |
| 471 | [3-[(4-oxo-1H-quinolin-3-yl)carbonylamino]-4-propyl-phenyl]aminoformic acid methyl ester |
| 472 | [4-ethyl-3-[(4-oxo-1H-quinolin-3-yl)carbonylamino]phenyl]aminoformic acid ethyl ester |
| 473 | 1-isopropyl-4-oxo-N-(2-tert-butylphenyl)-1H-quinoline-3-carboxamide |
| 474 | N-(3-methyl-2-oxo-3H-benzooxazol-5-yl)-4-oxo-1H-quinoline-3-carboxamide |
| 475 | N-(2,5-dichloro-3-pyridyl)-4-oxo-1H-quinoline-3-carboxamide |
| 476 | N-(2-cyano-5-hydroxy-4-tert-butyl-phenyl)-4-oxo-1H-quinoline-3-carboxamide |
| 477 | N-(5-fluoro-2-pyridyl)-4-oxo-1H-quinoline-3-carboxamide |
| 478 | 4-oxo-N-(3-tert-butyl-1H-indol-6-yl)-1H-quinoline-3-carboxamide |
| 479 | N-(1H-indol-6-yl)-5-methoxy-4-oxo-1H-quinoline-3-carboxamide |
| 480 | 1-ethyl-6-methoxy-4-oxo-N-phenyl-1H-quinoline-3-carboxamide |
| 481 | N-(2-naphthyl)-4-oxo-1H-quinoline-3-carboxamide |
| 482 | [7-[(4-oxo-1H-quinolin-3-yl)carbonylamino]tetralin-1-yl]aminoformic acid ethyl ester |
| 483 | N-[2-fluoro-5-hydroxy-4-(1-methylcycloheptyl)-phenyl]-4-hydroxy-quinoline-3-carboxamide |
| 484 | N-(3-methylamino-4-tert-butyl-phenyl)-4-oxo-1H-quinoline-3-carboxamide |
| 485 | N-(3-dimethylamino-4-tert-butyl-phenyl)-4-oxo-1H-quinoline-3-carboxamide |

In another embodiment, the present invention provides compounds useful as intermediates in the synthesis of compounds of formula I. In one embodiment, such compounds have formula A-I:

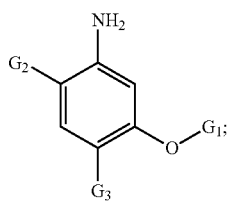

or a salt thereof;
wherein:

$G_1$ is hydrogen, R', C(O)R', C(S)R', S(O)R', S(O)$_2$R', Si(CH$_3$)$_2$R', P(O)(OR')$_3$, P(S)(OR')$_3$, or B(OR')$_2$;

$G_2$ is halo, CN, CF$_3$, isopropyl, or phenyl wherein said isopropyl or phenyl is optionally substituted with up to 3 substituents independently selected from WR$^W$, wherein W and R$^W$ are as defined above for formula I and embodiments thereof;

$G_3$ is an isopropyl or a C3-C10 cycloaliphatic ring, wherein said $G_3$ is optionally substituted with up to 3 substituents independently selected from WR$^W$, wherein W and R$^W$ are as defined above for formula I and embodiments thereof;

provided that when $G_1$ is methoxy, $G_3$ is tert-butyl, then $G_2$ is not 2-amino-4-methoxy-5-tert-butyl-phenyl.

In one embodiment, the present invention provides compounds of formula A-I, provided that when $G_2$ and $G_3$ each is t-butyl, then $G_1$ is not hydrogen.

In another embodiment:

$G_1$ is hydrogen;

$G_2$ is halo or isopropyl, wherein said isopropyl is optionally substituted with up to 3 substituents independently selected from R'; and $G_3$ is an isopropyl or a C3-C10 cycloaliphatic ring, wherein said $G_3$ is optionally substituted with up to 3 substituents independently selected from R'.

In another embodiment:

$G_1$ is hydrogen;

$G_2$ is halo, preferably fluoro; and $G_3$ is a C3-C10 cycloaliphatic ring, wherein said $G_3$ is optionally substituted with up to 3 substituents independently selected from methyl, ethyl, propyl, or butyl.

In another embodiment:

$G_1$ is hydrogen;

$G_2$ is CN, halo, or CF$_3$; and $G_3$ is an isopropyl or a C3-C10 cycloaliphatic ring, wherein said $G_3$ is optionally substituted with up to 3 substituents independently selected from R'.

In another embodiment:

$G_1$ is hydrogen;

$G_2$ is phenyl is optionally substituted with up to 3 substituents independently selected from —OC1-C4 alkyl, CF$_3$, halo, or CN; and $G_3$ is an isopropyl or a C3-C10 cycloaliphatic ring, wherein said $G_3$ is optionally substituted with up to 3 substituents independently selected from R'.

Exemplary $G_3$ include optionally substituted cyclopentyl, cyclohexyl, cycloheptyl, or adamantyl. Or, G3 is C3-C8 branched aliphatic chain. Exemplary G3 include isopropyl, t-butyl, 3,3-diethyl-prop-3-yl, or 3,3-diethyl-2,2-dimethyl-prop-3-yl.

In another embodiment:

$G_1$ is hydrogen;

$G_2$ is t-butyl; and $G_3$ is a t-butyl.

In another embodiment, the present invention provides a compound of formula A-II:

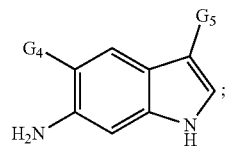

or a salt thereof, wherein:

$G_4$ is hydrogen, halo, CN, CF$_3$, CHF$_2$, CH$_2$F, optionally substituted C1-C6 aliphatic, aralkyl, or a phenyl ring optionally substituted with up to 4 WR$^W$ substituents;

$G_5$ is hydrogen or an optionally substituted C1-C6 aliphatic;

provided that both, $G_4$ and $G_5$, are not simultaneously hydrogen;

wherein said indole ring system is further optionally substituted with up to 3 substituents independently selected from $WR^W$.

In one embodiment, $G_4$ is hydrogen. Or, $G_5$ is hydrogen.

In another embodiment, $G_4$ is hydrogen, and $G_5$ is C1-C6 aliphatic, wherein said aliphatic is optionally substituted with C1-C6 alkyl, halo, cyano, or $CF_3$, and wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, $G_4$ is hydrogen, and $G_5$ is cyano, methyl, ethyl, propyl, isopropyl, butyl, sec-butyl, t-butyl, cyanomethyl, methoxyethyl, $CH_2C(O)OMe$, $(CH_2)_2NHC(O)O$-tert-But, or cyclopentyl.

In another embodiment, $G_5$ is hydrogen, and $G_4$ is halo, C1-C6 aliphatic or phenyl, wherein said aliphatic or phenyl is optionally substituted with C1-C6 alkyl, halo, cyano, or $CF_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, $G_5$ is hydrogen, and $G_4$ is halo, ethoxycarbonyl, t-butyl, 2-methoxyphenyl, 2-ethoxyphenyl, 4-C(O)NH(CH$_2$)$_2$—NMe$_2$, 2-methoxy-4-chloro-phenyl, pyridine-3-yl, 4-isopropylphenyl, 2,6-dimethoxyphenyl, sec-butylaminocarbonyl, ethyl, t-butyl, or piperidin-1-ylcarbonyl.

In a related embodiment of formula A-II, the nitrogen ring atom of said indole ring is substituted with C1-C6 aliphatic, C(O)(C1-C6 aliphatic), or benzyl, wherein said aliphatic or benzyl is optionally substituted with C1-C6 alkyl, halo, cyano, or $CF_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment the nitrogen ring atom of said indole ring is substituted with acyl, benzyl, C(O)CH$_2$N(Me) C(O)CH$_2$NHMe, or ethoxycarbonyl.

4. General Synthetic Schemes

Compounds of the present invention are readily prepared by methods known in the art. Illustrated below are exemplary methods for the preparation of compounds of the present invention.

The scheme below illustrates the synthesis of acid precursors of the compounds of the present invention.

Synthesis of Acid Precursors P-IV-A, P-IV-B or P-IV-C:

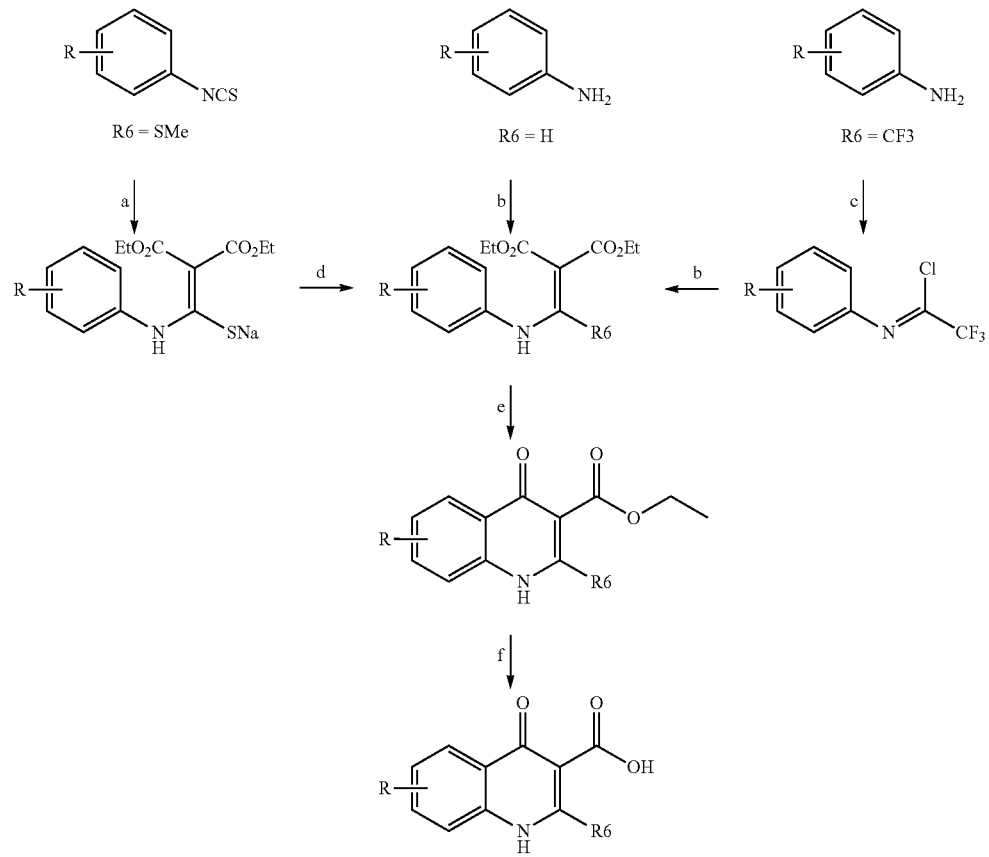

a) (CO$_2$Et)$_2$CH$_2$; b) (CO$_2$Et)$_2$CH═CH(OEt); c) CF$_3$CO$_2$H, PPh$_3$, CCl$_4$, Et$_3$N; d) MeI; e) PPA or diphenylether; f) NaOH.

Synthesis of Acid Precursors P-IV-A, P-IV-B or P-IV-C:

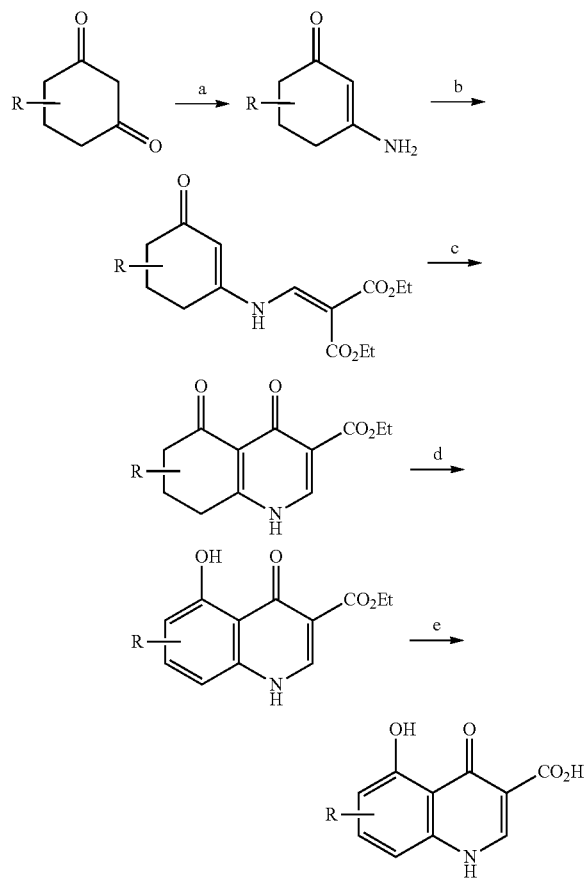

a) AcONH₄; b) EtOCHC(CO₂Et)₂, 130° C.; c) Ph₂O, ΔT; d) I₂, EtOH; e) NaOH.

Synthesis of Acid Precursors P-IV-A, P-IV-B or P-IV-C

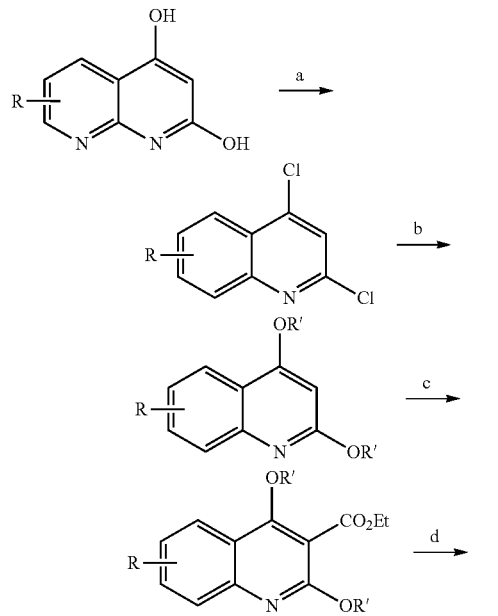

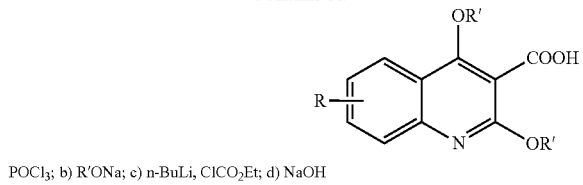

POCl₃; b) R'ONa; c) n-BuLi, ClCO₂Et; d) NaOH

Synthesis of Amine Precursor P-III-A:

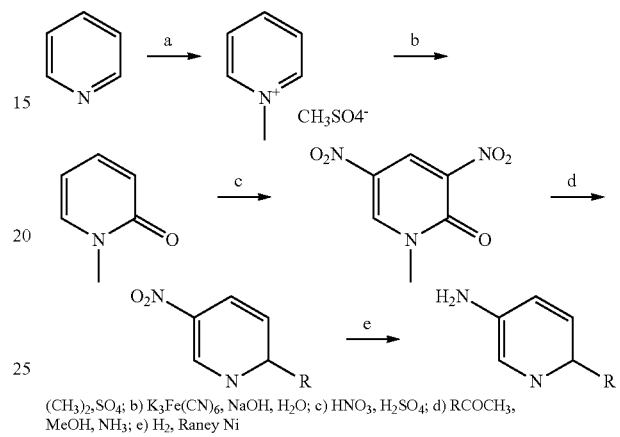

(CH₃)₂SO₄; b) K₃Fe(CN)₆, NaOH, H₂O; c) HNO₃, H₂SO₄; d) RCOCH₃, MeOH, NH₃; e) H₂, Raney Ni

Synthesis of Amine Precursor P-IV-A:

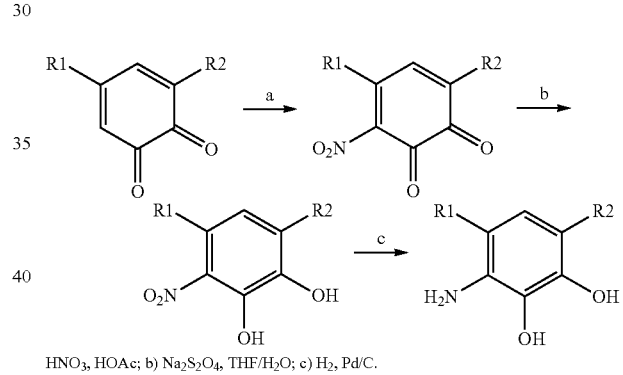

HNO₃, HOAc; b) Na₂S₂O₄, THF/H₂O; c) H₂, Pd/C.

Synthesis of Amine Precursor P-V-A-1:

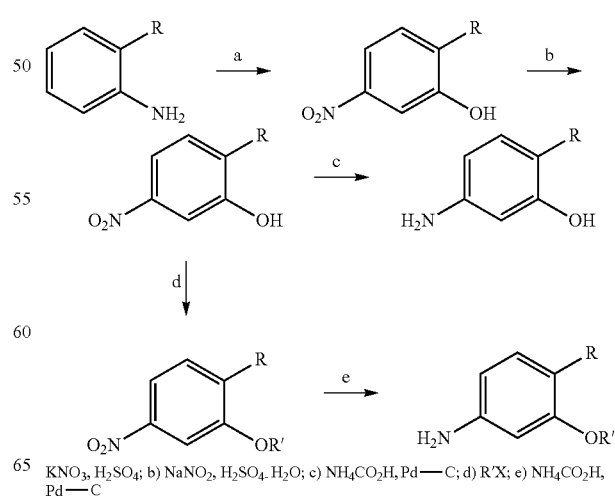

KNO₃, H₂SO₄; b) NaNO₂, H₂SO₄, H₂O; c) NH₄CO₂H, Pd—C; d) R'X; e) NH₄CO₂H, Pd—C

Synthesis of Amine Precursor P-V-A-1:
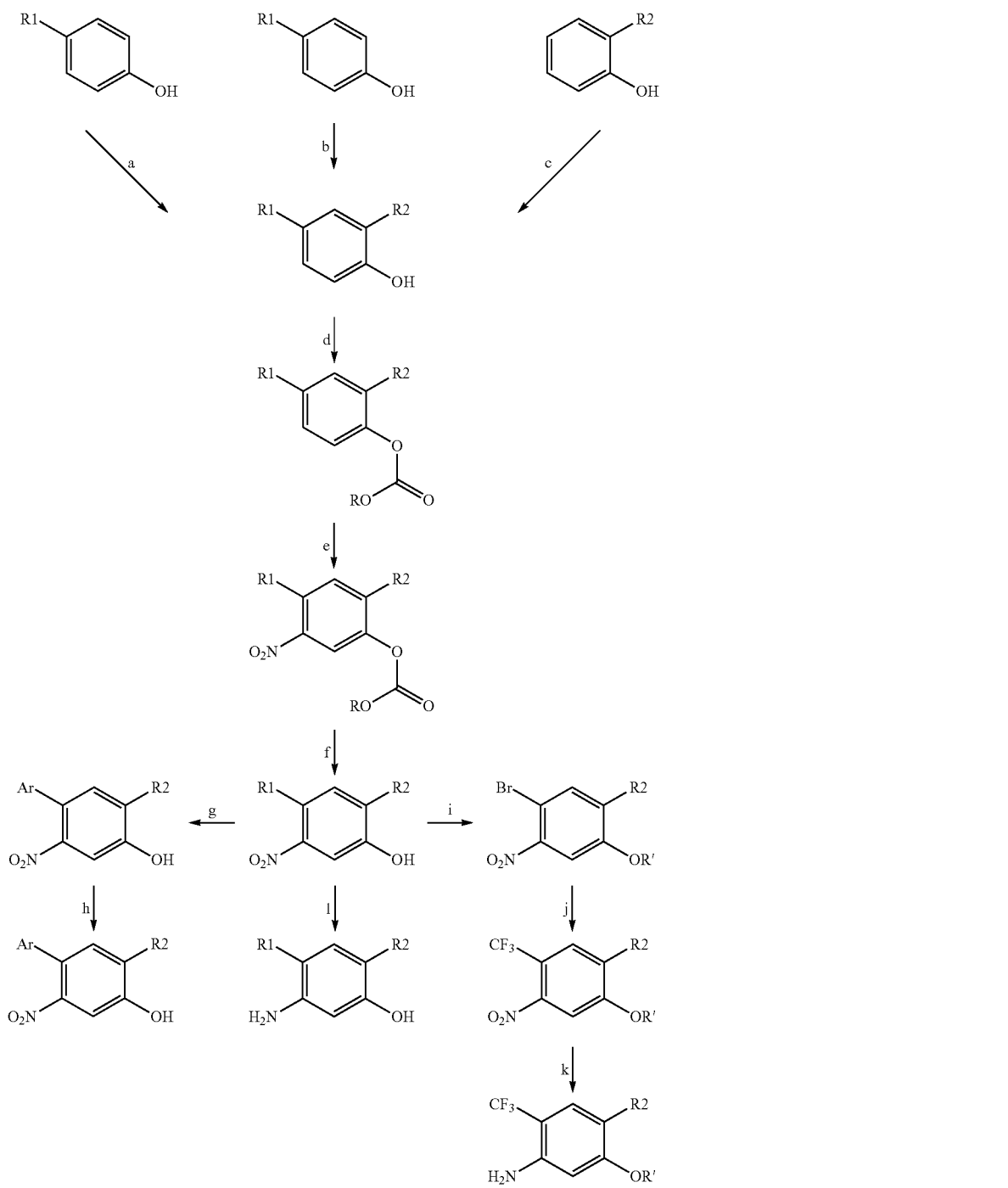
a) $SO_2Cl_2$, R2 = Cl; b) R2OH, R2 = alkyl; c) NBS, R1 = Br; d) $ClCO_2R$, TEA; e) $HNO_3$, $H_2SO_4$; f) base; g) $ArB(OH)_2$, R1 = Br; h) [H]; I) R'X, R1 = Br; j) $ClCF_2CO_2Me$; k) [H]; l) [H].
Synthesis of Amine Precursor P-V-A-1:
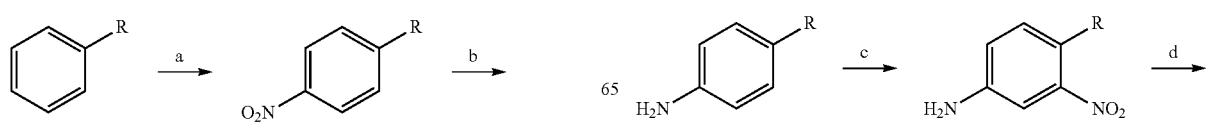

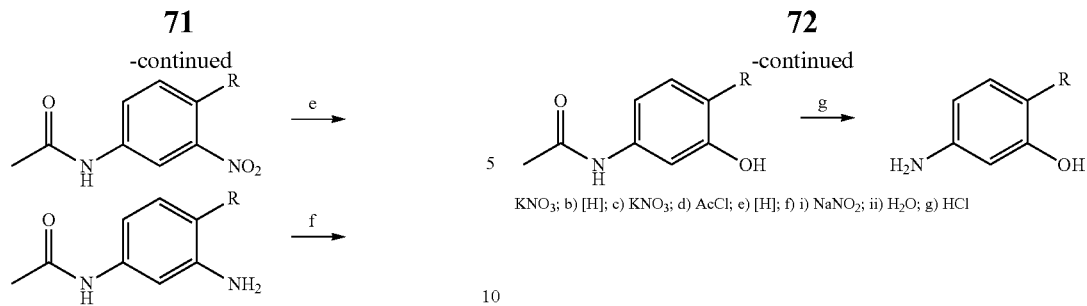
KNO₃; b) [H]; c) KNO₃; d) AcCl; e) [H]; f) i) NaNO₂; ii) H₂O; g) HCl
Synthesis of Amine Precursor P-V-A-1:
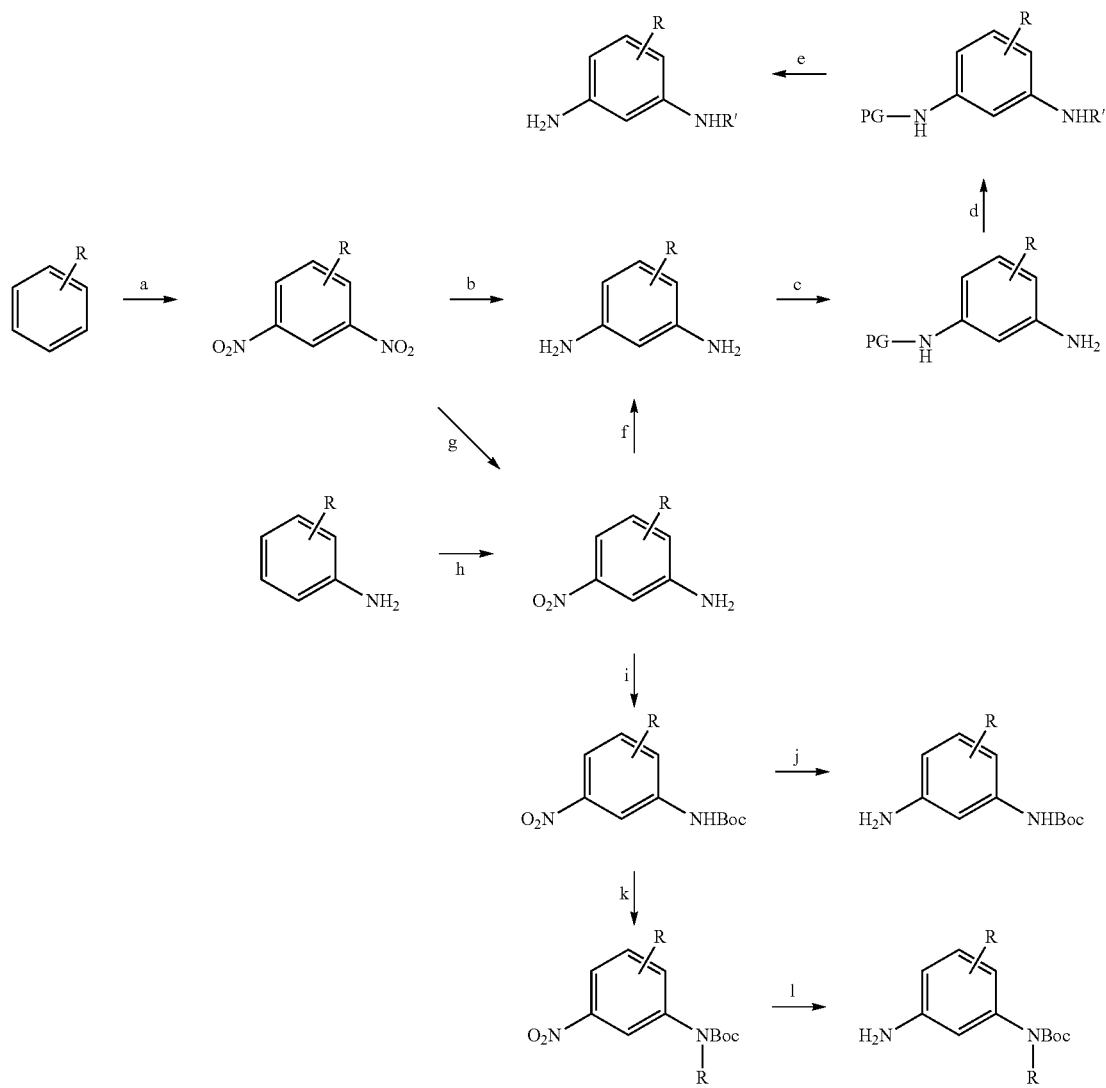
HNO₃, H₂SO₄; b) [H]; c) protection; d) R'CHO; e) deprotection; f) [H]; g) Na₂S, S, H₂O; h) nitration; i) (BOC)₂O; j) [H]; RX; l) [H]; PG = protecting group
Synthesis of Amine Precursors P-V-A-1 or P-V-A-2:
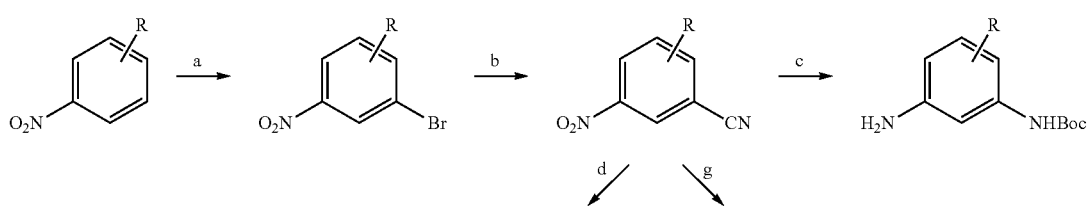

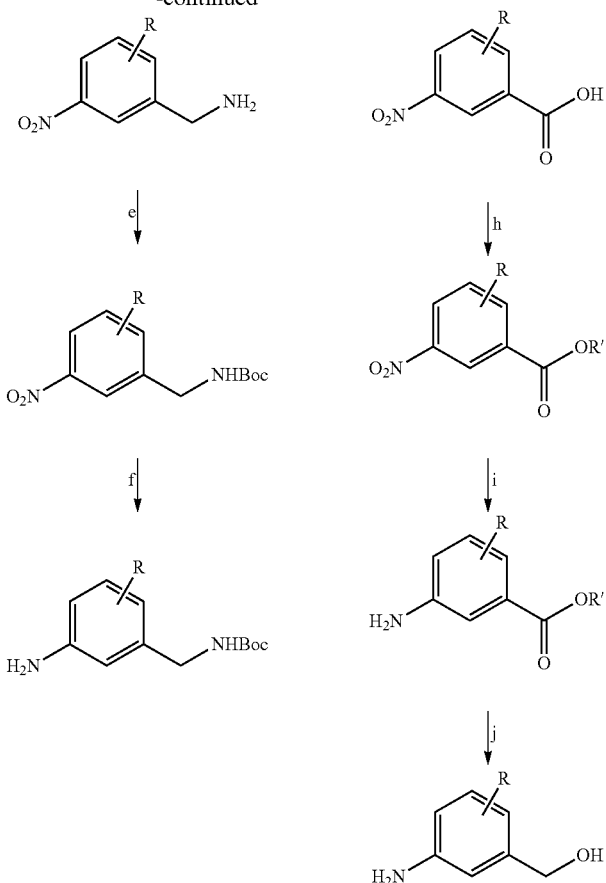
a) Br$_2$; b) Zn(CN)$_2$, Pd(PPh)$_3$; c) [H]; d) BH$_3$; d) (BOC)$_2$O; f) [H]; g) H$_2$SO$_4$, H$_2$O; h) R'X; i) [H]; j) LiAlH$_4$
Synthesis of Amine Precursors P-V-A-1 or P-V-A-2:
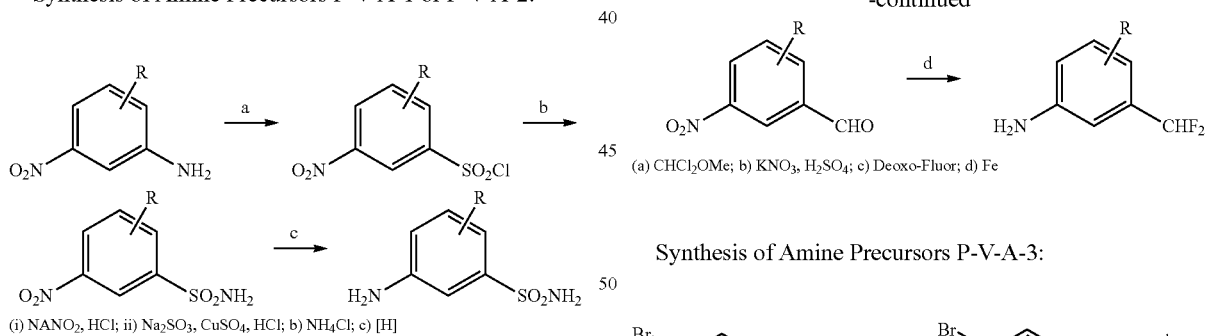
(i) NANO$_2$, HCl; ii) Na$_2$SO$_3$, CuSO$_4$, HCl; b) NH$_4$Cl; c) [H]
Synthesis of Amine Precursors P-V-A-1:
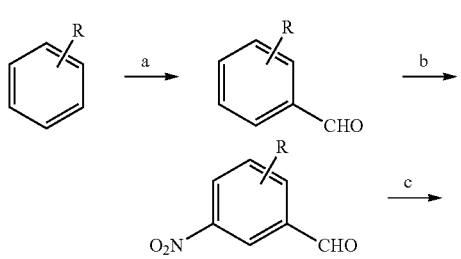
(a) CHCl$_2$OMe; b) KNO$_3$, H$_2$SO$_4$; c) Deoxo-Fluor; d) Fe
Synthesis of Amine Precursors P-V-A-3:
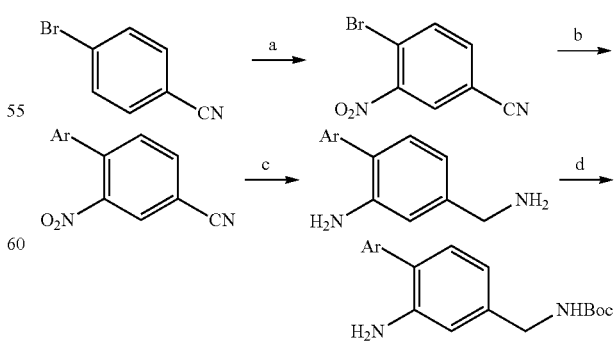
Ar = Aryl or Heteraryl
(a) Nitration: b) ArB(OH)$_2$, Pd; c) BH$_3$; d) (BOC)$_2$O

75
Synthesis of Amine Precursors P-V-B-1:
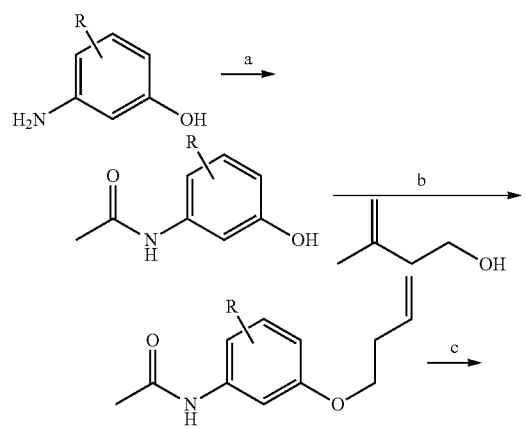
a) AcCl; b) DEAD; c) AlCl₃; d) NaOH
Synthesis of Amine Precursors P-V-B-1:
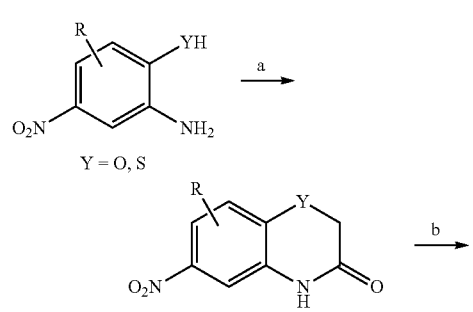
Y = O, S
76
-continued
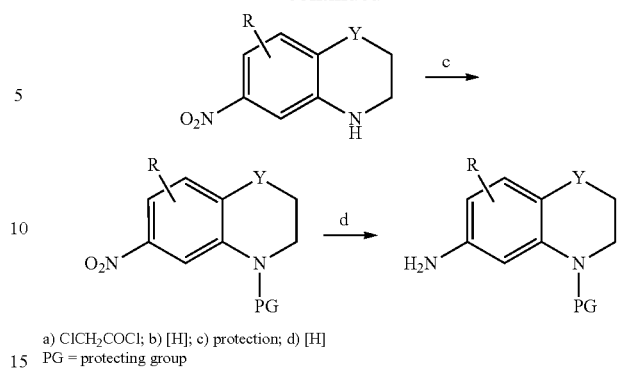
a) ClCH₂COCl; b) [H]; c) protection; d) [H]
PG = protecting group
Synthesis of Amine Precursors P-V-B-1:
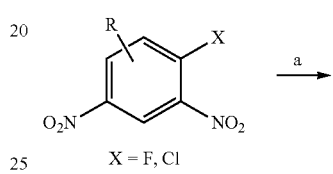
X = F, Cl
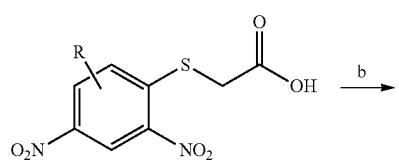
a) HSCH₂CO₂H; b) [H]
Synthesis of Amine Precursors P-V-B-2:
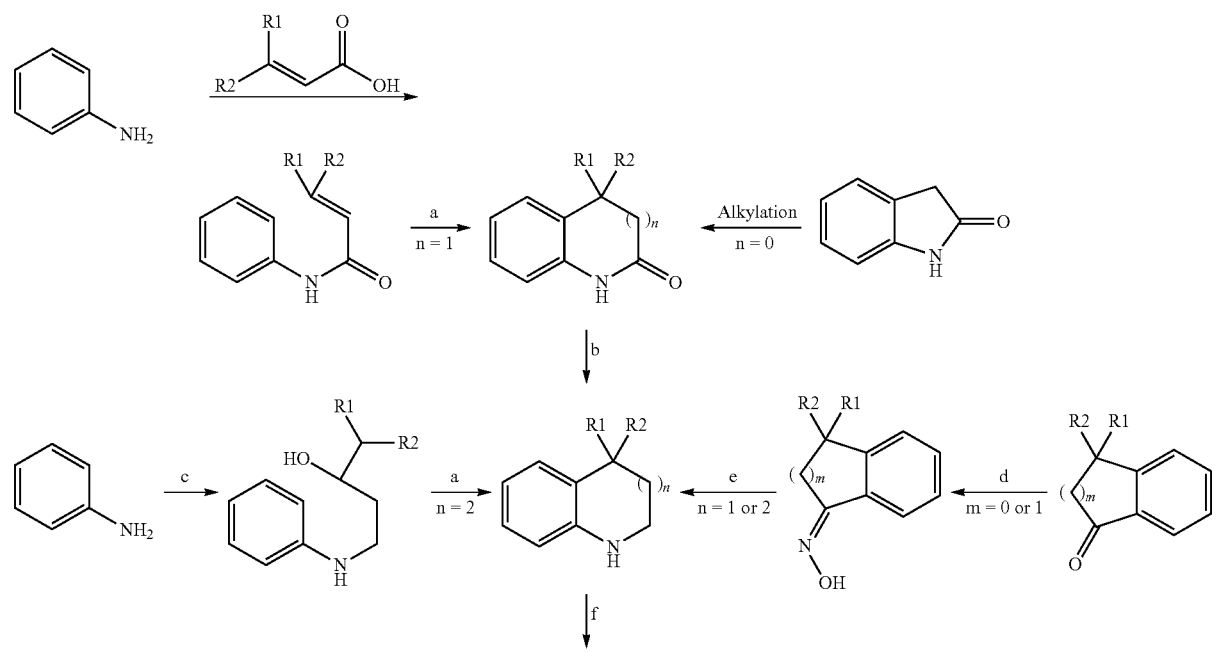

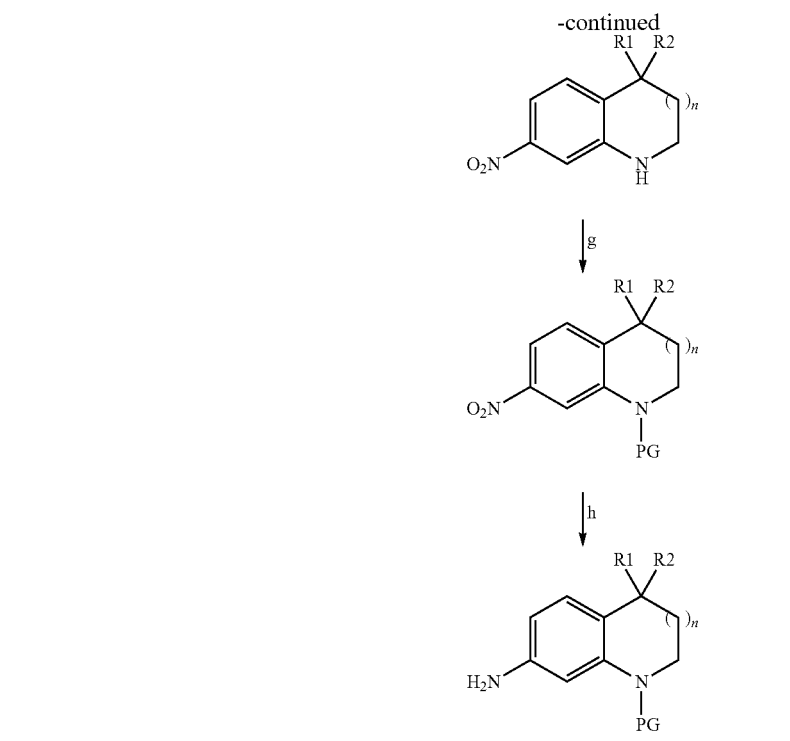

a) AlCl₃; b) [H]; c) i) R1R2CHCOCH₂CH₂Cl; ii) NaBH₄; d) NH₂OH; e) DIBAL—H; f) nitration; g) protection; h) [H]

PG = protecting group

Synthesis of Amine Precursors P-V-B-3:

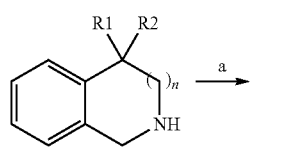

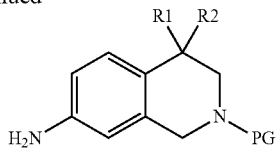

a) Nitration; b) Protection; c) [H]
PG = protecting group

Synthesis of Amine Precursors P-V-B-5:

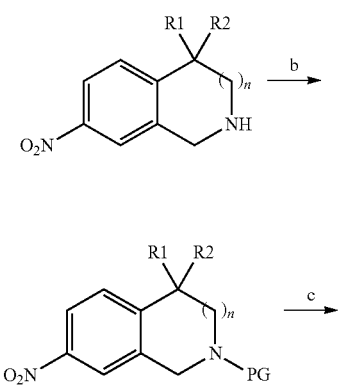

a) when X = Cl, Br, I: RX, K₂CO₃; DMF or CH₃CN; when X = OH: RX, TFFH, DIEA, THF b) H₂, Pd—C, EtOH or SnCl₂•2H₂O, EtOH or SnCl₂•H₂O, DIEA, EtOH.

Synthesis of Amine Precursors P-V-B-5:

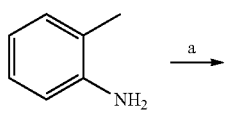

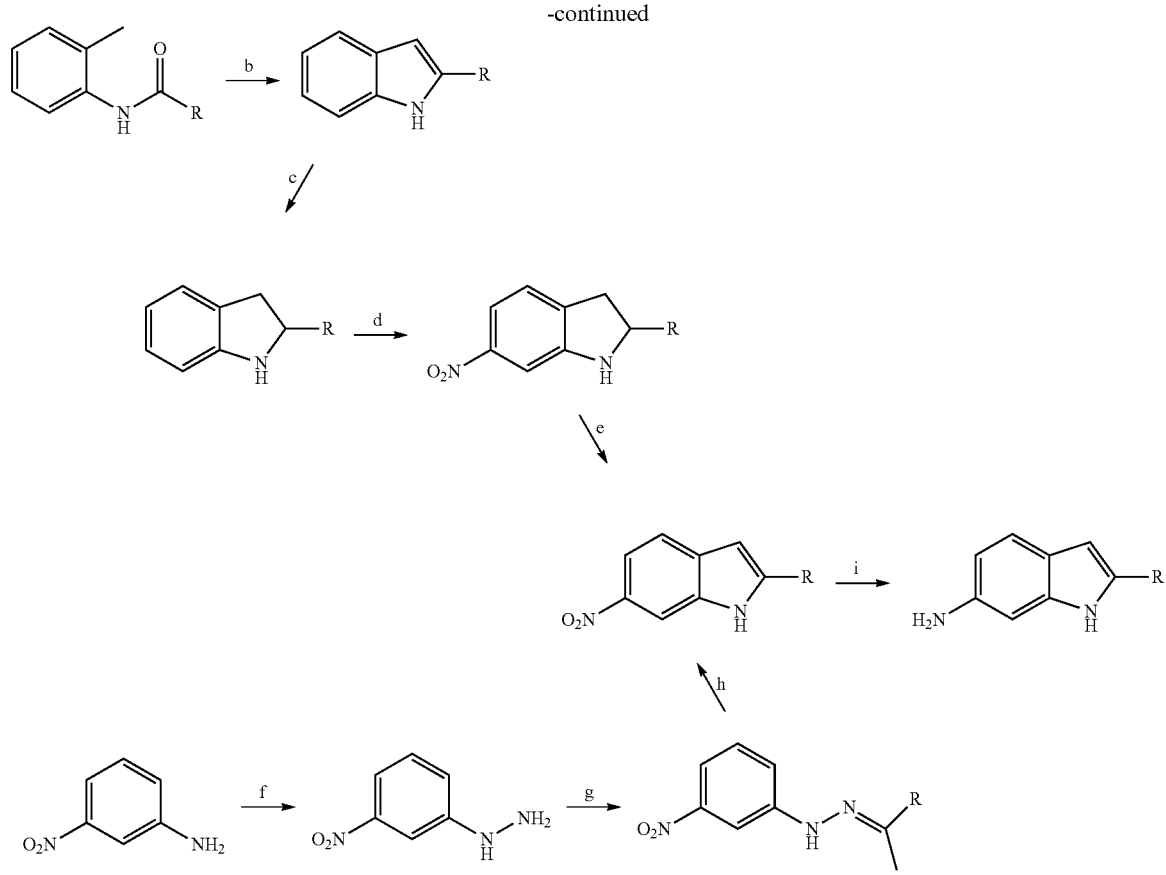

a) RCOCl, Et$_3$N, CH$_2$Cl$_2$; b) n-BuLi, THF; c) NaBH$_4$, AcOH; d) KNO$_3$; H$_2$SO$_4$; e) DDQ, 1,4-dioxane; f) NaNO$_2$, HCl, SnCl$_2$·2H$_2$O, H$_2$O; g) MeCOR, EtOH; h) PPA; i) LiAlH$_4$, THF or H$_2$, Raney Ni, EtOH or MeOH Synthesis of Amine Precursors V-B-5:

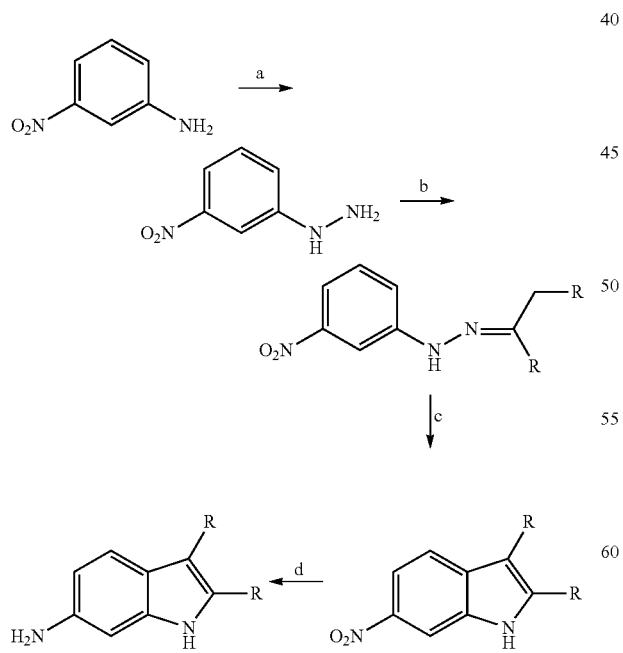

a) NaNO$_2$, HCl, SnCl$_2$·2H$_2$O, H$_2$O; b) RCH$_2$COR, AcOH, EtOH; c) H$_3$PO$_4$, toluene; d) H$_2$, Pd—C, EtOH Synthesis of Amine Precursors P-V-B-5:

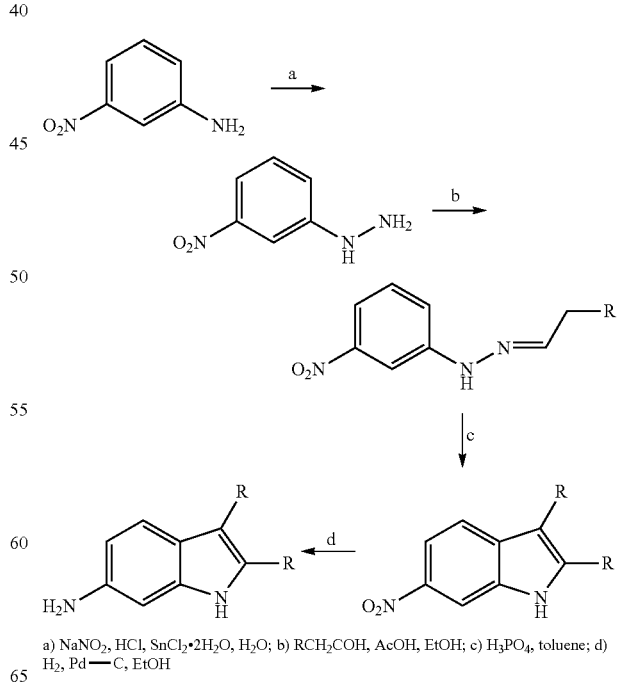

a) NaNO$_2$, HCl, SnCl$_2$·2H$_2$O, H$_2$O; b) RCH$_2$COH, AcOH, EtOH; c) H$_3$PO$_4$, toluene; d) H$_2$, Pd—C, EtOH Synthesis of Amine Precursors P-V-B-5:

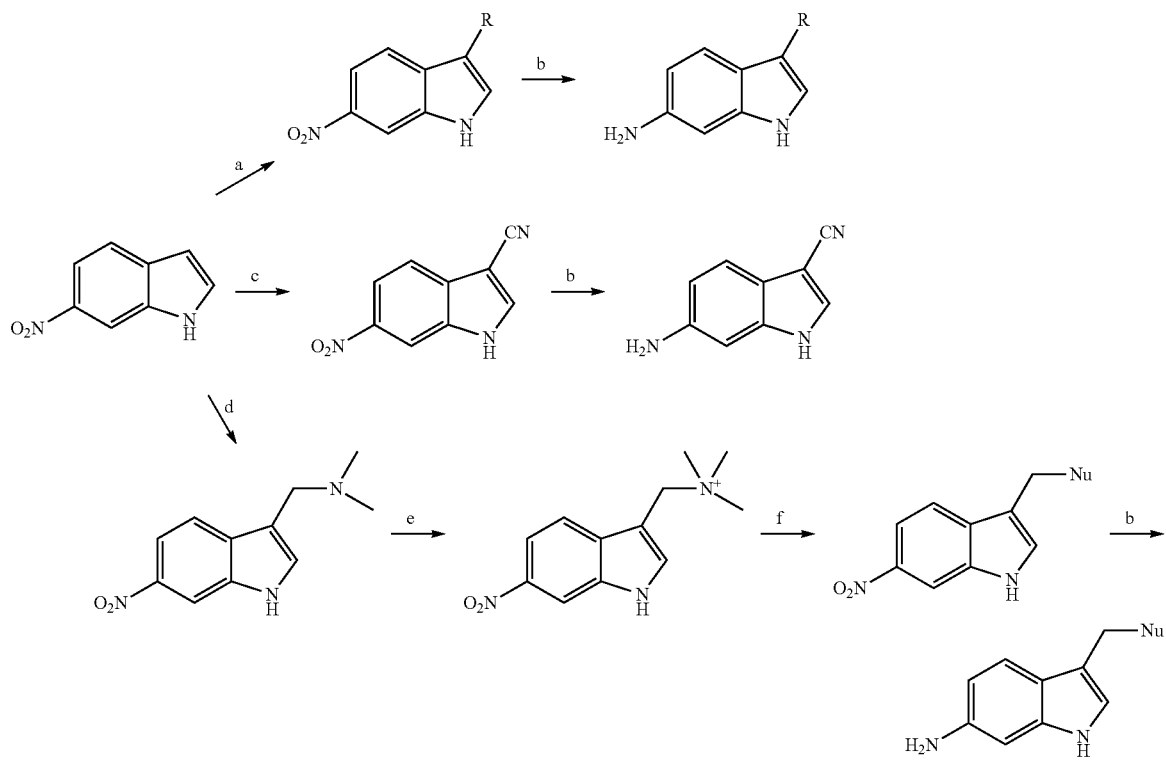

a) RX ( X = Br, I), zinc triflate, TBAI, DIEA, toluene; b) H$_2$, Raney Ni, EtOH or H$_2$, Pd—C, EtOH or SnCl$_2$·2H$_2$O, EtOH; c) ClSO$_2$NCO, DMF, CH$_3$CN; d) Me$_2$NH, H$_2$CO, AcOH; e) MeI, DMF, THF, H$_2$O; f) MNu (M = Na, K, Li; Nu = nucleophile)

Synthesis of Amine Precursors P-V-B-5:

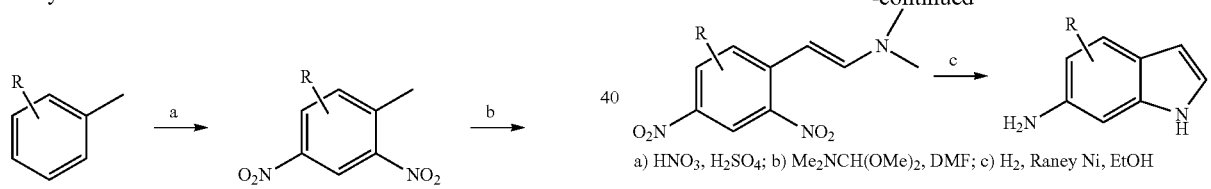

a) HNO$_3$, H$_2$SO$_4$; b) Me$_2$NCH(OMe)$_2$, DMF; c) H$_2$, Raney Ni, EtOH

Synthesis of Amine Precursors P-V-B-5:

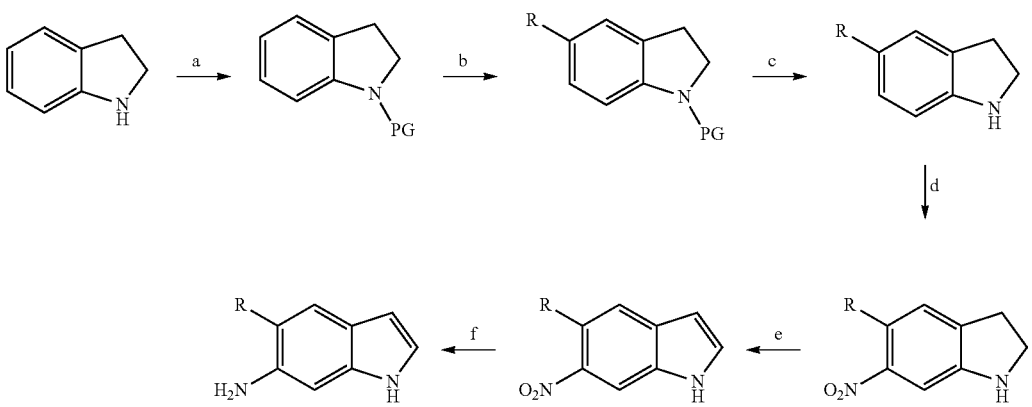

a) When PG = SO$_2$Ph: PhSO$_2$Cl, Et$_3$N, DMAP, CH$_2$Cl$_2$; When PG = Ac: AcCl, NaHCO$_3$, CH$_2$Cl$_2$; b) When R = RCO: (RCO)$_2$O, AlCl$_3$, CH$_2$Cl; When R= Br$_2$, AcOH; c) HBr or HCl; d) KNO$_3$, H$_2$SO$_4$; e) MnO$_2$, CH$_2$Cl$_2$ or DDQ, 1,4-dioxane; f) H$_2$, Raney Ni, EtOH.

Synthesis of Amine Precursors P-V-B-5:

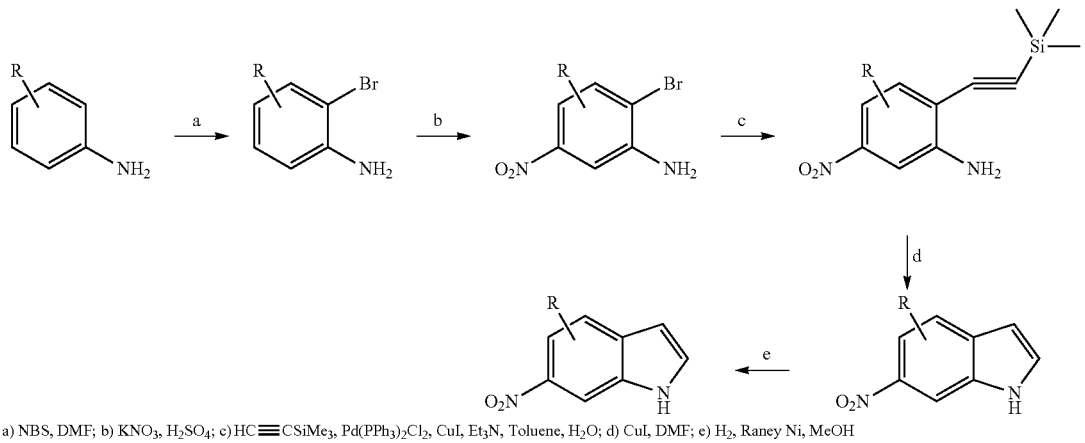

a) NBS, DMF; b) KNO₃, H₂SO₄; c) HC≡CSiMe₃, Pd(PPh₃)₂Cl₂, CuI, Et₃N, Toluene, H₂O; d) CuI, DMF; e) H₂, Raney Ni, MeOH Synthesis of Amine Precursors P-V-A-3 and P-V-A-6:

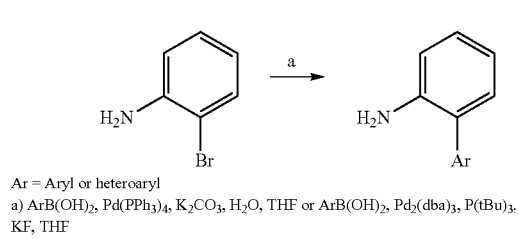

Ar = Aryl or heteroaryl
a) ArB(OH)₂, Pd(PPh₃)₄, K₂CO₃, H₂O, THF or ArB(OH)₂, Pd₂(dba)₃, P(tBu)₃, KF, THF Synthesis of Amine Precursors P-V-A-4:

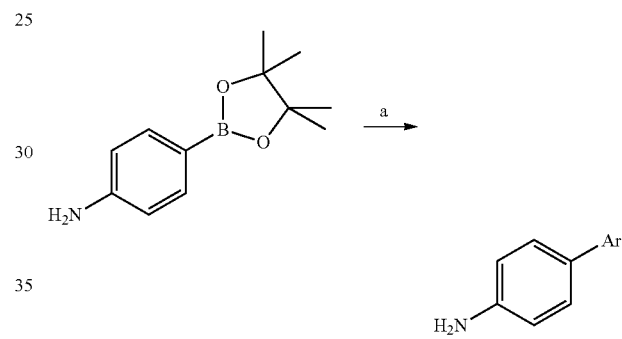

a) ArBr, Pd(OAc)₂, PS—PPh₃, K₂CO₃, DMF

Synthesis of Amine Precursors P-V-A-4:

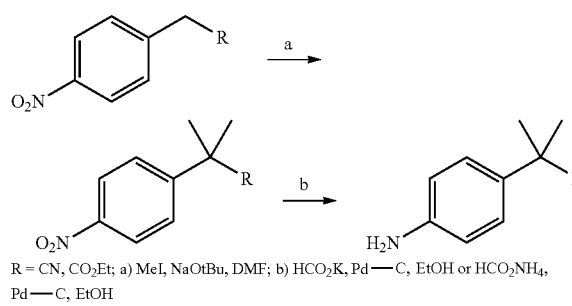

R = CN, CO₂Et; a) MeI, NaOtBu, DMF; b) HCO₂K, Pd—C, EtOH or HCO₂NH₄, Pd—C, EtOH

Synthesis of Amine Precursors P-V-B-4:

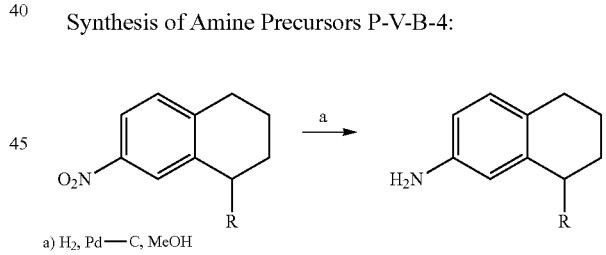

a) H₂, Pd—C, MeOH

Synthesis of Amine Precursors P-V-B-4:

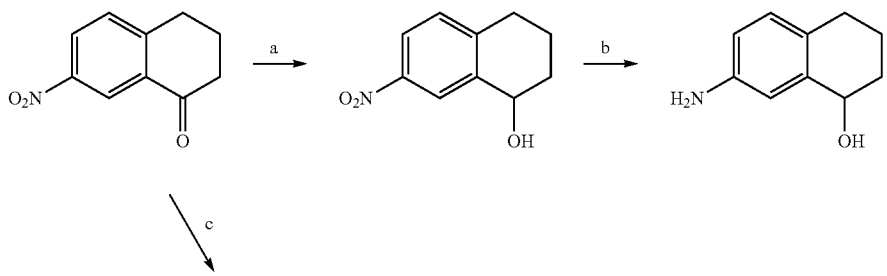

85 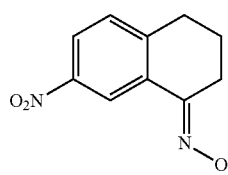 → d → 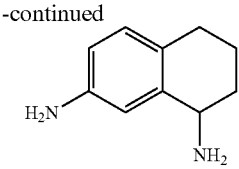 → e → 86 a) NaBH₄, MeOH; b) H₂, Pd—C, MeOH; c) NH₂OH, Pyridine; d) H₂, Pd—C, MeOH; e) Boc₂O, Et₃N, MeOH Synthesis of Compounds of Formula I:

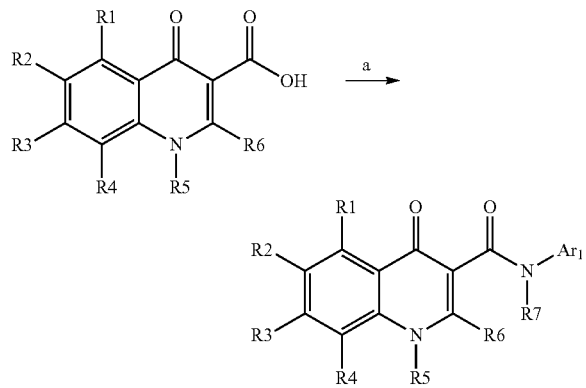

a) Ar₁R7NH, coupling reagent, base, solvent. Examples of conditions used: HATU, DIEA, DMF; BOP, DIEA, DMF; HBTU, Et₃N, CH₂Cl₂; PFPTFA, pyridine.

Synthesis of Compounds of Formula I':

R5 = aliphatic: a) R5X (X = Br, I), Cs₂CO₃, DMF

Synthesis of Compounds of formula V-B-5:

a) NAOH, THF; b) HNR₂, HATU, DIEA, DMF

Synthesis of Compounds of formula V-B-5:

WRʷ = aryl or heteroaryl: a) ArB(OH)₂, (dppf)PdCl₂, K₂CO₃, DMF

Synthesis of Compounds of Formula V-A-2 & V-A-5:
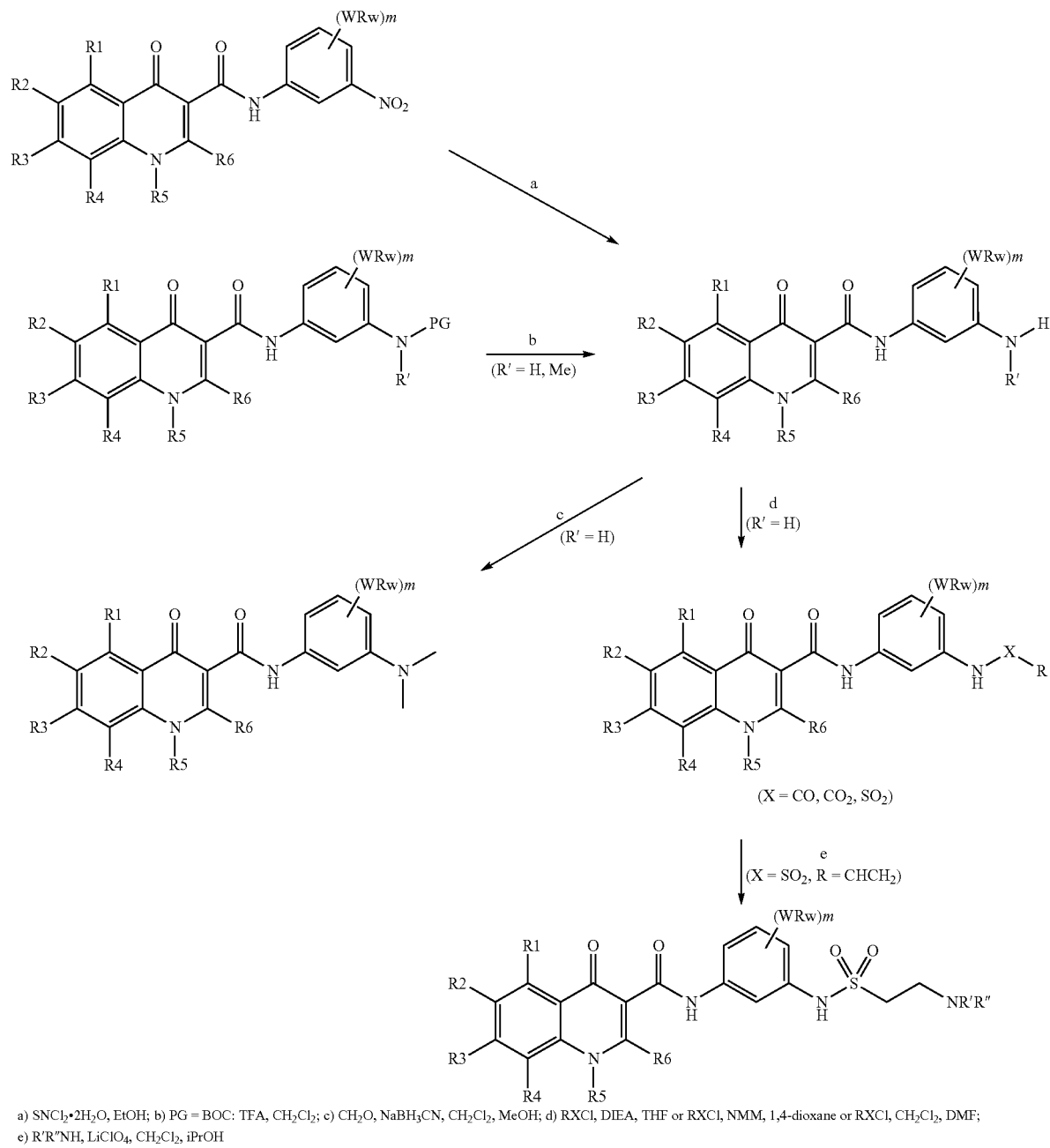
a) SnCl₂•2H₂O, EtOH; b) PG = BOC: TFA, CH₂Cl₂; c) CH₂O, NaBH₃CN, CH₂Cl₂, MeOH; d) RXCl, DIEA, THF or RXCl, NMM, 1,4-dioxane or RXCl, CH₂Cl₂, DMF; e) R'R"NH, LiClO₄, CH₂Cl₂, iPrOH
Synthesis of Compounds of Formula V-B-2:
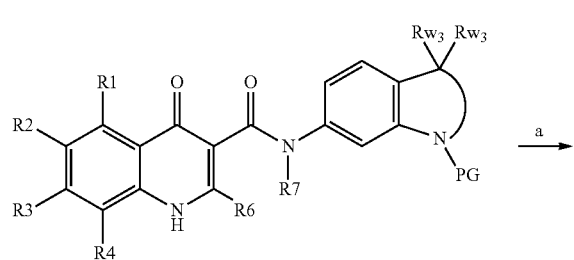
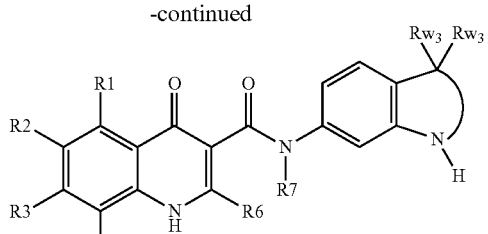
a) When PG = BOC: TFA, CH₂Cl₂; When PG = Ac: NaOH or HCl, EtOH or THF Synthesis of Compounds of Formula V-A-2:

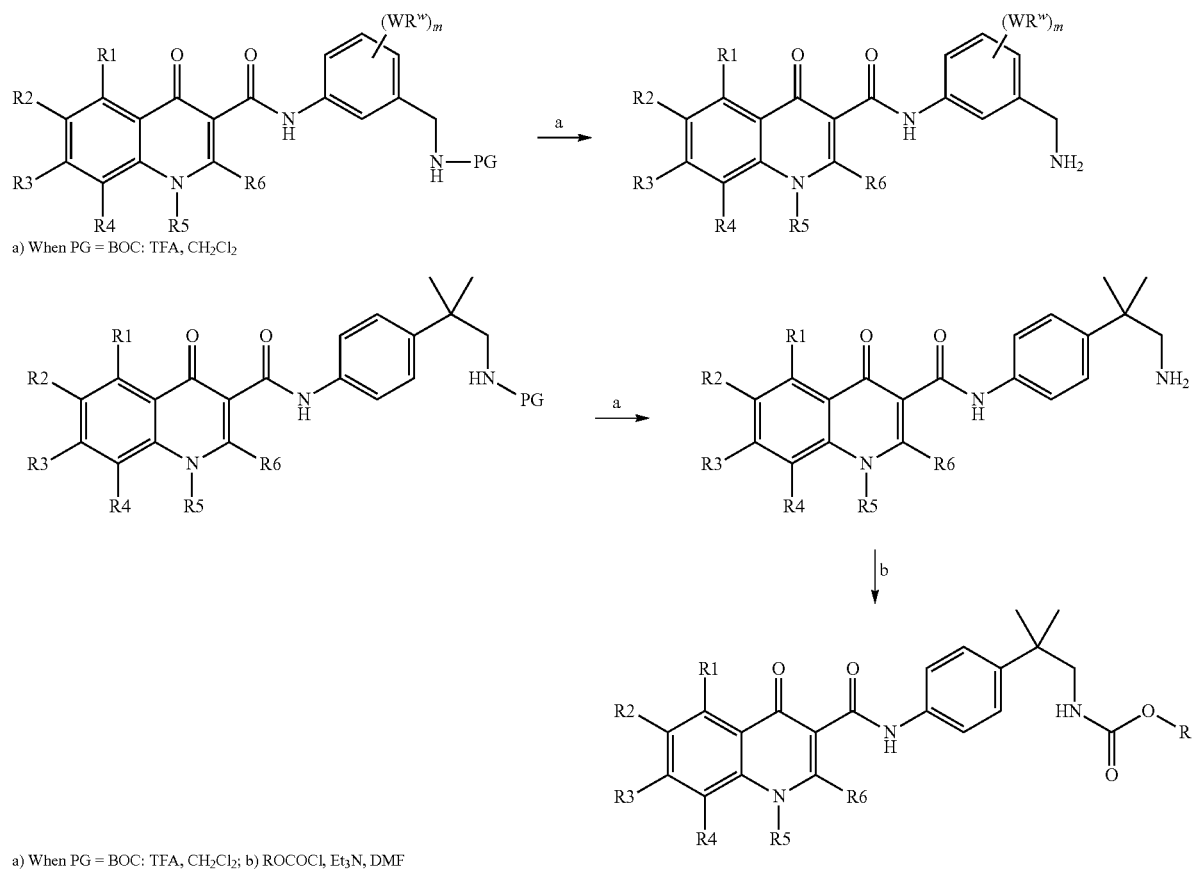

a) When PG = BOC: TFA, CH$_2$Cl$_2$ a) When PG = BOC: TFA, CH$_2$Cl$_2$; b) ROCOCl, Et$_3$N, DMF Synthesis of Compounds of Formula V-A-4:

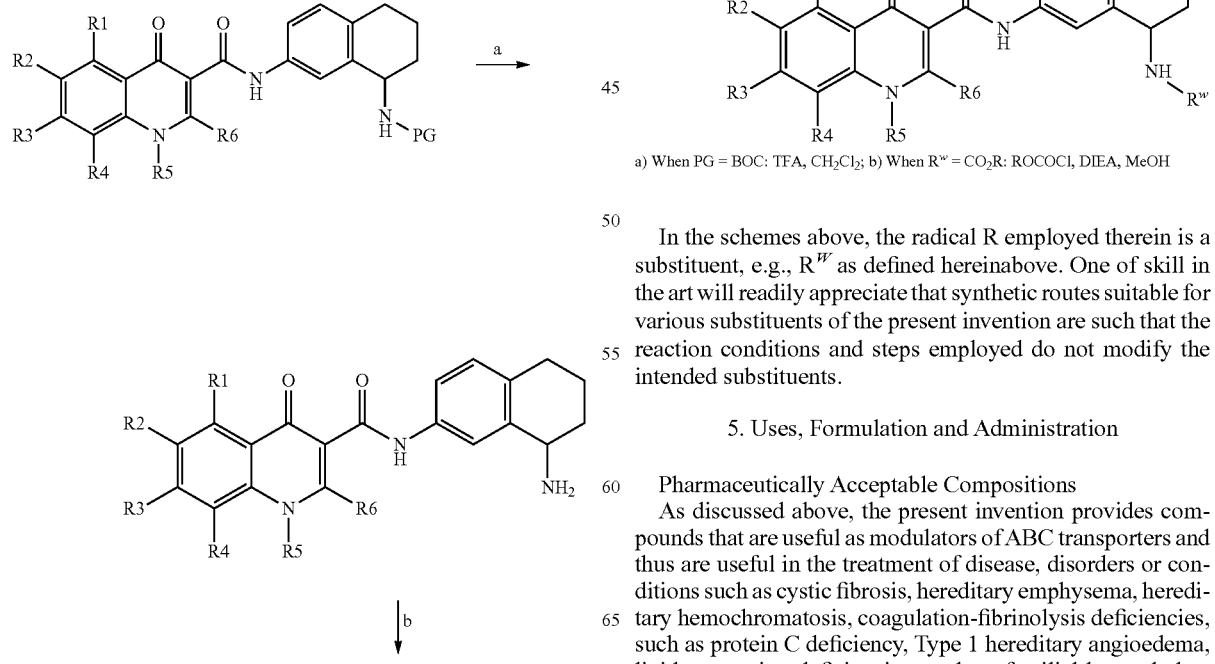

a) When PG = BOC: TFA, CH$_2$Cl$_2$; b) When R$^w$ = CO$_2$R: ROCOCl, DIEA, MeOH In the schemes above, the radical R employed therein is a substituent, e.g., R$^W$ as defined hereinabove. One of skill in the art will readily appreciate that synthetic routes suitable for various substituents of the present invention are such that the reaction conditions and steps employed do not modify the intended substituents.

5. Uses, Formulation and Administration

Pharmaceutically Acceptable Compositions

As discussed above, the present invention provides compounds that are useful as modulators of ABC transporters and thus are useful in the treatment of disease, disorders or conditions such as cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity, e.g., CFTR. In certain embodiments, the present invention provides a method of treating a condition, disease, or disorder implicated by a deficiency of the ABC transporter activity, the method comprising administering a composition comprising a compound of formula (I) to a subject, preferably a mammal, in need thereof.

In certain embodiments, the present invention provides a method of treating cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, comprising the step of administering to said mammal an effective amount of a composition comprising a compound of the present invention.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

The compounds and compositions, according to the method of the present invention, may be administered using any amount and any route of administration effective for treating or lessening the severity of one or more of cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

In one embodiment, the compounds and compositions of the present invention are useful for treating or lessening the severity of cystic fibrosis in a patient.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator*

*Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, 0 absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity, e.g., CFTR, in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I) or any of the above embodiments; and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Example 1

General Scheme to Prepare Acid Moities

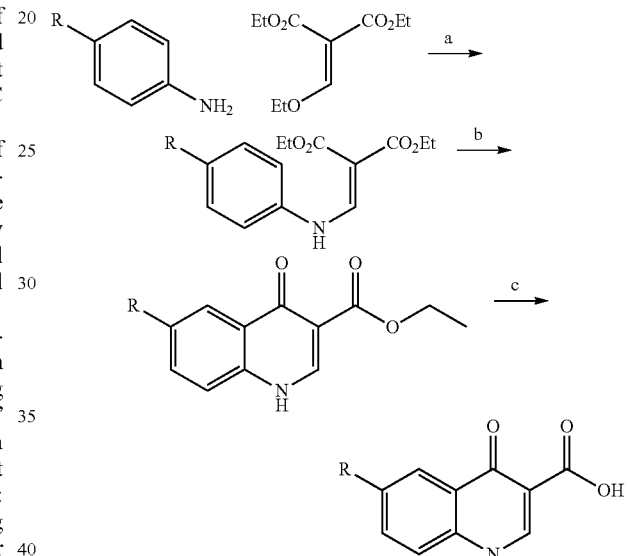

a) 140-150° C.; b) PPA, POCl$_3$, 70° C. or diphenyl ether, 220° C.; c) i) 2N NaOH ii) 2N HCl Specific Example 2-Phenylaminomethylene-malonic acid diethyl ester

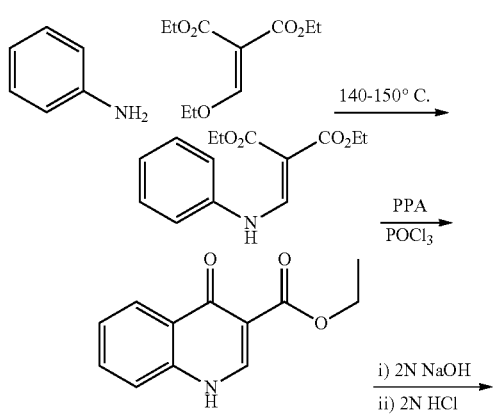

-continued

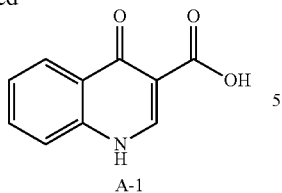

A-1

A mixture of aniline (25.6 g, 0.28 mol) and diethyl 2-(ethoxymethylene)malonate (62.4 g, 0.29 mol) was heated at 140-150° C. for 2 h. The mixture was cooled to room temperature and dried under reduced pressure to afford 2-phenylaminomethylene-malonic acid diethyl ester as a solid, which was used in the next step without further purification. $^1$H NMR (d-DMSO) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.1 mol), polyphosphoric acid (270 g) and phosphoryl chloride (750 g). The mixture was heated to about 70° C. and stirred for 4 h. The mixture was cooled to room temperature, and filtered. The residue was treated with aqueous $Na_2CO_3$ solution, filtered, washed with water and dried. 4-Hydroxyquinoline-3-carboxylic acid ethyl ester was obtained as a pale brown solid (15.2 g, 70%). The crude product was used in next step without further purification.

A-1; 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h under reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid (A-1) as a pale white solid (10.5 g, 92%). $^1$H NMR (d-DMSO) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Specific Example

A-2; 6-Fluoro-4-hydroxy-quinoline-3-carboxylic acid

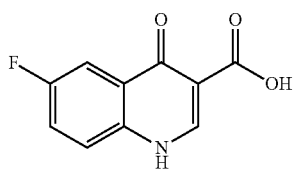 [SMILES: O=C(O)c1c[nH]c2ccc(F)cc2c1=O]

6-Fluoro-4-hydroxy-quinoline-3-carboxylic acid (A-2) was synthesized following the general scheme above starting from 4-fluoro-phenylamine. Overall yield (53%). $^1$H NMR (DMSO-d$_6$) δ 15.2 (br s, 1H), 8.89 (s, 1H), 7.93-7.85 (m, 2H), 7.80-7.74 (m, 1H); ESI-MS 207.9 m/z (MH$^+$).

Example 2

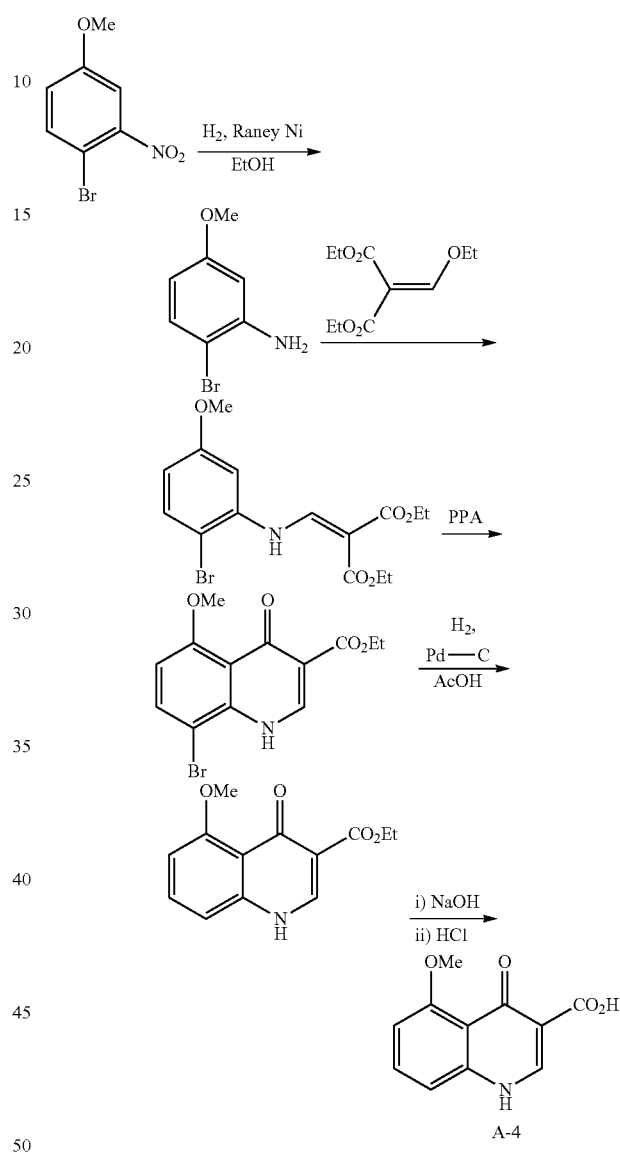

2-Bromo-5-methoxy-phenylamine

A mixture of 1-bromo-4-methoxy-2-nitro-benzene (10 g, 43 mmol) and Raney Ni (5 g) in ethanol (100 mL) was stirred under $H_2$ (1 atm) for 4 h at room temperature. Raney Ni was filtered off and the filtrate was concentrated under reduced pressure. The resulting solid was purified by column chromatography to give 2-bromo-5-methoxy-phenylamine (7.5 g, 86%).

2-[(2-Bromo-5-methoxy-phenylamino)-methylene]-malonic acid diethyl ester

A mixture of 2-bromo-5-methoxy-phenylamine (540 mg, 2.64 mmol) and diethyl 2-(ethoxymethylene)malonate (600 mg, 2.7 mmol) was stirred at 100° C. for 2 h. After cooling, the reaction mixture was recrystallized from methanol (10 mL) to give 2-[(2-bromo-5-methoxy-phenylamino)-methylene]-malonic acid diethyl ester as a yellow solid (0.8 g, 81%).

8-Bromo-5-methoxy-4-oxo-1,4-dihydro-quinoline-3-carboxylic acid ethyl ester

2-[(2-Bromo-5-methoxy-phenylamino)-methylene]-malonic acid diethyl ester (9 g, 24.2 mmol) was slowly added to polyphosphoric acid (30 g) at 120° C. The mixture was stirred at this temperature for additional 30 min and then cooled to room temperature. Absolute ethanol (30 mL) was added and the resulting mixture was refluxed for 30 min. The mixture was basified with aqueous sodium bicarbonate at 25° C. and extracted with EtOAc (4×100 mL). The organic layers were combined, dried and the solvent evaporated to give 8-bromo-5-methoxy-4-oxo-1,4-dihydro-quinoline-3-carboxylic acid ethyl ester (2.3 g, 30%).

5-Methoxy-4-oxo-1,4-dihydro-quinoline-3-carboxylic acid ethyl ester

A mixture of 8-bromo-5-methoxy-4-oxo-1,4-dihydro-quinoline-3-carboxylic acid ethyl ester (2.3 g, 7.1 mmol), sodium acetate (580 mg, 7.1 mmol) and 10% Pd/C (100 mg) in glacial acetic acid (50 ml) was stirred under H$_2$ (2.5 atm) overnight. The catalyst was removed via filtration, and the reaction mixture was concentrated under reduced pressure. The resulting oil was dissolved in CH$_2$Cl$_2$ (100 mL) and washed with aqueous sodium bicarbonate solution and water. The organic layer was dried, filtered and concentrated. The crude product was purified by column chromatography to afford 5-methoxy-4-oxo-1,4-dihydro-quinoline-3-carboxylic acid ethyl ester as a yellow solid (1 g, 57%).

A-4; 5-Methoxy-4-oxo-1,4-dihydro-quinoline-3-carboxylic acid

A mixture of 5-methoxy-4-oxo-1,4-dihydro-quinoline-3-carboxylic acid ethyl ester (1 g, 7.1 mmol) in 10% NaOH solution (50 mL) was heated to reflux overnight and then cooled to room temperature. The mixture was extracted with ether. The aqueous phase was separated and acidified with conc. HCl solution to pH 1-2. The resulting precipitate was collected by filtration to give 5-methoxy-4-oxo-1,4-dihydro-quinoline-3-carboxylic acid (A-4) (530 mg, 52%). $^1$H NMR (DMSO) δ: 15.9 (s, 1H), 13.2 (br, 1H), 8.71 (s, 1H), 7.71 (t, J=8.1 Hz, 1H), 7.18 (d, J=8.4 Hz, 1H), 6.82 (d, J=8.4 Hz, 1H), 3.86 (s, 3H); ESI-MS 219.9 m/z (MH$^+$).

Example 3

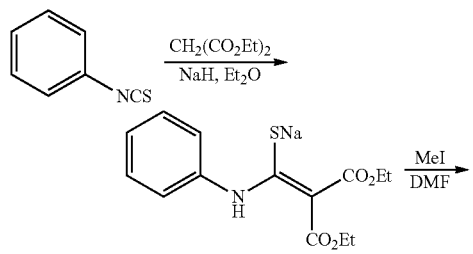

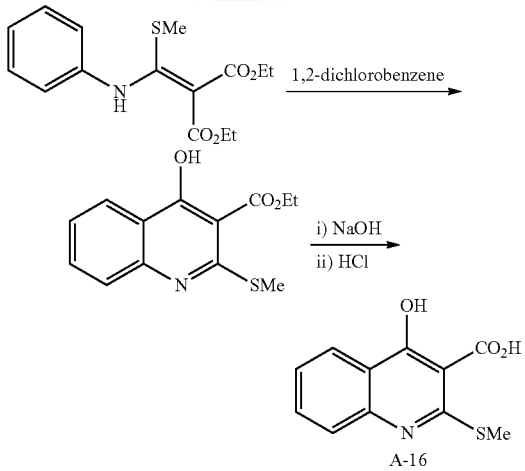

Sodium 2-(mercapto-phenylamino-methylene)-malonic acid diethyl ester

To a suspension of NaH (60% in mineral oil, 6 g, 0.15 mol) in Et$_2$O at room temperature was added dropwise, over a 30 minutes period, ethyl malonate (24 g, 0.15 mol). Phenyl isothiocyanate (20.3 g, 0.15 mol) was then added dropwise with stifling over 30 min. The mixture was refluxed for 1 h and then stirred overnight at room temperature. The solid was separated, washed with anhydrous ether (200 mL), and dried under vacuum to yield sodium 2-(mercapto-phenylamino-methylene)-malonic acid diethyl ester as a pale yellow powder (46 g, 97%).

2-(Methylsulfanyl-phenylamino-methylene)-malonic acid diethyl ester

Over a 30 min period, methyl iodide (17.7 g, 125 mmol) was added dropwise to a solution of sodium 2-(mercapto-phenylamino-methylene)-malonic acid diethyl ester (33 g, 104 mmol) in DMF (100 mL) cooled in an ice bath. The mixture was stirred at room temperature for 1 h, and then poured into ice water (300 mL). The resulting solid was collected via filtration, washed with water and dried to give 2-(methylsulfanyl-phenylamino-methylene)-malonic acid diethyl ester as a pale yellow solid (27 g, 84%).

4-Hydroxy-2-methylsulfanyl-quinoline-3-carboxylic acid ethyl ester

A mixture of 2-(methylsulfanyl-phenylamino-methylene)-malonic acid diethyl ester (27 g, 87 mmol) in 1,2-dichlorobenzene (100 mL) was heated to reflux for 1.5 h. The solvent was removed under reduced pressure and the oily residue was triturated with hexane to afford a pale yellow solid that was purified by preparative HPLC to yield 4-hydroxy-2-methylsulfanyl-quinoline-3-carboxylic acid ethyl ester (8 g, 35%).

A-16; 2-Methylsulfanyl-4-oxo-1,4-dihydro-quinoline-3-carboxylic acid

4-Hydroxy-2-methylsulfanyl-quinoline-3-carboxylic acid ethyl ester (8 g, 30 mmol) was heated under reflux in NaOH solution (10%, 100 mL) for 1.5 h. After cooling, the mixture was acidified with concentrated HCl to pH 4. The resulting solid was collected via filtration, washed with water (100 mL) and MeOH (100 mL) to give 2-methylsulfanyl-4-oxo-1,4-dihydro-quinoline-3-carboxylic acid (A-16) as a white solid (6 g, 85%). $^1$H NMR (CDCl$_3$) δ 16.4 (br s, 1H), 11.1 (br s, 1H), 8.19 (d, J=8 Hz, 1H), 8.05 (d, J=8 Hz, 1H), 7.84 (t, J=8, 8 Hz, 1H), 7.52 (t, J=8 Hz, 1H), 2.74 (s, 3H); ESI-MS 235.9 m/z (MH$^+$).

Example 4

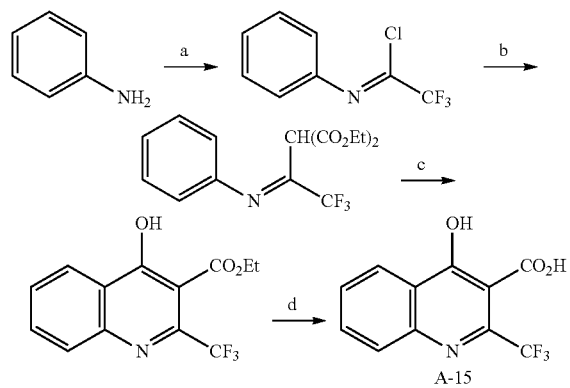

a) PPh$_3$, Et$_3$N, CCl$_4$, CF$_3$CO$_2$H; b) diethyl malonate; c) T~ 200° C.; d) 10% NaOH 2,2,2-Trifluoro-N-phenyl-acetimidoyl chloride A mixture of Ph$_3$P (138.0 g, 526 mmol), Et$_3$N (21.3 g, 211 mmol), CCl$_4$ (170 mL) and TFA (20 g, 175 mmol) was stirred for 10 min in an ice-bath. Aniline (19.6 g, 211 mmol) was dissolved in CCl$_4$ (20 mL) was added. The mixture was stirred at reflux for 3 h. The solvent was removed under vacuum and hexane was added. The precipitates (Ph$_3$PO and Ph$_3$P) were filtered off and washed with hexane. The filtrate was distilled under reduced pressure to yield 2,2,2-trifluoro-N-phenyl-acetimidoyl chloride (19 g), which was used in the next step without further purification.

2-(2,2,2-Trifluoro-1-phenylimino-ethyl)-malonic acid diethyl ester

To a suspension of NaH (3.47 g, 145 mmol, 60% in mineral oil) in THF (200 mL) was added diethyl malonate (18.5 g, 116 mmol) at 0° C. The mixture was stirred for 30 min at this temperature and 2,2,2-trifluoro-N-phenyl-acetimidoyl chloride (19 g, 92 mmol) was added at 0° C. The reaction mixture was allowed to warm to room temperature and stirred overnight. The mixture was diluted with CH$_2$Cl$_2$, washed with saturated sodium bicarbonate solution and brine. The combined organic layers were dried over Na$_2$SO$_4$, filtered and concentrated to provide 2-(2,2,2-trifluoro-1-phenylimino-ethyl)-malonic acid diethyl ester, which was used directly in the next step without further purification.

4-Hydroxy-2-trifluoromethyl-quinoline-3-carboxylic acid ethyl ester 2-(2,2,2-Trifluoro-1-phenylimino-ethyl)-malonic acid diethyl ester was heated at 210° C. for 1 h with continuous stirring. The mixture was purified by column chromatography (petroleum ether) to yield 4-hydroxy-2-trifluoromethyl-quinoline-3-carboxylic acid ethyl ester (12 g, 24% over 3 steps).

A-15; 4-Hydroxy-2-trifluoromethyl-quinoline-3-carboxylic acid

A suspension of 4-hydroxy-2-trifluoromethyl-quinoline-3-carboxylic acid ethyl ester (5 g, 17.5 mmol) in 10% aqueous NaOH solution was heated at reflux for 2 h. After cooling, dichloromethane was added and the aqueous phase was separated and acidified with concentrated HCl to pH 4. The resulting precipitate was collected via filtration, washed with water and Et$_2$O to provide 4-hydroxy-2-trifluoromethyl-quinoline-3-carboxylic acid (A-15) (3.6 g, 80%). $^1$H NMR (DMSO-d$_6$) δ 8.18-8.21 (d, J=7.8 Hz, 1H), 7.92-7.94 (d, J=8.4 Hz, 1H), 7.79-7.83 (t, J=14.4 Hz, 1H), 7.50-7.53 (t, J=15 Hz, 1H); ESI-MS 257.0 m/z (MH$^+$).

Example 5

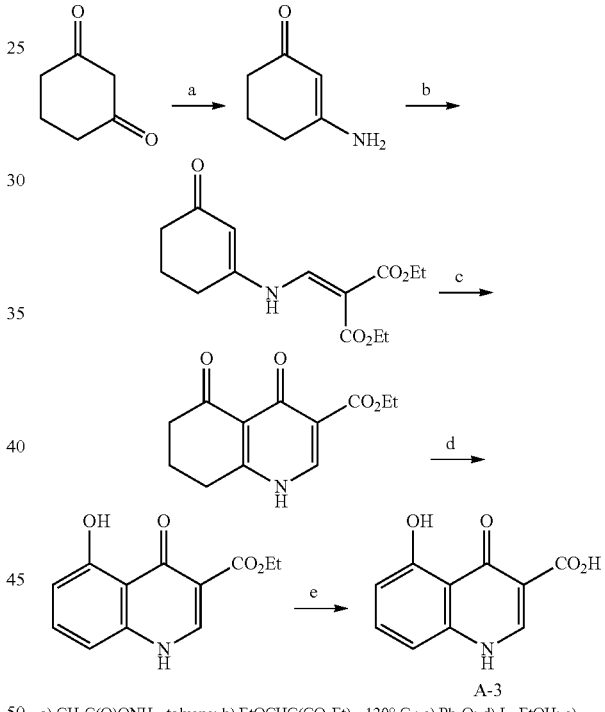

a) CH$_3$C(O)ONH$_4$, toluene; b) EtOCHC(CO$_2$Et)$_2$, 130° C.; c) Ph$_2$O; d) I$_2$, EtOH; e) NaOH 3-Amino-cyclohex-2-enone A mixture of cyclohexane-1,3-dione (56.1 g, 0.5 mol) and AcONH$_4$ (38.5 g, 0.5 mol) in toluene was heated at reflux for 5 h with a Dean-stark apparatus. The resulting oily layer was separated and concentrated under reduced pressure to give 3-amino-cyclohex-2-enone (49.9 g, 90%), which was used directly in the next step without further purification.

2-[(3-Oxo-cyclohex-1-enylamino)-methylene]-malonic acid diethyl ester

A mixture of 3-amino-cyclohex-2-enone (3.3 g, 29.7 mmol) and diethyl 2-(ethoxymethylene)malonate (6.7 g, 31.2 mmol) was stirred at 130° C. for 4 h. The reaction mixture was concentrated under reduced pressure and the resulting oil was purified by column chromatography (silica gel, ethyl acetate) to give 2-[(3-oxo-cyclohex-1-enylamino)-methylene]-malonic acid diethyl ester (7.5 g, 90%).

4,5-Dioxo-1,4,5,6,7,8-hexahydro-quinoline-3-carboxylic acid ethyl ester

A mixture of 2-[(3-oxo-cyclohex-1-enylamino)-methylene]-malonic acid diethyl ester (2.8 g, 1 mmol) and diphenylether (20 mL) was refluxed for 15 min. After cooling, n-hexane (80 mL) was added. The resulting solid was isolated via filtration and recrystallized from methanol to give 4,5-dioxo-1,4,5,6,7,8-hexahydro-quinoline-3-carboxylic acid ethyl ester (1.7 g 72%).

5-Hydroxy-4-oxo-1,4-dihydro-quinoline-3-carboxylic acid ethyl ester

To a solution of 4,5-dioxo-1,4,5,6,7,8-hexahydro-quinoline-3-carboxylic acid ethyl ester (1.6 g, 6.8 mmol) in ethanol (100 mL) was added iodine (4.8 g, 19 mmol). The mixture was refluxed for 19 h and then concentrated under reduced pressure. The resulting solid was washed with ethyl acetate, water and acetone, and then recrystallized from DMF to give 5-hydroxy-4-oxo-1,4-dihydro-quinoline-3-carboxylic acid ethyl ester (700 mg, 43%).

A-3;
5-Hydroxy-4-oxo-1,4-dihydro-quinoline-3-carboxylic acid

A mixture of 5-hydroxy-4-oxo-1,4-dihydro-quinoline-3-carboxylic acid ethyl ester (700 mg, 3 mmol) in 10% NaOH (20 ml) was heated at reflux overnight. After cooling, the mixture was extracted with ether. The aqueous phase was separated and acidified with conc. HCl to pH 1-2. The resulting precipitate was collected via filtration to give 5-hydroxy-4-oxo-1,4-dihydro-quinoline-3-carboxylic acid (A-3) (540 mg, 87%). $^1$H NMR (DMSO-d$_6$) δ 13.7 (br, 1H), 13.5 (br, 1H), 12.6 (s, 1H), 8.82 (s, 1H), 7.68 (t, J=8.1 Hz, 1H), 7.18 (d, J=8.4 Hz, 1H), 6.82 (d, J=8.4 Hz, 1H); ESI-MS 205.9 m/z (MH$^+$).

Example 6

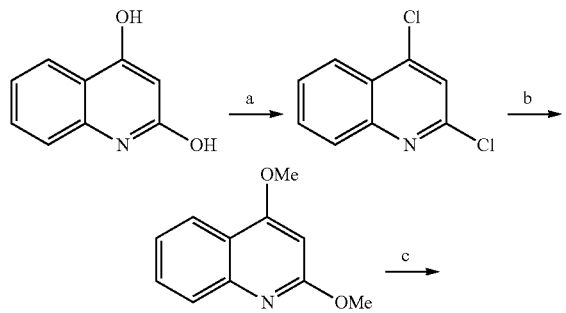

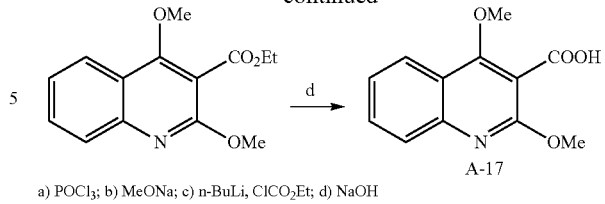

a) POCl$_3$; b) MeONa; c) n-BuLi, ClCO$_2$Et; d) NaOH 2,4-Dichloroquinoline

A suspension of quinoline-2,4-diol (15 g, 92.6 mmol) in POCl$_3$ was heated at reflux for 2 h. After cooling, the solvent was removed under reduced pressure to yield 2,4-dichloroquinoline, which was used without further purification.

2,4-Dimethoxyquinoline

To a suspension of 2,4-dichloroquinoline in MeOH (100 mL) was added sodium methoxide (50 g). The mixture was heated at reflux for 2 days. After cooling, the mixture was filtered. The filtrate was concentrated under reduced pressure to yield a residue that was dissolved in water and extracted with CH$_2$Cl$_2$. The combined organic layers were dried over Na$_2$SO$_4$ and concentrated to give 2,4-dimethoxyquinoline as a white solid (13 g, 74% over 2 steps).

Ethyl 2,4-dimethoxyquinoline-3-carboxylate

To a solution of 2,4-dimethoxyquinoline (11.5 g, 60.8 mmol) in anhydrous THF was added dropwise n-BuLi (2.5 M in hexane, 48.6 mL, 122 mmol) at 0° C. After stirring for 1.5 h at 0° C., the mixture was added to a solution of ethyl chloroformate in anhydrous THF and stirred at 0° C. for additional 30 min and then at room temperature overnight. The reaction mixture was poured into water and extracted with CH$_2$Cl$_2$. The organic layer was dried over Na$_2$SO$_4$ and concentrated under vacuum. The resulting residue was purified by column chromatography (petroleum ether/EtOAc=50/1) to give ethyl 2,4-dimethoxyquinoline-3-carboxylate (9.6 g, 60%).

A-17; 2,4-Dimethoxyquinoline-3-carboxylic acid

Ethyl 2,4-dimethoxyquinoline-3-carboxylate (1.5 g, 5.7 mmol) was heated at reflux in NaOH solution (10%, 100 mL) for 1 h. After cooling, the mixture was acidified with concentrated HCl to pH 4. The resulting precipitate was collected via filtration and washed with water and ether to give 2,4-dimethoxyquinoline-3-carboxylic acid (A-17) as a white solid (670 mg, 50%). $^1$H NMR (CDCl$_3$) δ 8.01-8.04 (d, J=12 Hz, 1H), 7.66-7.76 (m, 2H), 7.42-7.47 (t, J=22 Hz, 2H), 4.09 (s, 3H). 3.97 (s, 3H); ESI-MS 234.1 m/z (MH$^+$).

Commercially Available Acids

| Acid | Name |
|---|---|
| A-5 | 6,8-Difluoro-4-oxo-1,4-dihydro-quinoline-3-carboxylic acid |
| A-6 | 6-[(4-Fluoro-phenyl)-methyl-sulfamoyl]-4-oxo-1,4-dihydro-quinoline-3-carboxylic acid |
| A-7 | 6-(4-Methyl-piperidine-1-sulfonyl)-4-oxo-1,4-dihydro-quinoline-3-carboxylic acid |
| A-8 | 4-Oxo-6-(pyrrolidine-1-sulfonyl)-1,4-dihydro-quinoline-3-carboxylic acid |

-continued

| Acid | Name |
|---|---|
| A-10 | 6-Ethyl-4-oxo-1,4-dihydro-quinoline-3-carboxylic acid |
| A-11 | 6-Ethoxy-4-oxo-1,4-dihydro-quinoline-3-carboxylic acid |
| A-12 | 4-Oxo-7-trifluoromethyl-1,4-dihydro-quinoline-3-carboxylic acid |
| A-13 | 7-Chloro-4-oxo-1,4-dihydro-quinoline-3-carboxylic acid |
| A-14 | 4-Oxo-5,7-bis-trifluoromethyl-1,4-dihydro-quinoline-3-carboxylic acid |
| A-20 | 1-Methyl-4-oxo-1,4-dihydro-quinoline-3-carboxylic acid |
| A-21 | 1-Isopropyl-4-oxo-1,4-dihydro-quinoline-3-carboxylic acid |
| A-22 | 1,6-Dimethyl-4-oxo-1,4-dihydro-quinoline-3-carboxylic acid |
| A-23 | 1-Ethyl-6-methoxy-4-oxo-1,4-dihydro-quinoline-3-carboxylic acid |
| A-24 | 6-Chloro-4-oxo-1,4-dihydro-quinoline-3-carboxylic acid |

Amine Moieties

N-1 Substituted 6-aminoindoles

Example 1

General Scheme:

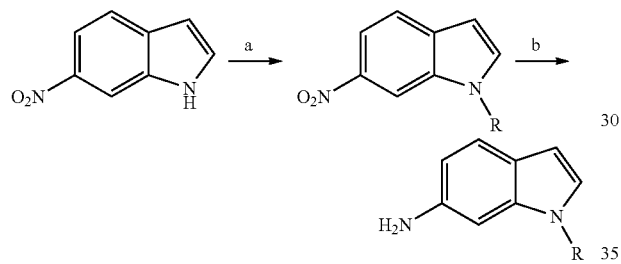

a) RX (X = Cl, Br, I), $K_2CO_3$, DMF or $CH_3CN$; b) $H_2$, Pd—C, EtOH or $SnCl_2 \cdot 2H_2O$, EtOH.

Specific Example

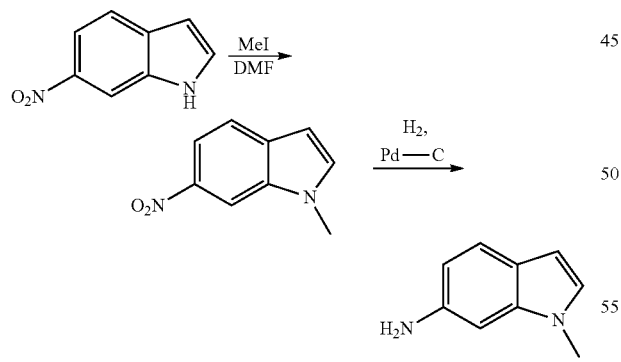

1-Methyl-6-nitro-1H-indole

To a solution of 6-nitroindole (4.05 g 25 mmol) in DMF (50 mL) was added $K_2CO_3$ (8.63 g, 62.5 mmol) and MeI (5.33 g, 37.5 mmol). After stifling at room temperature overnight, the mixture was poured into water and extracted with ethyl acetate. The combined organic layers were dried over $Na_2SO_4$ and concentrated under vacuum to give the product 1-methyl-6-nitro-1H-indole (4.3 g, 98%).

B-1; 1-Methyl-1H-indol-6-ylamine

A suspension of 1-methyl-6-nitro-1H-indole (4.3 g, 24.4 mmol) and 10% Pd—C (0.43 g) in EtOH (50 mL) was stirred under $H_2$ (1 atm) at room temperature overnight. After filtration, the filtrate was concentrated and acidified with HCl-MeOH (4 mol/L) to give 1-methyl-1H-indol-6-ylamine hydrochloride salt (B-1) (1.74 g, 49%) as a grey powder. $^1$H NMR (DMSO-$d_6$): δ 9.10 (s, 2H), 7.49 (d, J=8.4 Hz, 1H), 7.28 (d, J=2.0 Hz, 1H), 7.15 (s, 1H), 6.84 (d, J=8.4 Hz, 1H), 6.38 (d, J=2.8 Hz, 1H), 3.72 (s, 3H); ESI-MS 146.08 m/z (MH$^+$).

Other Examples

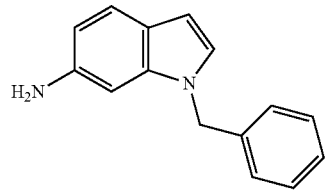 [SMILES: Nc1ccc2ccn(Cc3ccccc3)c2c1]

B-2; 1-Benzyl-1H-indol-6-ylamine

1-Benzyl-1H-indol-6-ylamine (B-2) was synthesized following the general scheme above starting from 6-nitroindole and benzyl bromide. Overall yield (~40%). HPLC ret. time 2.19 min, 10-99% $CH_3CN$, 5 min run; ESI-MS 223.3 m/z (MH$^+$).

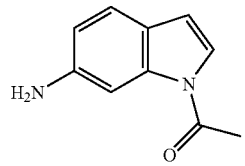

B-3; 1-(6-Amino-indol-1-yl)-ethanone 1-(6-Amino-indol-1-yl)-ethanone (B-3) was synthesized following the general scheme above starting from 6-nitroindole and acetyl chloride. Overall yield (~40%). HPLC ret. time 0.54 min, 10-99% $CH_3CN$, 5 min run; ESI-MS 175.1 m/z (MH+).

Example 2

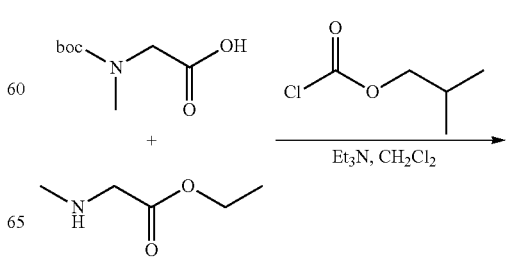

111

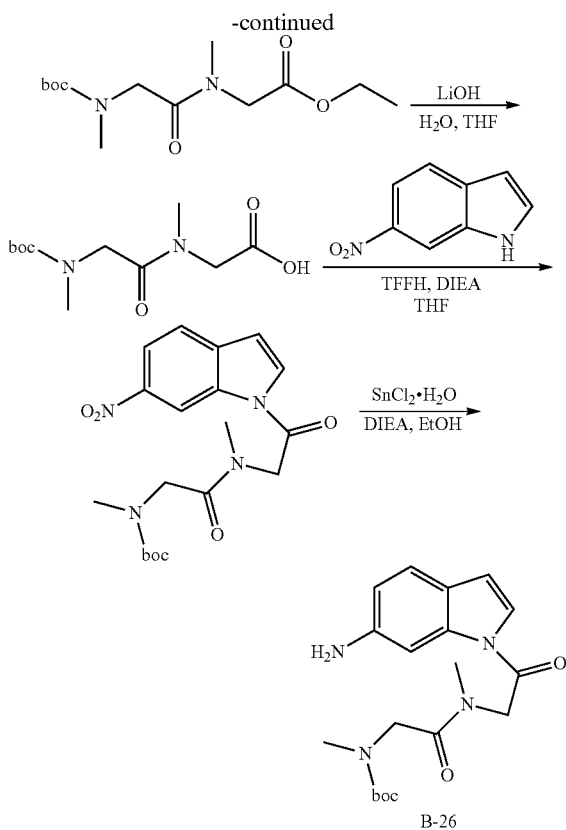

B-26

{[2-(tert-Butoxycarbonyl-methyl-amino)-acetyl]-methyl-amino}-acetic acid ethyl ester To a stirred solution of (tert-butoxycarbonyl-methyl-amino)-acetic acid (37 g, 0.2 mol) and Et$_3$N (60.6 g, 0.6 mol) in CH$_2$Cl$_2$ (300 mL) was added isobutyl chloroformate (27.3 g, 0.2 mmol) dropwise at −20° C. under argon. After stirring for 0.5 h, methylamino-acetic acid ethyl ester hydrochloride (30.5 g, 129 mmol) was added dropwise at −20° C. The mixture was allowed to warm to room temperature (c.a. 1 h) and quenched with water (500 mL). The organic layer was separated, washed with 10% citric acid solution, dried over Na$_2$SO$_4$, filtered and concentrated. The residue was purified by column chromatography (petroleum ether/EtOAc 1:1) to give {[2-(tert-butoxycarbonyl-methyl-amino)-acetyl]-methyl-amino}-acetic acid ethyl ester (12.5 g, 22%).

{[2-(tert-Butoxycarbonyl-methyl-amino)-acetyl]-methyl-amino}-acetic acid

A suspension of {[2-(tert-butoxycarbonyl-methyl-amino)-acetyl]-methyl-amino}-acetic acid ethyl ester (12.3 g, 42.7 mmol) and LiOH (8.9 g, 214 mmol) in H$_2$O (20 mL) and THF (100 mL) was stirred overnight. Volatile solvent was removed under vacuum and the residue was extracted with ether (2×100 mL). The aqueous phase was acidified to pH 3 with dilute HCl solution, and then extracted with CH$_2$Cl$_2$ (2×300 mL). The combined organic layers were washed with brine, dried over Na$_2$SO$_4$ and concentrated under vacuum to give {[2-(tert-butoxycarbonyl-methyl-amino)-acetyl]-methyl-amino}-acetic acid as a colorless oil (10 g, 90%). $^1$H NMR (CDCl$_3$) δ7.17 (br s, 1H), 4.14-4.04 (m, 4H), 3.04-2.88 (m, 6H), 1.45-1.41 (m, 9H); ESI-MS 282.9 m/z (M+Na$^+$).

112

Methyl-({methyl-[2-(6-nitro-indol-1-yl)-2-oxo-ethyl]-carbamoyl}-methyl)-carbamic acid tert-butyl ester To a mixture of {[2-(tert-butoxycarbonyl-methyl-amino)-acetyl]-methyl-amino}-acetic acid (13.8 g, 53 mmol) and TFFH (21.0 g, 79.5 mmol) in anhydrous THF (125 mL) was added DIEA (27.7 mL, 159 mmol) at room temperature under nitrogen. The solution was stirred at room temperature for 20 min. A solution of 6-nitroindole (8.6 g, 53 mmol) in THF (75 mL) was added and the reaction mixture was heated at 60° C. for 18 h. The solvent was evaporated and the crude mixture was re-partitioned between EtOAc and water. The organic layer was separated, washed with water (×3), dried over Na$_2$SO$_4$ and concentrated. Diethyl ether followed by EtOAc was added. The resulting solid was collected via filtration, washed with diethyl ether and air dried to yield methyl-({methyl-[2-(6-nitro-indol-1-yl)-2-oxo-ethyl]-carbamoyl}-methyl)-carbamic acid tert-butyl ester (6.42 g, 30%). $^1$H NMR (400 MHz, DMSO-d6) δ 1.37 (m, 9H), 2.78 (m, 3H), 2.95 (d, J=1.5 Hz, 1H), 3.12 (d, J=2.1 Hz, 2H), 4.01 (d, J=13.8 Hz, 0.6H), 4.18 (d, J=12.0 Hz, 1.4H), 4.92 (d, J=3.4 Hz, 1.4H), 5.08 (d, J=11.4 Hz, 0.6H), 7.03 (m, 1H), 7.90 (m, 1H), 8.21 (m, 1H), 8.35 (d, J=3.8 Hz, 1H), 9.18 (m, 1H); HPLC ret. time 3.12 min, 10-99% CH$_3$CN, 5 min run; ESI-MS 405.5 m/z (MH$^+$).

B-26; ({[2-(6-Amino-indol-1-yl)-2-oxo-ethyl]-methyl-carbamoyl}-methyl)-methyl-carbamic acid tert-butyl ester A mixture of methyl-({methyl-[2-(6-nitro-indol-1-yl)-2-oxo-ethyl]-carbamoyl}-methyl)-carbamic acid tert-butyl ester (12.4 g, 30.6 mmol), SnCl$_2$.2H$_2$O (34.5 g, 153.2 mmol) and DIEA (74.8 mL, 429 mmol) in ethanol (112 mL) was heated to 70° C. for 3 h. Water and EtOAc were added and the mixture was filtered through a short plug of Celite. The organic layer was separated, dried over Na$_2$SO$_4$ and concentrated to yield ({[2-(6-Amino-indol-1-yl)-2-oxo-ethyl]-methyl-carbamoyl}-methyl)-methyl-carbamic acid tert-butyl ester (B-26) (11.4 g, quant.).
HPLC ret. time 2.11 min, 10-99% CH$_3$CN, 5 min run; ESI-MS 375.3 m/z (MH$^+$).

2-Substituted 6-aminoindoles

Example 1

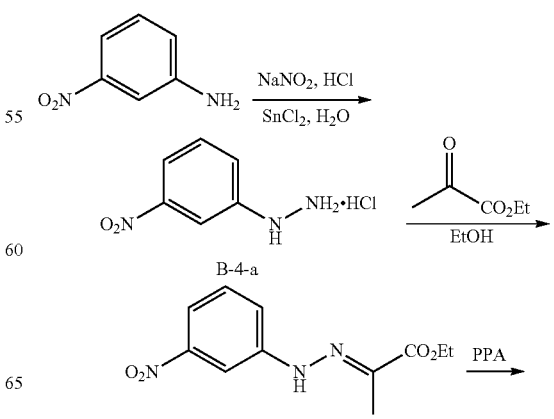

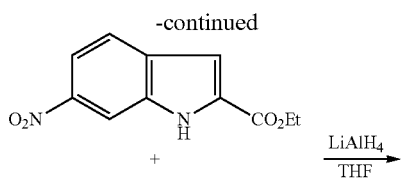

B-4-b

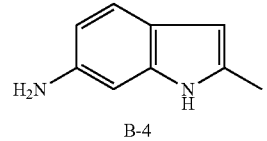

B-4

B-4-a; (3-Nitro-phenyl)-hydrazine hydrochloride salt

3-Nitro-phenylamine (27.6 g, 0.2 mol) was dissolved in a mixture of H₂O (40 mL) and 37% HCl (40 mL). A solution of NaNO₂ (13.8 g, 0.2 mol) in H₂O (60 mL) was added at 0° C., followed by the addition of SnCl₂.H₂O (135.5 g, 0.6 mol) in 37% HCl (100 mL) at that temperature. After stirring at 0° C. for 0.5 h, the solid was isolated via filtration and washed with water to give (3-nitro-phenyl)-hydrazine hydrochloride salt (B-4-a) (27.6 g, 73%).

2-[(3-Nitro-phenyl)-hydrazono]-propionic acid ethyl ester (3-Nitro-phenyl)-hydrazine hydrochloride salt (B-4-a) (30.2 g, 0.16 mol) and 2-oxo-propionic acid ethyl ester (22.3 g, 0.19 mol) was dissolved in ethanol (300 mL). The mixture was stirred at room temperature for 4 h. The solvent was evaporated under reduced pressure to give 2-[(3-nitro-phenyl)-hydrazono]-propionic acid ethyl ester, which was used directly in the next step.

B-4-b; 4-Nitro-1H-indole-2-carboxylic acid ethyl ester and 6-Nitro-1H-indole-2-carboxylic acid ethyl ester 2-[(3-Nitro-phenyl)-hydrazono]-propionic acid ethyl ester from the preceding step was dissolved in toluene (300 mL). PPA (30 g) was added. The mixture was heated at reflux overnight and then cooled to room temperature. The solvent was removed to give a mixture of 4-nitro-1H-indole-2-carboxylic acid ethyl ester and 6-nitro-1H-indole-2-carboxylic acid ethyl ester (B-4-b) (15 g, 40%).

B-4; 2-Methyl-1H-indol-6-ylamine

To a suspension of LiAlH₄ (7.8 g, 0.21 mol) in THF (300 mL) was added dropwise a mixture of 4-nitro-1H-indole-2-carboxylic acid ethyl ester and 6-nitro-1H-indole-2-carboxylic acid ethyl ester (B-4-b) (6 g, 25.7 mmol) in THF (50 mL) at 0° C. under N₂. The mixture was heated at reflux overnight and then cooled to 0° C. H₂O (7.8 mL) and 10% NaOH (7.8 mL) were added to the mixture at 0° C. The insoluble solid was removed via filtration. The filtrate was dried over Na₂SO₄, filtered and concentrated under reduced pressure.

The crude residue was purified by column chromatography to afford 2-methyl-1H-indol-6-ylamine (B-4) (0.3 g, 8%). ¹H NMR (CDCl₃) δ 7.57 (br s, 1H), 7.27 (d, J=8.8 Hz, 1H), 6.62 (s, 1H), 6.51-6.53 (m, 1H), 6.07 (s, 1H), 3.59-3.25 (br s, 2H), 2.37 (s, 3H); ESI-MS 147.2 m/z (MH⁺).

Example 2

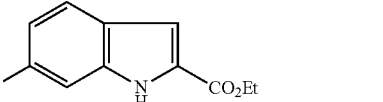

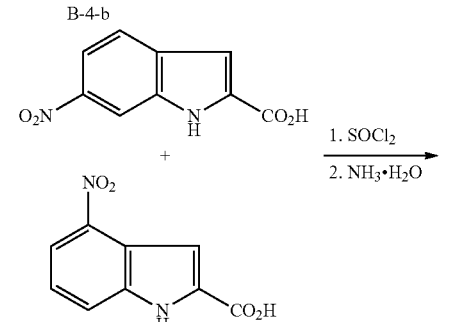

B-5

6-Nitro-1H-indole-2-carboxylic acid and 4-Nitro-1H-indole-2-carboxylic acid

A mixture of 4-nitro-1H-indole-2-carboxylic acid ethyl ester and 6-nitro-1H-indole-2-carboxylic acid ethyl ester (B-4-b) (0.5 g, 2.13 mmol) in 10% NaOH (20 mL) was heated at reflux overnight and then cooled to room temperature. The mixture was extracted with ether. The aqueous phase was separated and acidified with HCl to pH 1-2. The resulting solid was isolated via filtration to give a mixture of 6-nitro-1H-indole-2-carboxylic acid and 4-nitro-1H-indole-2-carboxylic acid (0.3 g, 68%).

6-Nitro-1H-indole-2-carboxylic acid amide and 4-Nitro-1H-indole-2-carboxylic acid amide A mixture of 6-nitro-1H-indole-2-carboxylic acid and 4-nitro-1H-indole-2-carboxylic acid (12 g, 58 mmol) and $SOCl_2$ (50 mL, 64 mmol) in benzene (150 mL) was refluxed for 2 h. The benzene and excessive $SOCl_2$ was removed under reduced pressure. The residue was dissolved in $CH_2Cl_2$ (250 mL). $NH_4OH$ (21.76 g, 0.32 mol) was added dropwise at 0° C. The mixture was stirred at room temperature for 1 h. The resulting solid was isolated via filtration to give a crude mixture of 6-nitro-1H-indole-2-carboxylic acid amide and 4-nitro-1H-indole-2-carboxylic acid amide (9 g, 68%), which was used directly in the next step.

6-Nitro-1H-indole-2-carbonitrile and 4-Nitro-1H-indole-2-carbonitrile

A mixture of 6-nitro-1H-indole-2-carboxylic acid amide and 4-nitro-1H-indole-2-carboxylic acid amide (5 g, 24 mmol) was dissolved in $CH_2Cl_2$ (200 mL). $Et_3N$ (24.24 g, 0.24 mol) was added, followed by the addition of $(CF_3CO)_2O$ (51.24 g, 0.24 mol) at room temperature. The mixture was stirred for 1 h and poured into water (100 mL). The organic layer was separated. The aqueous layer was extracted with EtOAc (100 mL×3). The combined organic layers were dried over $Na_2SO_4$, filtered and concentrated under reduced pressure. The crude residue was purified by column chromatography to give a mixture of 6-nitro-1H-indole-2-carbonitrile and 4-nitro-1H-indole-2-carbonitrile (2.5 g, 55%).

B-5; 6-Amino-1H-indole-2-carbonitrile

A mixture of 6-nitro-1H-indole-2-carbonitrile and 4-nitro-1H-indole-2-carbonitrile (2.5 g, 13.4 mmol) and Raney Ni (500 mg) in EtOH (50 mL) was stirred at room temperature under $H_2$ (1 atm) for 1 h. Raney Ni was filtered off. The filtrate was evaporated under reduced pressure and purified by column chromatography to give 6-amino-1H-indole-2-carbonitrile (B-5) (1 g, 49%).

$^1$H NMR (DMSO-$d_6$) δ 12.75 (br s, 1H), 7.82 (d, J=8 Hz, 1H), 7.57 (s, 1H), 7.42 (s, 1H), 7.15 (d, J=8 Hz, 1H); ESI-MS 158.2 m/z (MH$^+$).

Example 3

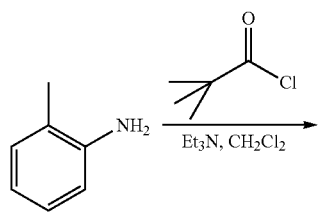

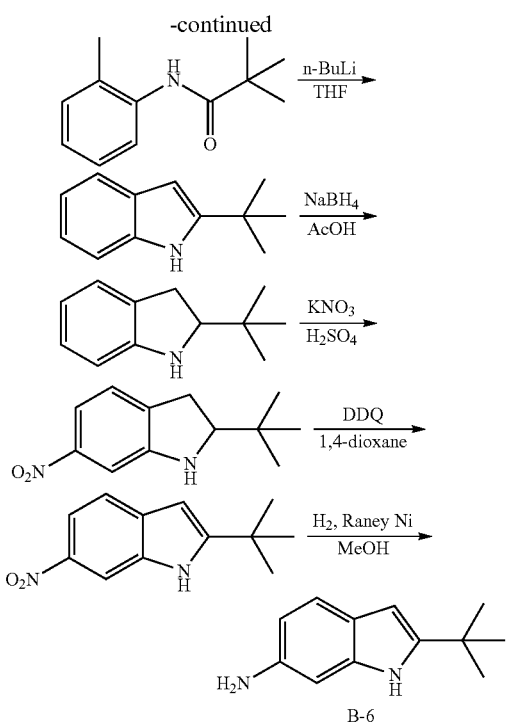

2,2-Dimethyl-N-o-tolyl-propionamide

To a solution of o-tolylamine (21.4 g, 0.20 mol) and $Et_3N$ (22.3 g, 0.22 mol) in $CH_2Cl_2$ was added 2,2-dimethyl-propionyl chloride (25.3 g, 0.21 mol) at 10° C. The mixture was stirred overnight at room temperature, washed with aq. HCl (5%, 80 mL), saturated $NaHCO_3$ solution and brine, dried over $Na_2SO_4$ and concentrated under vacuum to give 2,2-dimethyl-N-o-tolyl-propionamide (35.0 g, 92%).

2-tert-Butyl-1H-indole

To a solution of 2,2-dimethyl-N-o-tolyl-propionamide (30.0 g, 159 mmol) in dry THF (100 mL) was added dropwise n-BuLi (2.5 M, in hexane, 190 mL) at 15° C. The mixture was stirred overnight at 15° C., cooled in an ice-water bath and treated with saturated $NH_4Cl$ solution. The organic layer was separated and the aqueous layer was extracted with ethyl acetate. The combined organic layers were dried over anhydrous $Na_2SO_4$, filtered, and concentrated in vacuum. The residue was purified by column chromatography to give 2-tert-butyl-1H-indole (23.8 g, 88%).

2-tert-Butyl-2,3-dihydro-1H-indole

To a solution of 2-tert-butyl-1H-indole (5.0 g, 29 mmol) in AcOH (20 mL) was added $NaBH_4$ at 10° C. The mixture was stirred for 20 min at 10° C., treated dropwise with $H_2O$ under ice cooling, and extracted with ethyl acetate. The combined organic layers were dried over anhydrous $Na_2SO_4$, filtered, and concentrated under vacuum to give a mixture of starting material and 2-tert-butyl-2,3-dihydro-1H-indole (4.9 g), which was used directly in the next step.

2-tert-Butyl-6-nitro-2,3-dihydro-1H-indole

To a solution of the mixture of 2-tert-butyl-2,3-dihydro-1H-indole and 2-tert-butyl-1H-indole (9.7 g) in $H_2SO_4$ (98%, 80 mL) was slowly added KNO₃ (5.6 g, 55.7 mmol) at 0° C. The reaction mixture was stirred at room temperature for 1 h, carefully poured into cracked ice, basified with Na₂CO₃ to pH-8 and extracted with ethyl acetate. The combined extracts were washed with brine, dried over anhydrous Na₂SO₄ and concentrated under vacuum. The residue was purified by column chromatography to give 2-tert-butyl-6-nitro-2,3-dihydro-1H-indole (4.0 g, 32% over 2 steps).

2-tert-Butyl-6-nitro-1H-indole

To a solution of 2-tert-butyl-6-nitro-2,3-dihydro-1H-indole (2.0 g, 9.1 mmol) in 1,4-dioxane (20 mL) was added DDQ at room temperature. After refluxing for 2.5 h, the mixture was filtered and the filtrate was concentrated under vacuum. The residue was purified by column chromatography to give 2-tert-butyl-6-nitro-1H-indole (1.6 g, 80%).

B-6; 2-tert-Butyl-1H-indol-6-ylamine

To a solution of 2-tert-butyl-6-nitro-1H-indole (1.3 g, 6.0 mmol) in MeOH (10 mL) was added Raney Ni (0.2 g). The mixture was stirred at room temperature under H₂ (1 atm) for 3 h. The reaction mixture was filtered and the filtrate was concentrated. The residue was washed with petroleum ether to give 2-tert-butyl-1H-indol-6-ylamine (B-6) (1.0 g, 89%).
¹H NMR (DMSO-d₆) δ 10.19 (s, 1H), 6.99 (d, J=8.1 Hz, 1H), 6.46 (s, 1H), 6.25 (dd, J=1.8, 8.1 Hz, 1H), 5.79 (d, J=1.8 Hz, 1H), 4.52 (s, 2H), 1.24 (s, 9H); ESI-MS 189.1 m/z (MH⁺).

3-Substituted 6-aminoindoles

Example 1

N-(3-Nitro-phenyl)-N'-propylidene-hydrazine

Sodium hydroxide solution (10%, 15 mL) was added slowly to a stirred suspension of (3-nitro-phenyl)-hydrazine hydrochloride salt (B-4-a) (1.89 g, 10 mmol) in ethanol (20 mL) until pH 6. Acetic acid (5 mL) was added to the mixture followed by propionaldehyde (0.7 g, 12 mmol). After stifling for 3 h at room temperature, the mixture was poured into ice-water and the resulting precipitate was isolated via filtration, washed with water and dried in air to obtain N-(3-nitrophenyl)-N'-propylidene-hydrazine, which was used directly in the next step.

3-Methyl-4-nitro-1H-indole and 3-Methyl-6-nitro-1H-indole

A mixture of N-(3-nitro-phenyl)-N'-propylidene-hydrazine dissolved in 85% H₃PO₄ (20 mL) and toluene (20 mL) was heated at 90-100° C. for 2 h. After cooling, toluene was removed under reduced pressure. The resultant oil was basified with 10% NaOH to pH 8. The aqueous layer was extracted with EtOAc (100 mL×3). The combined organic layers were dried, filtered and concentrated under reduced pressure to afford a mixture of 3-methyl-4-nitro-1H-indole and 3-methyl-6-nitro-1H-indole (1.5 g, 86% over two steps), which was used directly in the next step.

B-7; 3-Methyl-1H-indol-6-ylamine

A mixture of 3-methyl-4-nitro-1H-indole and 3-methyl-6-nitro-1H-indole (3 g, 17 mol) and 10% Pd—C (0.5 g) in ethanol (30 mL) was stirred overnight under H₂ (1 atm) at room temperature. Pd—C was filtered off and the filtrate was concentrated under reduced pressure. The residue was purified by column chromatography to give 3-methyl-1H-indol-6-ylamine (B-7) (0.6 g, 24%).
¹H NMR (CDCl₃) δ 7.59 (br s, 1H), 7.34 (d, J=8.0 Hz, 1H), 6.77 (s, 1H), 6.64 (s, 1H), 6.57 (m, 1H), 3.57 (br s, 2H), 2.28 (s, 3H); ESI-MS 147.2 m/z (MH⁺).

Example 2

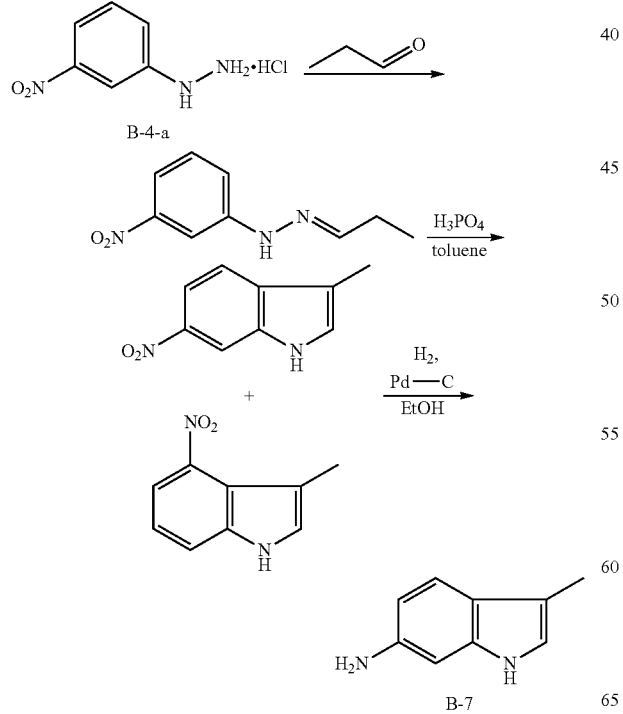

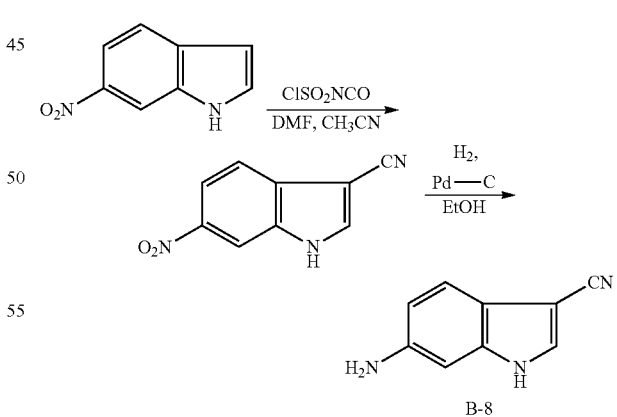

6-Nitro-1H-indole-3-carbonitrile

To a solution of 6-nitroindole (4.86 g 30 mmol) in DMF (24.3 mL) and CH₃CN (243 mL) was added dropwise a solution of ClSO₂NCO (5 mL, 57 mmol) in CH₃CN (39 mL) at 0° C. After addition, the reaction was allowed to warm to room temperature and stirred for 2 h. The mixture was poured into ice-water, basified with sat. NaHCO$_3$ solution to pH 7-8 and extracted with ethyl acetate. The organic layer was washed with brine, dried over Na$_2$SO$_4$ and concentrated to give 6-nitro-1H-indole-3-carbonitrile (4.6 g, 82%).

B-8; 6-Amino-1H-indole-3-carbonitrile

A suspension of 6-nitro-1H-indole-3-carbonitrile (4.6 g, 24.6 mmol) and 10% Pd—C (0.46 g) in EtOH (50 mL) was stirred under H$_2$ (1 atm) at room temperature overnight. After filtration, the filtrate was concentrated and the residue was purified by column chromatography (Pet. Ether/EtOAc=3/1) to give 6-amino-1H-indole-3-carbonitrile (B-8) (1 g, 99%) as a pink powder. 1H NMR (DMSO-d$_6$) δ 11.51 (s, 1H), 7.84 (d, J=2.4 Hz, 1H), 7.22 (d, J=8.4 Hz, 1H), 6.62 (s, 1H), 6.56 (d, J=8.4 Hz, 1H), 5.0 (s, 2H); ESI-MS 157.1 m/z (MH$^+$).

Example 3

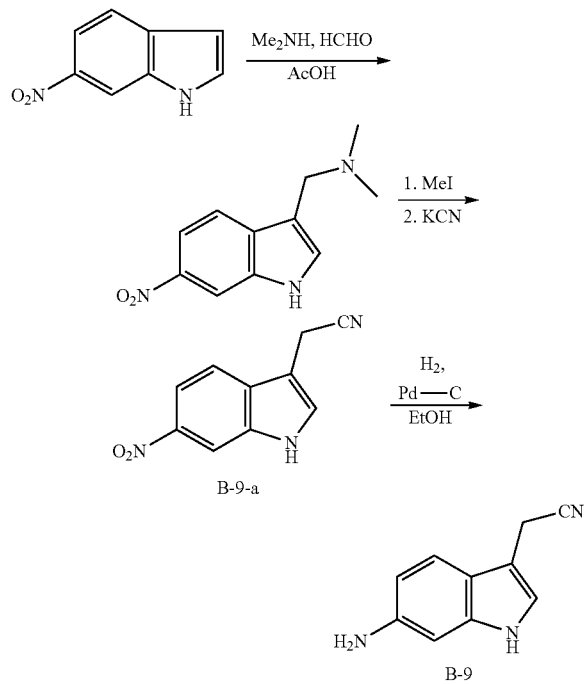

Dimethyl-(6-nitro-1H-indol-3-ylmethyl)-amine

A solution of dimethylamine (25 g, 0.17 mol) and formaldehyde (14.4 mL, 0.15 mol) in acetic acid (100 mL) was stirred at 0° C. for 30 min. To this solution was added 6-nitro-1H-indole (20 g, 0.12 mol). After stifling for 3 days at room temperature, the mixture was poured into 15% aq. NaOH solution (500 mL) at 0° C. The precipitate was collected via filtration and washed with water to give dimethyl-(6-nitro-1H-indol-3-ylmethyl)-amine (23 g, 87%).

B-9-a; (6-Nitro-1H-indol-3-yl)-acetonitrile

To a mixture of DMF (35 mL) and MeI (74.6 g, 0.53 mol) in water (35 mL) and THF (400 mL) was added dimethyl-(6-nitro-1H-indol-3-ylmethyl)-amine (23 g, 0.105 mol). After the reaction mixture was refluxed for 10 min, potassium cyanide (54.6 g, 0.84 mol) was added and the mixture was kept refluxing overnight. The mixture was then cooled to room temperature and filtered. The filtrate was washed with brine (300 mL×3), dried over Na$_2$SO$_4$, filtered and concentrated. The residue was purified by column chromatography to give (6-nitro-1H-indol-3-yl)-acetonitrile (B-9-a) (7.5 g, 36%).

B-9; (6-Amino-1H-indol-3-yl)-acetonitrile

A mixture of (6-nitro-1H-indol-3-yl)-acetonitrile (B-9-a) (1.5 g, 74.5 mml) and 10% Pd—C (300 mg) in EtOH (50 mL) was stirred at room temperature under H$_2$ (1 atm) for 5 h. Pd—C was removed via filtration and the filtrate was evaporated to give (6-amino-1H-indol-3-yl)-acetonitrile (B-9) (1.1 g, 90%). $^1$H NMR (DMSO-d$_6$) δ 10.4 (br s, 1H), 7.18 (d, J=8.4 Hz, 1H), 6.94 (s, 1H), 6.52 (s, 1H), 6.42 (dd, J=8.4, 1.8 Hz, 1H), 4.76 (s, 2H), 3.88 (s, 2H); ESI-MS 172.1 m/z (MH$^+$).

Example 4

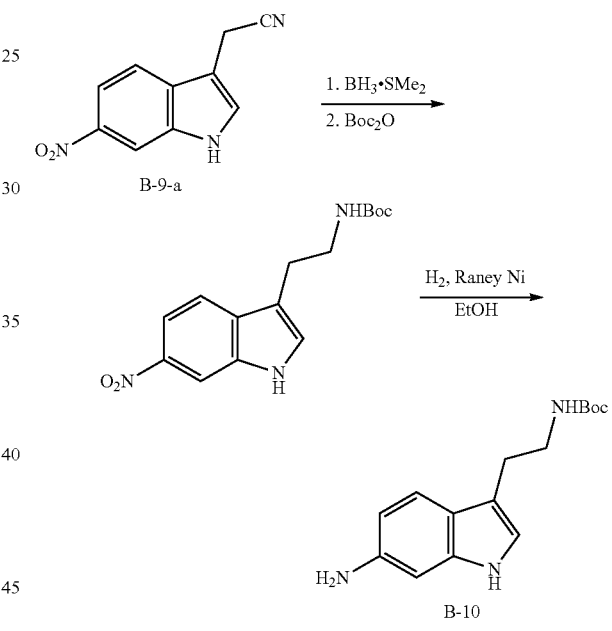

[2-(6-Nitro-1H-indol-3-yl)-ethyl]-carbamic acid tert-butyl ester

To a solution of (6-nitro-1H-indol-3-yl)-acetonitrile (B-9-a) (8.6 g, 42.8 mmol) in dry THF (200 mL) was added a solution of 2 M borane-dimethyl sulfide complex in THF (214 mL. 0.43 mol) at 0° C. The mixture was heated at reflux overnight under nitrogen. The mixture was then cooled to room temperature and a solution of (Boc)$_2$O (14 g, 64.2 mmol) and Et$_3$N (89.0 mL, 0.64 mol) in THF was added. The reaction mixture was kept stirring overnight and then poured into ice-water. The organic layer was separated and the aqueous phase was extracted with EtOAc (200×3 mL). The combined organic layers were washed with water and brine, dried over Na$_2$SO$_4$, filtered and concentrated under reduced pressure. The crude was purified by column chromatography to give [2-(6-nitro-1H-indol-3-yl)-ethyl]-carbamic acid tert-butyl ester (5 g, 38%).

B-10; [2-(6-Amino-1H-indol-3-yl)-ethyl]-carbamic acid tert-butyl ester

A mixture of [2-(6-nitro-1H-indol-3-yl)-ethyl]carbamic acid tert-butyl ester (5 g, 16.4 mmol) and Raney Ni (1 g) in EtOH (100 mL) was stirred at room temperature under $H_2$ (1 atm) for 5 h. Raney Ni was filtered off and the filtrate was evaporated under reduced pressure. The crude product was purified by column chromatography to give [2-(6-amino-1H-indol-3-yl)-ethyl]-carbamic acid tert-butyl ester (B-10) (3 g, 67%). $^1$H NMR (DMSO-$d_6$) δ 10.1 (br s, 1H), 7.11 (d, J=8.4 Hz, 1H), 6.77-6.73 (m, 2H), 6.46 (d, J=1.5 Hz, 1H), 6.32 (dd, J=8.4, 2.1 Hz, 1H), 4.62 (s, 2H), 3.14-3.08 (m, 2H), 2.67-2.62 (m, 2H), 1.35 (s, 9H); ESI-MS 275.8 m/z (MH$^+$).

Example 5

General Scheme:

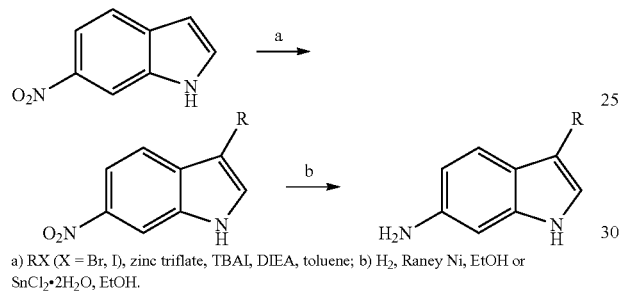

a) RX (X = Br, I), zinc triflate, TBAI, DIEA, toluene; b) $H_2$, Raney Ni, EtOH or SnCl$_2$•2H$_2$O, EtOH.

Specific Example

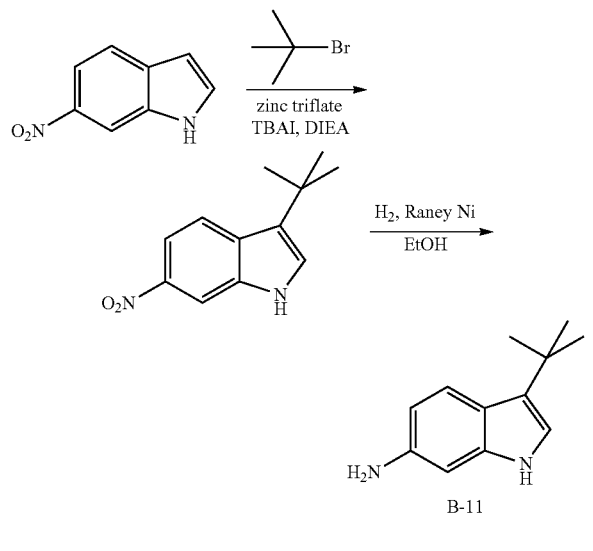

3-tert-Butyl-6-nitro-1H-indole

To a mixture of 6-nitroindole (1 g, 6.2 mmol), zinc triflate (2.06 g, 5.7 mmol) and TBAI (1.7 g, 5.16 mmol) in anhydrous toluene (11 mL) was added DIEA (1.47 g, 11.4 mmol) at room temperature under nitrogen. The reaction mixture was stirred for 10 min at 120° C., followed by addition of t-butyl bromide (0.707 g, 5.16 mmol). The resulting mixture was stirred for 45 min at 120° C. The solid was filtered off and the filtrate was concentrated to dryness and purified by column chromatography on silica gel (Pet.Ether./EtOAc 20:1) to give 3-tert-butyl-6-nitro-1H-indole as a yellow solid (0.25 g, 19%). $^1$H NMR (CDCl$_3$) δ 8.32 (d, J=2.1 Hz, 1H), 8.00 (dd, J=2.1, 14.4 Hz, 1H), 7.85 (d, J=8.7 Hz, 1H), 7.25 (s, 1H), 1.46 (s, 9H).

B-11; 3-tert-Butyl-1H-indol-6-ylamine

A suspension of 3-tert-butyl-6-nitro-1H-indole (3.0 g, 13.7 mmol) and Raney Ni (0.5 g) in ethanol was stirred at room temperature under $H_2$ (1 atm) for 3 h. The catalyst was filtered off and the filtrate was concentrated to dryness. The residue was purified by column chromatography on silica gel (Pet.Ether./EtOAc 4:1) to give 3-tert-butyl-1H-indol-6-ylamine (B-11) (2.0 g, 77.3%) as a gray solid. $^1$H NMR (CDCl$_3$): δ 7.58 (m, 2H), 6.73 (d, J=1.2 Hz, 1H), 6.66 (s, 1H), 6.57 (dd, J=0.8, 8.6 Hz, 1H), 3.60 (br s, 2H), 1.42 (s, 9H).

Other Examples

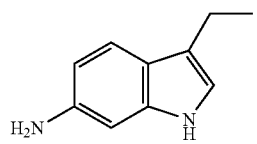

B-12; 3-Ethyl-1H-indol-6-ylamine

3-Ethyl-1H-indol-6-ylamine (B-12) was synthesized following the general scheme above starting from 6-nitroindole and ethyl bromide. Overall yield (42%). HPLC ret. time 1.95 min, 10-99% CH$_3$CN, 5 min run; ESI-MS 161.3 m/z (MH$^+$).

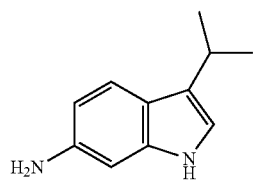

B-13; 3-Isopropyl-1H-indol-6-ylamine

3-Isopropyl-1H-indol-6-ylamine (B-13) was synthesized following the general scheme above starting from 6-nitroindole and isopropyl iodide. Overall yield (17%). HPLC ret. time 2.06 min, 10-99% CH$_3$CN, 5 min run; ESI-MS 175.2 m/z (MH$^+$).

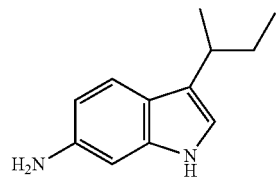

B-14; 3-sec-Butyl-1H-indol-6-ylamine 3-sec-Butyl-1H-indol-6-ylamine (B-14) was synthesized following the general scheme above starting from 6-nitroindole and 2-bromobutane. Overall yield (20%). HPLC ret. time 2.32 min, 10-99% CH$_3$CN, 5 min run; ESI-MS 189.5 m/z (MH$^+$).

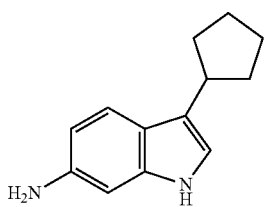 [SMILES: Nc1ccc2c(C3CCCC3)c[nH]c2c1]

B-15; 3-Cyclopentyl-1H-indol-6-ylamine

3-Cyclopentyl-1H-indol-6-ylamine (B-15) was synthesized following the general scheme above starting from 6-nitroindole and iodo-cyclopentane. Overall yield (16%). HPLC ret. time 2.39 min, 10-99% CH$_3$CN, 5 min run; ESI-MS 201.5 m/z (MH$^+$).

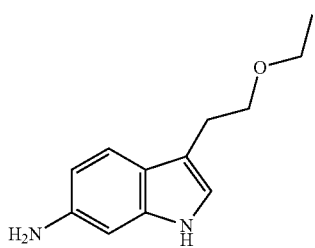

B-16; 3-(2-Ethoxy-ethyl)-1H-indol-6-ylamine 3-(2-Ethoxy-ethyl)-1H-indol-6-ylamine (B-16) was synthesized following the general scheme above starting from 6-nitroindole and 1-bromo-2-ethoxy-ethane. Overall yield (15%). HPLC ret. time 1.56 min, 10-99% CH$_3$CN, 5 min run; ESI-MS 205.1 m/z (MH$^+$).

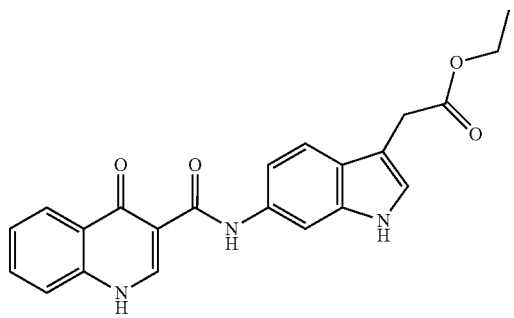 [SMILES: CCOC(=O)Cc1c[nH]c2cc(NC(=O)c3c[nH]c4ccccc4c3=O)ccc12]

B-17; (6-Amino-1H-indol-3-yl)-acetic acid ethyl ester (6-Amino-1H-indol-3-yl)-acetic acid ethyl ester (B-17) was synthesized following the general scheme above starting from 6-nitroindole and iodo-acetic acid ethyl ester. Overall yield (24%).

HPLC ret. time 0.95 min, 10-99% CH$_3$CN, 5 min run; ESI-MS 219.2 m/z (MH$^+$).

4-Substituted 6-aminoindole

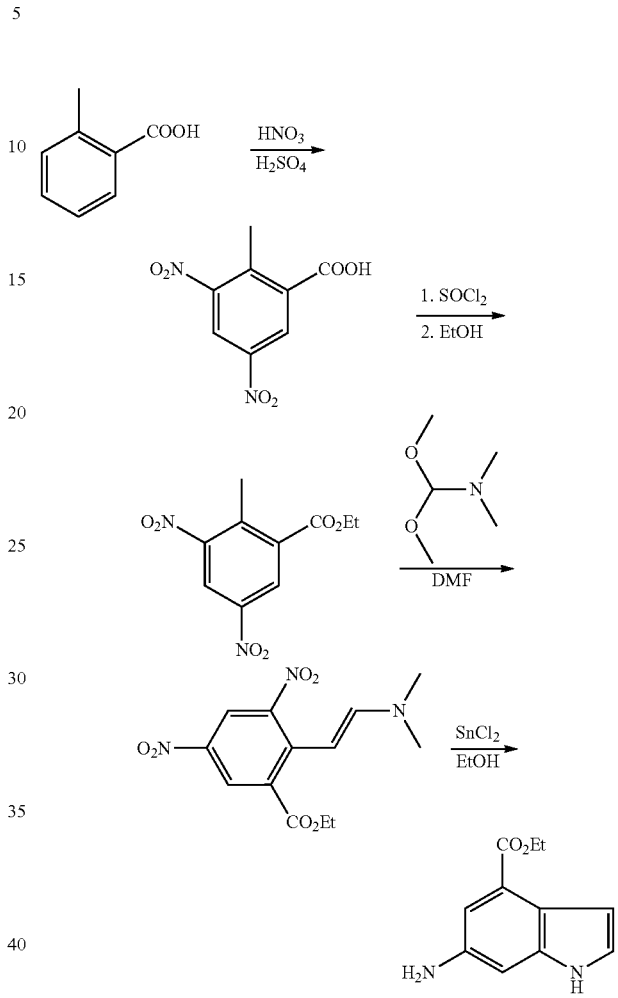

2-Methyl-3,5-dinitro-benzoic acid

To a mixture of HNO$_3$ (95%, 80 mL) and H$_2$SO$_4$ (98%, 80 mL) was slowly added 2-methylbenzoic acid (50 g, 0.37 mol) at 0° C. After addition, the reaction mixture was stirred for 1.5 h while keeping the temperature below 30° C., poured into ice-water and stirred for 15 min. The resulting precipitate was collected via filtration and washed with water to give 2-methyl-3,5-dinitro-benzoic acid (70 g, 84%).

2-Methyl-3,5-dinitro-benzoic acid ethyl ester

A mixture of 2-methyl-3,5-dinitro-benzoic acid (50 g, 0.22 mol) in SOCl$_2$ (80 mL) was heated at reflux for 4 h and then was concentrated to dryness. CH$_2$Cl$_2$ (50 mL) and EtOH (80 mL) were added. The mixture was stirred at room temperature for 1 h, poured into ice-water and extracted with EtOAc (3×100 mL). The combined extracts were washed with sat. Na$_2$CO$_3$ (80 mL), water (2×100 mL) and brine (100 mL), dried over Na$_2$SO$_4$ and concentrated to dryness to give 2-methyl-3,5-dinitro-benzoic acid ethyl ester (50 g, 88%).

2-(2-Dimethylamino-vinyl)-3,5-dinitro-benzoic acid ethyl ester

A mixture of 2-methyl-3,5-dinitro-benzoic acid ethyl ester (35 g, 0.14 mol) and dimethoxymethyl-dimethyl-amine (32 g, 0.27 mol) in DMF (200 mL) was heated at 100° C. for 5 h. The mixture was poured into ice-water. The precipitate was collected via filtration and washed with water to give 2-(2-dimethylamino-vinyl)-3,5-dinitro-benzoic acid ethyl ester (11.3 g, 48%).

B-18; 6-Amino-1H-indole-4-carboxylic acid ethyl ester

A mixture of 2-(2-dimethylamino-vinyl)-3,5-dinitro-benzoic acid ethyl ester (11.3 g, 0.037 mol) and $SnCl_2$ (83 g. 0.37 mol) in ethanol was heated at reflux for 4 h. The mixture was concentrated to dryness and the residue was poured into water and basified with sat. $Na_2CO_3$ solution to pH 8. The precipitate was filtered off and the filtrate was extracted with ethyl acetate (3×100 mL). The combined extracts were washed with water (2×100 mL) and brine (150 mL), dried over $Na_2SO_4$ and concentrated to dryness. The residue was purified by column chromatography on silica gel to give 6-amino-1H-indole-4-carboxylic acid ethyl ester (B-18) (3 g, 40%). $^1$H NMR (DMSO-$d_6$) δ 10.76 (br s, 1H), 7.11-7.14 (m, 2H), 6.81-6.82 (m, 1H), 6.67-6.68 (m, 1H), 4.94 (br s, 2H), 4.32-4.25 (q, J=7.2 Hz, 2H), 1.35-1.31 (t, J=7.2, 3 H). ESI-MS 205.0 m/z (MH$^+$).

5-Substituted 6-aminoindoles

Example 1

General Scheme:

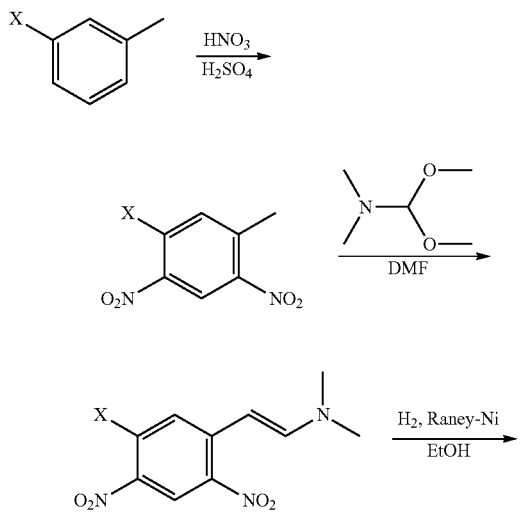

Specific Example

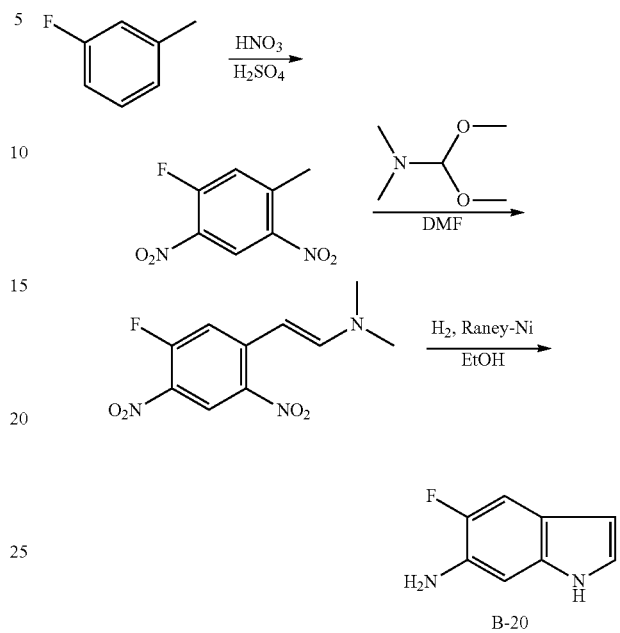

1-Fluoro-5-methyl-2,4-dinitro-benzene

To a stirred solution of $HNO_3$ (60 mL) and $H_2SO_4$ (80 mL), cooled in an ice bath, was added 1-fluoro-3-methyl-benzene (27.5 g, 25 mmol) at such a rate that the temperature did not rise over 35° C. The mixture was allowed to stir for 30 min at room temperature and poured into ice water (500 mL). The resulting precipitate (a mixture of the desired product and 1-fluoro-3-methyl-2,4-dinitro-benzene, approx. 7:3) was collected via filtration and purified by recrystallization from 50 mL isopropyl ether to give 1-fluoro-5-methyl-2,4-dinitro-benzene as a white solid (18 g, 36%).

[2-(5-Fluoro-2,4-dinitro-phenyl)-vinyl]-dimethyl-amine

A mixture of 1-fluoro-5-methyl-2,4-dinitro-benzene (10 g, 50 mmol), dimethoxymethyl-dimethylamine (11.9 g, 100 mmol) and DMF (50 mL) was heated at 100° C. for 4 h. The solution was cooled and poured into water. The red precipitate was collected via filtration, washed with water adequately and dried to give [2-(5-fluoro-2,4-dinitro-phenyl)-vinyl]-dimethyl-amine (8 g, 63%).

B-20; 5-Fluoro-1H-indol-6-ylamine

A suspension of [2-(5-fluoro-2,4-dinitro-phenyl)-vinyl]-dimethyl-amine (8 g, 31.4 mmol) and Raney Ni (8 g) in EtOH (80 mL) was stirred under $H_2$ (40 psi) at room temperature for 1 h. After filtration, the filtrate was concentrated and the residue was purified by chromatography (Pet.Ether/EtOAc=5/1) to give 5-fluoro-1H-indol-6-ylamine (B-20) as a brown solid (1 g, 16%). $^1$H NMR (DMSO-$d_6$) δ 10.56 (br s, 1H), 7.07 (d, J=12 Hz, 1H), 7.02 (m, 1H), 6.71 (d, J=8 Hz, 1H), 6.17 (s, 1H), 3.91 (br s, 2H); ESI-MS 150.1 m/z (MH+).

Other Examples

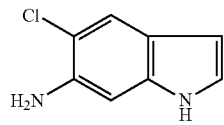

B-21; 5-Chloro-1H-indol-6-ylamine

5-Chloro-1H-indol-6-ylamine (B-21) was synthesized following the general scheme above starting from 1-chloro-3-methyl-benzene. Overall yield (7%). $^1$H NMR (CDCl$_3$) 6.7.85 (br s, 1H), 7.52 (s, 1H), 7.03 (s, 1H), 6.79 (s, 1H), 6.34 (s, 1H), 3.91 (br s, 2H); ESI-MS 166.0 m/z (MH+).

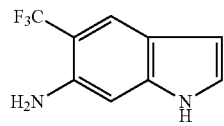 [SMILES: Nc1cc2[nH]ccc2cc1C(F)(F)F]

B-22; 5-Trifluoromethyl-1H-indol-6-ylamine

5-Trifluoromethyl-1H-indol-6-ylamine (B-22) was synthesized following the general scheme above starting from 1-methyl-3-trifluoromethyl-benzene. Overall yield (2%). $^1$H NMR (DMSO-d$_6$) 10.79 (br s, 1H), 7.55 (s, 1H), 7.12 (s, 1H), 6.78 (s, 1H), 6.27 (s, 1H), 4.92 (s, 2H); ESI-MS 200.8 m/z (MH+).

Example 2

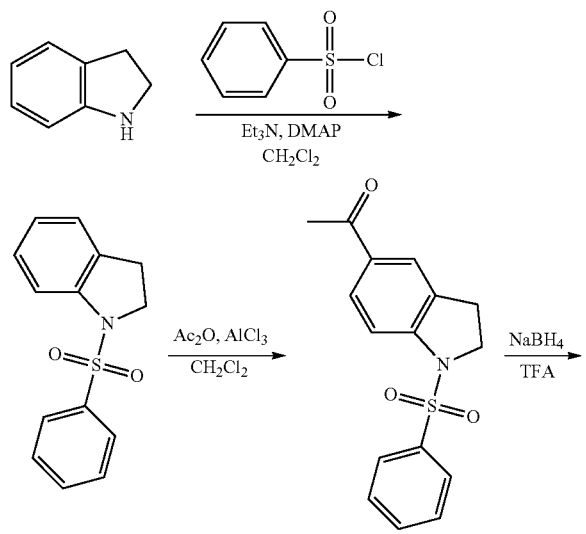

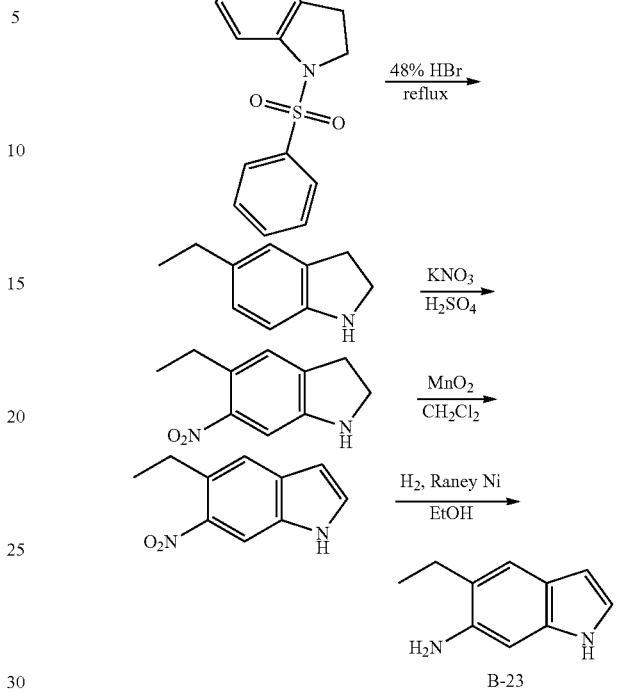

1-Benzenesulfonyl-2,3-dihydro-1H-indole

To a mixture of DMAP (1.5 g), benzenesulfonyl chloride (24 g, 136 mmol) and 2,3-dihydro-1H-indole (14.7 g, 124 mmol) in CH$_2$Cl$_2$ (200 mL) was added dropwise Et$_3$N (19 g, 186 mmol) in an ice-water bath. After addition, the mixture was stirred at room temperature overnight, washed with water, dried over Na$_2$SO$_4$ and concentrated to dryness under reduced pressure to provide 1-benzenesulfonyl-2,3-dihydro-1H-indole (30.9 g, 96%).

1-(1-Benzenesulfonyl-2,3-dihydro-1H-indol-5-yl)-ethanone

To a stirling suspension of AlCl$_3$ (144 g, 1.08 mol) in CH$_2$Cl$_2$ (1070 mL) was added acetic anhydride (54 mL). The mixture was stirred for 15 minutes. A solution of 1-benzenesulfonyl-2,3-dihydro-1H-indole (46.9 g, 0.18 mol) in CH$_2$Cl$_2$ (1070 mL) was added dropwise. The mixture was stirred for 5 h and quenched by the slow addition of crushed ice. The organic layer was separated and the aqueous layer was extracted with CH$_2$Cl$_2$. The combined organic layers were washed with saturated aqueous NaHCO$_3$ and brine, dried over Na$_2$SO$_4$ and concentrated under vacuum to yield 1-(1-benzenesulfonyl-2,3-dihydro-1H-indol-5-yl)-ethanone (42.6 g, 79%).

1-Benzenesulfonyl-5-ethyl-2,3-dihydro-1H-indole

To magnetically stirred TFA (1600 mL) was added at 0° C. sodium borohydride (64 g, 1.69 mol) over 1 h. To this mixture was added dropwise a solution of 1-(1-benzenesulfonyl-2,3-dihydro-1H-indol-5-yl)-ethanone (40 g, 0.13 mol) in TFA (700 mL) over 1 h. The mixture was stirred overnight at 25°

C., diluted with H$_2$O (1600 ml), and basified with sodium hydroxide pellets at 0° C. The organic layer was separated and the aqueous layer was extracted with CH$_2$Cl$_2$. The combined organic layers were washed with brine, dried over Na$_2$SO$_4$ and concentrated under reduced pressure. The residue was purified by column chromatography on silica gel to give 1-benzenesulfonyl-5-ethyl-2,3-dihydro-1H-indole (16.2 g, 43%).

5-Ethyl-2,3-dihydro-1H-indole

A mixture of 1-benzenesulfonyl-5-ethyl-2,3-dihydro-1H-indole (15 g, 0.05 mol) in HBr (48%, 162 mL) was heated at reflux for 6 h. The mixture was basified with sat. NaOH solution to pH 9 and extracted with ethyl acetate. The organic layer was washed with brine, dried over Na$_2$SO$_4$ and concentrated under reduced pressure. The residue was purified by column chromatography on silica gel to give 5-ethyl-2,3-dihydro-1H-indole (2.5 g, 32%).

5-Ethyl-6-nitro-2,3-dihydro-1H-indole

To a solution of 5-ethyl-2,3-dihydro-1H-indole (2.5 g, 17 mmol) in H$_2$SO$_4$ (98%, 20 mL) was slowly added KNO$_3$ (1.7 g, 17 mmol) at 0° C. After addition, the mixture was stirred at 0-10° C. for 10 min, carefully poured into ice, basified with NaOH solution to pH 9 and extracted with ethyl acetate. The combined extracts were washed with brine, dried over Na$_2$SO$_4$ and concentrated to dryness. The residue was purified by column chromatography on silica gel to give 5-ethyl-6-nitro-2,3-dihydro-1H-indole (1.9 g, 58%).

5-Ethyl-6-nitro-1H-indole

To a solution of 5-ethyl-6-nitro-2,3-dihydro-1H-indole (1.9 g, 9.9 mmol) in CH$_2$Cl$_2$ (30 mL) was added MnO$_2$ (4 g, 46 mmol). The mixture was stirred at room temperature for 8 h. The solid was filtered off and the filtrate was concentrated to dryness to give crude 5-ethyl-6-nitro-1H-indole (1.9 g, quant.).

B-23; 5-Ethyl-1H-indol-6-ylamine

A suspension of 5-ethyl-6-nitro-1H-indole (1.9 g, 10 mmol) and Raney Ni (1 g) was stirred under H$_2$ (1 atm) at room temperature for 2 h. The catalyst was filtered off and the filtrate was concentrated to dryness. The residue was purified by column chromatography on silica gel to give 5-ethyl-1H-indol-6-ylamine (B-23) (760 mg, 48%). $^1$H NMR (CDCl$_3$) δ 7.90 (br s, 1H), 7.41 (s, 1H), 7.00 (s, 1H), 6.78 (s, 2H), 6.39 (s, 1H), 3.39 (br s, 2H), 2.63 (q, J=7.2 Hz, 2H), 1.29 (t, J=6.9 Hz, 3H); ESI-MS 161.1 m/z (MH$^+$).

Example 3

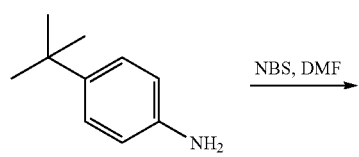

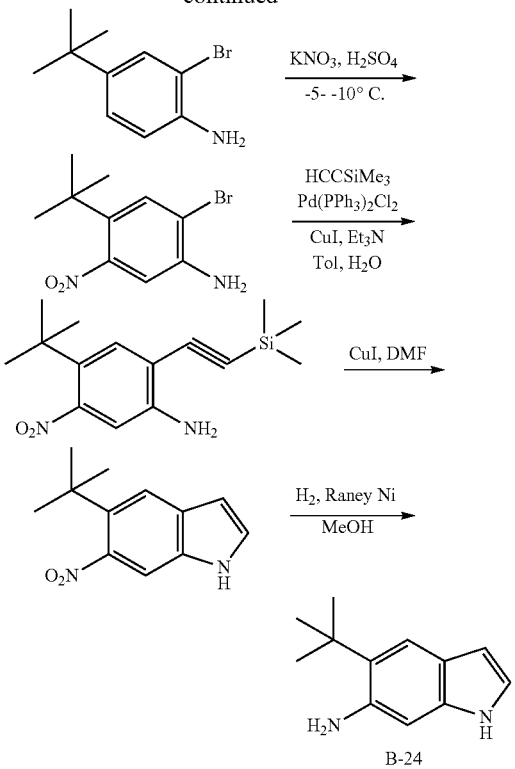

B-24

2-Bromo-4-tert-butyl-phenylamine

To a solution of 4-tert-butyl-phenylamine (447 g, 3 mol) in DMF (500 mL) was added dropwise NBS (531 g, 3 mol) in DMF (500 mL) at room temperature. Upon completion, the reaction mixture was diluted with water and extracted with EtOAc. The organic layer was washed with water, brine, dried over Na$_2$SO$_4$ and concentrated. The crude product was directly used in the next step without further purification.

2-Bromo-4-tert-butyl-5-nitro-phenylamine

2-Bromo-4-tert-butyl-phenylamine (162 g, 0.71 mol) was added dropwise to H$_2$SO$_4$ (410 mL) at room temperature to yield a clear solution. This clear solution was then cooled down to −5 to −10° C. A solution of KNO$_3$ (82.5 g, 0.82 mol) in H$_2$SO$_4$ (410 mL) was added dropwise while the temperature was maintained between −5 to −10° C. Upon completion, the reaction mixture was poured into ice/water and extracted with EtOAc. The combined organic layers were washed with 5% Na$_2$CO$_3$ and brine, dried over Na$_2$SO$_4$ and concentrated. The residue was purified by a column chromatography (EtOAc/petroleum ether 1/10) to give 2-bromo-4-tert-butyl-5-nitro-phenylamine as a yellow solid (152 g, 78%).

4-tert-Butyl-5-nitro-2-trimethylsilanylethynyl-phenylamine

To a mixture of 2-bromo-4-tert-butyl-5-nitro-phenylamine (27.3 g, 100 mmol) in toluene (200 mL) and water (100 mL) was added Et$_3$N (27.9 mL, 200 mmol), Pd(PPh$_3$)$_2$Cl$_2$ (2.11 g, 3 mmol), CuI (950 mg, 0.5 mmol) and trimethylsilyl acetylene (21.2 mL, 150 mmol) under a nitrogen atmosphere. The reaction mixture was heated at 70° C. in a sealed pressure flask for 2.5 h, cooled down to room temperature and filtered through a short plug of Celite. The filter cake was washed with EtOAc. The combined filtrate was washed with 5% NH₄OH solution and water, dried over Na₂SO₄ and concentrated. The crude product was purified by column chromatography (0-10% EtOAc/petroleum ether) to provide 4-tert-butyl-5-nitro-2-trimethylsilanylethynyl-phenylamine as a brown viscous liquid (25 g, 81%).

5-tert-Butyl-6-nitro-1H-indole

To a solution of 4-tert-butyl-5-nitro-2-trimethylsilanylethynyl-phenylamine (25 g, 86 mmol) in DMF (100 mL) was added CuI (8.2 g, 43 mmol) under a nitrogen atmosphere. The mixture was heated at 135° C. in a sealed pressure flask overnight, cooled down to room temperature and filtered through a short plug of Celite. The filter cake was washed with EtOAc. The combined filtrate was washed with water, dried over Na₂SO₄ and concentrated. The crude product was purified by column chromatography (10-20% EtOAc/Hexane) to provide 5-tert-butyl-6-nitro-1H-indole as a yellow solid (12.9 g, 69%).

B-24; 5-tert-Butyl-1H-indol-6-ylamine

Raney Ni (3 g) was added to 5-tert-butyl-6-nitro-1H-indole (14.7 g, 67 mmol) in methanol (100 mL). The mixture was stirred under hydrogen (1 atm) at 30° C. for 3 h. The catalyst was filtered off. The filtrate was dried over Na₂SO₄ and concentrated. The crude dark brown viscous oil was purified by column chromatography (10-20% EtOAc/petroleum ether) to give 5-tert-butyl-1H-indol-6-ylamine (B-24) as a gray solid (11 g, 87%). ¹H NMR (300 MHz, DMSO-d6) δ 10.3 (br s, 1H), 7.2 (s, 1H), 6.9 (m, 1H), 6.6 (s, 1H), 6.1 (m, 1H), 4.4 (br s, 2H), 1.3 (s, 9H).

Example 4

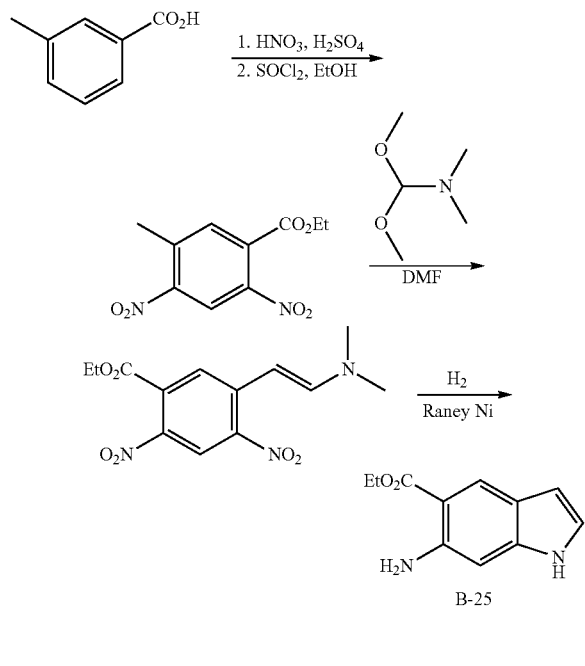

5-Methyl-2,4-dinitro-benzoic acid

To a mixture of HNO₃ (95%, 80 mL) and H₂SO₄ (98%, 80 mL) was slowly added 3-methylbenzoic acid (50 g, 0.37 mol) at 0° C. After addition, the mixture was stirred for 1.5 h while maintaining the temperature below 30° C. The mixture was poured into ice-water and stirred for 15 min. The precipitate was collected via filtration and washed with water to give a mixture of 3-methyl-2,6-dinitro-benzoic acid and 5-methyl-2,4-dinitro-benzoic acid (70 g, 84%). To a solution of this mixture in EtOH (150 mL) was added dropwise SOCl₂ (53.5 g, 0.45 mol). The mixture was heated at reflux for 2 h and concentrated to dryness under reduced pressure. The residue was dissolved in EtOAc (100 mL) and extracted with 10% Na₂CO₃ solution (120 mL). The organic layer was found to contain 5-methyl-2,4-dinitro-benzoic acid ethyl ester while the aqueous layer contained 3-methyl-2,6-dinitro-benzoic acid. The organic layer was washed with brine (50 mL), dried over Na₂SO₄ and concentrated to dryness to provide 5-methyl-2,4-dinitro-benzoic acid ethyl ester (20 g, 20%).

5-(2-Dimethylamino-vinyl)-2,4-dinitro-benzoic acid ethyl ester

A mixture of 5-methyl-2,4-dinitro-benzoic acid ethyl ester (39 g, 0.15 mol) and dimethoxymethyl-dimethylamine (32 g, 0.27 mol) in DMF (200 mL) was heated at 100° C. for 5 h. The mixture was poured into ice water. The precipitate was collected via filtration and washed with water to afford 5-(2-dimethylamino-vinyl)-2,4-dinitro-benzoic acid ethyl ester (15 g, 28%).

B-25; 6-Amino-1H-indole-5-carboxylic acid ethyl ester

A mixture of 5-(2-dimethylamino-vinyl)-2,4-dinitro-benzoic acid ethyl ester (15 g, 0.05 mol) and Raney Ni (5 g) in EtOH (500 mL) was stirred under H₂ (50 psi) at room temperature for 2 h. The catalyst was filtered off and the filtrate was concentrated to dryness. The residue was purified by column chromatography on silica gel to give 6-amino-1H-indole-5-carboxylic acid ethyl ester (B-25) (3 g, 30%). ¹H NMR (DMSO-d₆) δ 10.68 (s, 1H), 7.99 (s, 1H), 7.01-7.06 (m, 1H), 6.62 (s, 1H), 6.27-6.28 (m, 1H), 6.16 (s, 2H), 4.22 (q, J=7.2 Hz, 2H), 1.32-1.27 (t, J=7.2 Hz, 3H).

Example 5

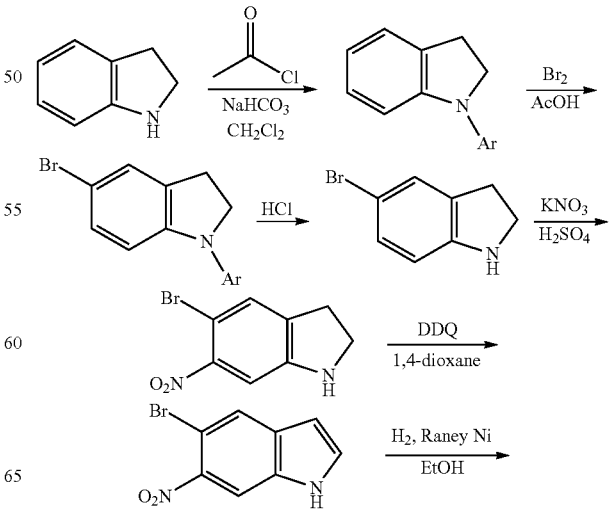

-continued

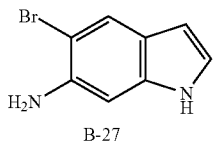

1-(2,3-Dihydro-indol-1-yl)-ethanone

To a suspension of NaHCO$_3$ (504 g, 6.0 mol) and 2,3-dihydro-1H-indole (60 g, 0.5 mol) in CH$_2$Cl$_2$ (600 mL) cooled in an ice-water bath, was added dropwise acetyl chloride (78.5 g, 1.0 mol). The mixture was stirred at room temperature for 2 h. The solid was filtered off and the filtrate was concentrated to give 1-(2,3-dihydro-indol-1-yl)-ethanone (82 g, 100%).

1-(5-Bromo-2,3-dihydro-indol-1-yl)-ethanone

To a solution of 1-(2,3-dihydro-indol-1-yl)-ethanone (58.0 g, 0.36 mol) in acetic acid (3000 mL) was added Br$_2$ (87.0 g, 0.54 mol) at 10° C. The mixture was stirred at room temperature for 4 h. The precipitate was collected via filtration to give crude 1-(5-bromo-2,3-dihydro-indol-1-yl)-ethanone (100 g, 96%), which was used directly in the next step.

5-Bromo-2,3-dihydro-1H-indole

A mixture of crude 1-(5-bromo-2,3-dihydro-indol-1-yl)-ethanone (100 g, 0.34 mol) in HCl (20%, 1200 mL) was heated at reflux for 6 h. The mixture was basified with Na$_2$CO$_3$ to pH 8.5-10 and then extracted with ethyl acetate. The combined organic layers were washed with brine, dried over Na$_2$SO$_4$ and concentrated under reduced pressure. The residue was purified by column chromatography on silica gel to give 5-bromo-2,3-dihydro-1H-indole (37 g, 55%).

5-Bromo-6-nitro-2,3-dihydro-1H-indole

To a solution of 5-bromo-2,3-dihydro-1H-indole (45 g, 0.227 mol) in H$_2$SO$_4$ (98%, 200 mL) was slowly added KNO$_3$ (23.5 g, 0.23 mol) at 0° C. After addition, the mixture was stirred at 0-10° C. for 4 h, carefully poured into ice, basified with Na$_2$CO$_3$ to pH 8 and extracted with ethyl acetate. The combined organic extracts were washed with brine, dried over Na$_2$SO$_4$ and concentrated to dryness. The residue was purified by column chromatography on silica gel to give 5-bromo-6-nitro-2,3-dihydro-1H-indole (42 g, 76%).

5-Bromo-6-nitro-1H-indole

To a solution of 5-bromo-6-nitro-2,3-dihydro-1H-indole (20 g, 82.3 mmol) in 1,4-dioxane (400 mL) was added DDQ (30 g, 0.13 mol). The mixture was stirred at 80° C. for 2 h. The solid was filtered off and the filtrate was concentrated to dryness. The residue was purified by column chromatography on silica gel to afford 5-bromo-6-nitro-1H-indole (7.5 g, 38%).

B-27; 5-Bromo-1H-indol-6-ylamine

A mixture of 5-bromo-6-nitro-1H-indole (7.5 g, 31.1 mmol) and Raney Ni (1 g) in ethanol was stirred under H$_2$ (1 atm) at room temperature for 2 h. The catalyst was filtered off and the filtrate was concentrated to dryness. The residue was purified by column chromatography on silica gel to give 5-bromo-1H-indol-6-ylamine (B-27) (2 g, 30%). $^1$H NMR (DMSO-d$_6$) δ 10.6 (s, 1H), 7.49 (s, 1H), 6.79-7.02 (m, 1H), 6.79 (s, 1H), 6.14-6.16 (m, 1H), 4.81 (s, 2H).

7-Substituted 6-aminoindole

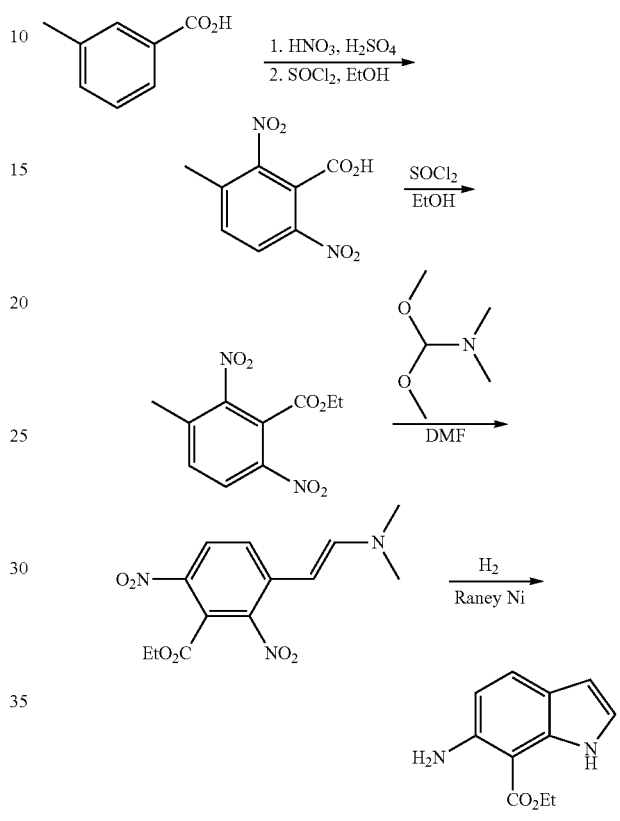

3-Methyl-2,6-dinitro-benzoic acid

To a mixture of HNO$_3$ (95%, 80 mL) and H$_2$SO$_4$ (98%, 80 mL) was slowly added 3-methylbenzoic acid (50 g, 0.37 mol) at 0° C. After addition, the mixture was stirred for 1.5 h while maintaining the temperature below 30° C. The mixture was poured into ice-water and stirred for 15 min. The precipitate was collected via filtration and washed with water to give a mixture of 3-methyl-2,6-dinitro-benzoic acid and 5-methyl-2,4-dinitro-benzoic acid (70 g, 84%). To a solution of this mixture in EtOH (150 mL) was added dropwise SOCl$_2$ (53.5 g, 0.45 mol). The mixture was heated to reflux for 2 h and concentrated to dryness under reduced pressure. The residue was dissolved in EtOAc (100 mL) and extracted with 10% Na$_2$CO$_3$ solution (120 mL). The organic layer was found to contain 5-methyl-2,4-dinitro-benzoic acid ethyl ester. The aqueous layer was acidified with HCl to pH 2-3 and the resulting precipitate was collected via filtration, washed with water and dried in air to give 3-methyl-2,6-dinitro-benzoic acid (39 g, 47%).

3-Methyl-2,6-dinitro-benzoic acid ethyl ester

A mixture of 3-methyl-2,6-dinitro-benzoic acid (39 g, 0.15 mol) and SOCl$_2$ (80 mL) was heated at reflux for 4 h. The excess SOCl$_2$ was removed under reduced pressure and the residue was added dropwise to a solution of EtOH (100 mL) and Et$_3$N (50 mL). The mixture was stirred at 20° C. for 1 h and concentrated to dryness. The residue was dissolved in EtOAc (100 mL), washed with Na$_2$CO$_3$ (10%, 40 mL×2), water (50 mL×2) and brine (50 mL), dried over Na$_2$SO$_4$ and concentrated to give 3-methyl-2,6-dinitro-benzoic acid ethyl ester (20 g, 53%).

3-(2-Dimethylamino-vinyl)-2,6-dinitro-benzoic acid ethyl ester

A mixture of 3-methyl-2,6-dinitro-benzoic acid ethyl ester (35 g, 0.14 mol) and dimethoxymethyl-dimethylamine (32 g, 0.27 mol) in DMF (200 mL) was heated at 100° C. for 5 h. The mixture was poured into ice water and the precipitate was collected via filtration and washed with water to give 3-(2-dimethylamino-vinyl)-2,6-dinitro-benzoic acid ethyl ester (25 g, 58%).

B-19; 6-Amino-1H-indole-7-carboxylic acid ethyl ester

A mixture of 3-(2-dimethylamino-vinyl)-2,6-dinitro-benzoic acid ethyl ester (30 g, 0.097 mol) and Raney Ni (10 g) in EtOH (1000 mL) was stirred under H$_2$ (50 psi) for 2 h. The catalyst was filtered off, and the filtrate was concentrated to dryness. The residue was purified by column chromatography on silica gel to give 6-amino-1H-indole-7-carboxylic acid ethyl ester (B-19) as an off-white solid (3.2 g, 16%). $^1$H NMR (DMSO-d$_6$) δ 10.38 (s, 1H), 7.44-7.41 (d, J=8.7 Hz, 1H), 6.98 (t, 1H), 6.65 (s, 2H), 6.50-6.46 (m, 1H), 6.27-6.26 (m, 1H), 4.43-4.36 (q, J=7.2 Hz, 2H), 1.35 (t, J=7.2 Hz, 3H).

Phenols

Example 1

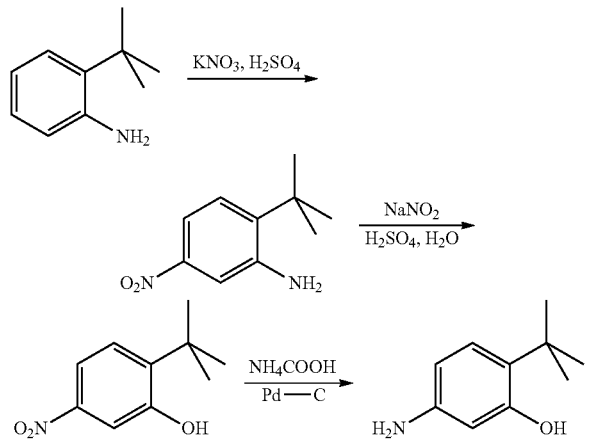

2-tert-Butyl-5-nitroaniline

To a cooled solution of sulfuric acid (90%, 50 mL) was added dropwise 2-tert-butyl-phenylamine (4.5 g, 30 mmol) at 0° C. Potassium nitrate (4.5 g, 45 mmol) was added in portions at 0° C. The reaction mixture was stirred at 0-5° C. for 5 min, poured into ice-water and then extracted with EtOAc three times. The combined organic layers were washed with brine and dried over Na$_2$SO$_4$. After removal of solvent, the residue was purified by recrystallization using 70% EtOH—H$_2$O to give 2-tert-butyl-5-nitroaniline (3.7 g, 64%). $^1$H NMR (400 MHz, CDCl$_3$) δ 7.56 (dd, J=8.7, 2.4 Hz, 1H), 7.48 (d, J=2.4 Hz, 1H), 7.36 (d, J=8.7 Hz, 1H), 4.17 (s, 2H), 1.46 (s, 9H); HPLC ret. time 3.27 min, 10-99% CH$_3$CN, 5 min run; ESI-MS 195.3 m/z (MH$^+$).

C-1-a; 2-tert-Butyl-5-nitrophenol

To a mixture of 2-tert-butyl-5-nitroaniline (1.94 g, 10 mmol) in 40 mL of 15% H$_2$SO$_4$ was added dropwise a solution of NaNO$_2$ (763 mg, 11.0 mmol) in water (3 mL) at 0° C. The resulting mixture was stirred at 0-5° C. for 5 min. Excess NaNO$_2$ was neutralized with urea, then 5 mL of H$_2$SO$_4$—H$_2$O (v/v 1:2) was added and the mixture was refluxed for 5 min. Three additional 5 mL aliquots of H$_2$SO$_4$—H$_2$O (v/v 1:2) were added while heating at reflux. The reaction mixture was cooled to room temperature and extracted with EtOAc twice. The combined organic layers were washed with brine and dried over MgSO$_4$. After removal of solvent, the residue was purified by column chromatography (0-10% EtOAc-Hexane) to give 2-tert-butyl-5-nitrophenol (C-1-a) (1.2 g, 62%). $^1$H NMR (400 MHz, CDCl$_3$) δ 7.76 (dd, J=8.6, 2.2 Hz, 1H), 7.58 (d, J=2.1 Hz, 1H), 7.43 (d, J=8.6 Hz, 1H), 5.41 (s, 1H), 1.45 (s, 9H);

HPLC ret. time 3.46 min, 10-99% CH$_3$CN, 5 min run.

C-1; 2-tert-Butyl-5-aminophenol

To a refluxing solution of 2-tert-butyl-5-nitrophenol (C-1-a) (196 mg, 1.0 mmol) in EtOH (10 mL) was added ammonium formate (200 mg, 3.1 mmol), followed by 140 mg of 10% Pd—C. The reaction mixture was refluxed for additional 30 min, cooled to room temperature and filtered through a plug of Celite. The filtrate was concentrated to dryness and purified by column chromatography (20-30% EtOAc-Hexane) to give 2-tert-butyl-5-aminophenol (C-1) (144 mg, 87%). $^1$H NMR (400 MHz, DMSO-d$_6$) δ 8.76 (s, 1H), 6.74 (d, J=8.3 Hz, 1H), 6.04 (d, J=2.3 Hz, 1H), 5.93 (dd, J=8.2, 2.3 Hz, 1H), 4.67 (s, 2H), 1.26 (s, 9H); HPLC ret. time 2.26 min, 10-99% CH$_3$CN, 5 min run; ESI-MS 166.1 m/z (MH$^+$).

Example 2

General scheme:

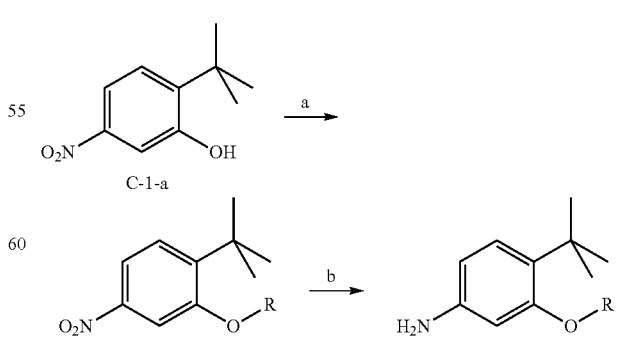

a) RX (X = Br, I), K$_2$CO$_3$ or Cs$_2$CO$_3$, DMF; b) HCO$_2$NH$_4$ or HCO$_2$K, Pd—C, EtOH

Specific Example

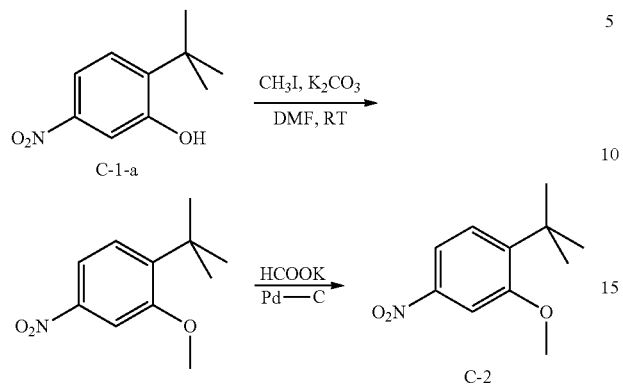

1-tert-Butyl-2-methoxy-4-nitrobenzene

To a mixture of 2-tert-butyl-5-nitrophenol (C-1-a) (100 mg, 0.52 mmol) and K$_2$CO$_3$ (86 mg, 0.62 mmol) in DMF (2 mL) was added CH$_3$I (40 uL, 0.62 mmol). The reaction mixture was stirred at room temperature for 2 h, diluted with water and extracted with EtOAc. The combined organic layers were washed with brine and dried over MgSO$_4$. After filtration, the filtrate was evaporated to dryness to give 1-tert-butyl-2-methoxy-4-nitrobenzene (82 mg, 76%) that was used without further purification. $^1$H NMR (400 MHz, CDCl$_3$) δ 7.77 (t, J=4.3 Hz, 1H), 7.70 (d, J=2.3 Hz, 1H), 7.40 (d, J=8.6 Hz, 1H), 3.94 (s, 3H), 1.39 (s, 9H).

C-2; 4-tert-Butyl-3-methoxyaniline

To a refluxing solution of 1-tert-butyl-2-methoxy-4-nitrobenzene (82 mg, 0.4 mmol) in EtOH (2 mL) was added potassium formate (300 mg, 3.6 mmol) in water (1 mL), followed by 10% Pd—C (15 mg). The reaction mixture was refluxed for additional 60 min, cooled to room temperature and filtered through Celite. The filtrate was concentrated to dryness to give 4-tert-butyl-3-methoxyaniline (C-2) (52 mg, 72%) that was used without further purification. HPLC ret. time 2.29 min, 10-99% CH$_3$CN, 5 min run; ESI-MS 180.0 m/z (MH$^+$).

Other Examples

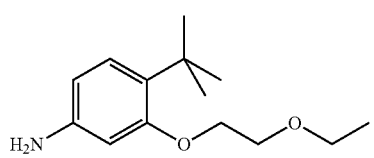

C-3; 3-(2-Ethoxyethoxy)-4-tert-butylbenzenamine 3-(2-Ethoxyethoxy)-4-tert-butylbenzenamine (C-3) was synthesized following the general scheme above starting from 2-tert-butyl-5-nitrophenol (C-1-a) and 1-bromo-2-ethoxyethane. $^1$H NMR (400 MHz, CDCl$_3$) δ 6.97 (d, J=7.9 Hz, 1H), 6.17 (s, 1H), 6.14 (d, J=2.3 Hz, 1H), 4.00 (t, J=5.2 Hz, 2H), 3.76 (t, J=5.2 Hz, 2H), 3.53 (q, J=7.0 Hz, 2H), 1.27 (s, 9H), 1.16 (t, J=7.0 Hz, 3H); HPLC ret. time 2.55 min, 10-99% CH$_3$CN, 5 min run; ESI-MS 238.3 m/z (MH$^+$).

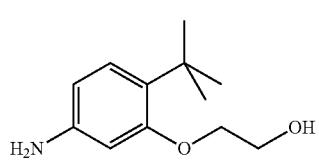

C-4; 2-(2-tert-Butyl-5-aminophenoxy)ethanol 2-(2-tert-Butyl-5-aminophenoxy)ethanol (C-4) was synthesized following the general scheme above starting from 2-tert-butyl-5-nitrophenol (C-1-a) and 2-bromoethanol. HPLC ret. time 2.08 min, 10-99% CH$_3$CN, 5 min run; ESI-MS 210.3 m/z (MH$^+$).

Example 3

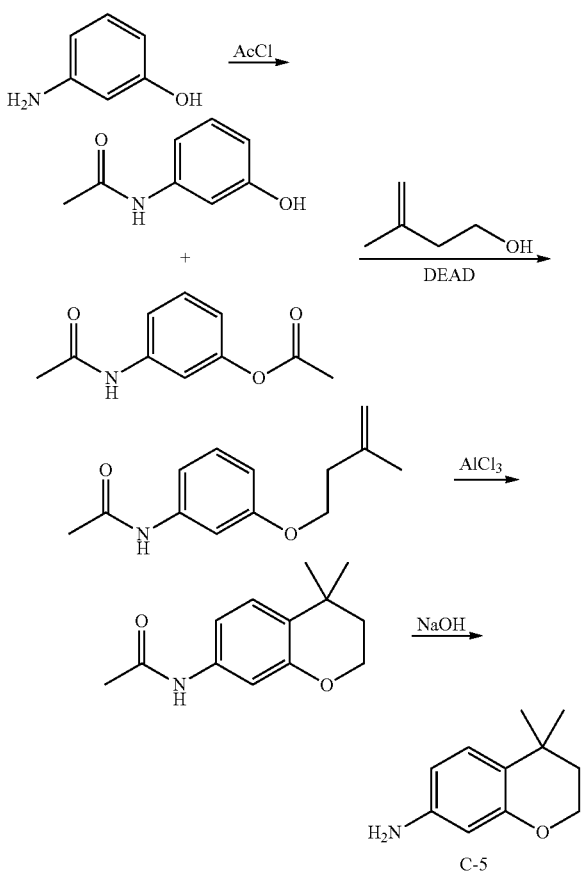

N-(3-Hydroxy-phenyl)-acetamide and acetic acid 3-formylamino-phenyl ester

To a well stirred suspension of 3-amino-phenol (50 g, 0.46 mol) and NaHCO$_3$ (193.2 g, 2.3 mol) in chloroform (1 L) was added dropwise chloroacetyl chloride (46.9 g, 0.6 mol) over a period of 30 min at 0° C. After the addition was complete, the reaction mixture was refluxed overnight and then cooled to room temperature. The excess NaHCO₃ was removed via filtration. The filtrate was poured into water and extracted with EtOAc (300×3 mL). The combined organic layers were washed with brine (500 mL), dried over anhydrous Na₂SO₄ and concentrated under reduced pressure to give a mixture of N-(3-hydroxy-phenyl)-acetamide and acetic acid 3-formylamino-phenyl ester (35 g, 4:1 by NMR analysis). The mixture was used directly in the next step.

N-[3-(3-Methyl-but-3-enyloxy)-phenyl]-acetamide

A suspension of the mixture of N-(3-hydroxy-phenyl)-acetamide and acetic acid 3-formylamino-phenyl ester (18.12 g, 0.12 mol), 3-methyl-but-3-en-1-ol (8.6 g, 0.1 mol), DEAD (87 g, 0.2 mol) and Ph₃P (31.44 g, 0.12 mol) in benzene (250 mL) was heated at reflux overnight and then cooled to room temperature. The reaction mixture was poured into water and the organic layer was separated. The aqueous phase was extracted with EtOAc (300×3 mL). The combined organic layers were washed with brine, dried over anhydrous Na₂SO₄ and concentrated. The residue was purified by column chromatography to give N-[3-(3-methyl-but-3-enyloxy)-phenyl]-acetamide (11 g, 52%).

N-(4,4-Dimethyl-chroman-7-yl)-acetamide

A mixture of N-[3-(3-methyl-but-3-enyloxy)-phenyl]-acetamide (2.5 g, 11.4 mmol) and AlCl₃ (4.52 g, 34.3 mmol) in fluoro-benzene (50 mL) was heated at reflux overnight. After cooling, the reaction mixture was poured into water. The organic layer was separated and the aqueous phase was extracted with EtOAc (40×3 mL). The combined organic layers were washed with brine, dried over anhydrous Na₂SO₄ and concentrated under vacuum. The residue was purified by column chromatography to give N-(4,4-dimethyl-chroman-7-yl)-acetamide (1.35 g, 54%).

C-5; 3,4-Dihydro-4,4-dimethyl-2H-chromen-7-amine

A mixture of N-(4,4-dimethyl-chroman-7-yl)-acetamide (1.35 g, 6.2 mmol) in 20% HCl solution (30 mL) was heated at reflux for 3 h and then cooled to room temperature. The reaction mixture was basified with 10% aq. NaOH to pH 8 and extracted with EtOAc (30×3 mL). The combined organic layers were washed with brine, dried over anhydrous Na₂SO₄ and concentrated to give 3,4-dihydro-4,4-dimethyl-2H-chromen-7-amine (C-5) (1 g, 92%). ¹H NMR (DMSO-d₆) δ 6.87 (d, J=8.4 Hz, 1H), 6.07 (dd, J=8.4, 2.4 Hz, 1H), 5.87 (d, J=2.4 Hz, 1H), 4.75 (s, 2H), 3.99 (t, J=5.4 Hz, 2H), 1.64 (t, J=5.1 Hz, 2H), 1.15 (s, 6H); ESI-MS 178.1 m/z (MH⁺).

Example 4

General scheme:

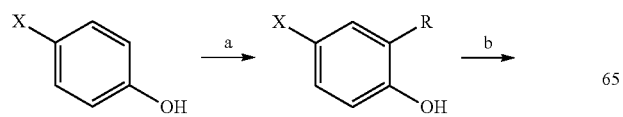

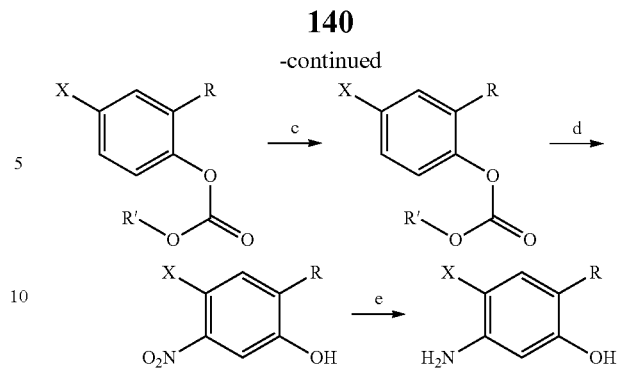

X = F, Cl; a) ROH, H₂SO₄ or MeSO₃H, CH₂Cl₂; b) R'CO₂Cl, Et₃N, 1,4-dioxane or CHCl₃; c) HNO₃, H₂SO₄ or KNO₃, H₂SO₄ or HNO₃, AcOH; d) piperidine, CH₂Cl₂; e) HCO₂NH₄, Pd—C, EtOH or SnCl₂·2H₂O, EtOH or H₂, Pd—C, MeOH.

Specific Example

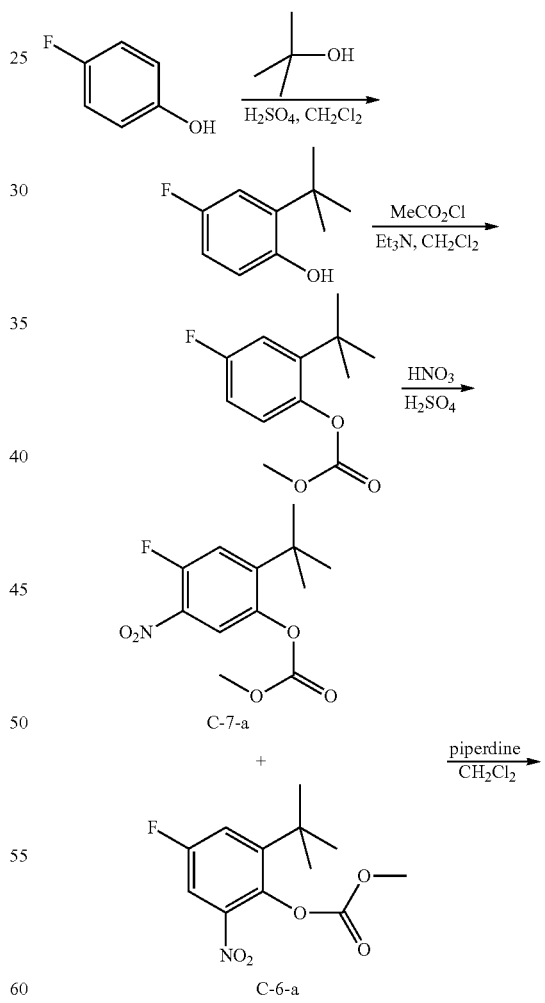

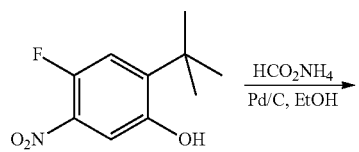

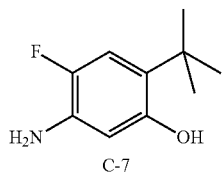

2-tert-Butyl-4-fluorophenol

4-Fluorophenol (5 g, 45 mmol) and tert-butanol (5.9 mL, 63 mmol) were dissolved in CH$_2$Cl$_2$ (80 mL) and treated with concentrated sulfuric acid (98%, 3 mL). The mixture was stirred at room temperature overnight. The organic layer was washed with water, neutralized with NaHCO$_3$, dried over MgSO$_4$ and concentrated. The residue was purified by column chromatography (5-15% EtOAc-Hexane) to give 2-tert-butyl-4-fluorophenol (3.12 g, 42%). $^1$H NMR (400 MHz, DMSO-d$_6$) δ 9.32 (s, 1H), 6.89 (dd, J=11.1, 3.1 Hz, 1H), 6.84-6.79 (m, 1H), 6.74 (dd, J=8.7, 5.3 Hz, 1H), 1.33 (s, 9H).

2-tert-Butyl-4-fluorophenyl methyl carbonate

To a solution of 2-tert-butyl-4-fluorophenol (2.63 g, 15.7 mmol) and NEt$_3$ (3.13 mL, 22.5 mmol) in dioxane (45 mL) was added methyl chloroformate (1.27 mL, 16.5 mmol). The mixture was stirred at room temperature for 1 h. The precipitate was removed via filtration. The filtrate was then diluted with water and extracted with ether. The ether extract was washed with water and dried over MgSO$_4$. After removal of solvent, the residue was purified by column chromatography to give 2-tert-butyl-4-fluorophenyl methyl carbonate (2.08 g, 59%). $^1$H NMR (400 MHz, DMSO-d$_6$) δ 7.24 (dd, J=8.8, 5.4 Hz, 1H), 7.17-7.10 (m, 2H), 3.86 (s, 3H), 1.29 (s, 9H).

2-tert-Butyl-4-fluoro-5-nitrophenyl methyl carbonate (C-7-a) and 2-tert-butyl-4-fluoro-6-nitrophenyl methyl carbonate (C-6-a)

To a solution of 2-tert-butyl-4-fluorophenyl methyl carbonate (1.81 g, 8 mmol) in H$_2$SO$_4$ (98%, 1 mL) was added slowly a cooled mixture of H$_2$SO$_4$ (1 mL) and HNO$_3$ (1 mL) at 0° C. The mixture was stirred for 2 h while warming to room temperature, poured into ice and extracted with diethyl ether. The ether extract was washed with brine, dried over MgSO$_4$ and concentrated. The residue was purified by column chromatography (0-10% EtOAc-Hexane) to give 2-tert-butyl-4-fluoro-5-nitrophenyl methyl carbonate (C-7-a) (1.2 g, 55%) and 2-tert-butyl-4-fluoro-6-nitrophenyl methyl carbonate (C-6-a) (270 mg, 12%). 2-tert-Butyl-4-fluoro-5-nitrophenyl methyl carbonate (C-7-a): $^1$H NMR (400 MHz, DMSO-d$_6$) δ 8.24 (d, J=7.1 Hz, 1H), 7.55 (d, J=13.4 Hz, 1H), 3.90 (s, 3H), 1.32 (s, 9H). 2-tert-butyl-4-fluoro-6-nitrophenyl methyl carbonate (C-6-a): $^1$H NMR (400 MHz, DMSO-d$_6$) δ 8.04 (dd, J=7.6, 3.1 Hz, 1H), 7.69 (dd, J=10.1, 3.1 Hz, 1H), 3.91 (s, 3H), 1.35 (s, 9H).

2-tert-Butyl-4-fluoro-5-nitrophenol

To a solution of 2-tert-butyl-4-fluoro-5-nitrophenyl methyl carbonate (C-7-a) (1.08 g, 4 mmol) in CH$_2$Cl$_2$ (40 mL) was added piperidine (3.94 mL, 10 mmol). The mixture was stirred at room temperature for 1 h and extracted with 1N NaOH (3×). The aqueous layer was acidified with 1N HCl and extracted with diethyl ether. The ether extract was washed with brine, dried (MgSO$_4$) and concentrated to give 2-tert-butyl-4-fluoro-5-nitrophenol (530 mg, 62%). $^1$H NMR (400 MHz, DMSO-d$_6$) δ 10.40 (s, 1H), 7.49 (d, J=6.8 Hz, 1H), 7.25 (d, J=13.7 Hz, 1H), 1.36 (s, 9H).

C-7; 2-tert-Butyl-5-amino-4-fluorophenol

To a refluxing solution of 2-tert-butyl-4-fluoro-5-nitrophenol (400 mg, 1.88 mmol) and ammonium formate (400 mg, 6.1 mmol) in EtOH (20 mL) was added 5% Pd—C (260 mg). The mixture was refluxed for additional 1 h, cooled and filtered through Celite. The solvent was removed by evaporation to give 2-tert-butyl-5-amino-4-fluorophenol (C-7) (550 mg, 83%). $^1$H NMR (400 MHz, DMSO-d$_6$) δ 8.83 (br s, 1H), 6.66 (d, J=13.7 Hz, 1H), 6.22 (d, J=8.5 Hz, 1H), 4.74 (br s, 2H), 1.26 (s, 9H); HPLC ret. time 2.58 min, 10-99% CH$_3$CN, 5 min run; ESI-MS 184.0 m/z (MH$^+$).

Other Examples

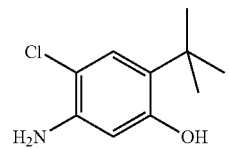

C-10; 2-tert-Butyl-5-amino-4-chlorophenol 2-tert-Butyl-5-amino-4-chlorophenol (C-10) was synthesized following the general scheme above starting from 4-chlorophenol and tert-butanol. Overall yield (6%). HPLC ret. time 3.07 min, 10-99% CH$_3$CN, 5 min run; ESI-MS 200.2 m/z (MH$^+$).

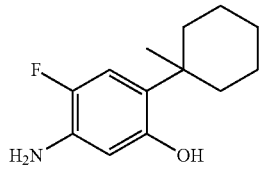 [SMILES: CC1(c2cc(F)c(N)cc2O)CCCCC1]

C-13; 5-Amino-4-fluoro-2-(1-methylcyclohexyl)phenol

5-Amino-4-fluoro-2-(1-methylcyclohexyl)phenol (C-13) was synthesized following the general scheme above starting from 4-fluorophenol and 1-methylcyclohexanol. Overall yield (3%).

HPLC ret. time 3.00 min, 10-99% CH$_3$CN, 5 min run; ESI-MS 224.2 m/z (MH$^+$).

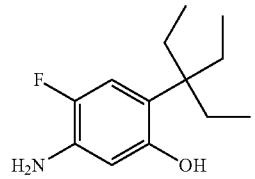

C-19; 5-Amino-2-(3-ethylpentan-3-yl)-4-fluoro-phenol

5-Amino-2-(3-ethylpentan-3-yl)-4-fluoro-phenol (C-19) was synthesized following the general scheme above starting from 4-fluorophenol and 3-ethyl-3-pentanol. Overall yield (1%).

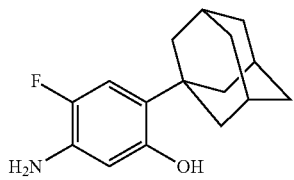

C-20; 2-Admantyl-5-amino-4-fluoro-phenol

2-Admantyl-5-amino-4-fluoro-phenol (C-20) was synthesized following the general scheme above starting from 4-fluorophenol and adamantan-1-ol.

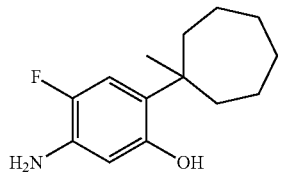

C-21; 5-Amino-4-fluoro-2-(1-methylcycloheptyl)phenol

5-Amino-4-fluoro-2-(1-methylcycloheptyl)phenol (C-21) was synthesized following the general scheme above starting from 4-fluorophenol and 1-methyl-cycloheptanol.

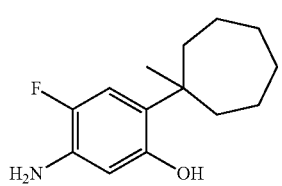 [SMILES: CC1(c2cc(F)c(N)cc2O)CCCCCC1]

C-22; 5-Amino-4-fluoro-2-(1-methylcyclooctyl)phenol

5-Amino-4-fluoro-2-(1-methylcyclooctyl)phenol (C-22) was synthesized following the general scheme above starting from 4-fluorophenol and 1-methyl-cyclooctanol.

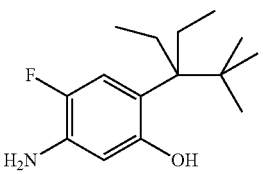

C-23; 5-Amino-2-(3-ethyl-2,2-dimethylpentan-3-yl)-4-fluoro-phenol

5-Amino-2-(3-ethyl-2,2-dimethylpentan-3-yl)-4-fluoro-phenol (C-23) was synthesized following the general scheme above starting from 4-fluorophenol and 3-ethyl-2,2-dimethyl-pentan-3-ol.

Example 5

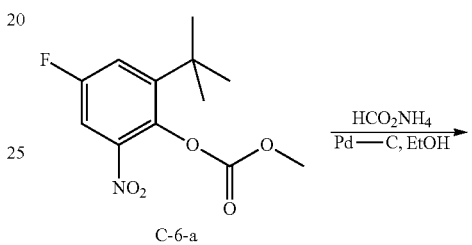

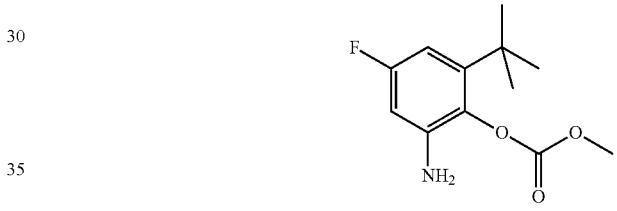

C-6; 2-tert-Butyl-4-fluoro-6-aminophenyl methyl carbonate

To a refluxing solution of 2-tert-butyl-4-fluoro-6-nitrophenyl methyl carbonate (250 mg, 0.92 mmol) and ammonium formate (250 mg, 4 mmol) in EtOH (10 mL) was added 5% Pd—C (170 mg). The mixture was refluxed for additional 1 h, cooled and filtered through Celite. The solvent was removed by evaporation and the residue was purified by column chromatography (0-15%, EtOAc-Hexane) to give 2-tert-butyl-4-fluoro-6-aminophenyl methyl carbonate (C-6) (60 mg, 27%). HPLC ret. time 3.35 min, 10-99% $CH_3CN$, 5 min run; ESI-MS 242.0 m/z ($MH^+$).

Example 6

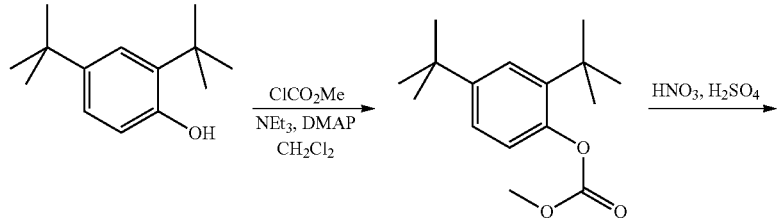

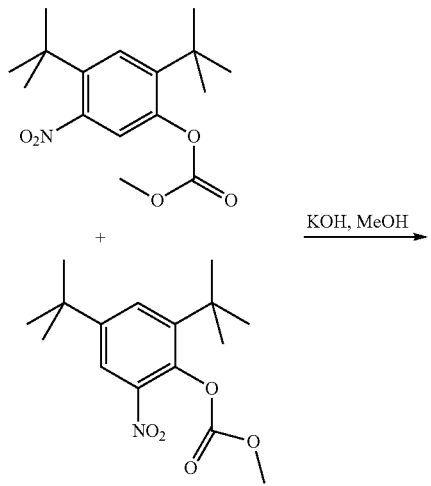
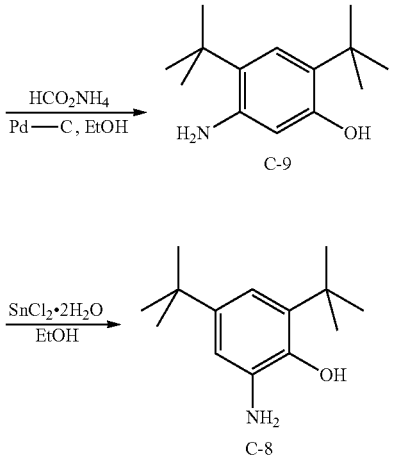

Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et$_3$N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d$_6$) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Carbonic acid 2,4-di-tert-butyl-5-nitro-phenyl ester methyl ester and Carbonic acid 2,4-di-tert-butyl-6-nitro-phenyl ester methyl ester To a stifling mixture of carbonic acid 2,4-di-tert-butyl-phenyl ester methyl ester (4.76 g, 18 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO$_4$), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

2,4-Di-tert-butyl-5-nitro-phenol and 2,4-Di-tert-butyl-6-nitro-phenol

The mixture of carbonic acid 2,4-di-tert-butyl-5-nitro-phenyl ester methyl ester and carbonic acid 2,4-di-tert-butyl-6-nitro-phenyl ester methyl ester (4.2 g, 12.9 mmol) was dissolved in MeOH (65 mL) and KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO$_4$), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d$_6$) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl$_3$) δ 11.48 (s, 1H), 7.98 (d, J=2.5 Hz, 1H), 7.66 (d, J=2.4 Hz, 1H), 1.47 (s, 9H), 1.34 (s, 9H).

C-9; 5-Amino-2,4-di-tert-butyl-phenol

To a refluxing solution of 2,4-di-tert-butyl-5-nitro-phenol (1.86 g, 7.4 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d$_6$) δ 8.64 (s, 1H, OH), 6.84 (s, 1H), 6.08 (s, 1H), 4.39 (s, 2H, NH$_2$), 1.27 (m, 18H);

HPLC ret. time 2.72 min, 10-99% CH$_3$CN, 5 min run; ESI-MS 222.4 m/z (MH$^+$).

C-8; 6-Amino-2,4-di-tert-butyl-phenol

A solution of 2,4-di-tert-butyl-6-nitro-phenol (27 mg, 0.11 mmol) and SnCl$_2$.2H$_2$O (121 mg, 0.54 mmol) in EtOH (1.0 mL) was heated in microwave oven at 100° C. for 30 min. The mixture was diluted with EtOAc and water, basified with sat. NaHCO$_3$ and filtered through Celite. The organic layer was separated and dried over Na$_2$SO$_4$. Solvent was removed by evaporation to provide 6-amino-2,4-di-tert-butyl-phenol (C-8), which was used without further purification.

HPLC ret. time 2.74 min, 10-99% CH$_3$CN, 5 min run; ESI-MS 222.5 m/z (MH$^+$).

Example 7

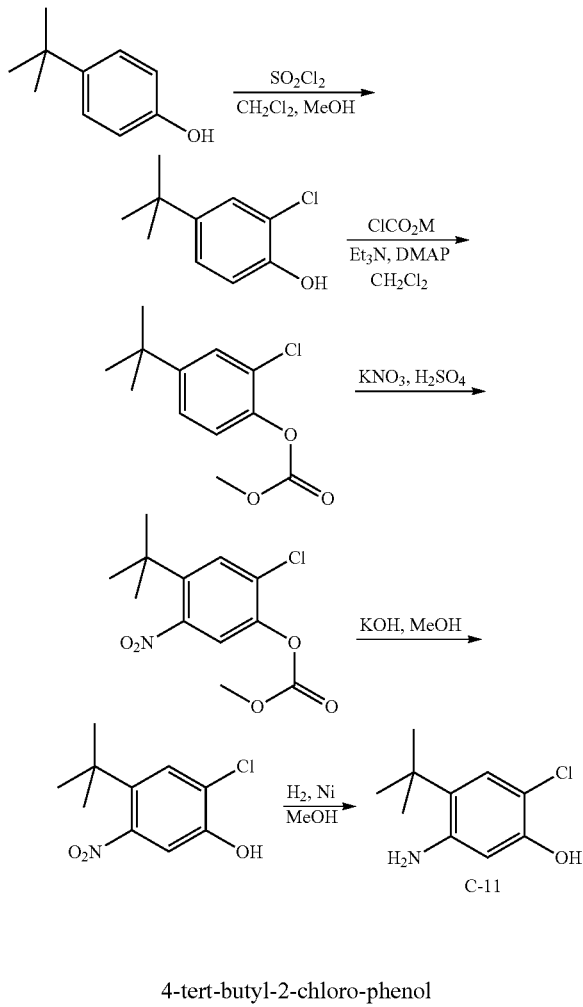

4-tert-butyl-2-chloro-phenol

To a solution of 4-tert-butyl-phenol (40.0 g, 0.27 mol) and SO$_2$Cl$_2$ (37.5 g, 0.28 mol) in CH$_2$Cl$_2$ was added MeOH (9.0 g, 0.28 mol) at 0° C. After addition was complete, the mixture was stirred overnight at room temperature and then water (200 mL) was added. The resulting solution was extracted with ethyl acetate. The combined organic layers were dried over anhydrous Na$_2$SO$_4$, filtered and concentrated under vacuum. The residue was purified by column chromatography (Pet. Ether/EtOAc, 50:1) to give 4-tert-butyl-2-chloro-phenol (47.0 g, 95%).

4-tert-Butyl-2-chlorophenyl methyl carbonate

To a solution of 4-tert-butyl-2-chlorophenol (47.0 g, 0.25 mol) in dichloromethane (200 mL) was added Et$_3$N (50.5 g, 0.50 mol), DMAP (1 g) and methyl chloroformate (35.4 g, 0.38 mol) at 0° C. The reaction was allowed to warm to room temperature and stirred for additional 30 min. The reaction mixture was washed with H$_2$O and the organic layer was dried over Na$_2$SO$_4$ and concentrated to give 4-tert-butyl-2-chlorophenyl methyl carbonate (56.6 g, 92%), which was used directly in the next step.

4-tert-Butyl-2-chloro-5-nitrophenyl methyl carbonate 4-tert-Butyl-2-chlorophenyl methyl carbonate (36.0 g, 0.15 mol) was dissolved in conc. H$_2$SO$_4$ (100 mL) at 0° C. KNO$_3$ (0.53 g, 5.2 mmol) was added in portions over 25 min. The reaction was stirred for 1.5 h and poured into ice (200 g). The aqueous layer was extracted with dichloromethane. The combined organic layers were washed with aq. NaHCO$_3$, dried over Na$_2$SO$_4$ and concentrated under vacuum to give 4-tert-butyl-2-chloro-5-nitrophenyl methyl carbonate (41.0 g), which was used without further purification.

4-tert-Butyl-2-chloro-5-nitro-phenol

Potassium hydroxide (10.1 g, 181 mmol) was added to 4-tert-butyl-2-chloro-5-nitrophenyl methyl carbonate (40.0 g, 139 mmol) in MeOH (100 mL). After 30 min, the reaction was acidified with 1N HCl and extracted with dichloromethane. The combined organic layers were combined, dried over Na$_2$SO$_4$ and concentrated under vacuum. The crude residue was purified by column chromatography (Pet. Ether/EtOAc, 30:1) to give 4-tert-butyl-2-chloro-5-nitro-phenol (23.0 g, 68% over 2 steps).

C-11; 4-tert-Butyl-2-chloro-5-amino-phenol

To a solution of 4-tert-butyl-2-chloro-5-nitro-phenol (12.6 g, 54.9 mmol) in MeOH (50 mL) was added Ni (1.2 g). The reaction was shaken under H$_2$ (1 atm) for 4 h. The reaction mixture was filtered and the filtrate was concentrated. The residue was purified by column chromatography (P.E./EtOAc, 20:1) to give 4-tert-butyl-2-chloro-5-amino-phenol (C-11) (8.5 g, 78%). $^1$H NMR (DMSO-d$_6$) δ 9.33 (s, 1H), 6.80 (s, 1H), 6.22 (s, 1H), 4.76 (s, 1H), 1.23 (s, 9H); ESI-MS 200.1 m/z (MH$^+$).

Example 8

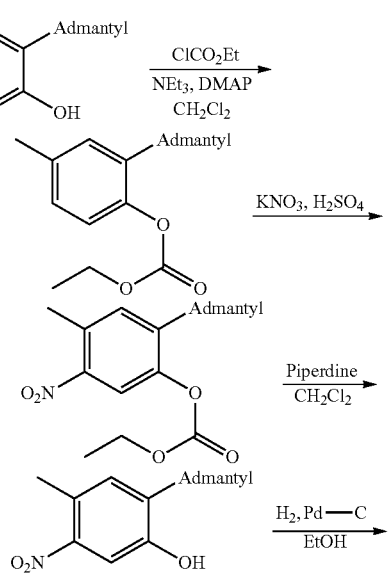

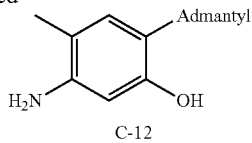

C-12

2-Admantyl-4-methyl-phenyl ethyl carbonate

Ethyl chloroformate (0.64 mL, 6.7 mmol) was added dropwise to a solution of 2-admantyl-4-methylphenol (1.09 g, 4.5 mmol), Et$_3$N (1.25 mL, 9 mmol) and DMAP (catalytic amount) in dichloromethane (8 mL) cooled in an ice-water bath to 0° C. The mixture was allowed to warm to room temperature while stirring overnight, then filtered and the filtrate was concentrated. The residue was purified by column chromatography (10-20% ethyl acetate-hexanes) to yield 2-admantyl-4-methyl-phenyl ethyl carbonate as a yellow oil (1.32 g, 94%).

2-Admantyl-4-methyl-5-nitrophenyl ethyl carbonate

To a cooled solution of 2-admantyl-4-methyl-phenyl ethyl carbonate (1.32 g, 4.2 mmol) in H$_2$SO$_4$ (98%, 10 mL) was added KNO$_3$ (510 mg, 5.0 mmol) in small portions at 0° C. The mixture was stirred for 3 h while warming to room temperature, poured into ice and then extracted with dichloromethane. The combined organic layers were washed with NaHCO$_3$ and brine, dried over MgSO$_4$ and concentrated to dryness. The residue was purified by column chromatography (0-10% EtOAc-Hexane) to yield 2-admantyl-4-methyl-5-nitrophenyl ethyl carbonate (378 mg, 25%).

2-Admantyl-4-methyl-5-nitrophenol

To a solution of 2-admantyl-4-methyl-5-nitrophenyl ethyl carbonate (378 mg, 1.05 mmol) in CH$_2$Cl$_2$ (5 mL) was added piperidine (1.0 mL). The solution was stirred at room temperature for 1 h, adsorbed onto silica gel under reduced pressure and purified by flash chromatography on silica gel (0-15%, EtOAc-Hexanes) to provide 2-admantyl-4-methyl-5-nitrophenol (231 mg, 77%).

C-12; 2-Admantyl-4-methyl-5-aminophenol

To a solution of 2-admantyl-4-methyl-5-nitrophenol (231 mg, 1.6 mmol) in EtOH (2 mL) was added Pd-5% wt on carbon (10 mg). The mixture was stirred under H$_2$ (1 atm) overnight and then filtered through Celite. The filtrate was evaporated to dryness to provide 2-admantyl-4-methyl-5-aminophenol (C-12), which was used without further purification. HPLC ret. time 2.52 min, 10-99% CH$_3$CN, 5 min run; ESI-MS 258.3 m/z (MH$^+$).

Example 9

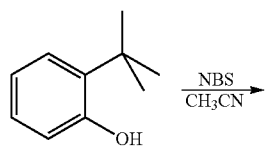

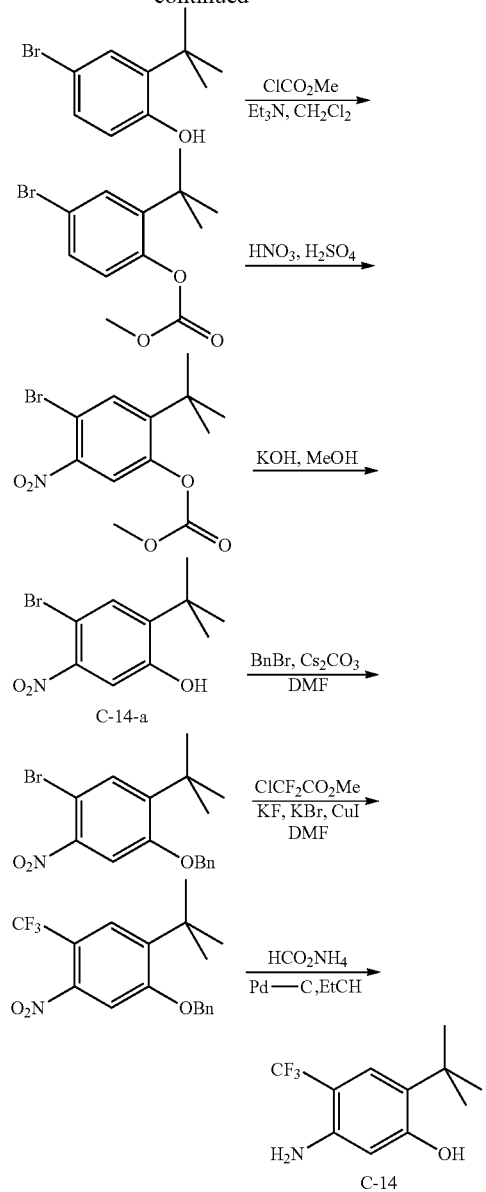

C-14

2-tert-Butyl-4-bromophenol

To a solution of 2-tert-butylphenol (250 g, 1.67 mol) in CH$_3$CN (1500 mL) was added NBS (300 g, 1.67 mol) at room temperature. After addition, the mixture was stirred at room temperature overnight and then the solvent was removed. Petroleum ether (1000 mL) was added, and the resulting white precipitate was filtered off. The filtrate was concentrated under reduced pressure to give the crude 2-tert-butyl-4-bromophenol (380 g), which was used without further purification.

Methyl (2-tert-butyl-4-bromophenyl) carbonate

To a solution of 2-t-butyl-4-bromophenol (380 g, 1.67 mol) in dichloromethane (1000 mL) was added Et$_3$N (202 g, 2 mol) at room temperature. Methyl chloroformate (155 mL) was added dropwise to the above solution at 0° C. After addition, the mixture was stirred at 0° C. for 2 h, quenched with saturated ammonium chloride solution and diluted with water. The organic layer was separated and washed with water and brine, dried over $Na_2SO_4$, and concentrated to provide the crude methyl (2-tert-butyl-4-bromophenyl) carbonate (470 g), which was used without further purification.

Methyl (2-tert-butyl-4-bromo-5-nitrophenyl) carbonate

Methyl (2-tert-butyl-4-bromophenyl) carbonate (470 g, 1.67 mol) was dissolved in conc. $H_2SO_4$ (1000 ml) at 0° C. $KNO_3$ (253 g, 2.5 mol) was added in portions over 90 min. The reaction mixture was stirred at 0° C. for 2 h and poured into ice-water (20 L). The resulting precipitate was collected via filtration and washed with water thoroughly, dried and recrystallized from ether to give methyl (2-tert-butyl-4-bromo-5-nitrophenyl) carbonate (332 g, 60% over 3 steps).

C-14-a; 2-tert-Butyl-4-bromo-5-nitro-phenol

To a solution of methyl (2-tert-butyl-4-bromo-5-nitrophenyl) carbonate (121.5 g, 0.366 mol) in methanol (1000 mL) was added potassium hydroxide (30.75 g, 0.549 mol) in portions. After addition, the mixture was stirred at room temperature for 3 h and acidified with 1N HCl to pH 7. Methanol was removed and water was added. The mixture was extracted with ethyl acetate and the organic layer was separated, dried over $Na_2SO_4$ and concentrated to give 2-tert-butyl-4-bromo-5-nitro-phenol (C-14-a) (100 g, 99%).

1-tert-Butyl-2-(benzyloxy)-5-bromo-4-nitrobenzene

To a mixture of 2-tert-butyl-4-bromo-5-nitrophenol (C-14-a) (1.1 g, 4 mmol) and $Cs_2CO_3$ (1.56 g, 4.8 mmol) in DMF (8 mL) was added benzyl bromide (500 μL, 4.2 mmol). The mixture was stirred at room temperature for 4 h, diluted with $H_2O$ and extracted twice with EtOAc. The combined organic layers were washed with brine and dried over $MgSO_4$. After removal of solvent, the residue was purified by column chloromatography (0-5% EtOAc-Hexane) to yield 1-tert-butyl-2-(benzyloxy)-5-bromo-4-nitrobenzene (1.37 g, 94%). $^1$H NMR (400 MHz, $CDCl_3$) 7.62 (s, 1H), 7.53 (s, 1H), 7.43 (m, 5H), 5.22 (s, 2H), 1.42 (s, 9H).

1-tert-Butyl-2-(benzyloxy)-5-(trifluoromethyl)-4-nitrobenzene

A mixture of 1-tert-butyl-2-(benzyloxy)-5-bromo-4-nitrobenzene (913 mg, 2.5 mmol), KF (291 mg, 5 mmol), KBr (595 mg, 5 mmol), CuI (570 mg, 3 mmol), methyl chlorodifluoroacetate (1.6 mL, 15 mmol) and DMF (5 mL) was stirred at 125° C. in a sealed tube overnight, cooled to room temperature, diluted with water and extracted three times with EtOAc. The combined organic layers were washed with brine and dried over anhydrous $MgSO_4$. After removal of the solvent, the residue was purified by column chromatography (0-5% EtOAc-Hexane) to yield 1-tert-butyl-2-(benzyloxy)-5-(trifluoromethyl)-4-nitrobenzene (591 mg, 67%). $^1$H NMR (400 MHz, $CDCl_3$) 7.66 (s, 1H), 7.37 (m, 5H), 7.19 (s, 1H), 5.21 (s, 2H), 1.32 (s, 9H).

C-14; 5-Amino-2-tert-butyl-4-trifluoromethyl-phenol

To a refluxing solution of 1-tert-butyl-2-(benzyloxy)-5-(trifluoromethyl)-4-nitrobenzene (353 mg, 1.0 mmol) and ammonium formate (350 mg, 5.4 mmol) in EtOH (10 mL) was added 10% Pd—C (245 mg). The mixture was refluxed for additional 2 h, cooled to room temperature and filtered through Celite. After removal of solvent, the residue was purified by column chromatography to give 5-Amino-2-tert-butyl-4-trifluoromethyl-phenol (C-14) (120 mg, 52%).

$^1$H NMR (400 MHz, $CDCl_3$) δ 7.21 (s, 1H), 6.05 (s, 1H), 1.28 (s, 9H); HPLC ret. time 3.46 min, 10-99% $CH_3CN$, 5 min run; ESI-MS 234.1 m/z ($MH^+$).

Example 10

General Scheme:

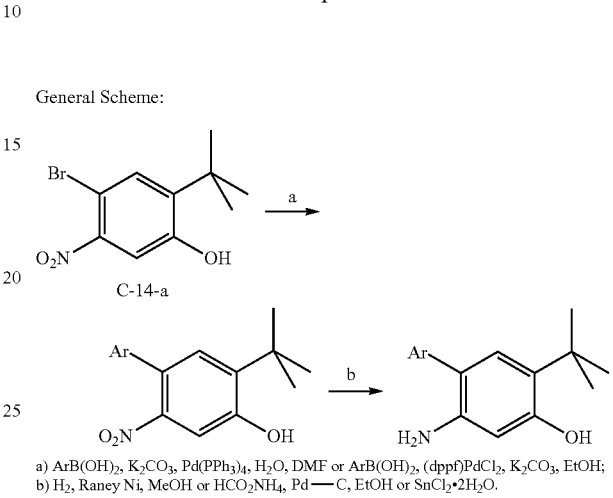

a) $ArB(OH)_2$, $K_2CO_3$, $Pd(PPh_3)_4$, $H_2O$, DMF or $ArB(OH)_2$, (dppf)$PdCl_2$, $K_2CO_3$, EtOH; b) $H_2$, Raney Ni, MeOH or $HCO_2NH_4$, Pd—C, EtOH or $SnCl_2 \cdot 2H_2O$.

Specific Example

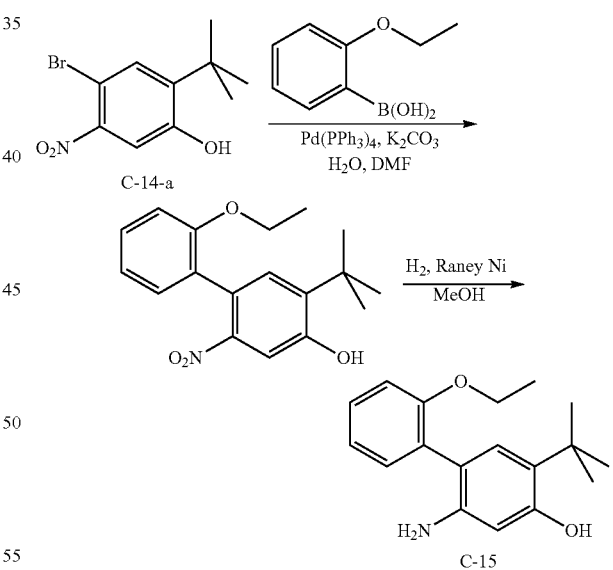

2-tert-Butyl-4-(2-ethoxyphenyl)-5-nitrophenol

To a solution of 2-tert-butyl-4-bromo-5-nitrophenol (C-14-a) (8.22 g, 30 mmol) in DMF (90 mL) was added 2-ethoxyphenyl boronic acid (5.48 g, 33 mmol), potassium carbonate (4.56 g, 33 mmol), water (10 ml) and $Pd(PPh_3)_4$ (1.73 g, 1.5 mmol). The mixture was heated at 90° C. for 3 h under nitrogen. The solvent was removed under reduced pressure. The residue was partitioned between water and ethyl acetate. The combined organic layers were washed with water and brine, dried and purified by column chromatography (petroleum ether-ethyl acetate, 10:1) to afford 2-tert-butyl-4-(2-ethoxyphenyl)-5-nitrophenol (9.2 g, 92%). $^1$HNMR (DMSO-d$_6$) δ 10.38 (s, 1H), 7.36 (s, 1H), 7.28 (m, 2H), 7.08 (s, 1H), 6.99 (t, 1H, J=7.35 Hz), 6.92 (d, 1H, J=8.1 Hz), 3.84 (q, 2H, J=6.6 Hz), 1.35 (s, 9H), 1.09 (t, 3H, J=6.6 Hz); ESI-MS 314.3 m/z (MH$^+$).

C-15;
2-tert-Butyl-4-(2-ethoxyphenyl)-5-aminophenol

To a solution of 2-tert-butyl-4-(2-ethoxyphenyl)-5-nitrophenol (3.0 g, 9.5 mmol) in methanol (30 ml) was added Raney Ni (300 mg). The mixture was stirred under H$_2$ (1 atm) at room temperature for 2 h. The catalyst was filtered off and the filtrate was concentrated. The residue was purified by column chromatography (petroleum ether-ethyl acetate, 6:1) to afford 2-tert-butyl-4-(2-ethoxyphenyl)-5-aminophenol (C-15) (2.35 g, 92%). $^1$HNMR (DMSO-d$_6$) δ 8.89 (s, 1H), 7.19 (t, 1H, J=4.2 Hz), 7.10 (d, 1H, J=1.8 Hz), 7.08 (d, 1H, J=1.8 Hz), 6.94 (t, 1H, J=3.6 Hz), 6.67 (s, 1H), 6.16 (s, 1H), 4.25 (s, 1H), 4.00 (q, 2H, J=6.9 Hz), 1.26 (s, 9H), 1.21 (t, 3H, J=6.9 Hz); ESI-MS 286.0 m/z (MH$^+$).

Other Examples

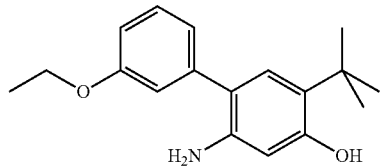 [SMILES: CCOc1cccc(-c2cc(C(C)(C)C)c(O)cc2N)c1]

C-16;
2-tert-Butyl-4-(3-ethoxyphenyl)-5-aminophenol 2-tert-Butyl-4-(3-ethoxyphenyl)-5-aminophenol (C-16) was synthesized following the general scheme above starting from 2-tert-butyl-4-bromo-5-nitrophenol (C-14-a) and 3-ethoxyphenyl boronic acid. HPLC ret. time 2.77 min, 10-99% CH$_3$CN, 5 min run; ESI-MS 286.1 m/z (MH$^+$).

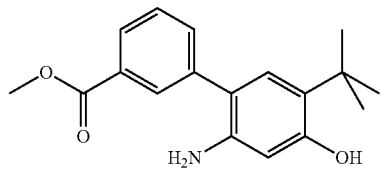 [SMILES: COC(=O)c1cccc(-c2cc(C(C)(C)C)c(O)cc2N)c1]

C-17; 2-tert-Butyl-4-(3-methoxycarbonylphenyl)-5-aminophenol (C-17)

2-tert-Butyl-4-(3-methoxycarbonylphenyl)-5-aminophenol (C-17) was synthesized following the general scheme above starting from 2-tert-butyl-4-bromo-5-nitrophenol (C-14-a) and 3-(methoxycarbonyl)phenylboronic acid. HPLC ret. time 2.70 min, 10-99% CH$_3$CN, 5 min run; ESI-MS 300.5 m/z (MH$^+$).

Example 11

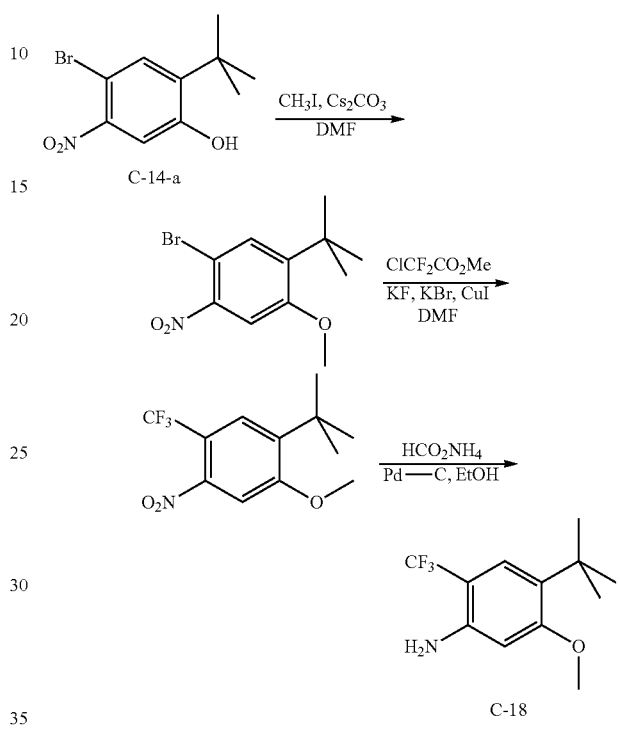

1-tert-Butyl-2-methoxy-5-bromo-4-nitrobenzene

To a mixture of 2-tert-butyl-4-bromo-5-nitrophenol (C-14-a) (1.5 g, 5.5 mmol) and Cs$_2$CO$_3$ (2.2 g, 6.6 mmol) in DMF (6 mL) was added methyl iodide (5150 μL, 8.3 mmol). The mixture was stirred at room temperature for 4 h, diluted with H$_2$O and extracted twice with EtOAc. The combined organic layers were washed with brine and dried over MgSO$_4$. After removal of solvent, the residue was washed with hexane to yield 1-tert-butyl-2-methoxy-5-bromo-4-nitrobenzene (1.1 g, 69%). $^1$H NMR (400 MHz, CDCl$_3$) δ 7.58 (s, 1H), 7.44 (s, 1H), 3.92 (s, 3H), 1.39 (s, 9H).

1-tert-Butyl-2-methoxy-5-(trifluoromethyl)-4-nitrobenzene

A mixture of 1-tert-butyl-2-methoxy-5-bromo-4-nitrobenzene (867 mg, 3.0 mmol), KF (348 mg, 6 mmol), KBr (714 mg, 6 mmol), CuI (684 mg, 3.6 mmol), methyl chlorodifluoroacetate (2.2 mL, 21.0 mmol) in DMF (5 mL) was stirred at 125° C. in a sealed tube overnight, cooled to room temperature, diluted with water and extracted three times with EtOAc. The combined organic layers were washed with brine and dried over anhydrous MgSO$_4$. After removal of the solvent, the residue was purified by column chromatography (0-5% EtOAc-Hexane) to yield 1-tert-butyl-2-methoxy-5-(trifluoromethyl)-4-nitrobenzene (512 mg, 61%). $^1$H NMR (400 MHz, CDCl$_3$) δ 7.60 (s, 1H), 7.29 (s, 1H), 3.90 (s, 3H), 1.33 (s, 9H).

C-18; 1-tert-Butyl-2-methoxy-5-(trifluoromethyl)-4-aminobenzene

To a refluxing solution of 1-tert-butyl-2-methoxy-5-(trifluoromethyl)-4-nitrobenzene (473 mg, 1.7 mmol) and ammonium formate (473 mg, 7.3 mmol) in EtOH (10 mL) was added 10% Pd—C (200 mg). The mixture was refluxed for 1 h, cooled and filtered through Celite. The solvent was removed by evaporation to give 1-tert-butyl-2-methoxy-5-(trifluoromethyl)-4-aminobenzene (C-18) (403 mg, 95%). $^1$H NMR (400 MHz, CDCl$_3$) δ 7.19 (s, 1H), 6.14 (s, 1H), 4.02 (bs, 2H), 3.74 (s, 3H), 1.24 (s, 9H).

Example 12

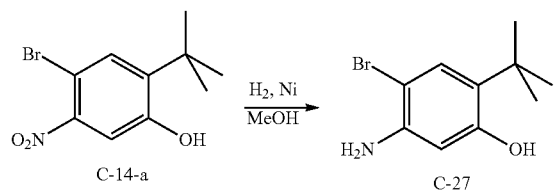

C-27; 2-tert-Butyl-4-bromo-5-amino-phenol

To a solution of 2-tert-butyl-4-bromo-5-nitrophenol (C-14-a) (12 g, 43.8 mmol) in MeOH (90 mL) was added Ni (2.4 g). The reaction mixture was stirred under H$_2$ (1 atm) for 4 h. The mixture was filtered and the filtrate was concentrated. The crude product was recrystallized from ethyl acetate and petroleum ether to give 2-tert-butyl-4-bromo-5-amino-phenol (C-27) (7.2 g, 70%). $^1$H NMR (DMSO-d$_6$) δ 9.15 (s, 1H), 6.91 (s, 1H), 6.24 (s, 1H), 4.90 (br s, 2H), 1.22 (s, 9H); ESI-MS 244.0 m/z (MH$^+$).

Example 13

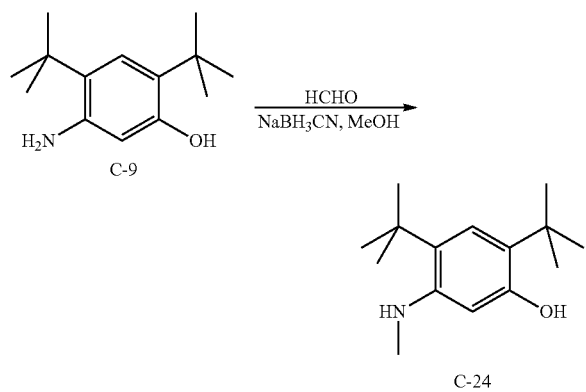

C-24; 2,4-Di-tert-butyl-6-(N-methylamino)phenol

A mixture of 2,4-di-tert-butyl-6-amino-phenol (C-9) (5.08 g, 23 mmol), NaBH$_3$CN (4.41 g, 70 mmol) and paraformaldehyde (2.1 g, 70 mmol) in methanol (50 mL) was stirred at reflux for 3 h. After removal of the solvent, the residue was purified by column chromatography (petroleum ether-EtOAc, 30:1) to give 2,4-di-tert-butyl-6-(N-methylamino) phenol (C-24) (800 mg, 15%). $^1$HNMR (DMSO-d$_6$) δ 8.67 (s, 1H), 6.84 (s, 1H), 5.99 (s, 1H), 4.36 (q, J=4.8 Hz, 1H), 2.65 (d, J=4.8 Hz, 3H), 1.23 (s, 18H); ESI-MS 236.2 m/z (MH$^+$).

Example 14

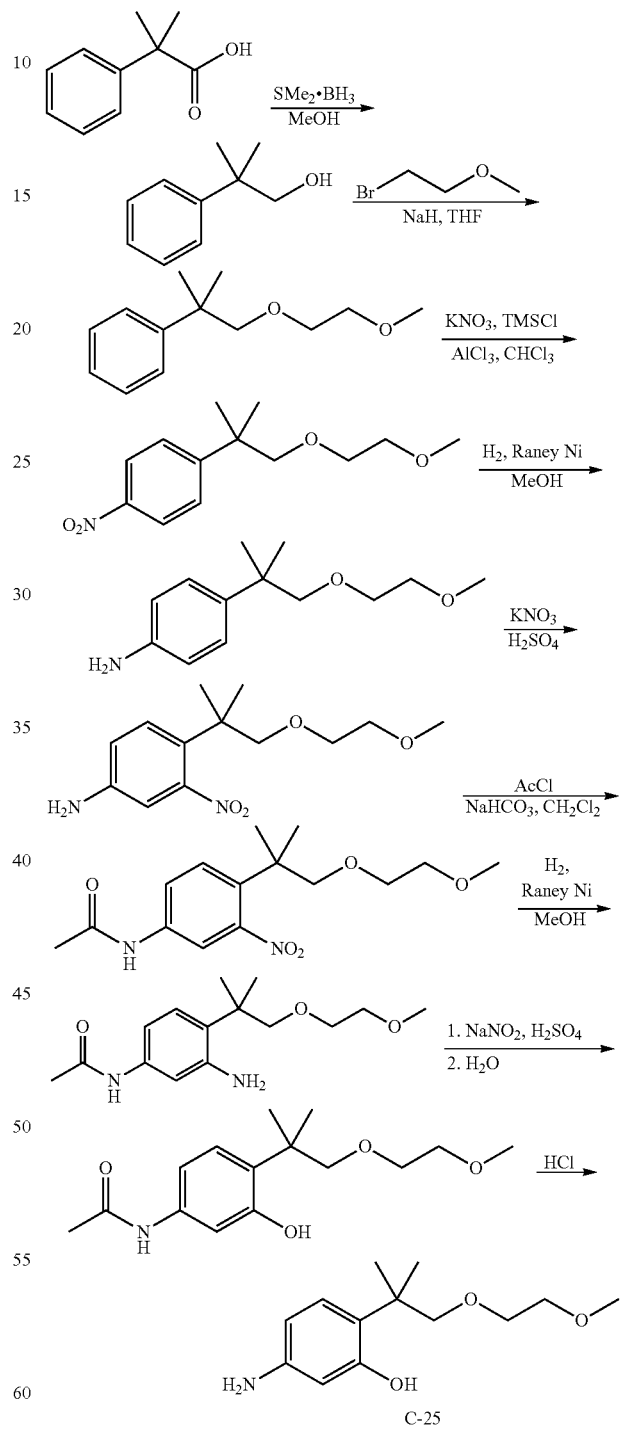

2-Methyl-2-phenyl-propan-1-ol

To a solution of 2-methyl-2-phenyl-propionic acid (82 g, 0.5 mol) in THF (200 mL) was added dropwise borane-dimethyl sulfide (2M, 100 mL) at 0-5° C. The mixture was stirred at this temperature for 30 min and then heated at reflux for 1 h. After cooling, methanol (150 mL) and water (50 mL) were added. The mixture was extracted with EtOAc (100 mL×3), and the combined organic layers were washed with water and brine, dried over Na$_2$SO$_4$ and concentrated to give 2-methyl-2-phenyl-propan-1-ol as an oil (70 g, 77%).

2-(2-Methoxy-ethoxy)-1,1-dimethyl-ethyl]-benzene

To a suspension of NaH (29 g, 0.75 mol) in THF (200 mL) was added dropwise a solution of 2-methyl-2-phenyl-propan-1-ol (75 g, 0.5 mol) in THF (50 mL) at 0° C. The mixture was stirred at 20° C. for 30 min and then a solution of 1-bromo-2-methoxy-ethane (104 g, 0.75 mol) in THF (100 mL) was added dropwise at 0° C. The mixture was stirred at 20° C. overnight, poured into water (200 mL) and extracted with EtOAc (100 mL×3). The combined organic layers were washed with water and brine, dried over Na$_2$SO$_4$, and concentrated. The residue was purified by column chromatography (silica gel, petroleum ether) to give 2-(2-Methoxy-ethoxy)-1,1-dimethyl-ethyl]-benzene as an oil (28 g, 27%).

1-[2-(2-Methoxy-ethoxy)-1,1-dimethyl-ethyl]-4-nitro-benzene

To a solution of 2-(2-methoxy-ethoxy)-1,1-dimethyl-ethyl]-benzene (52 g, 0.25 mol) in CHCl$_3$ (200 mL) was added KNO$_3$ (50.5 g, 0.5 mol) and TMSCl (54 g, 0.5 mol). The mixture was stirred at 20° C. for 30 min and then AlCl$_3$ (95 g, 0.7 mol) was added. The reaction mixture was stirred at 20° C. for 1 h and poured into ice-water. The organic layer was separated and the aqueous layer was extracted with CHCl$_3$ (50 mL×3). The combined organic layers were washed with water and brine, dried over Na$_2$SO$_4$, and concentrated. The residue was purified by column chromatography (silica gel, petroleum ether) to obtain 1-[2-(2-methoxy-ethoxy)-1,1-dimethyl-ethyl]-4-nitro-benzene (6 g, 10%).

4-[2-(2-Methoxy-ethoxy)-1,1-dimethyl-ethyl]-phenylamine

A suspension of 1-[2-(2-methoxy-ethoxy)-1,1-dimethyl-ethyl]-4-nitro-benzene (8.1 g, 32 mmol) and Raney Ni (1 g) in MeOH (50 mL) was stirred under H$_2$ (1 atm) at room temperature for 1 h. The catalyst was filtered off and the filtrate was concentrated to obtain 4-[2-(2-methoxy-ethoxy)-1,1-dimethyl-ethyl]-phenylamine (5.5 g, 77%).

4-[2-(2-Methoxy-ethoxy)-1,1-dimethyl-ethyl]-3-nitro-phenylamine

To a solution of 4-[2-(2-methoxy-ethoxy)-1,1-dimethyl-ethyl]-phenylamine (5.8 g, 26 mmol) in H$_2$SO$_4$ (20 mL) was added KNO$_3$ (2.63 g, 26 mmol) at 0° C. After addition was complete, the mixture was stirred at this temperature for 20 min and then poured into ice-water. The mixture was extracted with EtOAc (50 mL×3). The combined organic layers were washed with water and brine, dried over Na$_2$SO$_4$, and concentrated. The residue was purified by column chromatography (petroleum ether-EtOAc, 100:1) to give 4-[2-(2-methoxy-ethoxy)-1,1-dimethyl-ethyl]-3-nitro-phenylamine (5 g, 71%).

N-{4-[2-(2-Methoxy-ethoxy)-1,1-dimethyl-ethyl]-3-nitro-phenyl}-acetamide

To a suspension of NaHCO$_3$ (10 g, 0.1 mol) in dichloromethane (50 mL) was added 4-[2-(2-methoxy-ethoxy)-1,1-dimethyl-ethyl]-3-nitro-phenylamine (5 g, 30 mmol) and acetyl chloride (3 mL, 20 mmol) at 0-5° C. The mixture was stirred overnight at 15° C. and then poured into water (200 mL). The organic layer was separated and the aqueous layer was extracted with dichloromethane (50 mL×2). The combined organic layers were washed with water and brine, dried over Na$_2$SO$_4$, and concentrated to dryness to give N-{4-[2-(2-methoxy-ethoxy)-1,1-dimethyl-ethyl]-3-nitro-phenyl}-acetamide (5.0 g, 87%).

N-{3-Amino-4-[2-(2-methoxy-ethoxy)-1,1-dimethyl-ethyl]-phenyl}-acetamide

A mixture of N-{4-[2-(2-methoxy-ethoxy)-1,1-dimethyl-ethyl]-3-nitro-phenyl}-acetamide (5 g, 16 mmol) and Raney Ni (1 g) in MeOH (50 mL) was stirred under H$_2$ (1 atm) at room temperature 1 h. The catalyst was filtered off and the filtrate was concentrated. The residue was purified by column chromatography (petroleum ether-EtOAc, 100:1) to give N-{3-amino-4-(2-(2-methoxy-ethoxy)-1,1-dimethyl-ethyl]-phenyl}-acetamide (1.6 g, 35%).

N-{3-Hydroxy-4-[2-(2-methoxy-ethoxy)-1,1-dimethyl-ethyl]-phenyl}-acetamide

To a solution of N-{3-amino-4-[2-(2-methoxy-ethoxy)-1,1-dimethyl-ethyl]-phenyl}-acetamide (1.6 g, 5.7 mmol) in H$_2$SO$_4$ (15%, 6 mL) was added NaNO$_2$ at 0-5° C. The mixture was stirred at this temperature for 20 min and then poured into ice water. The mixture was extracted with EtOAc (30 mL×3). The combined organic layers were washed with water and brine, dried over Na$_2$SO$_4$ and concentrated. The residue was purified by column chromatography (petroleum ether-EtOAc, 100:1) to give N-{3-hydroxy-4-[2-(2-methoxy-ethoxy)-1,1-dimethyl-ethyl]-phenyl}-acetamide (0.7 g, 38%).

C-25; 2-(1-(2-Methoxyethoxy)-2-methylpropan-2-yl)-5-aminophenol

A mixture of N-{3-hydroxy-4-[2-(2-methoxy-ethoxy)-1,1-dimethyl-ethyl]-phenyl}-acetamide (1 g, 3.5 mmol) and HCl (5 mL) was heated at reflux for 1 h. The mixture was basified with Na$_2$CO$_3$ solution to pH 9 and then extracted with EtOAc (20 mL×3). The combined organic layers were washed with water and brine, dried over Na$_2$SO$_4$ and concentrated to dryness. The residue was purified by column chromatography (petroleum ether-EtOAc, 100:1) to obtain 2-(1-(2-methoxyethoxy)-2-methylpropan-2-yl)-5-aminophenol (C-25) (61 mg, 6%). $^1$HNMR (CDCl$_3$) δ 9.11 (br s, 1H), 6.96-6.98 (d, J=8 Hz, 1H), 6.26-6.27 (d, J=4 Hz, 1H), 6.17-6.19 (m, 1H), 3.68-3.69 (m, 2H), 3.56-3.59 (m, 4H), 3.39 (s, 3H), 1.37 (s, 6H); ESI-MS 239.9 m/z (MH$^+$).

Example 15

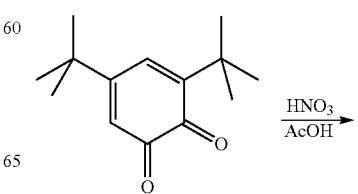

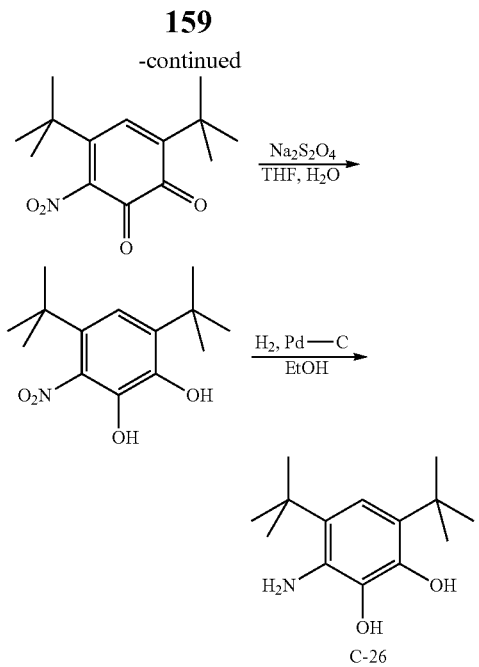

4,6-di-tert-Butyl-3-nitrocyclohexa-3,5-diene-1,2-dione

To a solution of 3,5-di-tert-butylcyclohexa-3,5-diene-1,2-dione (4.20 g, 19.1 mmol) in acetic acid (115 mL) was slowly added HNO$_3$ (15 mL). The mixture was heated at 60° C. for 40 min before it was poured into H$_2$O (50 mL). The mixture was allowed to stand at room temperature for 2 h, then was placed in an ice bath for 1 h. The solid was collected and washed with water to provide 4,6-di-tert-butyl-3-nitrocyclohexa-3,5-diene-1,2-dione (1.2 g, 24%). $^1$H NMR (400 MHz, DMSO-d$_6$) δ 6.89 (s, 1H), 1.27 (s, 9H), 1.24 (s, 9H).

4,6-Di-tert-butyl-3-nitrobenzene-1,2-diol

In a separatory funnel was placed THF/H$_2$O (1:1, 400 mL), 4,6-di-tert-butyl-3-nitrocyclohexa-3,5-diene-1,2-dione (4.59 g, 17.3 mmol) and Na$_2$S$_2$O$_4$ (3 g, 17.3 mmol). The separatory funnel was stoppered and was shaken for 2 min. The mixture was diluted with EtOAc (20 mL). The layers were separated and the organic layer was washed with brine, dried over MgSO$_4$ and concentrated to provide 4,6-di-tert-butyl-3-nitrobenzene-1,2-diol (3.4 g, 74%), which was used without further purification. $^1$H NMR (400 MHz, DMSO-d$_6$) δ 9.24 (s, 1H), 8.76 (s, 1H), 6.87 (s, 1H), 1.35 (s, 9H), 1.25 (s, 9H).

C-26; 4,6-Di-tert-butyl-3-aminobenzene-1,2-diol

To a solution of 4,6-di-tert-butyl-3-nitrobenzene-1,2-diol (1.92 g, 7.2 mmol) in EtOH (70 mL) was added Pd-5% wt. on carbon (200 mg). The mixture was stirred under H$_2$ (1 atm) for 2 h. The reaction was recharged with Pd-5% wt. on carbon (200 mg) and stirred under H$_2$ (1 atm) for another 2 h. The mixture was filtered through Celite and the filtrate was concentrated and purified by column chromatography (10-40% ethyl acetate-hexanes) to give 4,6-di-tert-butyl-3-aminobenzene-1,2-diol (C-26) (560 mg, 33%). $^1$H NMR (400 MHz, CDCl$_3$) δ 7.28 (s, 1H), 1.42 (s, 9H), 1.38 (s, 9H).

Anilines

Example 1

General Scheme

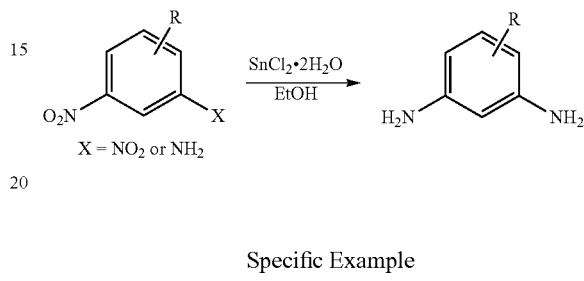

Specific Example

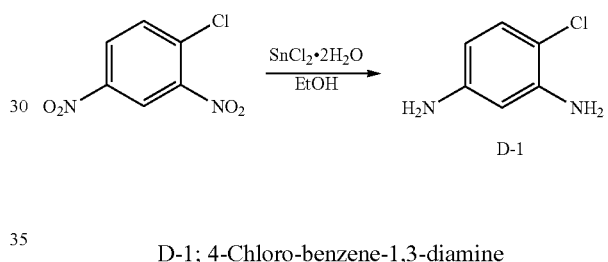

D-1; 4-Chloro-benzene-1,3-diamine

A mixture of 1-chloro-2,4-dinitro-benzene (100 mg, 0.5 mmol) and SnCl$_2$.2H$_2$O (1.12 g, 5 mmol) in ethanol (2.5 mL) was stirred at room temperature overnight. Water was added and then the mixture was basified to pH 7-8 with saturated NaHCO$_3$ solution. The solution was extracted with ethyl acetate. The combined organic layers were washed with brine, dried over Na$_2$SO$_4$, filtered and concentrated to yield 4-chloro-benzene-1,3-diamine (D-1) (79 mg, quant.).

HPLC ret. time 0.38 min, 10-99% CH$_3$CN, 5 min run; ESI-MS 143.1 m/z (MH$^+$)

Other Examples

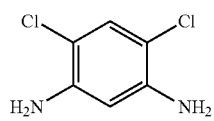

D-2; 4,6-Dichloro-benzene-1,3-diamine 4,6-Dichloro-benzene-1,3-diamine (D-2) was synthesized following the general scheme above starting from 1,5-dichloro-2,4-dinitro-benzene. Yield (95%). HPLC ret. time 1.88 min, 10-99% CH$_3$CN, 5 min run; ESI-MS 177.1 m/z (MH$^+$).

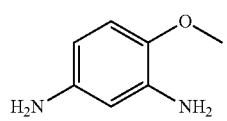

D-3; 4-Methoxy-benzene-1,3-diamine

4-Methoxy-benzene-1,3-diamine (D-3) was synthesized following the general scheme above starting from 1-methoxy-2,4-dinitro-benzene. Yield (quant.). HPLC ret. time 0.31 min, 10-99% $CH_3CN$, 5 min run.

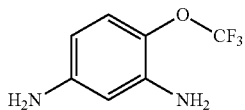

D-4; 4-Trifluoromethoxy-benzene-1,3-diamine

4-Trifluoromethoxy-benzene-1,3-diamine (D-4) was synthesized following the general scheme above starting from 2,4-dinitro-1-trifluoromethoxy-benzene. Yield (89%). HPLC ret. time 0.91 min, 10-99% $CH_3CN$, 5 min run; ESI-MS 193.3 m/z ($MH^+$).

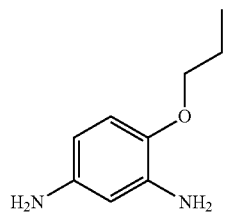

D-5; 4-Propoxybenzene-1,3-diamine

4-Propoxybenzene-1,3-diamine (D-5) was synthesized following the general scheme above starting from 5-nitro-2-propoxy-phenylamine. Yield (79%). HPLC ret. time 0.54 min, 10-99% $CH_3CN$, 5 min run; ESI-MS 167.5 m/z ($MH^+$).

Example 2

General scheme

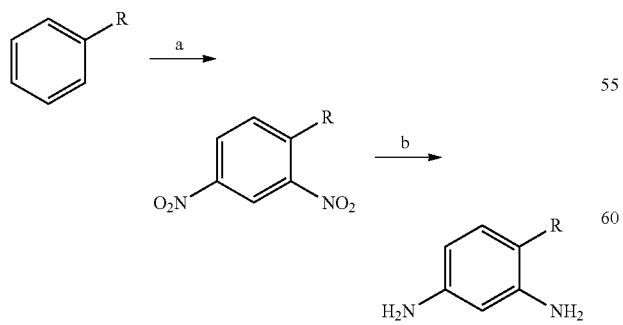

a) $HNO_3$, $H_2SO_4$; b) $SnCl_2 \cdot 2H_2O$, EtOH or $H_2$, Pd—C, MeOH

Specific Example

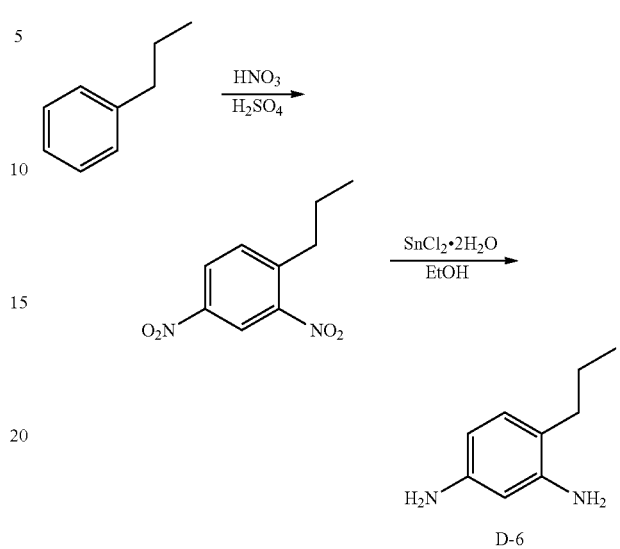

2,4-Dinitro-propylbenzene

A solution of propylbenzene (10 g, 83 mmol) in conc. $H_2SO_4$ (50 mL) was cooled at 0° C. for 30 min, and a solution of conc. $H_2SO_4$ (50 mL) and fuming $HNO_3$ (25 mL), previously cooled to 0° C., was added in portions over 15 min. The mixture was stirred at 0° C. for additional 30 min, and then allowed to warm to room temperature. The mixture was poured into ice (200 g)-water (100 mL) and extracted with ether (2×100 mL). The combined extracts were washed with $H_2O$ (100 mL) and brine (100 mL), dried over $MgSO_4$, filtered and concentrated to afford 2,4-dinitro-propylbenzene (15.6 g, 89%). $^1H$ NMR ($CDCl_3$, 300 MHz) δ 8.73 (d, J=2.2 Hz, 1H), 8.38 (dd, J=8.3, J=2.2, 1H), 7.6 (d, J=8.5 Hz, 1H), 2.96 (dd, 2H), 1.73 (m, 2H), 1.06 (t, J=7.4 Hz, 3H).

D-6; 4-Propyl-benzene-1,3-diamine

To a solution of 2,4-dinitro-propylbenzene (2.02 g, 9.6 mmol) in ethanol (100 mL) was added $SnCl_2$ (9.9 g, 52 mmol) followed by conc. HCl (10 mL). The mixture was refluxed for 2 h, poured into ice-water (100 mL), and neutralized with solid sodium bicarbonate. The solution was further basified with 10% NaOH solution to pH ~10 and extracted with ether (2×100 mL). The combined organic layers were washed with brine (100 mL), dried over $MgSO_4$, filtered, and concentrated to provide 4-propyl-benzene-1,3-diamine (D-6) (1.2 g, 83%). No further purification was necessary for use in the next step; however, the product was not stable for an extended period of time. $^1H$ NMR ($CDCl_3$, 300 MHz) δ 6.82 (d, J=7.9 Hz, 1H), 6.11 (dd, J=7.5, J=2.2 Hz, 1H), 6.06 (d, J=2.2 Hz, 1H), 3.49 (br s, 4H, $NH_2$), 2.38 (t, J=7.4 Hz, 2H), 1.58 (m, 2H), 0.98 (t, J=7.2 Hz, 3H); ESI-MS 151.5 m/z ($MH^+$).

Other Examples

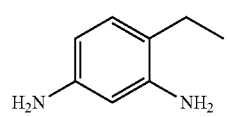

D-7; 4-Ethylbenzene-1,3-diamine

4-Ethylbenzene-1,3-diamine (D-7) was synthesized following the general scheme above starting from ethylbenezene. Overall yield (76%).

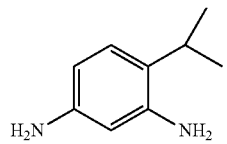

D-8; 4-Isopropylbenzene-1,3-diamine

4-Isopropylbenzene-1,3-diamine (D-8) was synthesized following the general scheme above starting from isopropylbenezene. Overall yield (78%).

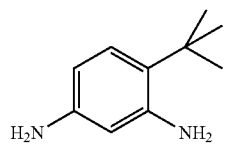

D-9; 4-tert-Butylbenzene-1,3-diamine 4-tert-Butylbenzene-1,3-diamine (D-9) was synthesized following the general scheme above starting from tert-butylbenzene. Overall yield (48%). $^1$H NMR (400 MHz, CDCl$_3$) δ 7.01 (d, J=8.3 Hz, 1H), 6.10 (dd, J=2.4, 8.3 Hz, 1H), 6.01 (d, J=2.4 Hz, 1H), 3.59 (br, 4H), 1.37 (s, 9H); $^{13}$C NMR (100 MHz, CDCl$_3$) δ 145.5, 145.3, 127.6, 124.9, 105.9, 104.5, 33.6, 30.1; ESI-MS 164.9 m/z (MH$^+$).

Example 3

General scheme

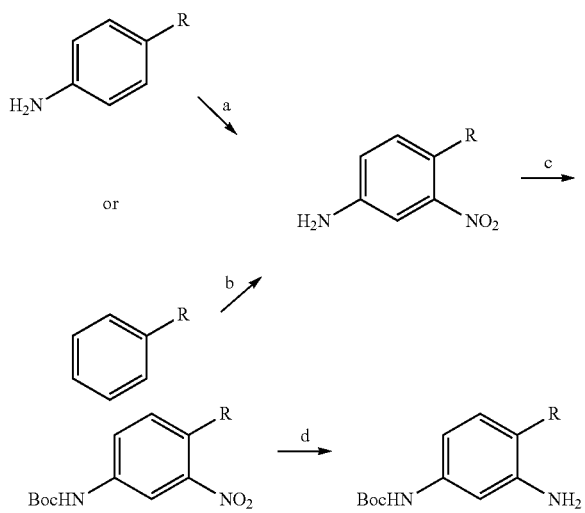

a) KNO$_3$, H$_2$SO$_4$; b) (i) HNO$_3$, H$_2$SO$_4$; (ii) Na$_2$S, S, H$_2$O; c) Boc$_2$O, NaOH, THF; d) H$_2$, Pd—C, MeOH

Specific Example

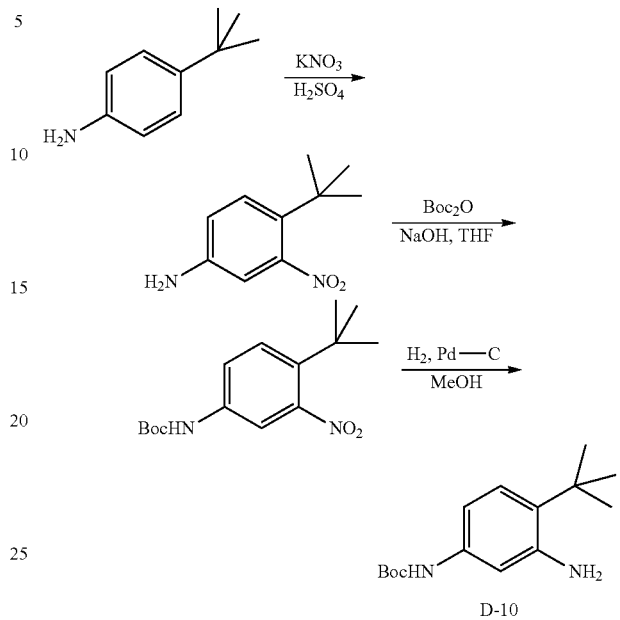

4-tert-Butyl-3-nitro-phenylamine

To a mixture of 4-tert-butyl-phenylamine (10.0 g, 67.01 mmol) dissolved in H$_2$SO$_4$ (98%, 60 mL) was slowly added KNO$_3$ (8.1 g, 80.41 mmol) at 0° C. After addition, the reaction was allowed to warm to room temperature and stirred overnight. The mixture was then poured into ice-water and basified with sat. NaHCO$_3$ solution to pH 8. The mixture was extracted several times with CH$_2$Cl$_2$. The combined organic layers were washed with brine, dried over Na$_2$SO$_4$ and concentrated. The residue was purified by column chromatography (petroleum ether-EtOAc, 10:1) to give 4-tert-butyl-3-nitro-phenylamine (10 g, 77%).

(4-tert-Butyl-3-nitro-phenyl)-carbamic acid tert-butyl ester

A mixture of 4-tert-butyl-3-nitro-phenylamine (4.0 g, 20.6 mmol) and Boc$_2$O (4.72 g, 21.6 mmol) in NaOH (2N, 20 mL) and THF (20 mL) was stirred at room temperature overnight. THF was removed under reduced pressure. The residue was dissolved in water and extracted with CH$_2$Cl$_2$. The organic layer was washed with NaHCO$_3$ and brine, dried over Na$_2$SO$_4$ and concentrated to afford (4-tert-butyl-3-nitro-phenyl)-carbamic acid tert-butyl ester (4.5 g, 74%).

D-10; (3-Amino-4-tert-butyl-phenyl)-carbamic acid tert-butyl ester

A suspension of (4-tert-butyl-3-nitro-phenyl)-carbamic acid tert-butyl ester (3.0 g, 10.19 mol) and 10% Pd—C (1 g) in MeOH (40 mL) was stirred under H$_2$ (1 atm) at room temperature overnight. After filtration, the filtrate was concentrated and the residue was purified by column chromatograph (petroleum ether-EtOAc, 5:1) to give (3-amino-4-tert-butyl-phenyl)-carbamic acid tert-butyl ester (D-10) as a brown oil (2.5 g, 93%). $^1$H NMR (CDCl$_3$) δ 7.10 (d, J=8.4 Hz, 1H), 6.92 (s, 1H), 6.50-6.53 (m, 1H), 6.36 (s, 1H), 3.62 (br s, 2H), 1.50 (s, 9H), 1.38 (s, 9H); ESI-MS 528.9 m/z (2M+H$^+$).

Other Examples

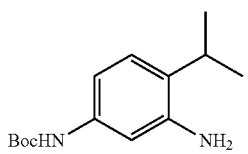

D-11; (3-Amino-4-isopropyl-phenyl)-carbamic acid tert-butyl ester (3-Amino-4-isopropyl-phenyl)-carbamic acid tert-butyl ester (D-11) was synthesized following the general scheme above starting from isopropylbenezene. Overall yield (56%).

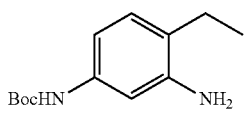 [SMILES: CCc1ccc(NC(=O)OC(C)(C)C)cc1N]

D-12; (3-Amino-4-ethyl-phenyl)-carbamic acid tert-butyl ester (3-Amino-4-ethyl-phenyl)-carbamic acid tert-butyl ester (D-12) was synthesized following the general scheme above starting from ethylbenzene. Overall yield (64%). $^1$H NMR (CD$_3$OD, 300 MHz) δ 6.87 (d, J=8.0 Hz, 1H), 6.81 (d, J=2.2 Hz, 1H), 6.63 (dd, J=8.1, J=2.2, 1H), 2.47 (q, J=7.4 Hz, 2H), 1.50 (s, 9H), 1.19 (t, J=7.4 Hz, 3H); ESI-MS 237.1 m/z (MH$^+$).

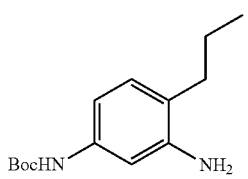

D-13; (3-Amino-4-propyl-phenyl)-carbamic acid tert-butyl ester (3-Amino-4-propyl-phenyl)-carbamic acid tert-butyl ester (D-13) was synthesized following the general scheme above starting from propylbenzene. Overall yield (48%).

Example 4

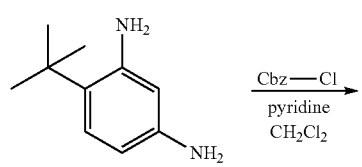

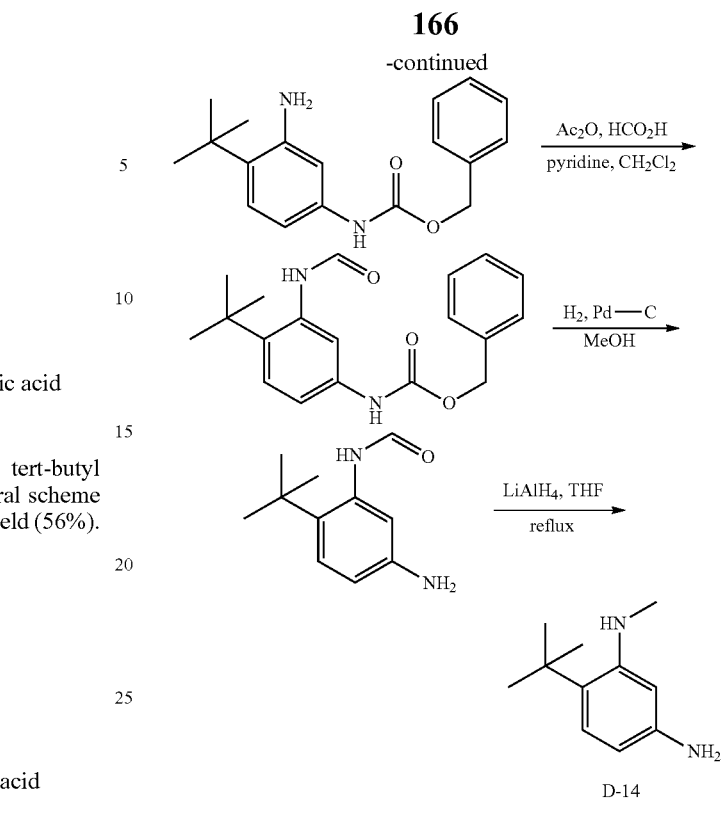

(3-Amino-4-tert-butyl-phenyl)-carbamic acid benzyl ester

A solution of 4-tert-butylbenzene-1,3-diamine (D-9) (657 mg, 4 mmol) and pyridine (0.39 mL, 4.8 mmol) in CH$_2$Cl$_2$/MeOH (12/1, 8 mL) was cooled to 0° C., and a solution of benzyl chloroformate (0.51 mL, 3.6 mmol) in CH$_2$Cl$_2$ (8 mL) was added dropwise over 10 min. The mixture was stirred at 0° C. for 15 min, then warmed to room temperature. After 1 h, the mixture was washed with 1M citric acid (2×20 mL), saturated aqueous sodium bicarbonate (20 mL), dried (Na$_2$SO$_4$), filtered and concentrated in vacuo to afford the crude (3-amino-4-tert-butyl-phenyl)-carbamic acid benzyl ester as a brown viscous gum (0.97 g), which was used without further purification. $^1$H NMR (400 MHz, CDCl$_3$) δ 7.41-7.32 (m, 6H), 7.12 (d, J=8.5 Hz, 1H), 6.89 (br s, 1H), 6.57 (dd, J=2.3, 8.5 Hz, 1H), 5.17 (s, 2H), 3.85 (br s, 2H), 1.38 (s, 9H); $^{13}$C NMR (100 MHz, CDCl$_3$, rotameric) δ 153.3 (br), 145.3, 136.56, 136.18, 129.2, 128.73, 128.59, 128.29, 128.25, 127.14, 108.63 (br), 107.61 (br), 66.86, 33.9, 29.7; ESI-MS 299.1 m/z (MH$^+$).

(4-tert-Butyl-3-formylamino-phenyl)-carbamic acid benzyl ester

A solution of (3-amino-4-tert-butyl-phenyl)-carbamic acid benzyl ester (0.97 g, 3.25 mmol) and pyridine (0.43 mL, 5.25 mmol) in CH$_2$Cl$_2$ (7.5 mL) was cooled to 0° C., and a solution of formic-acetic anhydride (3.5 mmol, prepared by mixing formic acid (158 μL, 4.2 mmol, 1.3 equiv) and acetic anhydride (0.32 mL, 3.5 mmol, 1.1 eq.) neat and ageing for 1 hour) in CH$_2$Cl$_2$ (2.5 mL) was added dropwise over 2 min. After the addition was complete, the mixture was allowed to warm to room temperature, whereupon it deposited a precipitate, and the resulting slurry was stirred overnight. The mixture was washed with 1 M citric acid (2×20 mL), saturated aqueous sodium bicarbonate (20 mL), dried (Na$_2$SO$_4$), and filtered. The cloudy mixture deposited a thin bed of solid above the drying agent, HPLC analysis showed this to be the desired formamide. The filtrate was concentrated to approximately 5 mL, and diluted with hexane (15 mL) to precipitate further formamide. The drying agent (Na$_2$SO$_4$) was slurried with methanol (50 mL), filtered, and the filtrate combined with material from the CH$_2$Cl$_2$/hexane recrystallisation. The resultant mixture was concentrated to afford (4-tert-butyl-3-formylamino-phenyl)-carbamic acid benzyl ester as an off-white solid (650 mg, 50% over 2 steps). $^1$H and $^{13}$C NMR (CD$_3$OD) show the product as a rotameric mixture. $^1$H NMR (400 MHz, CD$_3$OD, rotameric) δ 8.27 (s, 1H-a), 8.17 (s, 1H-b), 7.42-7.26 (m, 8H), 5.17 (s, 1H-a), 5.15 (s, 1H-b), 4.86 (s, 2H), 1.37 (s, 9H-a), 1.36 (s, 9H-b); $^{13}$C NMR (100 MHz, CD$_3$OD, rotameric) δ 1636.9, 163.5, 155.8, 141.40, 141.32, 139.37, 138.88, 138.22, 138.14, 136.4, 135.3, 129.68, 129.65, 129.31, 129.24, 129.19, 129.13, 128.94, 128.50, 121.4 (br), 118.7 (br), 67.80, 67.67, 35.78, 35.52, 31.65, 31.34; ESI-MS 327.5 m/z (MH$^+$).

N-(5-Amino-2-tert-butyl-phenyl)-formamide

A 100 mL flask was charged with (4-tert-butyl-3-formylamino-phenyl)-carbamic acid benzyl ester (650 mg, 1.99 mmol), methanol (30 mL) and 10% Pd—C (50 mg), and stirred under H$_2$ (1 atm) for 20 h. CH$_2$Cl$_2$ (5 mL) was added to quench the catalyst, and the mixture then filtered through Celite, and concentrated to afford N-(5-amino-2-tert-butyl-phenyl)-formamide as an off-white solid (366 mg, 96%). Rotameric by $^1$H and $^{13}$C NMR (DMSO-d$_6$). $^1$H NMR (400 MHz, DMSO-d$_6$, rotameric) δ 9.24 (d, J=10.4 Hz, 1H), 9.15 (s, 1H), 8.23 (d, J=1.5 Hz, 1H), 8.06 (d, J=10.4 Hz, 1H), 7.06 (d, J=8.5 Hz, 1H), 7.02 (d, J=8.5 Hz, 1H), 6.51 (d, J=2.5 Hz, 1H), 6.46 (dd, J=2.5, 8.5 Hz, 1H), 6.39 (dd, J=2.5, 8.5 Hz, 1H), 6.29 (d, J=2.5 Hz, 1H), 5.05 (s, 2H), 4.93 (s, 2H), 1.27 (s, 9H); $^{13}$C NMR (100 MHz, DMSO-d$_6$, rotameric) δ 164.0, 160.4, 147.37, 146.74, 135.38, 135.72, 132.48, 131.59, 127.31, 126.69, 115.15, 115.01, 112.43, 112.00, 33.92, 33.57, 31.33, 30.92; ESI-MS 193.1 m/z (MH$^+$).

D-14; 4-tert-butyl-N$^3$-methyl-benzene-1,3-diamine

A 100 mL flask was charged with N-(5-amino-2-tert-butyl-phenyl)-formamide (340 mg, 1.77 mmol) and purged with nitrogen. THF (10 mL) was added, and the solution was cooled to 0° C. A solution of lithium aluminum hydride in THF (4.4 mL, 1M solution) was added over 2 min. The mixture was then allowed to warm to room temperature. After refluxing for 15 h, the yellow suspension was cooled to 0° C., quenched with water (170 µL), 15% aqueous NaOH (170 µL), and water (510 µL) which were added sequentially and stirred at room temperature for 30 min. The mixture was filtered through Celite, and the filter cake washed with methanol (50 mL). The combined filtrates were concentrated in vacuo to give a gray-brown solid, which was partitioned between chloroform (75 mL) and water (50 mL). The organic layer was separated, washed with water (50 mL), dried (Na$_2$SO$_4$), filtered, and concentrated to afford 4-tert-butyl-N$^3$-methyl-benzene-1,3-diamine (D-14) as a brown oil which solidified on standing (313 mg, 98%). $^1$H NMR (400 MHz, CDCl$_3$) δ 7.01 (d, J=8.1 Hz, 1H), 6.05 (dd, J=2.4, 8.1 Hz, 1H), 6.03 (d, J=2.4 Hz, 1H), 3.91 (br s, 1H), 3.52 (br s, 2H), 2.86 (s, 3H), 1.36 (s, 9H); $^{13}$C NMR (100 MHz, CDCl$_3$) δ 148.4, 145.7, 127.0, 124.3, 103.6, 98.9, 33.5, 31.15, 30.31; ESI-MS 179.1 m/z (MH$^+$).

Example 5

General scheme:

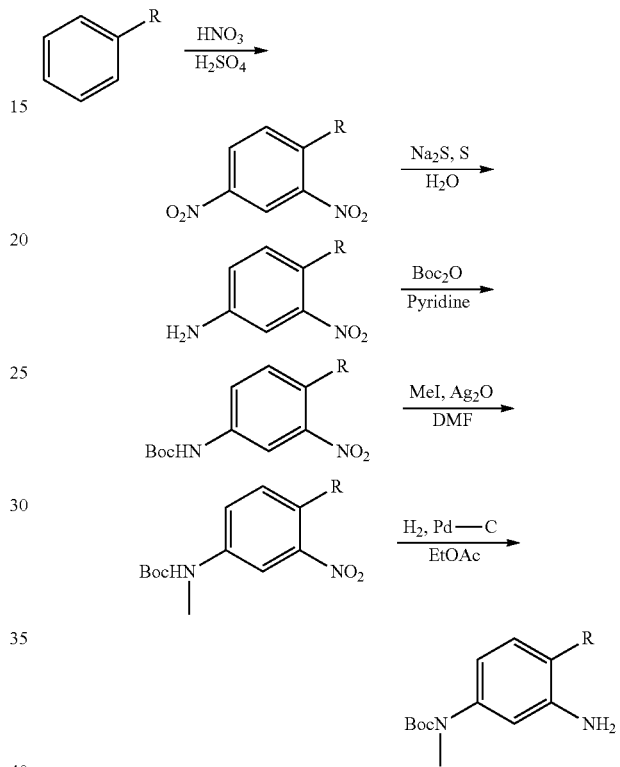

Specific Example

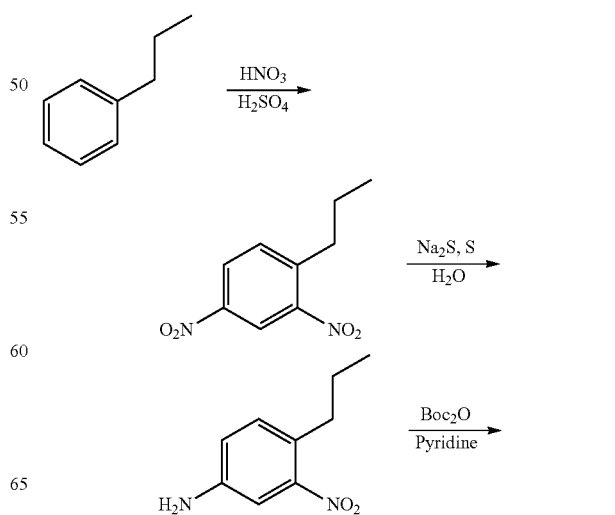

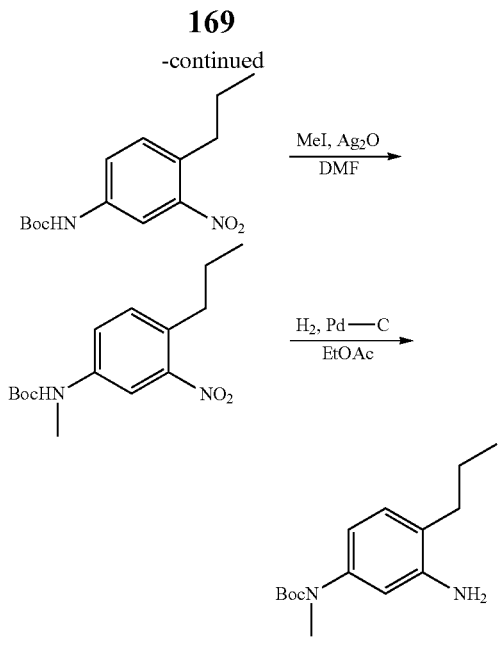

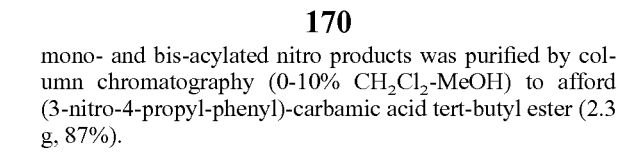

D-15

2,4-Dinitro-propylbenzene

A solution of propylbenzene (10 g, 83 mmol) in conc. $H_2SO_4$ (50 mL) was cooled at 0° C. for 30 mins, and a solution of conc. $H_2SO_4$ (50 mL) and fuming $HNO_3$ (25 mL), previously cooled to 0° C., was added in portions over 15 min. The mixture was stirred at 0° C. for additional 30 min. and then allowed to warm to room temperature. The mixture was poured into ice (200 g)-water (100 mL) and extracted with ether (2×100 mL). The combined extracts were washed with $H_2O$ (100 mL) and brine (100 mL), dried over $MgSO_4$, filtered and concentrated to afford 2,4-dinitro-propylbenzene (15.6 g, 89%). $^1$H NMR (CDCl$_3$, 300 MHz) δ 8.73 (d, J=2.2 Hz, 1H), 8.38 (dd, J=8.3, 2.2 Hz, 1H), 7.6 (d, J=8.5 Hz, 1H), 2.96 (m, 2H), 1.73 (m, 2H), 1.06 (t, J=7.4 Hz, 3H).

4-Propyl-3-nitroaniline

A suspension of 2,4-dinitro-propylbenzene (2 g, 9.5 mmol) in $H_2O$ (100 mL) was heated near reflux and stirred vigorously. A clear orange-red solution of polysulfide (300 mL (10 eq.), previously prepared by heating sodium sulfide nanohydrate (10.0 g), sulfur powder (2.60 g) and $H_2O$ (400 mL), was added dropwise over 45 mins. The red-brown solution was heated at reflux for 1.5 h. The mixture was cooled to 0° C. and then extracted with ether (2×200 mL). The combined organic extracts were dried over $MgSO_4$, filtered, and concentrated under reduced pressure to afford 4-propyl-3-nitroaniline (1.6 g, 93%), which was used without further purification.

(3-Nitro-4-propyl-phenyl)-carbamic acid tert-butyl ester

4-Propyl-3-nitroaniline (1.69 g, 9.4 mmol) was dissolved in pyridine (30 mL) with stirring. Boc anhydride (2.05 g, 9.4 mmol) was added. The mixture was stirred and heated at reflux for 1 h before the solvent was removed in vacuo. The oil obtained was re-dissolved in $CH_2Cl_2$ (300 mL) and washed with water (300 mL) and brine (300 mL), dried over $Na_2SO_4$, filtered, and concentrated. The crude oil that contained both mono- and bis-acylated nitro products was purified by column chromatography (0-10% $CH_2Cl_2$-MeOH) to afford (3-nitro-4-propyl-phenyl)-carbamic acid tert-butyl ester (2.3 g, 87%).

Methyl-(3-nitro-4-propyl-phenyl)-carbamic acid tert-butyl ester

To a solution of (3-nitro-4-propyl-phenyl)-carbamic acid tert-butyl ester (200 mg, 0.71 mmol) in DMF (5 mL) was added $Ag_2O$ (1.0 g, 6.0 mmol) followed by methyl iodide (0.20 mL, 3.2 mmol). The resulting suspension was stirred at room temperature for 18 h and filtered through a pad of Celite. The filter cake was washed with $CH_2Cl_2$ (10 mL). The filtrate was concentrated in vacuo. The crude oil was purified by column chromatography (0-10% $CH_2Cl_2$-MeOH) to afford methyl-(3-nitro-4-propyl-phenyl)-carbamic acid tert-butyl ester as a yellow oil (110 mg, 52%). $^1$H NMR (CDCl$_3$, 300 MHz) δ 7.78 (d, J=2.2 Hz, 1H), 7.42 (dd, J=8.2, 2.2 Hz, 1H), 7.26 (d, J=8.2 Hz, 1H), 3.27 (s, 3H), 2.81 (t, J=7.7 Hz, 2H), 1.66 (m, 2H), 1.61 (s, 9H), 0.97 (t, J=7.4 Hz, 3H).

D-15; (3-Amino-4-propyl-phenyl)-methyl-carbamic acid tert-butyl ester

To a solution of methyl-(3-nitro-4-propyl-phenyl)-carbamic acid tert-butyl ester (110 mg, 0.37 mmol) in EtOAc (10 ml) was added 10% Pd—C (100 mg). The resulting suspension was stirred at room temperature under $H_2$ (1 atm) for 2 days. The progress of the reaction was monitored by TLC. Upon completion, the reaction mixture was filtered through a pad of Celite. The filtrate was concentrated in vacuo to afford (3-Amino-4-propyl-phenyl)-methyl-carbamic acid tert-butyl ester (D-15) as a colorless crystalline compound (80 mg, 81%). ESI-MS 265.3 m/z (MH$^+$).

Other Examples

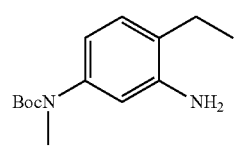 [SMILES: CCc1ccc(N(C)C(=O)OC(C)(C)C)cc1N]

D-16; (3-Amino-4-ethyl-phenyl)-methyl-carbamic acid tert-butyl ester (3-Amino-4-ethyl-phenyl)-methyl-carbamic acid tert-butyl ester (D-16) was synthesized following the general scheme above starting from ethylbenezene. Overall yield (57%).

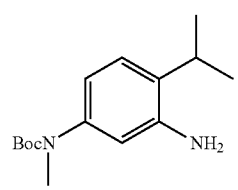 [SMILES: CC(C)c1ccc(N(C)C(=O)OC(C)(C)C)cc1N]

D-17; (3-Amino-4-isopropyl-phenyl)-methyl-carbamic acid tert-butyl ester (3-Amino-4-isopropyl-phenyl)-methyl-carbamic acid tert-butyl ester (D-17) was synthesized following the general scheme above starting from isopropylbenezene. Overall yield (38%).

Example 6

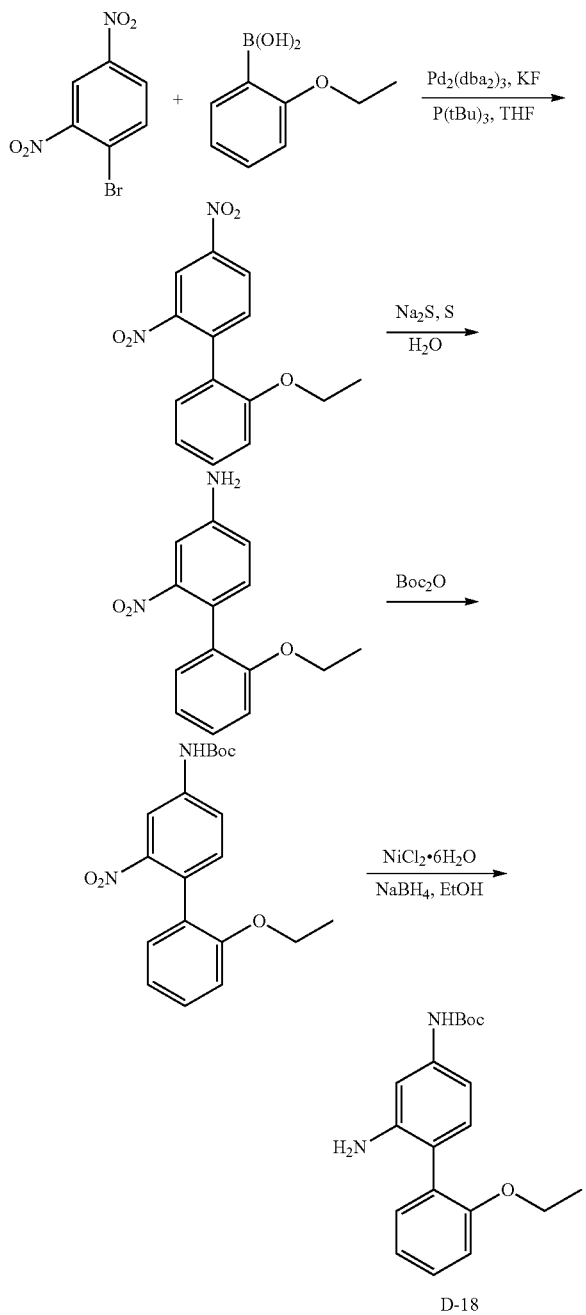

2'-Ethoxy-2,4-dinitro-biphenyl

A pressure flask was charged with 2-ethoxyphenylboronic acid (0.66 g, 4.0 mmol), KF (0.77 g, 13 mmol), Pd₂(dba)₃ (16 mg, 0.02 mmol), and 2,4-dinitro-bromobenzene (0.99 g, 4.0 mmol) in THF (5 mL). The vessel was purged with argon for 1 min followed by the addition of tri-tert-butylphosphine (0.15 ml, 0.48 mmol, 10% solution in hexanes). The reaction vessel was purged with argon for additional 1 min., sealed and heated at 80° C. overnight. After cooling to room temperature, the solution was filtered through a plug of Celite. The filter cake was rinsed with CH$_2$Cl$_2$ (10 mL), and the combined organic extracts were concentrated under reduced pressure to provide the crude product 2'-ethoxy-2,4-dinitro-biphenyl (0.95 g, 82%). No further purification was performed. $^1$H NMR (300 MHz, CDCl$_3$) δ 8.75 (s, 1H), 8.43 (d, J=8.7 Hz, 1H), 7.60 (d, J=8.4 Hz, 1H), 7.40 (t, J=7.8 Hz, 1H), 7.31 (d, J=7.5 Hz, 1H), 7.08 (t, J=7.5 Hz, 1H), 6.88 (d, J=8.4 Hz, 1H), 3.44 (q, J=6.6 Hz, 2H), 1.24 (t, J=6.6 Hz, 3H); HPLC ret. time 3.14 min, 10-100% CH$_3$CN, 5 min gradient.

2'-Ethoxy-2-nitrobiphenyl-4-yl amine

A clear orange-red solution of polysulfide (120 ml, 7.5 eq.), previously prepared by heating sodium sulfide monohydrate (10 g), sulfur (1.04 g) and water (160 ml), was added dropwise at 90° C. over 45 minutes to a suspension of 2'-ethoxy-2,4-dinitro-biphenyl (1.2 g, 4.0 mmol) in water (40 ml). The red-brown solution was heated at reflux for 1.5 h. The mixture was cooled to room temperature, and solid NaCl (5 g) was added. The solution was extracted with CH$_2$Cl$_2$ (3×50 mL), and the combined organic extracts was concentrated to provide 2'-ethoxy-2-nitrobiphenyl-4-yl amine (0.98 g, 95%) that was used in the next step without further purification. $^1$H NMR (300 MHz, CDCl$_3$) δ 7.26 (m, 2H), 7.17 (d, J=2.7 Hz, 1H), 7.11 (d, J=7.8 Hz, 1H), 7.00 (t, J=6.9 Hz, 1H), 6.83 (m, 2H), 3.91 (q, J=6.9 Hz, 2H), 1.23 (t, J=7.2 Hz, 3H); HPLC ret. time 2.81 min, 10-100% CH$_3$CN, 5 min gradient; ESI-MS 259.1 m/z (MH$^+$).

(2'-Ethoxy-2-nitrobiphenyl-4-yl)-carbamic acid tert-butyl ester

A mixture of 2'-ethoxy-2-nitrobipenyl-4-yl amine (0.98 g, 4.0 mmol) and Boc$_2$O (2.6 g, 12 mmol) was heated with a heat gun. Upon the consumption of the starting material as indicated by TLC, the crude mixture was purified by flash chromatography (silica gel, CH$_2$Cl$_2$) to provide (2'-ethoxy-2-nitrobiphenyl-4-yl)-carbamic acid tert-butyl ester (1.5 g, 83%). $^1$H NMR (300 MHz, CDCl$_3$) δ 7.99 (s, 1H), 7.55 (d, J=8.4 Hz, 1H), 7.25 (m, 3H), 6.99 (t, J=7.5 Hz, 1H), 6.82 (m, 2H), 3.88 (q, J=6.9 Hz, 2H), 1.50 (s, 9H), 1.18 (t, J=6.9 Hz, 3H); HPLC ret. time 3.30 min, 10-100% CH$_3$CN, 5 min gradient.

D-18; (2'-ethoxy-2-aminobiphenyl-4-yl)-carbamic acid tert-butyl ester

To a solution of NiCl$_2$.6H$_2$O (0.26 g, 1.1 mmol) in EtOH (5 mL) was added NaBH$_4$ (40 mg, 1.1 mmol) at −10° C. Gas evolution was observed and a black precipitate was formed. After stirring for 5 min, a solution of 2'-ethoxy-2-nitrobiphenyl-4-yl)carbamic acid tert-butyl ester (0.50 g, 1.1 mmol) in EtOH (2 mL) was added. Additional NaBH$_4$ (80 mg, 60 mmol) was added in 3 portions over 20 min. The reaction was stirred at 0° C. for 20 min followed by the addition of NH$_4$OH (4 mL, 25% aq. solution). The resulting solution was stirred for 20 min. The crude mixture was filtered through a short plug of silica. The silica cake was flushed with 5% MeOH in CH$_2$Cl$_2$ (10 mL), and the combined organic extracts was concentrated under reduced pressure to provide (2'-ethoxy-2-aminobiphenyl-4-yl)-carbamic acid tert-butyl ester (D-18)

(0.36 g, quant.), which was used without further purification. HPLC ret. time 2.41 min, 10-100% CH₃CN, 5 min gradient; ESI-MS 329.3 m/z (MH⁺).

Example 7

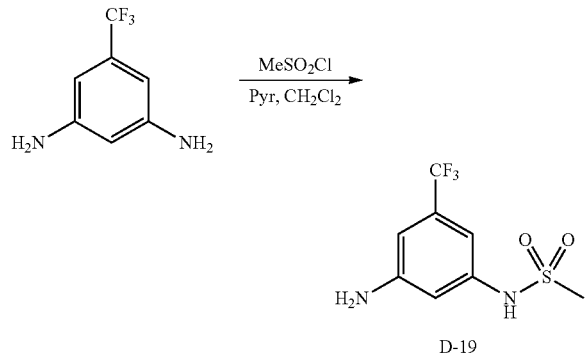

D-19; N-(3-Amino-5-trifluoromethyl-phenyl)-methanesulfonamide

A solution of 5-trifluoromethyl-benzene-1,3-diamine (250 mg, 1.42 mmol) in pyridine (0.52 mL) and CH₂Cl₂ (6.5 mL) was cooled to 0° C. Methanesulfonyl chloride (171 mg, 1.49 mmol) was slowly added at such a rate that the temperature of the solution remained below 10° C. The mixture was stirred at ~8° C. and then allowed to warm to room temperature after 30 min. After stirring at room temperature for 4 h, reaction was almost complete as indicated by LCMS analysis. The reaction mixture was quenched with sat. aq. NH₄Cl (10 mL) solution, extracted with CH₂Cl₂ (4×10 mL), dried over Na₂SO₄, filtered, and concentrated to yield N-(3-amino-5-trifluoromethyl-phenyl)-methanesulfonamide (D-19) as a reddish semi-solid (0.35 g, 97%), which was used without further purification. ¹H-NMR (CDCl₃, 300 MHz) δ 6.76 (m, 1H), 6.70 (m, 1H), 6.66 (s, 1H), 3.02 (s, 3H); ESI-MS 255.3 m/z (MH⁺).

Cyclic amines

Example 1

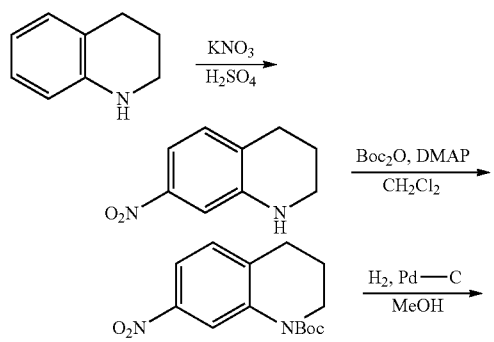

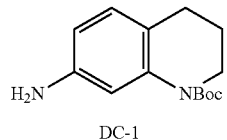

7-Nitro-1,2,3,4-tetrahydro-quinoline

To a mixture of 1,2,3,4-tetrahydro-quinoline (20.0 g, 0.15 mol) dissolved in H₂SO₄ (98%, 150 mL), KNO₃ (18.2 g, 0.18 mol) was slowly added at 0° C. The reaction was allowed to warm to room temperature and stirred over night. The mixture was then poured into ice-water and basified with sat. NaHCO₃ solution to pH 8. After extraction with CH₂Cl₂, the combined organic layers were washed with brine, dried over Na₂SO₄ and concentrated. The residue was purified by column chromatography (petroleum ether-EtOAc, 10:1) to give 7-nitro-1,2,3,4-tetrahydro-quinoline (6.6 g, 25%).

7-Nitro-3,4-dihydro-2H-quinoline-1-carboxylic acid tert-butyl ester

A mixture of 7-nitro-1,2,3,4-tetrahydro-quinoline (4.0 g, 5.61 mmol), Boc₂O (1.29 g, 5.89 mmol) and DMAP (0.4 g) in CH₂Cl₂ was stirred at room temperature overnight. After diluted with water, the mixture was extracted with CH₂Cl₂. The combined organic layers were washed with NaHCO₃ and brine, dried over Na₂SO₄ and concentrated to provide crude 7-nitro-3,4-dihydro-2H-quinoline-1-carboxylic acid tert-butyl ester that was used in the next step without further purification.

DC-1; tert-Butyl 7-amino-3,4-dihydroquinoline-1(2H)-carboxylate

A suspension of the crude 7-nitro-3,4-dihydro-2H-quinoline-1-carboxylic acid tert-butyl ester (4.5 g, 16.2 mol) and 10% Pd—C (0.45 g) in MeOH (40 mL) was stirred under H₂ (1 atm) at room temperature overnight. After filtration, the filtrate was concentrated and the residue was purified by column chromatography (petroleum ether-EtOAc, 5:1) to give tert-butyl 7-amino-3,4-dihydroquinoline-1(2H)-carboxylate (DC-1) as a brown solid (1.2 g, 22% over 2 steps). ¹H NMR (CDCl₃) δ 7.15 (d, J=2 Hz, 1H), 6.84 (d, J=8 Hz, 1H), 6.36-6.38 (m, 1H), 3.65-3.68 (m, 2H), 3.10 (br s, 2H), 2.66 (t, J=6.4 Hz, 2H), 1.84-1.90 (m, 2H), 1.52 (s, 9H); ESI-MS 496.8 m/z (2M+H⁺).

Example 2

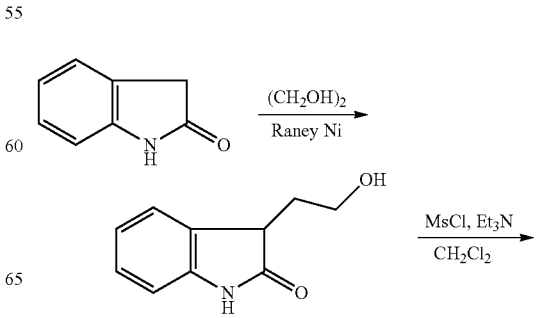

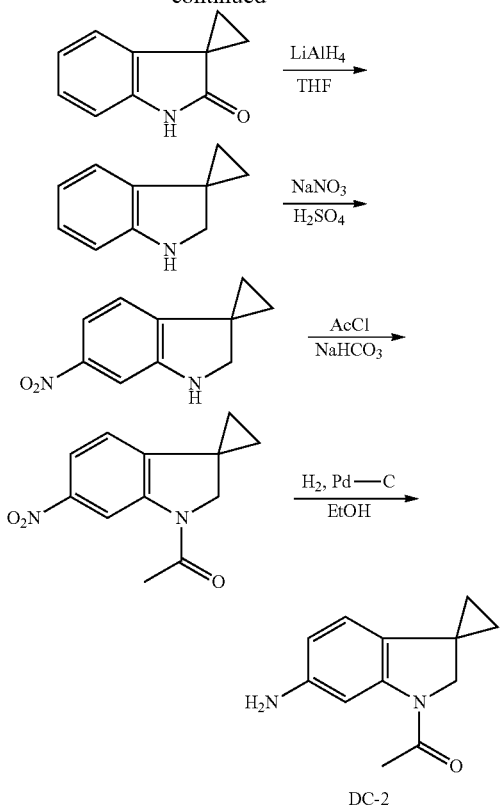

3-(2-Hydroxy-ethyl)-1,3-dihydro-indol-2-one

A stirling mixture of oxindole (5.7 g, 43 mmol) and Raney nickel (10 g) in ethane-1,2-diol (100 mL) was heated in an autoclave. After the reaction was complete, the mixture was filtered and the excess of diol was removed under vacuum. The residual oil was triturated with hexane to give 3-(2-hydroxy-ethyl)-1,3-dihydro-indol-2-one as a colorless crystalline solid (4.6 g, 70%).

1,2-Dihydro-3-spiro-1'-cyclopropyl-1H-indole-2-one

To a solution of 3-(2-hydroxy-ethyl)-1,3-dihydro-indol-2-one (4.6 g, 26 mmol) and triethylamine (10 mL) in $CH_2Cl_2$ (100 mL) was added MsCl (3.4 g, 30 mmol) dropwise at -20° C. The mixture was then allowed to warm up to room temperature and stirred overnight. The mixture was filtered and the filtrate was concentrated under vacuum. The residue was purified by column chromatography to give crude 1,2-dihydro-3-spiro-1'-cyclopropyl-1H-indole-2-one as a yellow solid (2.5 g), which was used directly in the next step.

1,2-Dihydro-3-spiro-1'-cyclopropyl-1H-indole

To a solution of 1,2-dihydro-3-spiro-1'-cyclopropyl-1H-indole-2-one (2.5 g crude) in THF (50 mL) was added $LiAlH_4$ (2 g, 52 mmol) portionwise. After heating the mixture to reflux, it was poured into crushed ice, basified with aqueous ammonia to pH 8 and extracted with EtOAc. The combined organic layers were washed with brine, dried over $Na_2SO_4$ and concentrated to give the crude 1,2-dihydro-3-spiro-1'-cyclopropyl-1H-indole as a yellow solid (about 2 g), which was used directly in the next step.

6-Nitro-1,2-dihydro-3-spiro-1'-cyclopropyl-1H-indole

To a cooled solution (-5° C. to -10° C.) of $NaNO_3$ (1.3 g, 15.3 mmol) in $H_2SO_4$ (98%, 30 mL) was added 1,2-dihydro-3-spiro-1'-cyclopropyl-1H-indole (2 g, crude) dropwise over a period of 20 min. After addition, the reaction mixture was stirred for another 40 min and poured over crushed ice (20 g). The cooled mixture was then basified with $NH_4OH$ and extracted with EtOAc. The organic layer was washed with brine, dried over $Na_2SO_4$, and concentrated under reduced pressure to yield 6-nitro-1,2-dihydro-3-spiro-1'-cyclopropyl-1H-indole as a dark gray solid (1.3 g)

1-Acetyl-6-nitro-1,2-dihydro-3-spiro-1'-cyclopropyl-1H-indole $NaHCO_3$ (5 g) was suspended in a solution of 6-nitro-1,2-dihydro-3-spiro-1'-cyclopropyl-1H-indole (1.3 g, crude) in $CH_2Cl_2$ (50 mL). While stirling vigorously, acetyl chloride (720 mg) was added dropwise. The mixture was stirred for 1 h and filtered. The filtrate was concentrated under vacuum. The residue was purified by flash column chromatography on silica gel to give 1-acetyl-6-nitro-1,2-dihydro-3-spiro-1'-cyclopropyl-1H-indole (0.9 g, 15% over 4 steps).

DC-2; 1-Acetyl-6-amino-1,2-dihydro-3-spiro-1'-cyclopropyl-1H-indole

A mixture of 1-acetyl-6-nitro-1,2-dihydro-3-spiro-1'-cyclopropyl-1H-indole (383 mg, 2 mmol) and Pd—C (10%, 100 mg) in EtOH (50 mL) was stirred at room temperature under $H_2$ (1 atm) for 1.5 h. The catalyst was filtered off and the filtrate was concentrated under reduced pressure. The residue was treated with HCl/MeOH to give 1-acetyl-6-amino-1,2-dihydro-3-spiro-1'-cyclopropyl-1H-indole (DC-2) (300 mg, 90%) as a hydrochloride salt.

Example 3

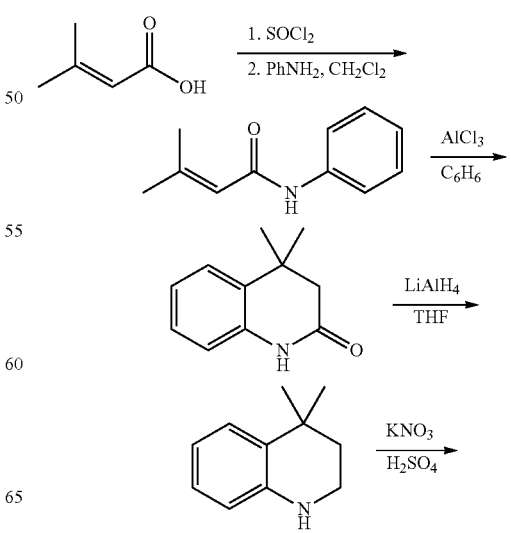

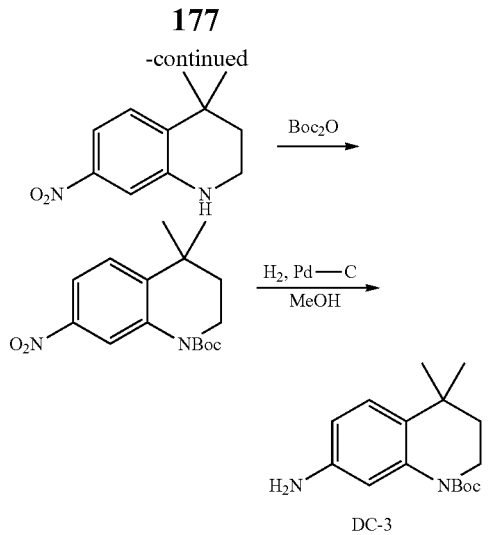

3-Methyl-but-2-enoic acid phenylamide

A mixture of 3-methyl-but-2-enoic acid (100 g, 1 mol) and SOCl₂ (119 g, 1 mol) was heated at reflux for 3 h. The excess SOCl₂ was removed under reduced pressure. CH₂Cl₂ (200 mL) was added followed by the addition of aniline (93 g, 1.0 mol) in Et₃N (101 g, 1 mol) at 0° C. The mixture was stirred at room temperature for 1 h and quenched with HCl (5%, 150 mL). The aqueous layer was separated and extracted with CH₂Cl₂. The combined organic layers were washed with water (2×100 mL) and brine (100 mL), dried over Na₂SO₄ and concentrated to give 3-methyl-but-2-enoic acid phenylamide (120 g, 80%).

4,4-Dimethyl-3,4-dihydro-1H-quinolin-2-one

AlCl₃ (500 g, 3.8 mol) was carefully added to a suspension of 3-methyl-but-2-enoic acid phenylamide (105 g, 0.6 mol) in benzene (1000 mL). The reaction mixture was stirred at 80° C. overnight and poured into ice-water. The organic layer was separated and the aqueous layer was extracted with ethyl acetate (250 mL×3). The combined organic layers were washed with water (200 mL×2) and brine (200 mL), dried over Na₂SO₄ and concentrated to give 4,4-dimethyl-3,4-dihydro-1H-quinolin-2-one (90 g, 86%).

4,4-Dimethyl-1,2,3,4-tetrahydro-quinoline

A solution of 4,4-dimethyl-3,4-dihydro-1H-quinolin-2-one (35 g, 0.2 mol) in THF (100 mL) was added dropwise to a suspension of LiAlH₄ (18 g, 0.47 mol) in THF (200 mL) at 0° C. After addition, the mixture was stirred at room temperature for 30 min and then slowly heated to reflux for 1 h. The mixture was then cooled to 0° C. Water (18 mL) and NaOH solution (10%, 100 mL) were carefully added to quench the reaction. The solid was filtered off and the filtrate was concentrated to give 4,4-dimethyl-1,2,3,4-tetrahydro-quinoline.

4,4-Dimethyl-7-nitro-1,2,3,4-tetrahydro-quinoline

To a mixture of 4,4-dimethyl-1,2,3,4-tetrahydro-quinoline (33 g, 0.2 mol) in H₂SO₄ (120 mL) was slowly added KNO₃ (20.7 g, 0.2 mol) at 0° C. After addition, the mixture was stirred at room temperature for 2 h, carefully poured into ice water and basified with Na₂CO₃ to pH 8. The mixture was extracted with ethyl acetate (3×200 mL). The combined extracts were washed with water and brine, dried over Na₂SO₄ and concentrated to give 4,4-dimethyl-7-nitro-1,2,3,4-tetrahydro-quinoline (21 g, 50%).

4,4-Dimethyl-7-nitro-3,4-dihydro-2H-quinoline-1-carboxylic acid tert-butyl ester A mixture of 4,4-dimethyl-7-nitro-1,2,3,4-tetrahydro-quinoline (25 g, 0.12 mol) and Boc₂O (55 g, 0.25 mol) was stirred at 80° C. for 2 days. The mixture was purified by silica gel chromatography to give 4,4-dimethyl-7-nitro-3,4-dihydro-2H-quinoline-1-carboxylic acid tert-butyl ester (8 g, 22%).

DC-3; tert-Butyl 7-amino-3,4-dihydro-4,4-dimethylquinoline-1(2H)-carboxylate A mixture of 4,4-dimethyl-7-nitro-3,4-dihydro-2H-quinoline-1 carboxylic acid tert-butyl ester (8.3 g, 0.03 mol) and Pd—C (0.5 g) in methanol (100 mL) was stirred under H₂ (1 atm) at room temperature overnight. The catalyst was filtered off and the filtrate was concentrated. The residue was washed with petroleum ether to give tert-butyl 7-amino-3,4-dihydro-4,4-dimethylquinoline-1(2H)-carboxylate (DC-3) (7.2 g, 95%). ¹H NMR (CDCl₃) δ 7.11-7.04 (m, 2H), 6.45-6.38 (m, 1H), 3.71-3.67 (m, 2H), 3.50-3.28 (m, 2H), 1.71-1.67 (m, 2H), 1.51 (s, 9H), 1.24 (s, 6H).

Example 4

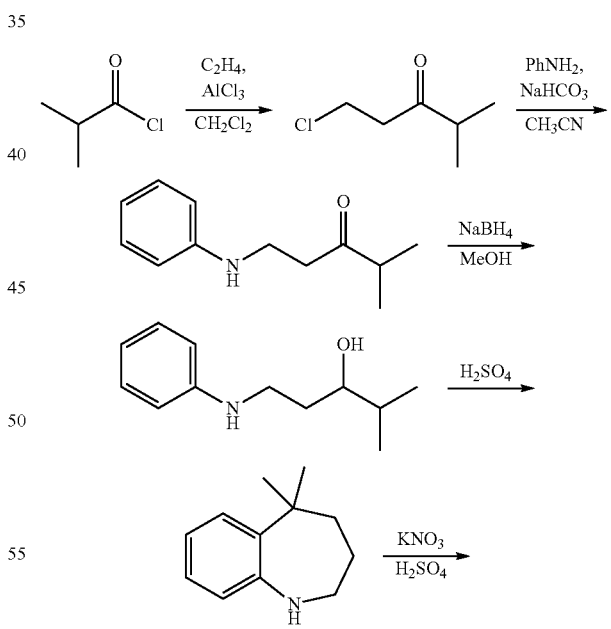

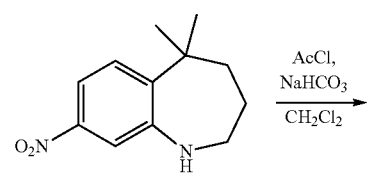

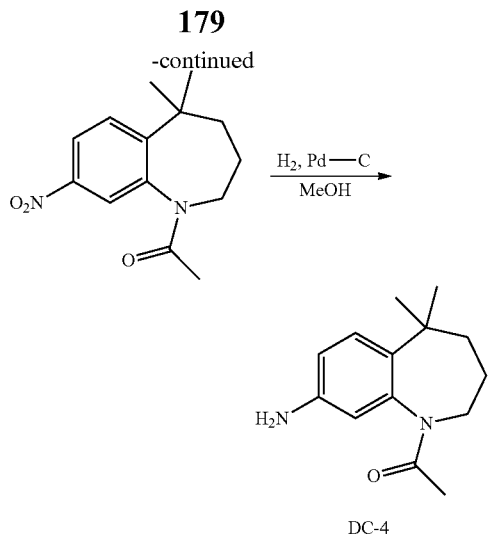

1-Chloro-4-methylpentan-3-one

Ethylene was passed through a solution of isobutyryl chloride (50 g, 0.5 mol) and AlCl₃ (68.8 g, 0.52 mol) in anhydrous CH₂Cl₂ (700 mL) at 5° C. After 4 h, the absorption of ethylene ceased, and the mixture was stirred at room temperature overnight. The mixture was poured into cold diluted HCl solution and extracted with CH₂Cl₂. The combined organic phases were washed with brine, dried over Na₂SO₄, filtered and concentrated to give the crude 1-chloro-4-methylpentan-3-one, which was used directly in the next step without further purification.

4-Methyl-1-(phenylamino)-pentan-3-one

A suspension of the crude 1-chloro-4-methylpentan-3-one (about 60 g), aniline (69.8 g, 0.75 mol) and NaHCO₃ (210 g, 2.5 mol) in CH₃CN (1000 mL) was heated at reflux overnight. After cooling, the insoluble salt was filtered off and the filtrate was concentrated. The residue was diluted with CH₂Cl₂, washed with 10% HCl solution (100 mL) and brine, dried over Na₂SO₄, filtered and concentrated to give the crude 4-methyl-1-(phenylamino)-pentan-3-one.

4-Methyl-1-(phenylamino)-pentan-3-ol

At −10° C., NaBH₄ (56.7 g, 1.5 mol) was gradually added to a mixture of the crude 4-methyl-1-(phenylamino)-pentan-3-one (about 80 g) in MeOH (500 mL). After addition, the reaction mixture was allowed to warm to room temperature and stirred for 20 min. The solvent was removed and the residue was repartitioned between water and CH₂Cl₂. The organic phase was separated, washed with brine, dried over Na₂SO₄, filtered and concentrated. The resulting gum was triturated with ether to give 4-methyl-1-(phenylamino)-pentan-3-ol as a white solid (22 g, 23%).

5,5-Dimethyl-2,3,4,5-tetrahydro-1H-benzo[b]azepine

A mixture of 4-methyl-1-(phenylamino)-pentan-3-ol (22 g, 0.11 mol) in 98% H₂SO₄ (250 mL) was stirred at 50° C. for 30 min. The reaction mixture was poured into ice-water basified with sat. NaOH solution to pH 8 and extracted with CH₂Cl₂. The combined organic phases were washed with brine, dried over Na₂SO₄, filtered and concentrated. The residue was purified by column chromatography (petroleum ether) to afford 5,5-dimethyl-2,3,4,5-tetrahydro-1H-benzo[b]azepine as a brown oil (1.5 g, 8%).

5,5-Dimethyl-8-nitro-2,3,4,5-tetrahydro-1H-benzo[b]azepine

At 0° C., KNO₃ (0.76 g, 7.54 mmol) was added portionwise to a solution of 5,5-dimethyl-2,3,4,5-tetrahydro-1H-benzo[b]azepine (1.1 g, 6.28 mmol) in H₂SO₄ (15 mL). After stirling 15 min at this temperature, the mixture was poured into ice water, basified with sat. NaHCO₃ to pH 8 and extracted with EtOAc. The organic layer was washed with brine, dried over Na₂SO₄ and concentrated to give crude 5,5-dimethyl-8-nitro-2,3,4,5-tetrahydro-1H-benzo[b]azepine (1.2 g), which was used directly in the next step without further purification.

1-(5,5-dimethyl-8-nitro-2,3,4,5-tetrahydrobenzo[b]azepin-1-yl)ethanone

Acetyl chloride (0.77 mL, 11 mmol) was added to a suspension of crude 5,5-dimethyl-8-nitro-2,3,4,5-tetrahydro-1H-benzo[b]azepine (1.2 g, 5.45 mmol) and NaHCO₃ (1.37 g, 16.3 mmol) in CH₂Cl₂ (20 mL). The mixture was heated at reflux for 1 h. After cooling, the mixture was poured into water and extracted with CH₂Cl₂. The organic layer was washed with brine, dried over Na₂SO₄ and concentrated. The residue was purified by column chromatography to afford 1-(5,5-dimethyl-8-nitro-2,3,4,5-tetrahydrobenzo[b]azepin-1-yl)ethanone (1.05 g, 64% over two steps).

DC-4; 1-(8-Amino-2,3,4,5-tetrahydro-5,5-dimethyl-benzo[b]azepin-1-yl)ethanone A suspension of 1-(5,5-dimethyl-8-nitro-2,3,4,5-tetrahydrobenzo[b]azepin-1-yl)ethanone (1.05 g, 40 mmol) and 10% Pd—C (0.2 g) in MeOH (20 mL) was stirred under H₂ (1 atm) at room temperature for 4 h. After filtration, the filtrate was concentrated to give 1-(8-amino-2,3,4,5-tetrahydro-5,5-dimethylbenzo[b]azepin-1-yl)ethanone as a white solid (DC-4) (880 mg, 94%).

¹H NMR (CDCl₃) δ 7.06 (d, J=8.0 Hz, 1H), 6.59 (dd, J=8.4, 2.4 Hz, 1H), 6.50 (br s, 1H), 4.18-4.05 (m, 1H), 3.46-3.36 (m, 1H), 2.23 (s, 3H), 1.92-1.85 (m, 1H), 1.61-1.51 (m, 3H), 1.21 (s, 3H), 0.73 (t, J=7.2 Hz, 3H); ESI-MS 233.0 m/z (MH⁺).

Example 5

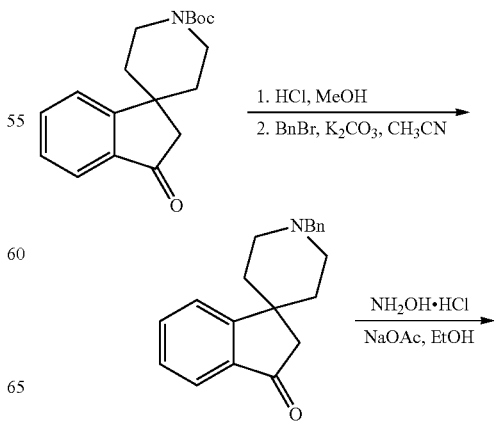

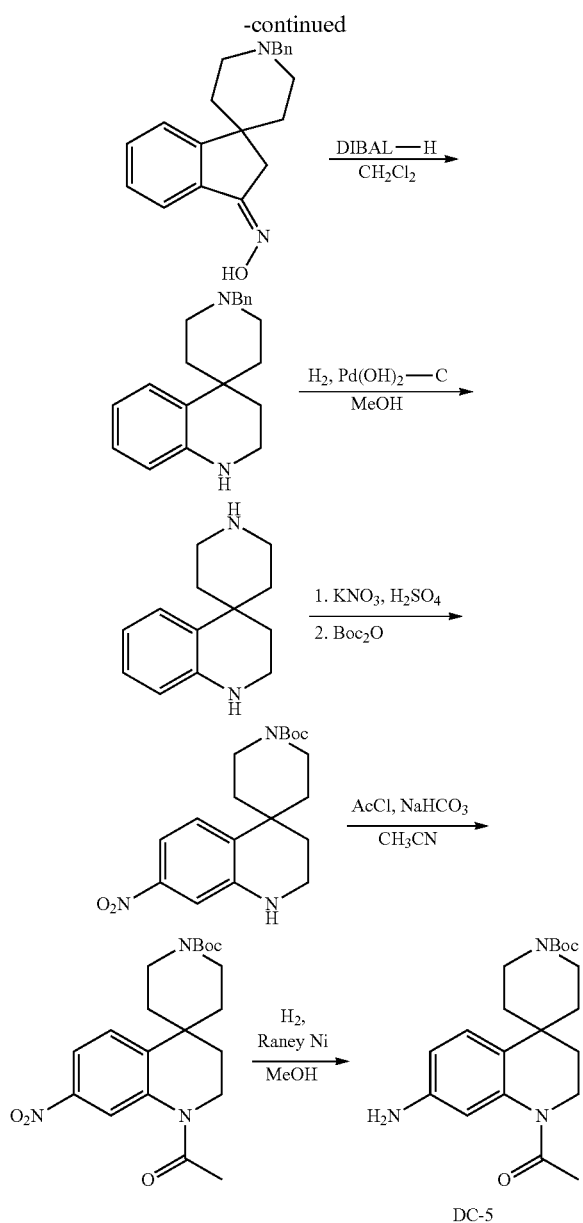

Spiro[1H-indene-1,4'-piperidin]-3(2H)-one, 1'-benzyl

A mixture of spiro[1H-indene-1,4'-piperidine]-1'-carboxylic acid, 2,3-dihydro-3-oxo-, 1,1-dimethylethyl ester (9.50 g, 31.50 mmol) in saturated HCl/MeOH (50 mL) was stirred at 25° C. overnight. The solvent was removed under reduced pressure to yield an off-white solid (7.50 g). To a solution of this solid in dry $CH_3CN$ (30 mL) was added anhydrous $K_2CO_3$ (7.85 g, 56.80 mmol). The suspension was stirred for 5 min, and benzyl bromide (5.93 g, 34.65 mmol) was added dropwise at room temperature. The mixture was stirred for 2 h, poured into cracked ice and extracted with $CH_2Cl_2$. The combined organic layers were dried over $Na_2SO_4$ and concentrated under vacuum to give crude spiro[1H-indene-1,4'-piperidin]-3(2H)-one, 1'-benzyl (7.93 g, 87%), which was used without further purification.

Spiro[1H-indene-1,4'-piperidin]-3(2H)-one, 1'-benzyl, oxime

To a solution of spiro[1H-indene-1,4'-piperidin]-3(2H)-one, 1'-benzyl (7.93 g, 27.25 mmol) in EtOH (50 mL) were added hydroxylamine hydrochloride (3.79 g, 54.50 mmol) and anhydrous sodium acetate (4.02 g, 49.01 mmol) in one portion. The mixture was refluxed for 1 h, and then cooled to room temperature. The solvent was removed under reduced pressure and 200 mL of water was added. The mixture was extracted with $CH_2Cl_2$. The combined organic layers were dried over $Na_2SO_4$ and concentrated to yield spiro[1H-indene-1,4'-piperidin]-3(2H)-one, 1'-benzyl, oxime (7.57 g, 91%), which was used without further purification.

1,2,3,4-Tetrahydroquinolin-4-spiro-4'-(N'-benzyl-piperidine)

To a solution of spiro[1H-indene-1,4'-piperidin]-3(2H)-one, 1'-benzyl, oxime (7.57 g, 24.74 mmol) in dry $CH_2Cl_2$ (150 mL) was added dropwise DIBAL-H (135.7 mL, 1M in toluene) at 0° C. The mixture was stirred at 0° C. for 3 h, diluted with $CH_2Cl_2$ (100 mL), and quenched with NaF (20.78 g, 495 mmol) and water (6.7 g, 372 mmol). The resulting suspension was stirred vigorously at 0° C. for 30 min. After filtration, the residue was washed with $CH_2Cl_2$. The combined filtrates were concentrated under vacuum to give an off-brown oil that was purified by column chromatography on silica gel ($CH_2Cl_2$—MeOH, 30:1) to afford 1,2,3,4-tetrahydroquinolin-4-spiro-4'-(N'-benzyl-piperidine) (2.72 g, 38%).

1,2,3,4-Tetrahydroquinolin-4-spiro-4'-piperidine

A suspension of 1,2,3,4-Tetrahydroquinolin-4-spiro-4'-(N'-benzyl-piperidine) (300 mg, 1.03 mmol) and $Pd(OH)_2$—C (30 mg) in MeOH (3 mL) was stirred under $H_2$ (55 psi) at 50° C. over night. After cooling, the catalyst was filtered off and washed with MeOH. The combined filtrates were concentrated under reduced pressure to yield 1,2,3,4-tetrahydroquinolin-4-spiro-4'-piperidine as a white solid (176 mg, 85%), which was used without further purification.

7'-Nitro-spiro[piperidine-4,4'(1'H)-quinoline], 2',3'-dihydro-carboxylic acid tert-butyl ester $KNO_3$ (69.97 mg, 0.69 mmol) was added portion-wise to a suspension of 1,2,3,4-tetrahydroquinolin-4-spiro-4'-piperidine (133 mg, 0.66 mmol) in 98% $H_2SO_4$ (2 mL) at 0° C. After the addition was complete, the reaction mixture was allowed to warm to room temperature and stirred for additional 2 h. The mixture was then poured into cracked ice and basified with 10% NaOH to pH~8. $Boc_2O$ (172 mg, 0.79 mmol) was added dropwise and the mixture was stirred at room temperature for 1 h. The mixture was then extracted with EtOAc and the combined organic layers were dried over $Na_2SO_4$, filtered and concentrated to yield crude 7'-nitro-spiro[piperidine-4,4' (1'H)-quinoline], 2',3'-dihydro-carboxylic acid tert-butyl ester (230 mg), which was used in the next step without further purification.

7'-nitro-spiro[piperidine-4,4'(1'H)-1-acetyl-quinoline], 2',3'-dihydro-carboxylic acid tert-butyl ester Acetyl chloride (260 mg, 3.30 mmol) was added dropwise to a suspension of 7'-nitro-spiro[piperidine-4,4'(1'H)-quinoline], 2',3'-dihydro-carboxylic acid tert-butyl ester (230 mg)

and NaHCO$_3$ (1.11 g, 13.17 mmol) in MeCN (5 mL) at room temperature. The reaction mixture was refluxed for 4 h. After cooling, the suspension was filtered and the filtrate was concentrated. The residue was purified by column chromatography (petroleum ether-EtOAc, 10:1) to provide 7'-nitro-spiro [piperidine-4,4'(1'H)-1-acetyl-quinoline], 2',3'-dihydro-carboxylic acid tert-butyl ester (150 mg, 58% over 2 steps)

DC-5; 7'-Amino-spiro[piperidine-4,4'(1'H)-1-acetyl-quinoline], 2',3'-dihydro-carboxylic acid tert-butyl ester A suspension of 7'-nitro-spiro[piperidine-4,4'(1'H)-1-acetyl-quinoline], 2',3'-dihydro-carboxylic acid tert-butyl ester (150 mg, 0.39 mmol) and Raney Ni (15 mg) in MeOH (2 mL) was stirred under H$_2$ (1 atm) at 25° C. overnight. The catalyst was removed via filtration and washed with MeOH. The combined filtrates were dried over Na$_2$SO$_4$, filtered, and concentrated to yield 7'-amino-spiro[piperidine-4,4'(1'H)-1-acetyl-quinoline], 2',3'-dihydro-carboxylic acid tert-butyl ester (DC-5) (133 mg, 96%).

Example 7

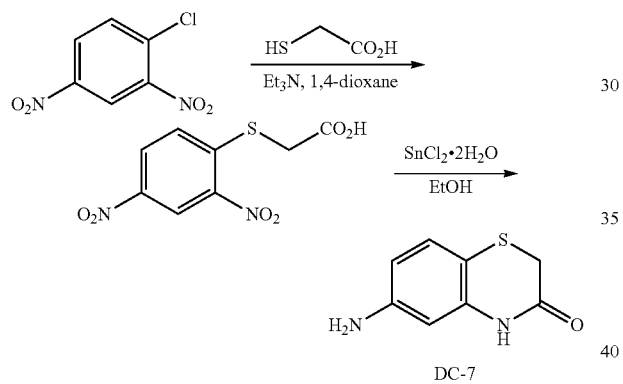

2-(2,4-Dinitrophenylthio)-acetic acid

Et$_3$N (1.5 g, 15 mmol) and mercapto-acetic acid (1 g, 11 mmol) were added to a solution of 1-chloro-2,4-dinitrobenzene (2.26 g, 10 mmol) in 1,4-dioxane (50 mL) at room temperature. After stirring at room temperature for 5 h, H$_2$O (100 mL) was added. The resulting suspension was extracted with ethyl acetate (100 mL×3). The ethyl acetate extract was washed with water and brine, dried over Na$_2$SO$_4$ and concentrated to give 2-(2,4-dinitrophenylthio)-acetic acid (2.3 g, 74%), which was used without further purification.

DC-7; 6-Amino-2H-benzo[b][1,4]thiazin-3(4H)-one

A solution of 2-(2,4-dinitrophenylthio)-acetic acid (2.3 g, 9 mmol) and tin (II) chloride dihydrate (22.6 g, 0.1 mol) in ethanol (30 mL) was refluxed overnight. After removal of the solvent under reduced pressure, the residual slurry was diluted with water (100 mL) and basified with 10% Na$_2$CO$_3$ solution to pH 8. The resulting suspension was extracted with ethyl acetate (3×100 mL). The ethyl acetate extract was washed with water and brine, dried over Na$_2$SO$_4$, and concentrated. The residue was washed with CH$_2$Cl$_2$ to yield 6-amino-2H-benzo[b][1,4]thiazin-3(4H)-one (DC-7) as a yellow powder (1 g, 52%). $^1$H NMR (DMSO-d$_6$) δ 10.24 (s, 1H), 6.88 (d, 1H, J=6 Hz), 6.19-6.21 (m, 2H), 5.15 (s, 2H), 3.28 (s, 2H); ESI-MS 181.1 m/z (MH$^+$).

Example 7

N-(2-Bromo-5-nitrophenyl)acetamide

Acetic anhydride (1.4 mL, 13.8 mmol) was added dropwise to a stirring solution of 2-bromo-5-nitroaniline (3 g, 13.8 mmol) in glacial acetic acid (30 mL) at 25° C. The reaction mixture was stirred at room temperature overnight, and then poured into water. The precipitate was collected via filtration, washed with water and dried under vacuum to provide N-(2-bromo-5-nitrophenyl)acetamide as an off white solid (3.6 g, 90%).

N-(2-Bromo-5-nitrophenyl)-N-(2-methylprop-2-enyl)acetamide

At 25° C., a solution of 3-bromo-2-methylpropene (3.4 g, 55.6 mmol) in anhydrous DMF (30 mL) was added dropwise to a solution of N-(2-bromo-5-nitrophenyl)acetamide (3.6 g, 13.9 mmol) and potassium carbonate (3.9 g, 27.8 mmol) in anhydrous DMF (50 mL). The reaction mixture was stirred at 25° C. overnight. The reaction mixture was then filtered and the filtrate was treated with sat. Na$_2$CO$_3$ solution. The organic layer was separated and the aqueous layer was extracted with EtOAc. The combined organic extracts were washed with water and brine, dried over MgSO$_4$, filtered and concentrated under vacuum to provide N-(2-bromo-5-nitrophenyl)-N-(2-methylprop-2-enyl)acetamide as a golden solid (3.1 g, 85%). ESI-MS 313 m/z (MH⁺).

1-(3,3-Dimethyl-6-nitroindolin-1-yl) ethanone

A solution of N-(2-bromo-5-nitrophenyl)-N-(2-methylprop-2-enyl)acetamide (3.1 g, 10.2 mmol), tetraethylammonium chloride hydrate (2.4 g, 149 mmol), sodium formate (1.08 g, 18 mmol), sodium acetate (2.76 g, 34.2 mmol) and palladium acetate (0.32 g, 13.2 mmol) in anhydrous DMF (50 mL) was stirred at 80° C. for 15 h under N₂ atmosphere. After cooling, the mixture was filtered through Celite. The Celite was washed with EtOAc and the combined filtrates were washed with sat. NaHCO₃. The separated organic layer was washed with water and brine, dried over MgSO₄, filtered and concentrated under reduced pressure to provide 1-(3,3-dimethyl-6-nitroindolin-1-yl)ethanone as a brown solid (2.1 g, 88%).

DC-8; 1-(6-Amino-3,3-dimethyl-2,3-dihydro-indol-1-yl)-ethanone

10% Pd—C (0.2 g) was added to a suspension of 1-(3,3-dimethyl-6-nitroindolin-1-yl)ethanone (2.1 g, 9 mmol) in MeOH (20 mL). The reaction was stirred under H₂ (40 psi) at room temperature overnight. Pd—C was filtered off and the filtrate was concentrated under vacuum to give a crude product, which was purified by column chromatography to yield 1-(6-amino-3,3-dimethyl-2,3-dihydro-indol-1-yl)-ethanone (DC-8) (1.3 g, 61%).

Example 8

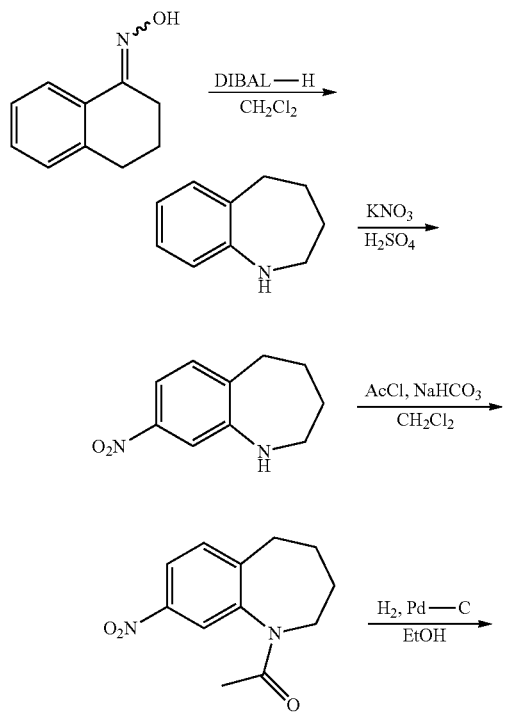

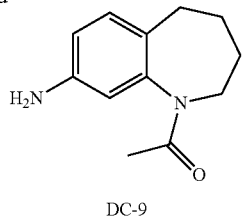

DC-9

2,3,4,5-Tetrahydro-1H-benzo[b]azepine

DIBAL (90 mL, 90 mmol) was added dropwise to a solution of 4-dihydro-2H-naphthalen-1-one oxime (3 g, 18 mmol) in dichloromethane (50 mL) at 0° C. The mixture was stirred at this temperature for 2 h. The reaction was quenched with dichloromethane (30 mL), followed by treatment with NaF (2 g. 0.36 mol) and H₂O (5 mL, 0.27 mol). Vigorous stifling of the resulting suspension was continued at 0° C. for 30 min. After filtration, the filtrate was concentrated. The residue was purified by flash column chromatography to give 2,3,4,5-tetrahydro-1H-benzo[b]azepine as a colorless oil (1.9 g, 70%).

8-Nitro-2,3,4,5-tetrahydro-1H-benzo[b]azepine

At –10° C., 2,3,4,5-tetrahydro-1H-benzo[b]azepine (1.9 g, 13 mmol) was added dropwise to a solution of KNO₃ (3 g, 30 mmol) in H₂SO₄ (50 mL). The mixture was stirred for 40 min, poured over crushed ice, basified with aq. ammonia to pH 13, and extracted with EtOAc. The combined organic phases were washed with brine, dried over Na₂SO₄ and concentrated to give 8-nitro-2,3,4,5-tetrahydro-1H-benzo[b]azepine as a black solid (1.3 g, 51%), which was used without further purification.

1-(8-Nitro-2,3,4,5-tetrahydro-benzo[b]azepin-1-yl)-ethanone

Acetyl chloride (1 g, 13 mmol) was added dropwise to a mixture of 8-nitro-2,3,4,5-tetrahydro-1H-benzo[b]azepine (1.3 g, 6.8 mmol) and NaHCO₃ (1 g, 12 mmol) in CH₂Cl₂ (50 mL). After stirring for 1 h, the mixture was filtered and the filtrate was concentrated. The residue was dissolved in CH₂Cl₂, washed with brine, dried over Na₂SO₄ and concentrated. The residue was purified by column chromatography to give 1-(8-nitro-2,3,4,5-tetrahydro-benzo[b]azepin-1-yl)-ethanone as a yellow solid (1.3 g, 80%).

DC-9; 1-(8-Amino-2,3,4,5-tetrahydro-benzo[b]azepin-1-yl)-ethanone

A mixture of 1-(8-nitro-2,3,4,5-tetrahydro-benzo[b]azepin-1-yl)-ethanone (1.3 g, 5.4 mmol) and Pd—C (10%, 100 mg) in EtOH (200 mL) was stirred under H₂ (1 atm) at room temperature for 1.5 h. The mixture was filtered through a layer of Celite and the filtrate was concentrated to give 1-(8-amino-2,3,4,5-tetrahydro-benzo[b]azepin-1-yl)-ethanone (DC-9) as a white solid (1 g, 90%). ¹H NMR (CDCl₃) δ 7.01 (d, J=6.0 Hz, 1H), 6.56 (dd, J=6.0, 1.8 Hz, 1H), 6.50 (d, J=1.8 Hz, 1H), 4.66-4.61 (m, 1H), 3.50 (br s, 2H), 2.64-2.55

(m, 3H), 1.94-1.91 (m, 5H), 1.77-1.72 (m, 1H), 1.32-1.30 (m, 1H); ESI-MS 204.1 m/z (MH+).

Example 9

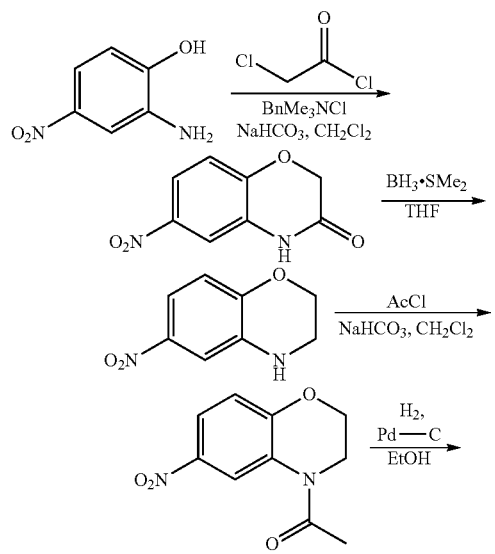

6-Nitro-4H-benzo[1,4]oxazin-3-one

At 0° C., chloroacetyl chloride (8.75 mL, 0.11 mol) was added dropwise to a mixture of 4-nitro-2-aminophenol (15.4 g, 0.1 mol), benzyltrimethylammonium chloride (18.6 g, 0.1 mol) and NaHCO$_3$ (42 g, 0.5 mol) in chloroform (350 ml) over a period of 30 min. After addition, the reaction mixture was stirred at 0° C. for 1 h, then at 50° C. overnight. The solvent was removed under reduced pressure and the residue was treated with water (50 ml). The solid was collected via filtration, washed with water and recrystallized from ethanol to provide 6-nitro-4H-benzo[1,4]oxazin-3-one as a pale yellow solid (8 g, 41%).

6-Nitro-3,4-dihydro-2H-benzo[1,4]oxazine

A solution of BH$_3$.Me$_2$S in THF (2 M, 7.75 mL, 15.5 mmol) was added dropwise to a suspension of 6-nitro-4H-benzo[1,4]oxazin-3-one (0.6 g, 3.1 mmol) in THF (10 mL). The mixture was stirred at room temperature overnight. The reaction was quenched with MeOH (5 mL) at 0° C. and then water (20 mL) was added. The mixture was extracted with Et$_2$O and the combined organic layers were washed with brine, dried over Na$_2$SO$_4$ and concentrated to give 6-nitro-3,4-dihydro-2H-benzo[1,4]oxazine as a red solid (0.5 g, 89%), which was used without further purification.

4-Acetyl-6-nitro-3,4-dihydro-2H-benzo[1,4]oxazine

Under vigorous stirring at room temperature, acetyl chloride (1.02 g, 13 mmol) was added dropwise to a mixture of 6-nitro-3,4-dihydro-2H-benzo[1,4]oxazine (1.8 g, 10 mmol) and NaHCO$_3$ (7.14 g, 85 mmol) in CH$_2$Cl$_2$ (50 mL). After addition, the reaction was stirred for 1 h at this temperature. The mixture was filtered and the filtrate was concentrated under vacuum. The residue was treated with Et$_2$O:hexane (1:2, 50 mL) under stirring for 30 min and then filtered to give 4-acetyl-6-nitro-3,4-dihydro-2H-benzo[1,4]oxazine as a pale yellow solid (2 g, 90%).

DC-10; 4-Acetyl-6-amino-3,4-dihydro-2H-benzo[1,4]oxazine

A mixture of 4-acetyl-6-nitro-3,4-dihydro-2H-benzo[1,4] oxazine (1.5 g, 67.6 mmol) and Pd—C (10%, 100 mg) in EtOH (30 mL) was stirred under H$_2$ (1 atm) overnight. The catalyst was filtered off and the filtrate was concentrated. The residue was treated with HCl/MeOH to give 4-acetyl-6-amino-3,4-dihydro-2H-benzo[1,4]oxazine hydrochloride (DC-10) as an off-white solid (1.1 g, 85%). $^1$H NMR (DMSO-d$_6$) δ 10.12 (br s, 2H), 8.08 (br s, 1H), 6.90-7.03 (m, 2H), 4.24 (t, J=4.8 Hz, 2H), 3.83 (t, J=4.8 Hz, 2H), 2.23 (s, 3H); ESI-MS 192.1 m/z (MH+).

Example 10

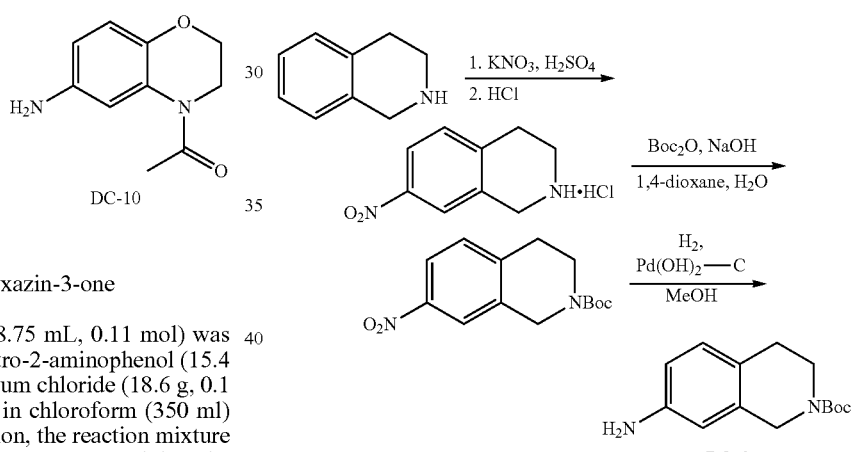

1,2,3,4-Tetrahydro-7-nitroisoquinoline hydrochloride 1,2,3,4-Tetrahydroisoquinoline (6.3 mL, 50.0 mmol) was added dropwise to a stirred ice-cold solution of concentrated H$_2$SO$_4$ (25 mL). KNO$_3$ (5.6 g, 55.0 mmol) was added portionwise while maintaining the temperature below 5° C. The mixture was stirred at room temperature overnight, carefully poured into an ice-cold solution of concentrated NH$_4$OH, and then extracted three times with CHCl$_3$. The combined organic layers were washed with brine, dried over Na$_2$SO$_4$ and concentrated. The resulting dark brown oil was taken up into EtOH, cooled in an ice bath and treated with concentrated HCl. The yellow precipitate was collected via filtration and recrystallized from methanol to give 1,2,3,4-tetrahydro-7-nitroisoquinoline hydrochloride as yellow solid (2.5 g, 23%). $^1$H NMR (400 MHz, DMSO-d$_6$) δ 9.86 (s, 2H), 8.22 (d, J=1.6 Hz, 1H), 8.11 (dd, J=8.5, 2.2 Hz, 1H), 7.53 (d, J=8.5 Hz, 1H), 4.38 (s, 2H), 3.38 (s, 2H), 3.17-3.14 (m, 2H); HPLC ret. time 0.51 min, 10-99% CH$_3$CN, 5 min run; ESI-MS 179.0 m/z (MH+).

tert-Butyl 3,4-dihydro-7-nitroisoquinoline-2(1H)-carboxylate

A mixture of 1,2,3,4-Tetrahydro-7-nitroisoquinoline (2.5 g, 11.6 mmol), 1,4-dioxane (24 mL), H$_2$O (12 mL) and 1N NaOH (12 mL) was cooled in an ice-bath, and Boc$_2$O (2.8 g, 12.8 mmol) was added. The mixture was stirred at room temperature for 2.5 h, acidified with a 5% KHSO$_4$ solution to pH 2-3, and then extracted with EtOAc. The organic layer was dried over MgSO$_4$ and concentrated to give tert-butyl 3,4-dihydro-7-nitroisoquinoline-2(1H)-carboxylate (3.3 g, quant.), which was used without further purification. $^1$H NMR (400 MHz, DMSO-d$_6$) δ 8.13 (d, J=2.3 Hz, 1H), 8.03 (dd, J=8.4, 2.5 Hz, 1H), 7.45 (d, J=8.5 Hz, 1H), 4.63 (s, 2H), 3.60-3.57 (m, 2H), 2.90 (t, J=5.9 Hz, 2H), 1.44 (s, 9H); HPLC ret. time 3.51 min, 10-99% CH$_3$CN, 5 min run; ESI-MS 279.2 m/z (MH$^+$).

DC-6; tert-Butyl 7-amino-3,4-dihydroisoquinoline-2(1H)-carboxylate

Pd(OH)$_2$ (330.0 mg) was added to a stirring solution of tert-butyl 3,4-dihydro-7-nitroisoquinoline-2(1H)-carboxylate (3.3 g, 12.0 mmol) in MeOH (56 mL) under N$_2$ atmosphere. The reaction mixture was stirred under H$_2$ (1 atm) at room temperature for 72 h. The solid was removed by filtration through Celite. The filtrate was concentrated and purified by column chromatography (15-35% EtOAc-Hexanes) to provide tert-butyl 7-amino-3,4-dihydroisoquinoline-2(1H)-carboxylate (DC-6) as a pink oil (2.0 g, 69%). $^1$H NMR (400 MHz, DMSO-d$_6$) δ 6.79 (d, J=8.1 Hz, 1H), 6.40 (dd, J=8.1, 2.3 Hz, 1H), 6.31 (s, 1H), 4.88 (s, 2H), 4.33 (s, 2H), 3.48 (t, J=5.9 Hz, 2H), 2.58 (t, J=5.9 Hz, 2H), 1.42 (s, 9H); HPLC ret. time 2.13 min, 10-99% CH$_3$CN, 5 min run; ESI-MS 249.0 m/z (MH$^+$).

Other Amines

Example 1

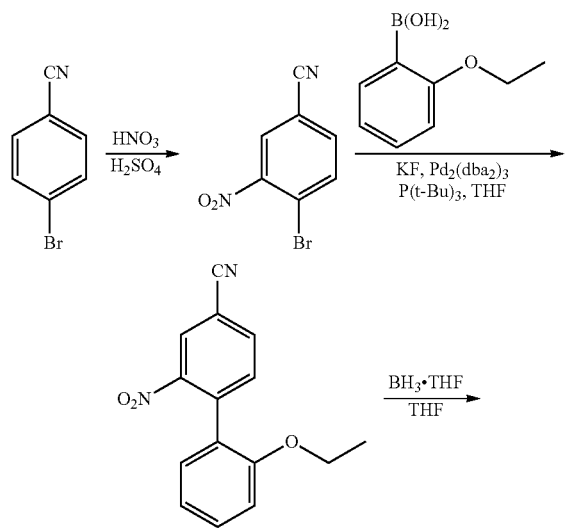

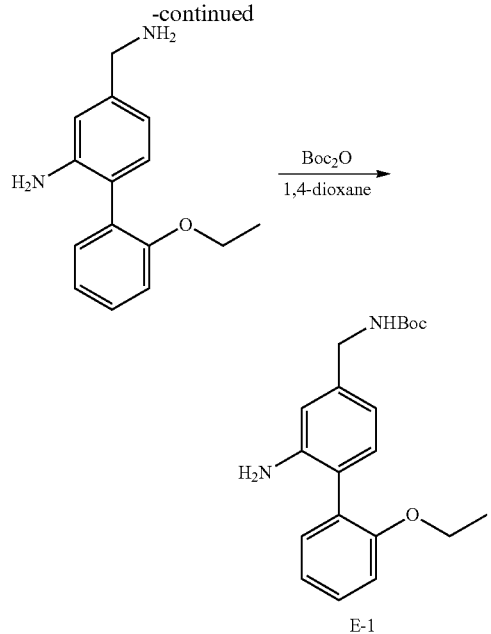

4-Bromo-3-nitrobenzonitrile

To a solution of 4-bromobenzonitrile (4.0 g, 22 mmol) in conc. H$_2$SO$_4$ (10 mL) was added dropwise at 0° C. nitric acid (6 mL). The reaction mixture was stirred at 0° C. for 30 min, and then at room temperature for 2.5 h. The resulting solution was poured into ice-water. The white precipitate was collected via filtration and washed with water until the washings were neutral. The solid was recrystallized from an ethanol/water mixture (1:1, 20 mL) twice to afford 4-bromo-3-nitrobenzonitrile as a white crystalline solid (2.8 g, 56%). $^1$H NMR (300 MHz, DMSO-d$_6$) δ 8.54 (s, 1H), 8.06 (d, J=8.4 Hz, 1H), 7.99 (d, J=8.4 Hz, 1H); $^{13}$C NMR (75 MHz, DMSO-d$_6$) δ 150.4, 137.4, 136.6, 129.6, 119.6, 117.0, 112.6; HPLC ret. time 1.96 min, 10-100% CH$_3$CN, 5 min gradient; ESI-MS 227.1 m/z (MH$^+$).

2'-Ethoxy-2-nitrobiphenyl-4-carbonitrile

A 50 mL round-bottom flask was charged with 4-bromo-3-nitrobenzonitrile (1.0 g 4.4 mmol), 2-ethoxyphenylboronic acid (731 mg, 4.4 mmol), Pd$_2$(dba)$_3$ (18 mg, 0.022 mmol) and potassium fluoride (786 mg, 13.5 mmol). The reaction vessel was evacuated and filled with argon. Dry THF (300 mL) was added followed by the addition of P(t-Bu)$_3$ (0.11 mL, 10% wt. in hexane). The reaction mixture was stirred at room temperature for 30 min., and then heated at 80° C. for 16 h. After cooling to room temperature, the resulting mixture was filtered through a Celite pad and concentrated. 2'-Ethoxy-2-nitrobiphenyl-4-carbonitrile was isolated as a yellow solid (1.12 g, 95%). $^1$H NMR (300 MHz, DMSO-d$_6$) δ 8.51 (s, 1H), 8.20 (d, J=8.1 Hz, 1H), 7.68 (d, J=8.4 Hz, 1H), 7.41 (t, J=8.4 Hz, 1H), 7.37 (d, J=7.5 Hz, 1H), 7.08 (t, J=7.5 Hz, 1H), 7.03 (d, J=8.1 Hz, 1H), 3.91 (q, J=7.2 Hz, 2H), 1.12 (t, J=7.2 Hz, 3H); $^{13}$C NMR (75 MHz, DMSO-d$_6$) δ 154.9, 149.7, 137.3, 137.2, 134.4, 131.5, 130.4, 128.4, 125.4, 121.8, 117.6, 112.3, 111.9, 64.1, 14.7; HPLC ret. time 2.43 min, 10-100% CH$_3$CN, 5 min gradient; ESI-MS 269.3 m/z (MH$^+$).

4-Aminomethyl-2'-ethoxy-biphenyl-2-ylamine

To a solution of 2'-ethoxy-2-nitrobiphenyl-4-carbonitrile (500 mg, 1.86 mmol) in THF (80 mL) was added a solution of BH$_3$.THF (5.6 mL, 10% wt. in THF, 5.6 mmol) at 0° C. over 30 min. The reaction mixture was stirred at 0° C. for 3 h and then at room temperature for 15 h. The reaction solution was chilled to 0° C., and a H$_2$O/THF mixture (3 mL) was added. After being agitated at room temperature for 6 h, the volatiles were removed under reduced pressure. The residue was dissolved in EtOAc (100 mL) and extracted with 1N HCl (2×100 mL). The aqueous phase was basified with 1N NaOH solution to pH 1 and extracted with EtOAc (3×50 mL). The combined organic layers were washed with water (50 mL), dried over Na$_2$SO$_4$, filtered, and evaporated. After drying under vacuum, 4-aminomethyl-2'-ethoxy-biphenyl-2-ylamine was isolated as a brown oil (370 mg, 82%). $^1$H NMR (300 MHz, DMSO-d$_6$) δ 7.28 (dt, J=7.2 Hz, J=1.8 Hz, 1H), 7.09 (dd, J=7.2 Hz, J=1.8 Hz, 1H), 7.05 (d, J=7.5 Hz, 1H), 6.96 (dt, J=7.2 Hz, J=0.9 Hz, 1H), 6.83 (d, J=7.5 Hz, 1H), 6.66 (d, J=1.2 Hz, 1H), 6.57 (dd, J=7.5 Hz, J=1.5 Hz, 1H), 4.29 (s, 2H), 4.02 (q, J=6.9 Hz, 2H), 3.60 (s, 2H), 1.21 (t, J=6.9 Hz, 3H); HPLC ret. time 1.54 min, 10-100% CH$_3$CN, 5 min gradient; ESI-MS 243.3 m/z (MH$^+$).

E-1; (2-Amino-2'-ethoxy-biphenyl-4-ylmethyl)carbamic acid tert-butyl ester

A solution of Boc$_2$O (123 mg, 0.565 mmol) in 1,4-dioxane (10 mL) was added over a period of 30 min. to a solution of 4-aminomethyl-2'-ethoxy-biphenyl-2-ylamine (274 mg, 1.13 mmol) in 1,4-dioxane (10 mL). The reaction mixture was stirred at room temperature for 16 h. The volatiles were removed on a rotary evaporator. The residue was purified by flash chromatography (silica gel, EtOAc—CH$_2$Cl$_2$, 1:4) to afford (2-Amino-2'-ethoxy-biphenyl-4-ylmethyl)carbamic acid tert-butyl ester (E-1) as a pale yellow oil (119 mg, 31%). $^1$H NMR (300 MHz, DMSO-d$_6$) δ 7.27 (m, 2H), 7.07 (dd, J=7.2 Hz, J=1.8 Hz, 1H), 7.03 (d, J=7.8 Hz, 1H), 6.95 (dt, J=7.2 Hz, J=0.9 Hz, 1H), 6.81 (d, J=7.5 Hz, 1H), 6.55 (s, 1H), 6.45 (dd, J=7.8 Hz, J=1.5 Hz, 1H), 4.47 (s, 2H), 4.00 (q, J=7.2 Hz, 2H), 1.38 (s, 9H), 1.20 (t, J=7.2 Hz, 3H);

HPLC ret. time 2.34 min, 10-100% CH$_3$CN, 5 min gradient; ESI-MS 343.1 m/z (MH$^+$).

Example 2

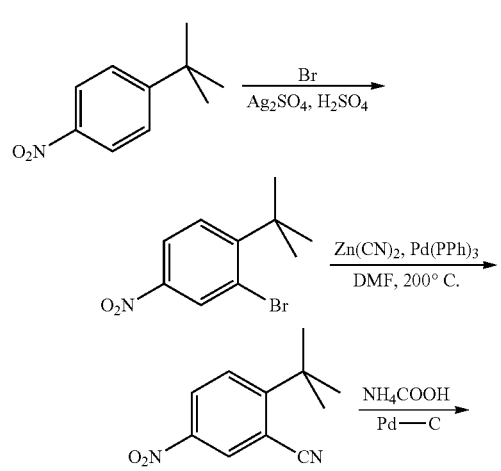

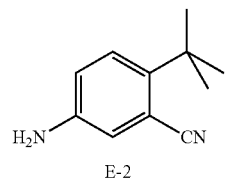

2-Bromo-1-tert-butyl-4-nitrobenzene

To a solution of 1-tert-butyl-4-nitrobenzene (8.95 g, 50 mmol) and silver sulfate (10 g, 32 mmol) in 50 mL of 90% sulfuric acid was added dropwise bromine (7.95 g, 50 mmol). Stirring was continued at room temperature overnight, and then the mixture was poured into dilute sodium hydrogen sulfite solution and was extracted with EtOAc three times. The combined organic layers were washed with brine and dried over MgSO$_4$. After filtration, the filtrate was concentrated to give 2-bromo-1-tert-butyl-4-nitrobenzene (12.7 g, 98%), which was used without further purification. $^1$H NMR (400 MHz, CDCl$_3$) δ 8.47 (d, J=2.5 Hz, 1H), 8.11 (dd, J=8.8, 2.5 Hz, 1H), 7.63 (d, J=8.8 Hz, 1H), 1.57 (s, 9H); HPLC ret. time 4.05 min, 10-100% CH$_3$CN, 5 min gradient.

2-tert-Butyl-5-nitrobenzonitrile

To a solution of 2-bromo-1-tert-butyl-4-nitrobenzene (2.13 g, 8.2 mmol) and Zn(CN)$_2$ (770 mg, 6.56 mmol) in DMF (10 mL) was added Pd(PPh$_3$)$_4$ (474 mg, 0.41 mmol) under a nitrogen atmosphere. The mixture was heated in a sealed vessel at 205° C. for 5 h. After cooling to room temperature, the mixture was diluted with water and extracted with EtOAc twice. The combined organic layers were washed with brine and dried over MgSO$_4$. After removal of solvent, the residue was purified by column chromatography (0-10% EtOAc-Hexane) to give 2-tert-butyl-5-nitrobenzonitrile (1.33 g, 80%). $^1$H NMR (400 MHz, CDCl$_3$) δ 8.55 (d, J=2.3 Hz, 1H), 8.36 (dd, J=8.8, 2.2 Hz, 1H), 7.73 (d, J=8.9 Hz, 1H), 1.60 (s, 9H); HPLC ret. time 3.42 min, 10-100% CH$_3$CN, 5 min gradient.

E-2; 2-tert-Butyl-5-aminobenzonitrile

To a refluxing solution of 2-tert-butyl-5-nitrobenzonitrile (816 mg, 4.0 mmol) in EtOH (20 mL) was added ammonium formate (816 mg, 12.6 mmol), followed by 10% Pd—C (570 mg). The reaction mixture was refluxed for additional 90 min, cooled to room temperature and filtered through Celite. The filtrate was concentrated to give 2-tert-butyl-5-aminobenzonitrile (E-2) (630 mg, 91%), which was used without further purification. HPLC ret. time 2.66 min, 10-99% CH$_3$CN, 5 min run; ESI-MS 175.2 m/z (MH$^+$).

Example 3

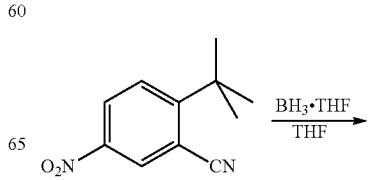

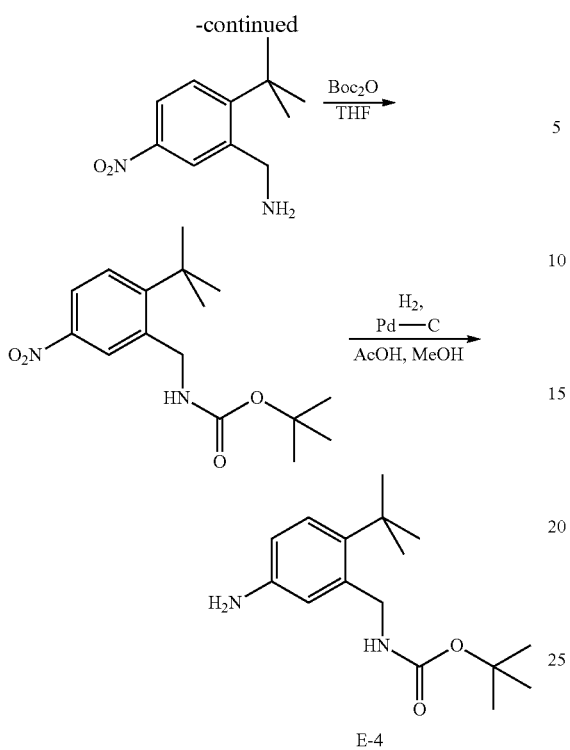

(2-tert-Butyl-5-nitrophenyl)methanamine

To a solution of 2-tert-butyl-5-nitrobenzonitrile (612 mg, 3.0 mmol) in THF (10 mL) was added a solution of $BH_3$·THF (12 mL, 1M in THF, 12.0 mmol) under nitrogen. The reaction mixture was stirred at 70° C. overnight and cooled to 0° C. Methanol (2 mL) was added followed by the addition of 1N HCl (2 mL). After refluxing for 30 min, the solution was diluted with water and extracted with EtOAc. The aqueous layer was basified with 1N NaOH and extracted with EtOAc twice. The combined organic layers were washed with brine and dried over $Mg_2SO_4$. After removal of solvent, the residue was purified by column chromatography (0-10% MeOH—$CH_2Cl_2$) to give (2-tert-butyl-5-nitrophenyl)methanamine (268 mg, 43%). $^1$H NMR (400 MHz, DMSO-$d_6$) δ 8.54 (d, J=2.7 Hz, 1H), 7.99 (dd, J=8.8, 2.8 Hz, 1H), 7.58 (d, J=8.8 Hz, 1H), 4.03 (s, 2H), 2.00 (t, J=2.1 Hz, 2H), 1.40 (s, 9H); HPLC ret. time 2.05 min, 10-100% $CH_3CN$, 5 min gradient; ESI-MS 209.3 m/z (MH$^+$).

tert-Butyl 2-tert-butyl-5-nitrobenzylcarbamate

A solution of (2-tert-butyl-5-nitrophenyl)methanamine (208 mg, 1 mmol) and Boc$_2$O (229 mg, 1.05 mmol) in THF (5 mL) was refluxed for 30 min. After cooling to room temperature, the solution was diluted with water and extracted with EtOAc. The combined organic layers were washed with brine and dried over MgSO$_4$. After filtration, the filtrate was concentrated to give tert-butyl 2-tert-butyl-5-nitrobenzylcarbamate (240 mg, 78%), which was used without further purification. $^1$H NMR (400 MHz, DMSO-$d_6$) δ 8.26 (d, J=2.3 Hz, 1H), 8.09 (dd, J=8.8, 2.5 Hz, 1H), 7.79 (t, J=5.9 Hz, 1H), 7.68 (d, J=8.8 Hz, 1H), 4.52 (d, J=6.0 Hz, 2H), 1.48 (s, 18H); HPLC ret. time 3.72 min, 10-100% $CH_3CN$, 5 min gradient.

E-4; tert-Butyl 2-tert-butyl-5-aminobenzylcarbamate

To a solution of tert-butyl 2-tert-butyl-5-nitrobenzylcarbamate (20 mg, 0.065 mmol) in 5% AcOH-MeOH (1 mL) was added 10% Pd—C (14 mg) under nitrogen atmosphere. The mixture was stirred under H$_2$ (1 atm) at room temperature for 1 h. The catalyst was removed via filtration through Celite, and the filtrate was concentrated to give tert-butyl 2-tert-butyl-5-aminobenzylcarbamate (E-4), which was used without further purification. $^1$H NMR (400 MHz, CDCl$_3$) δ 7.09 (d, J=8.5 Hz, 1H), 6.62 (d, J=2.6 Hz, 1H), 6.47 (dd, J=8.5, 2.6 Hz, 1H), 4.61 (br s, 1H), 4.40 (d, J=5.1 Hz, 2H), 4.15 (br s, 2H), 1.39 (s, 9H), 1.29 (s, 9H); HPLC ret. time 2.47 min, 10-100% $CH_3CN$, 5 min gradient; ESI-MS 279.3 m/z (MH$^+$).

Example 4

2-tert-Butyl-5-nitrobenzoic acid

A solution of 2-tert-butyl-5-nitrobenzonitrile (204 mg, 1 mmol) in 5 mL of 75% H$_2$SO$_4$ was microwaved at 200° C. for 30 min. The reaction mixture was poured into ice, extracted with EtOAc, washed with brine and dried over MgSO$_4$. After filtration, the filtrate was concentrated to give 2-tert-butyl-5-nitrobenzoic acid (200 mg, 90%), which was used without further purification. $^1$H NMR (400 MHz, CDCl$_3$) δ 8.36 (d, J=2.6 Hz, 1H), 8.24 (dd, J=8.9, 2.6 Hz, 1H), 7.72 (d, J=8.9 Hz, 1H) 1.51 (s, 9H); HPLC ret. time 2.97 min, 10-100% $CH_3CN$, 5 min gradient.

Methyl 2-tert-butyl-5-nitrobenzoate

To a mixture of 2-tert-butyl-5-nitrobenzoic acid (120 mg, 0.53 mmol) and K$_2$CO$_3$ (147 mg, 1.1 mmol) in DMF (5.0 mL) was added CH$_3$I (40 μL, 0.64 mmol). The reaction mixture was stirred at room temperature for 10 min, diluted with water and extracted with EtOAc. The combined organic layers were washed with brine and dried over MgSO$_4$. After filtration, the filtrate was concentrated to give methyl 2-tert-butyl-5-nitrobenzoate, which was used without further purification. $^1$H NMR (400 MHz, CDCl$_3$) δ 8.20 (d, J=2.6 Hz, 1H), 8.17 (t, J=1.8 Hz, 1H), 7.66 (d, J=8.6 Hz, 1H), 4.11 (s, 3H), 1.43 (s, 9H).

E-6; Methyl 2-tert-butyl-5-aminobenzoate

To a refluxing solution of 2-tert-butyl-5-nitrobenzoate (90 mg, 0.38 mmol) in EtOH (2.0 mL) was added potassium formate (400 mg, 4.76 mmol) in water (1 mL), followed by the addition of 20 mg of 10% Pd—C. The reaction mixture was refluxed for additional 40 min, cooled to room temperature and filtered through Celite. The filtrate was concentrated to give methyl 2-tert-butyl-5-aminobenzoate (E-6) (76 mg, 95%), which was used without further purification. $^1$H NMR (400 MHz, CDCl$_3$) δ 7.24 (d, J=8.6 Hz, 1H), 6.67 (dd, J=8.6, 2.7 Hz, 1H), 6.60 (d, J=2.7 Hz, 1H), 3.86 (s, 3H), 1.34 (s, 9H); HPLC ret. time 2.19 min, 10-99% CH$_3$CN, 5 min run; ESI-MS 208.2 m/z (MH$^+$).

Example 5

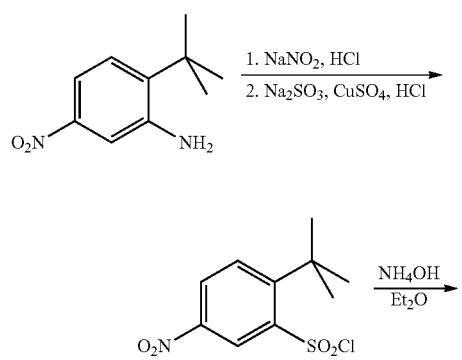

2-tert-Butyl-5-nitrobenzene-1-sulfonyl chloride

A suspension of 2-tert-butyl-5-nitrobenzenamine (0.971 g, 5 mmol) in conc. HCl (5 mL) was cooled to 5-10° C. and a solution of NaNO$_2$ (0.433 g, 6.3 mmol) in H$_2$O (0.83 mL) was added dropwise. Stirring was continued for 0.5 h, after which the mixture was vacuum filtered. The filtrate was added, simultaneously with a solution of Na$_2$SO$_3$ (1.57 g, 12.4 mmol) in H$_2$O (2.7 mL), to a stirred solution of CuSO$_4$ (0.190 g, 0.76 mmol) and Na$_2$SO$_3$ (1.57 g, 12.4 mmol) in HCl (11.7 mL) and H$_2$O (2.7 mL) at 3-5° C. Stirring was continued for 0.5 h and the resulting precipitate was filtered off, washed with water and dried to give 2-tert-butyl-5-nitrobenzene-1-sulfonyl chloride (0.235 g, 17%). $^1$H NMR (400 MHz, DMSO-d$_6$) δ 9.13 (d, J=2.5 Hz, 1H), 8.36 (dd, J=8.9, 2.5 Hz, 1H), 7.88 (d, J=8.9 Hz, 1H), 1.59 (s, 9H).

2-tert-Butyl-5-nitrobenzene-1-sulfonamide

To a solution of 2-tert-butyl-5-nitrobenzene-1-sulfonyl chloride (100 mg, 0.36 mmol) in ether (2 mL) was added aqueous NH$_4$OH (128 μL, 3.6 mmol) at 0° C. The mixture was stirred at room temperature overnight, diluted with water and extracted with ether. The combined ether extracts were washed with brine and dried over Na$_2$SO$_4$. After removal of solvent, the residue was purified by column chromatography (0-50% EtOAc-Hexane) to give 2-tert-butyl-5-nitrobenzene-1-sulfonamide (31.6 mg, 34%).

E-7; 2-tert-Butyl-5-aminobenzene-1-sulfonamide

A solution of 2-tert-butyl-5-nitrobenzene-1-sulfonamide (32 mg, 0.12 mmol) and SnCl$_2$.2H$_2$O (138 mg, 0.61 mmol) in EtOH (1.5 mL) was heated in microwave oven at 100° C. for 30 min. The mixture was diluted with EtOAc and water, basified with sat. NaHCO$_3$ and filtered through Celite. The organic layer was separated from water and dried over Na$_2$SO$_4$. Solvent was removed by evaporation to provide 2-tert-butyl-5-aminobenzene-1-sulfonamide (E-7) (28 mg, 100%), which was used without further purification. HPLC ret. time 1.99 min, 10-99% CH$_3$CN, 5 min run; ESI-MS 229.3 m/z (MH$^+$).

Example 6

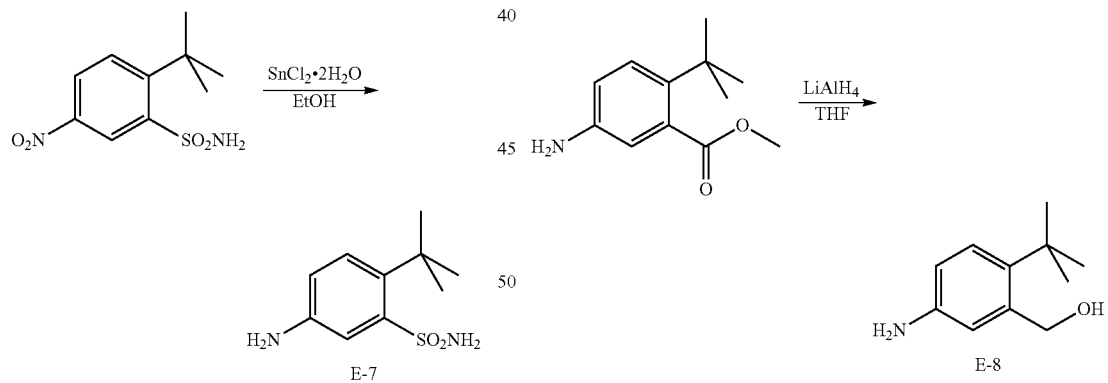

E-8; (2-tert-Butyl-5-aminophenyl)methanol

To a solution of methyl 2-tert-butyl-5-aminobenzoate (159 mg, 0.72 mmol) in THF (5 mL) was added dropwise LiAlH$_4$ (1.4 mL, 1M in THF, 1.4 mmol) at 0° C. The reaction mixture was refluxed for 2 h, diluted with H$_2$O and extracted with EtOAc. The combined organic layers were washed with brine and dried over MgSO$_4$. After filtration, the filtrate was concentrated to give (2-tert-butyl-5-aminophenyl)methanol (E-8) (25 mg, 20%), which was used without further purification. $^1$H NMR (400 MHz, CDCl$_3$) δ 7.17 (d, J=8.5 Hz, 1H), 6.87 (d, J=2.6 Hz, 1H), 6.56 (dd, J=8.4, 2.7 Hz, 1H), 4.83 (s, 2H), 1.36 (s, 9H).

Example 7

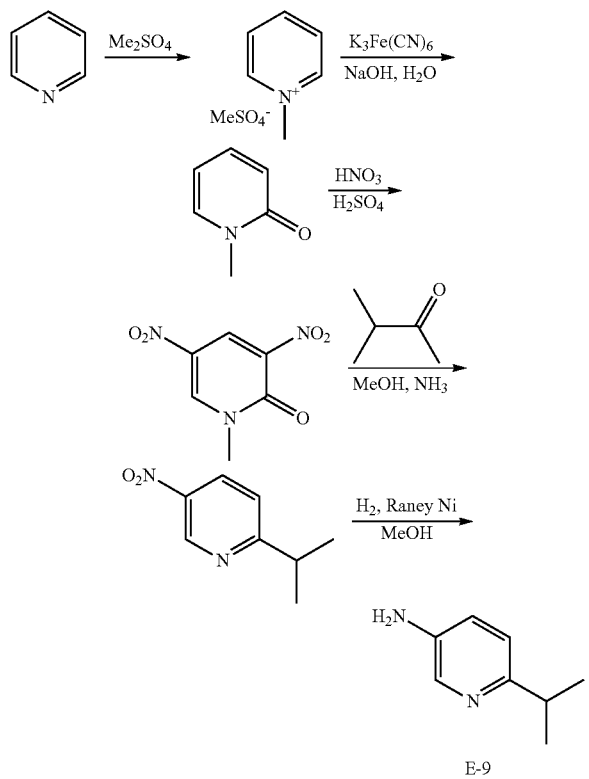

1-Methyl-pyridinium monomethyl sulfuric acid salt

Methyl sulfate (30 mL, 39.8 g, 0.315 mol) was added dropwise to dry pyridine (25.0 g, 0.316 mol) added dropwise. The mixture was stirred at room temperature for 10 min, then at 100° C. for 2 h. The mixture was cooled to room temperature to give crude 1-methyl-pyridinium monomethyl sulfuric acid salt (64.7 g, quant.), which was used without further purification.

1-Methyl-2-pyridone

A solution of 1-methyl-pyridinium monomethyl sulfuric acid salt (50 g, 0.243 mol) in water (54 mL) was cooled to 0° C. Separate solutions of potassium ferricyanide (160 g, 0.486 mol) in water (320 mL) and sodium hydroxide (40 g, 1.000 mol) in water (67 mL) were prepared and added dropwise from two separatory funnels to the well-stirred solution of 1-methyl-pyridinium monomethyl sulfuric acid salt, at such a rate that the temperature of reaction mixture did not rise above 10° C. The rate of addition of these two solutions was regulated so that all the sodium hydroxide solution had been introduced into the reaction mixture when one-half of the potassium Ferric Cyanide solution had been added. After addition was complete, the reaction mixture was allowed to warm to room temperature and stirred overnight. Dry sodium carbonate (91.6 g) was added, and the mixture was stirred for 10 min. The organic layer was separated, and the aqueous layer was extracted with CH$_2$Cl$_2$ (100 mL×3). The combined organic layers were dried and concentrated to yield 1-methyl-2-pyridone (25.0 g, 94%), which was used without further purification.

1-Methyl-3,5-dinitro-2-pyridone

1-Methyl-2-pyridone (25.0 g, 0.229 mol) was added to sulfuric acid (500 mL) at 0° C. After stirring for 5 min., nitric acid (200 mL) was added dropwise at 0° C. After addition, the reaction temperature was slowly raised to 100° C., and then maintained for 5 h. The reaction mixture was poured into ice, basified with potassium carbonate to pH 8 and extracted with CH$_2$Cl$_2$ (100 mL×3). The combined organic layers were dried over Na$_2$SO$_4$ and concentrated to yield 1-methyl-3,5-dinitro-2-pyridone (12.5 g, 28%), which was used without further purification.

2-Isopropyl-5-nitro-pyridine

To a solution of 1-methyl-3,5-dinitro-2-pyridone (8.0 g, 40 mmol) in methyl alcohol (20 mL) was added dropwise 3-methyl-2-butanone (5.1 mL, 48 mmol), followed by ammonia solution in methyl alcohol (10.0 g, 17%, 100 mmol). The reaction mixture was heated at 70° C. for 2.5 h under atmospheric pressure. The solvent was removed under vacuum and the residual oil was dissolved in CH$_2$Cl$_2$, and then filtered. The filtrate was dried over Na$_2$SO$_4$ and concentrated to afford 2-isopropyl-5-nitro-pyridine (1.88 g, 28%).

E-9; 2-Isopropyl-5-amino-pyridine

2-Isopropyl-5-nitro-pyridine (1.30 g, 7.82 mmol) was dissolved in methyl alcohol (20 mL), and Raney Ni (0.25 g) was added. The mixture was stirred under H$_2$ (1 atm) at room temperature for 2 h. The catalyst was filtered off, and the filtrate was concentrated under vacuum to give 2-isopropyl-5-amino-pyridine (E-9) (0.55 g, 52%). $^1$H NMR (CDCl$_3$) δ 8.05 (s, 1H), 6.93-6.99 (m, 2H), 3.47 (br s, 2H), 2.92-3.02 (m, 1H), 1.24-1.26 (m, 6H). ESI-MS 137.2 m/z (MH$^+$).

Example 8

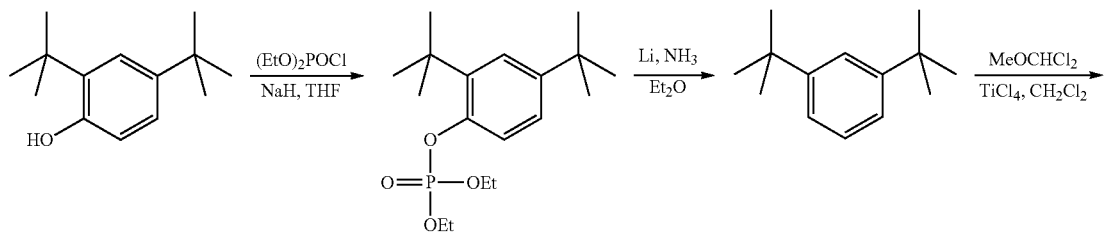

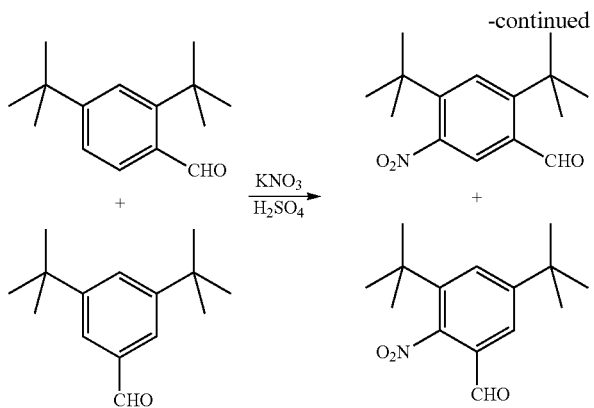
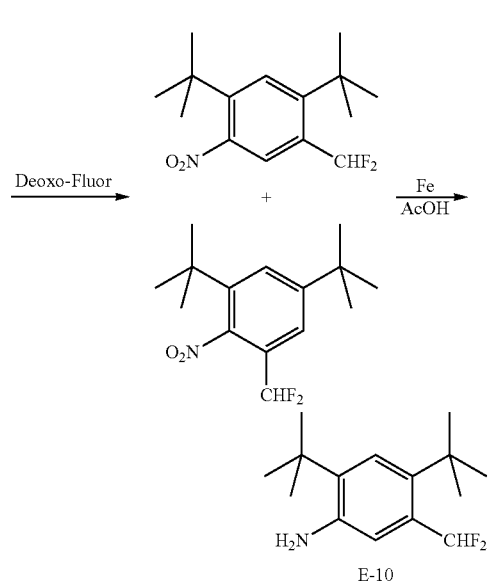

E-10

Phosphoric acid 2,4-di-tert-butyl-phenyl ester diethyl ester

To a suspension of NaH (60% in mineral oil, 6.99 g, 174.7 mmol) in THF (350 mL) was added dropwise a solution of 2,4-di-tert-butylphenol (35 g, 169.6 mmol) in THF (150 mL) at 0° C. The mixture was stirred at 0° C. for 15 min and then phosphorochloridic acid diethyl ester (30.15 g, 174.7 mmol) was added dropwise at 0° C. After addition, the mixture was stirred at this temperature for 15 min. The reaction was quenched with sat. NH$_4$Cl (300 mL). The organic layer was separated and the aqueous phase was extracted with Et$_2$O (350 mL×2). The combined organic layers were washed with brine, dried over anhydrous Na$_2$SO$_4$ and concentrated under vacuum to give crude phosphoric acid 2,4-di-tert-butyl-phenyl ester diethyl ester as a yellow oil (51 g, contaminated with some mineral oil), which was used directly in the next step.

1,3-Di-tert-butyl-benzene

To NH$_3$ (liquid, 250 mL) was added a solution of phosphoric acid 2,4-di-tert-butyl-phenyl ester diethyl ester (51 g, crude from last step, about 0.2 mol) in Et$_2$O (anhydrous, 150 mL) at −78° C. under N$_2$ atmosphere. Lithium metal was added to the solution in small pieces until a blue color persisted. The reaction mixture was stirred at −78° C. for 15 min and then quenched with sat. NH$_4$Cl solution until the mixture turned colorless. Liquid NH$_3$ was evaporated and the residue was dissolved in water, extracted with Et$_2$O (300 mL×2). The combined organic phases were dried over Na$_2$SO$_4$ and concentrated to give crude 1,3-di-tert-butyl-benzene as a yellow oil (30.4 g, 94% over 2 steps, contaminated with some mineral oil), which was used directly in next step.

2,4-Di-tert-butyl-benzaldehyde and 3,5-di-tert-butyl-benzaldehyde

To a stirred solution of 1,3-di-tert-butyl-benzene (30 g, 157.6 mmol) in dry CH$_2$Cl$_2$ (700 mL) was added TiCl$_4$ (37.5 g, 197 mmol) at 0° C., and followed by dropwise addition of MeOCHCl$_2$ (27.3 g, 236.4 mmol). The reaction was allowed to warm to room temperature and stirred for 1 h. The mixture was poured into ice-water and extracted with CH$_2$Cl$_2$. The combined organic phases were washed with NaHCO$_3$ and brine, dried over Na$_2$SO$_4$ and concentrated. The residue was purified by column chromatography (petroleum ether) to give a mixture of 2,4-di-tert-butyl-benzaldehyde and 3,5-di-tert-butyl-benzaldehyde (21 g, 61%).

2,4-Di-tert-butyl-5-nitro-benzaldehyde and 3,5-di-tert-butyl-2-nitro-benzaldehyde To a mixture of 2,4-di-tert-butyl-benzaldehyde and 3,5-di-tert-butyl-benzaldehyde in H$_2$SO$_4$ (250 mL) was added KNO$_3$ (7.64 g, 75.6 mmol) in portions at 0° C. The reaction mixture was stirred at this temperature for 20 min and then poured into crushed ice. The mixture was basified with NaOH solution to pH 8 and extracted with Et$_2$O (10 mL×3). The combined organic layers were washed with water and brine and concentrated. The residue was purified by column chromatography (petroleum ether) to give a mixture of 2,4-di-tert-butyl-5-nitro-benzaldehyde and 3,5-di-tert-butyl-2-nitro-benzaldehyde (2:1 by NMR) as a yellow solid (14.7 g, 82%). After further purification by column chromatography (petroleum ether), 2,4-di-tert-butyl-5-nitro-benzaldehyde (2.5 g, contains 10% 3,5-di-tert-butyl-2-nitro-benzaldehyde) was isolated.

1,5-Di-tert-butyl-2-difluoromethyl-4-nitro-benzene and 1,5-Di-tert-butyl-3-difluoromethyl-2-nitro-benzene 2,4-Di-tert-butyl-5-nitro-benzaldehyde (2.4 g, 9.11 mmol, contaminated with 10% 3,5-di-tert-butyl-2-nitro-benzaldehyde) in neat deoxofluor solution was stirred at room temperature for 5 h. The reaction mixture was poured into cooled sat. NaHCO$_3$ solution and extracted with dichloromethane. The combined organics were dried over Na$_2$SO$_4$, concentrated and purified by column chromatography (petroleum ether) to give 1,5-di-tert-butyl-2-difluoromethyl-4-nitro-benzene (1.5 g) and a mixture of 1,5-di-tert-butyl-2-difluoromethyl-4-nitro-benzene and 1,5-di-tert-butyl-3-difluoromethyl-2-nitro-benzene (0.75 g, contains 28% 1,5-di-tert-butyl-3-difluoromethyl-2-nitro-benzene).

E-10;
1,5-Di-tert-butyl-2-difluoromethyl-4-amino-benzene

To a suspension of iron powder (5.1 g, 91.1 mmol) in 50% acetic acid (25 ml) was added 1,5-di-tert-butyl-2-difluoromethyl-4-nitro-benzene (1.3 g, 4.56 mmol). The reaction mixture was heated at 115° C. for 15 min. Solid was filtered off was washed with acetic acid and $CH_2Cl_2$. The combined filtrate was concentrated and treated with HCl/MeOH. The precipitate was collected via filtration, washed with MeOH and dried to give 1,5-Di-tert-butyl-2-difluoromethyl-4-amino-benzene HCl salt (E-10) as a white solid (1.20 g, 90%). $^1$H NMR (DMSO-$d_6$) δ 7.35-7.70 (t, J=53.7 Hz, 1H), 7.56 (s, 1H), 7.41 (s, 1H), 1.33-1.36 (d, J=8.1 Hz, 1H); ESI-MS 256.3 m/z (MH$^+$).

Example 9

General scheme:

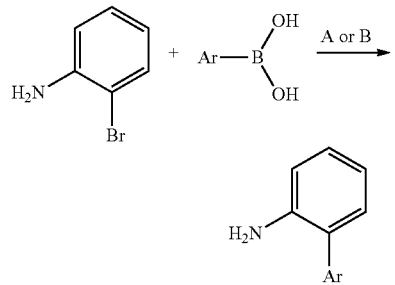

A) Pd(PPh$_3$)$_4$, K$_2$CO$_3$, H$_2$O, THF;
B) Pd$_2$(dba)$_3$, P(tBu)$_3$, KF, THF

Method A

In a 2-dram vial, 2-bromoaniline (100 mg, 0.58 mmol) and the corresponding aryl boronic acid (0.82 mmol) were dissolved in THF (1 mL). H$_2$O (500 µL) was added followed by K$_2$CO$_3$ (200 mg, 1.0 mmol) and Pd(PPh$_3$)$_4$ (100 mg, 0.1 mmol). The vial was purged with argon and sealed. The vial was then heated at 75° C. for 18 h. The crude sample was diluted in EtOAc and filtered through a silica gel plug. The organics were concentrated via Savant Speed-vac. The crude amine was used without further purification.

Method B

In a 2-dram vial, the corresponding aryl boronic acid (0.58 mmol) was added followed by KF (110 mg, 1.9 mmol). The solids were suspended in THF (2 mL), and then 2-bromoaniline (70 µL, 0.58 mmol) was added. The vial was purged with argon for 1 min. P($^t$Bu)$_3$ (100 µL, 10% sol. in hexanes) was added followed by Pd$_2$(dba)$_3$ (900 µL, 0.005 M in THF). The vial was purged again with argon and sealed. The vial was agitated on an orbital shaker at room temperature for 30 min and heated in a heating block at 80° C. for 16 h. The vial was then cooled to 20° C. and the suspension was passed through a pad of Celite. The pad was washed with EtOAc (5 mL). The organics were combined and concentrated under vacuum to give a crude amine that was used without further purification.

The table below includes the amines made following the general scheme above.

| Product | Name | Method |
|---|---|---|
| F-1 | 4'-Methyl-biphenyl-2-ylamine | A |
| F-2 | 3'-Methyl-biphenyl-2-ylamine | A |
| F-3 | 2'-Methyl-biphenyl-2-ylamine | A |
| F-4 | 2',3'-Dimethyl-biphenyl-2-ylamine | A |
| F-5 | (2'-Amino-biphenyl-4-yl)-methanol | A |
| F-6 | N*4'*,N*4'*-Dimethyl-biphenyl-2,4'-diamine | B |
| F-7 | 2'-Trifluoromethyl-biphenyl-2-ylamine | B |
| F-8 | (2'-Amino-biphenyl-4-yl)-acetonitrile | A |
| F-9 | 4'-Isobutyl-biphenyl-2-ylamine | A |
| F-10 | 3'-Trifluoromethyl-biphenyl-2-ylamine | B |
| F-11 | 2-Pyridin-4-yl-phenylamine | B |
| F-12 | 2-(1H-Indol-5-yl)-phenylamine | B |
| F-13 | 3',4'-Dimethyl-biphenyl-2-ylamine | A |
| F-14 | 4'-Isopropyl-biphenyl-2-ylamine | A |
| F-15 | 3'-Isopropyl-biphenyl-2-ylamine | A |
| F-16 | 4'-Trifluoromethyl-biphenyl-2-ylamine | B |
| F-17 | 4'-Methoxy-biphenyl-2-ylamine | B |
| F-18 | 3'-Methoxy-biphenyl-2-ylamine | B |
| F-19 | 2-Benzo[1,3]dioxol-5-yl-phenylamine | B |
| F-20 | 3'-Ethoxy-biphenyl-2-ylamine | B |
| F-21 | 4'-Ethoxy-biphenyl-2-ylamine | B |
| F-22 | 2'-Ethoxy-biphenyl-2-ylamine | B |
| F-23 | 4'-Methylsulfanyl-biphenyl-2-ylamine | B |
| F-24 | 3',4'-Dimethoxy-biphenyl-2-ylamine | B |
| F-25 | 2',6'-Dimethoxy-biphenyl-2-ylamine | B |
| F-26 | 2',5'-Dimethoxy-biphenyl-2-ylamine | B |
| F-27 | 2',4'-Dimethoxy-biphenyl-2-ylamine | B |
| F-28 | 5'-Chloro-2'-methoxy-biphenyl-2-ylamine | B |
| F-29 | 4'-Trifluoromethoxy-biphenyl-2-ylamine | B |
| F-30 | 3'-Trifluoromethoxy-biphenyl-2-ylamine | B |
| F-31 | 4'-Phenoxy-biphenyl-2-ylamine | B |
| F-32 | 2'-Fluoro-3'-methoxy-biphenyl-2-ylamine | B |
| F-33 | 2'-Phenoxy-biphenyl-2-ylamine | B |
| F-34 | 2-(2,4-Dimethoxy-pyrimidin-5-yl)-phenylamine | B |
| F-35 | 5'-Isopropyl-2'-methoxy-biphenyl-2-ylamine | B |
| F-36 | 2'-Trifluoromethoxy-biphenyl-2-ylamine | B |
| F-37 | 4'-Fluoro-biphenyl-2-ylamine | B |
| F-38 | 3'-Fluoro-biphenyl-2-ylamine | B |
| F-39 | 2'-Fluoro-biphenyl-2-ylamine | B |
| F-40 | 2'-Amino-biphenyl-3-carbonitrile | B |
| F-41 | 4'-Fluoro-3'-methyl-biphenyl-2-ylamine | B |
| F-42 | 4'-Chloro-biphenyl-2-ylamine | B |
| F-43 | 3'-Chloro-biphenyl-2-ylamine | B |
| F-44 | 3',5'-Difluoro-biphenyl-2-ylamine | B |
| F-45 | 2',3'-Difluoro-biphenyl-2-ylamine | B |
| F-46 | 3',4'-Difluoro-biphenyl-2-ylamine | B |
| F-47 | 2',4'-Difluoro-biphenyl-2-ylamine | B |
| F-48 | 2',5'-Difluoro-biphenyl-2-ylamine | B |
| F-49 | 3'-Chloro-4'-fluoro-biphenyl-2-ylamine | B |
| F-50 | 3',5'-Dichloro-biphenyl-2-ylamine | B |
| F-51 | 2',5'-Dichloro-biphenyl-2-ylamine | B |
| F-52 | 2',3'-Dichloro-biphenyl-2-ylamine | B |
| F-53 | 3',4'-Dichloro-biphenyl-2-ylamine | B |
| F-54 | 2'-Amino-biphenyl-4-carboxylic acid methyl ester | B |
| F-55 | 2'-Amino-biphenyl-3-carboxylic acid methyl ester | B |
| F-56 | 2'-Methylsulfanyl-biphenyl-2-ylamine | B |
| F-57 | N-(2'-Amino-biphenyl-3-yl)-acetamide | B |
| F-58 | 4'-Methanesulfinyl-biphenyl-2-ylamine | B |
| F-59 | 2',4'-Dichloro-biphenyl-2-ylamine | B |
| F-60 | 4'-Methanesulfonyl-biphenyl-2-ylamine | B |
| F-61 | 2'-Amino-biphenyl-2-carboxylic acid isopropyl ester | B |
| F-62 | 2-Furan-2-yl-phenylamine | B |
| F-63 | 1-[5-(2-Amino-phenyl)-thiophen-2-yl]-ethanone | B |
| F-64 | 2-Benzo[b]thiophen-2-yl-phenylamine | B |
| F-65 | 2-Benzo[b]thiophen-3-yl-phenylamine | B |
| F-66 | 2-Furan-3-yl-phenylamine | B |
| F-67 | 2-(4-Methyl-thiophen-2-yl)-phenylamine | B |
| F-68 | 5-(2-Amino-phenyl)-thiophene-2-carbonitrile | B |

Example 10

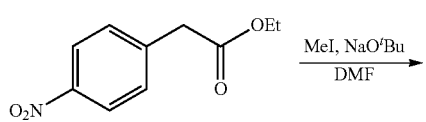

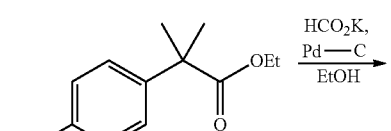

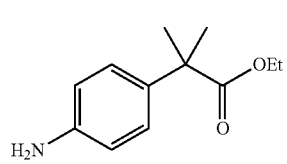

G-1

Ethyl 2-(4-nitrophenyl)-2-methylpropanoate

Sodium t-butoxide (466 mg, 4.85 mmol) was added to DMF (20 mL) at 0° C. The cloudy solution was re-cooled to 5° C. Ethyl 4-nitrophenylacetate (1.0 g, 4.78 mmol) was added. The purple slurry was cooled to 5° C. and methyl iodide (0.688 mL, 4.85 mmol) was added over 40 min. The mixture was stirred at 5-10° C. for 20 min, and then re-charged with sodium t-butoxide (466 mg, 4.85 mmol) and methyl iodide (0.699 mL, 4.85 mmol). The mixture was stirred at 5-10° C. for 20 min and a third charge of sodium t-butoxide (47 mg, 0.48 mmol) was added followed by methyl iodide (0.057 mL, 0.9 mmol). Ethyl acetate (100 mL) and HCl (0.1; N, 50 mL) were added. The organic layer was separated, washed with brine and dried over $Na_2SO_4$. After filtration, the filtrate was concentrated to provide ethyl 2-(4-nitrophenyl)-2-methylpropanoate (900 mg, 80%), which was used without further purification.

G-1; Ethyl 2-(4-aminophenyl)-2-methylpropanoate

A solution of ethyl 2-(4-nitrophenyl)-2-methylpropanoate (900 mg, 3.8 mmol) in EtOH (10 mL) was treated with 10% Pd—C (80 mg) and heated to 45° C. A solution of potassium formate (4.10 g, 48.8 mmol) in $H_2O$ (11 mL) was added over a period of 15 min. The reaction mixture was stirred at 65° C. for 2 h and then treated with additional 300 mg of Pd/C. The reaction was stirred for 1.5 h and then filtered through Celite. The solvent volume was reduced by approximately 50% under reduced pressure and extracted with EtOAc. The organic layers were dried over $Na_2SO_4$ and the solvent was removed under reduced pressure to yield ethyl 2-(4-aminophenyl)-2-methylpropanoate (G-1) (670 mg, 85%). $^1$H NMR (400 MHz, $CDCl_3$) δ 7.14 (d, J=8.5 Hz, 2H), 6.65 (d, J=8.6 Hz, 2H), 4.10 (q, J=7.1 Hz, 2H), 1.53 (s, 6H), 1.18 (t, J=7.1 Hz, 3H).

Example 11

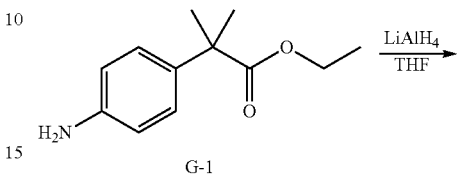

G-1

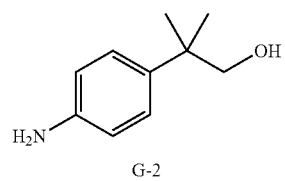

G-2

G-2; 2-(4-Aminophenyl)-2-methylpropan-1-ol

A solution of ethyl 2-(4-aminophenyl)-2-methylpropanoate (30 mg, 0.145 mmol) in THF (1 mL) was treated with $LiAlH_4$ (1M solution in THF, 0.226 mL, 0.226 mmol) at 0° C. and stirred for 15 min. The reaction was treated with 0.1N NaOH, extracted with EtOAc and the organic layers were dried over $Na_2SO_4$. The solvent was removed under reduced pressure to yield 2-(4-aminophenyl)-2-methylpropan-1-ol (G-2), which was used without further purification: $^1$H NMR (400 MHz, $CDCl_3$) δ 7.17 (d, J=8.5 Hz, 2H), 6.67 (d, J=8.5 Hz, 2H), 3.53 (s, 2H), 1.28 (s, 6H).

Example 12

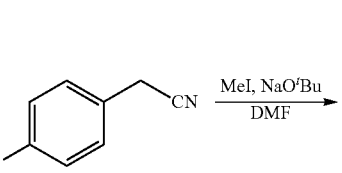

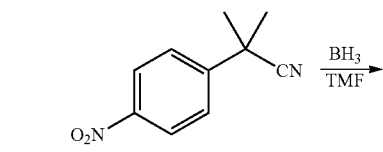

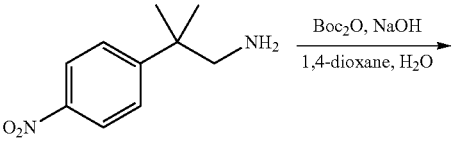

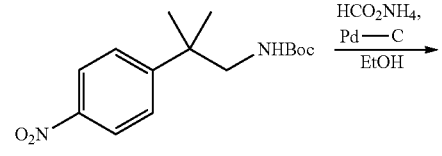

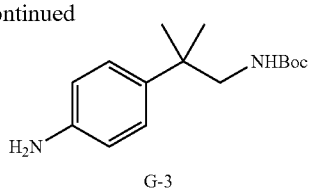

G-3

2-methyl-2-(4-nitrophenyl)propanenitrile

A suspension of sodium tert-butoxide (662 mg, 6.47 mmol) in DMF (20 mL) at 0° C. was treated with 4-nitrophenylacetonitrile (1000 mg, 6.18 mmol) and stirred for 10 min. Methyl iodide (400 μL, 6.47 mmol) was added dropwise over 15 min. The solution was stirred at 0-10° C. for 15 min and then at room temperature for additional 15 min. To this purple solution was added sodium tert-butoxide (662 mg, 6.47 mmol) and the solution was stirred for 15 min. Methyl iodide (400 μL, 6.47 mmol) was added dropwise over 15 min and the solution was stirred overnight. Sodium tert-butoxide (192 mg, 1.94 mmol) was added and the reaction was stirred at 0° C. for 10 minutes. Methyl iodide (186 μL, 2.98 mmol) was added and the reaction was stirred for 1 h. The reaction mixture was then partitioned between 1N HCl (50 mL) and EtOAc (75 mL). The organic layer was washed with 1 N HCl and brine, dried over $Na_2SO_4$ and concentrated to yield 2-methyl-2-(4-nitrophenyl)propanenitrile as a green waxy solid (1.25 g, 99%). $^1H$ NMR (400 MHz, $CDCl_3$) δ 8.24 (d, J=8.9 Hz, 2H), 7.66 (d, J=8.9 Hz, 2H), 1.77 (s, 6H).

2-Methyl-2-(4-nitrophenyl)propan-1-amine

To a cooled solution of 2-methyl-2-(4-nitrophenyl)propanenitrile (670 mg, 3.5 mmol) in THF (15 mL) was added $BH_3$ (1M in THF, 14 mL, 14 mmol) dropwise at 0° C. The mixture was warmed to room temperature and heated at 70° C. for 2 h. 1N HCl solution (2 mL) was added, followed by the addition of NaOH until pH>7. The mixture was extracted with ether and ether extract was concentrated to give 2-methyl-2-(4-nitrophenyl)propan-1-amine (610 mg, 90%), which was used without further purification. $^1H$ NMR (400 MHz, $CDCl_3$) δ 8.20 (d, J=9.0 Hz, 2H), 7.54 (d, J=9.0 Hz, 2H), 2.89 (s, 2H), 1.38 (s, 6H).

tert-Butyl 2-methyl-2-(4-nitrophenyl)propylcarbamate

To a cooled solution of 2-methyl-2-(4-nitrophenyl)propan-1-amine (600 mg, 3.1 mmol) and 1N NaOH (3 mL, 3 mmol) in 1,4-dioxane (6 mL) and water (3 mL) was added $Boc_2O$ (742 mg, 3.4 mmol) at 0° C. The reaction was allowed to warm to room temperature and stirred overnight. The reaction was made acidic with 5% $KHSO_4$ solution and then extracted with ethyl acetate. The organic layer was dried over $MgSO_4$ and concentrated to give tert-butyl 2-methyl-2-(4-nitrophenyl)propylcarbamate (725 mg, 80%), which was used without further purification. $^1H$ NMR (400 MHz, $CDCl_3$) δ 8.11 (d, J=8.9 Hz, 2H), 7.46 (d, J=8.8 Hz, 2H), 3.63 (s, 2H), 1.31-1.29 (m, 15H).

G-3; tert-Butyl 2-methyl-2-(4-aminophenyl)propylcarbamate

To a refluxing solution of tert-butyl 2-methyl-2-(4-nitrophenyl)propylcarbamate (725 mg, 2.5 mmol) and ammonium formate (700 mg, 10.9 mmol) in EtOH (25 mL) was added Pd-5% wt on carbon (400 mg). The mixture was refluxed for 1 h, cooled and filtered through Celite. The filtrate was concentrated to give tert-butyl 2-methyl-2-(4-aminophenyl)propylcarbamate (G-3) (550 mg, 83%), which was used without further purification. $^1H$ NMR (400 MHz, DMSO-$d_6$) δ 6.99 (d, J=8.5 Hz, 2H), 6.49 (d, J=8.6 Hz, 2H), 4.85 (s, 2H), 3.01 (d, J=6.3 Hz, 2H), 1.36 (s, 9H), 1.12 (s, 6H); HPLC ret. time 2.02 min, 10-99% $CH_3CN$, 5 min run; ESI-MS 265.2 m/z ($MH^+$).

Example 13

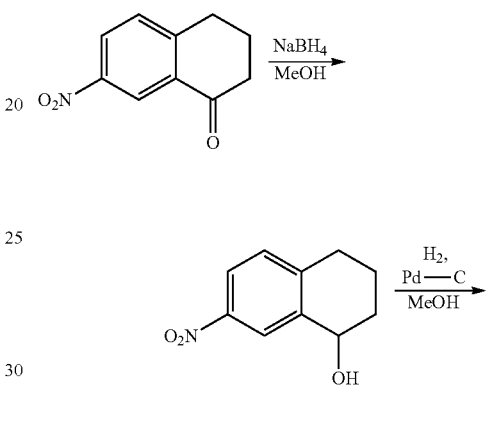

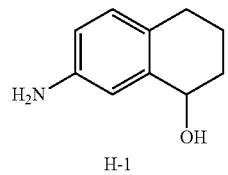

H-1

7-Nitro-1,2,3,4-tetrahydro-naphthalen-1-ol

7-Nitro-3,4-dihydro-2H-naphthalen-1-one (200 mg, 1.05 mmol) was dissolved in methanol (5 mL) and $NaBH_4$ ((78 mg, 2.05 mmol) was added in portions. The reaction was stirred at room temperature for 20 min and then concentrated and purified by column chromatography (10-50% ethyl acetate-hexanes) to yield 7-nitro-1,2,3,4-tetrahydro-naphthalen-1-ol (163 mg, 80%). $^1H$ NMR (400 MHz, $CD_3CN$) δ 8.30 (d, J=2.3 Hz, 1H), 8.02 (dd, J=8.5, 2.5 Hz, 1H), 7.33 (d, J=8.5 Hz, 1H), 4.76 (t, J=5.5 Hz, 1H), 2.96-2.80 (m, 2H), 2.10-1.99 (m, 2H), 1.86-1.77 (m, 2H);

HPLC ret. time 2.32 min, 10-99% $CH_3CN$, 5 min run.

H-1; 7-Amino-1,2,3,4-tetrahydro-naphthalen-1-ol 7-nitro-1,2,3,4-tetrahydro-naphthalen-1-ol (142 mg, 0.73 mmol) was dissolved in methanol (10 mL) and the flask was flushed with $N_2$ (g). 10% Pd—C (10 mg) was added and the reaction was stirred under $H_2$ (1 atm) at room temperature overnight. The reaction was filtered and the filtrate concentrated to yield 7-amino-1,2,3,4-tetrahydro-naphthalen-1-ol

Example 14

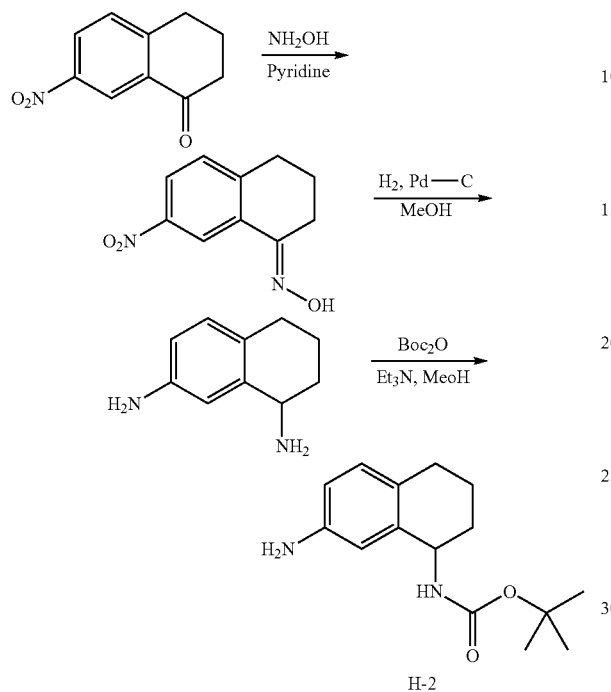

7-Nitro-3,4-dihydro-2H-naphthalen-1-one oxime

To a solution of 7-nitro-3,4-dihydro-2H-naphthalen-1-one (500 mg, 2.62 mmol) in pyridine (2 mL) was added hydroxylamine solution (1 mL, ~50% solution in water). The reaction was stirred at room temperature for 1 h, then concentrated and purified by column chromatography (10-50% ethyl acetate-hexanes) to yield 7-nitro-3,4-dihydro-2H-naphthalen-1-one oxime (471 mg, 88%). HPLC ret. time 2.67 min, 10-99% $CH_3CN$, 5 min run; ESI-MS 207.1 m/z (MH+).

1,2,3,4-Tetrahydro-naphthalene-1,7-diamine

7-Nitro-3,4-dihydro-2H-naphthalen-1-one oxime (274 mg, 1.33 mmol) was dissolved in methanol (10 mL) and the flask was flushed with $N_2$ (g). 10% Pd—C (50 mg) was added and the reaction was stirred under $H_2$ (1 atm) at room temperature overnight. The reaction was filtered and the filtrate was concentrated to yield 1,2,3,4-tetrahydro-naphthalene-1, 7-diamine (207 mg, 96%). $^1$H NMR (400 MHz, DMSO-$d_6$) δ 6.61-6.57 (m, 2H), 6.28 (dd, J=8.0, 2.4 Hz, 1H), 4.62 (s, 2H), 3.58 (m, 1H), 2.48-2.44 (m, 2H), 1.78-1.70 (m, 2H), 1.53-1.37 (m, 2H).

H-2; (7-Amino-1,2,3,4-tetrahydro-naphthalen-1-yl)-carbamic acid tert-butyl ester To a solution of 1,2,3,4-tetrahydro-naphthalene-1,7-diamine (154 mg, 0.95 mmol) and triethylamine (139 μL, 1.0 mmol) in methanol (2 mL) cooled to 0° C. was added di-tert-butyl dicarbonate (207 mg, 0.95 mmol). The reaction was stirred at 0° C. and then concentrated and purified by column chromatography (5-50% methanol-dichloromethane) to yield (7-amino-1,2,3,4-tetrahydro-naphthalen-1-yl)-carbamic acid tert-butyl ester (H-2) (327 mg, quant.). HPLC ret. time 1.95 min, 10-99% $CH_3CN$, 5 min run; ESI-MS 263.1 m/z (MH+).

Example 15

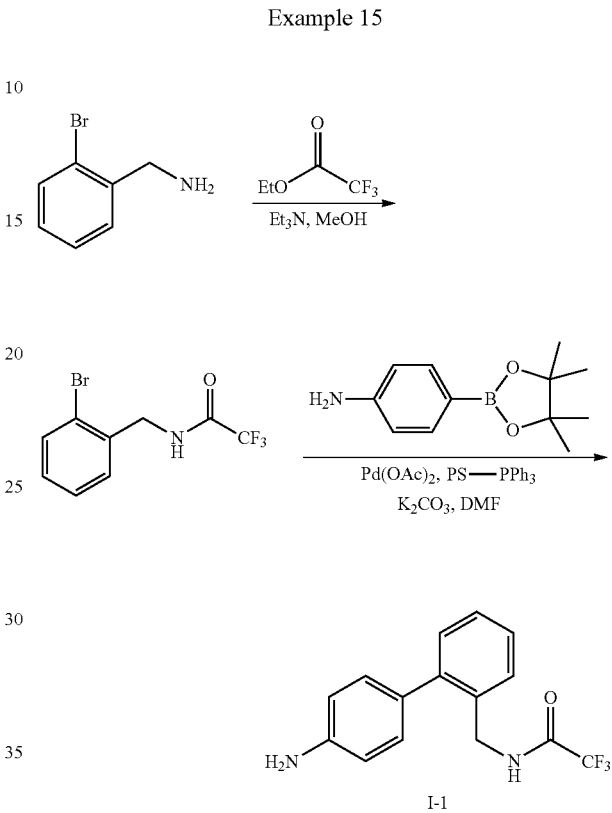

N-(2-Bromo-benzyl)-2,2,2-trifluoro-acetamide

To a solution of 2-bromobenzylamine (1.3 mL, 10.8 mmol) in methanol (5 mL) was added ethyl trifluoroacetate (1.54 mL, 21.6 mmol) and triethylamine (1.4 mL, 10.8 mmol) under a nitrogen atmosphere. The reaction was stirred at room temperature for 1 h. The reaction mixture was then concentrated under vacuum to yield N-(2-bromo-benzyl)-2,2,2-trifluoro-acetamide (3.15 g, quant.). HPLC ret. time 2.86 min, 10-99% $CH_3CN$, 5 min run; ESI-MS 283.9 m/z (MH+).

I-1; N-(4'-Amino-biphenyl-2-ylmethyl)-2,2,2-trifluoro-acetamide

A mixture of N-(2-bromo-benzyl)-2,2,2-trifluoro-acetamide (282 mg, 1.0 mmol), 4,4,4,5,5-tetramethyl-1,3,2-dioxaborolan-2-yl)aniline (284 mg, 1.3 mmol), Pd(OAc)$_2$ (20 mg, 0.09 mmol) and PS—PPh$_3$ (40 mg, 3 mmol/g, 0.12 mmol) was dissolved in DMF (5 mL) and 4M $K_2CO_3$ solution (0.5 mL) was added. The reaction was heated at 80° C. overnight. The mixture was filtered, concentrated and purified by column chromatography (0-50% ethyl acetate-hexanes) to yield N-(4'-amino-biphenyl-2-ylmethyl)-2,2,2-trifluoro-acetamide (1-1) (143 mg, 49%).

HPLC ret. time 1.90 min, 10-99% $CH_3CN$, 5 min run; ESI-MS 295.5 m/z (MH+).

Commercially Available Amines

| Amine | Name |
|---|---|
| J-1 | 2-methoxy-5-methylbenzenamine |
| J-2 | 2,6-diisopropylbenzenamine |
| J-3 | pyridin-2-amine |
| J-4 | 4-pentylbenzenamine |
| J-5 | isoquinolin-3-amine |
| J-6 | aniline |
| J-7 | 4-phenoxybenzenamine |
| J-8 | 2-(2,3-dimethylphenoxy)pyridin-3-amine |
| J-9 | 4-ethynylbenzenamine |
| J-10 | 2-sec-butylbenzenamine |
| J-11 | 2-amino-4,5-dimethoxybenzonitrile |
| J-12 | 2-tert-butylbenzenamine |
| J-13 | 1-(7-amino-3,4-dihydroisoquinolin-2(1H)-yl)ethanone |
| J-14 | 4-(4-methyl-4H-1,2,4-triazol-3-yl)benzenamine |
| J-15 | 2'-Aminomethyl-biphenyl-4-ylamine |
| J-16 | 1H-Indazol-6-ylamine |
| J-17 | 2-(2-methoxyphenoxy)-5-(trifluoromethyl)benzenamine |
| J-18 | 2-tert-butylbenzenamine |
| J-19 | 2,4,6-trimethylbenzenamine |
| J-20 | 5,6-dimethyl-1H-benzo[d]imidazol-2-amine |
| J-21 | 2,3-dihydro-1H-inden-4-amine |
| J-22 | 2-sec-butyl-6-ethylbenzenamine |
| J-23 | quinolin-5-amine |
| J-24 | 4-(benzyloxy)benzenamine |
| J-25 | 2'-Methoxy-biphenyl-2-ylamine |
| J-26 | benzo[c][1,2,5]thiadiazol-4-amine |
| J-27 | 3-benzylbenzenamine |
| J-28 | 4-isopropylbenzenamine |
| J-29 | 2-(phenylsulfonyl)benzenamine |
| J-30 | 2-methoxybenzenamine |
| J-31 | 4-amino-3-ethylbenzonitrile |
| J-32 | 4-methylpyridin-2-amine |
| J-33 | 4-chlorobenzenamine |
| J-34 | 2-(benzyloxy)benzenamine |
| J-35 | 2-amino-6-chlorobenzonitrile |
| J-36 | 3-methylpyridin-2-amine |
| J-37 | 4-aminobenzonitrile |
| J-38 | 3-chloro-2,6-diethylbenzenamine |
| J-39 | 3-phenoxybenzenamine |
| J-40 | 2-benzylbenzenamine |
| J-41 | 2-(2-fluorophenoxy)pyridin-3-amine |
| J-42 | 5-chloropyridin-2-amine |
| J-43 | 2-(trifluoromethyl)benzenamine |
| J-44 | (4-(2-aminophenyl)piperazin-1-yl)(phenyl)methanone |
| J-45 | 1H-benzo[d][1,2,3]triazol-5-amine |
| J-46 | 2-(1H-indol-2-yl)benzenamine |
| J-47 | 4-Methyl-biphenyl-3-ylamine |
| J-48 | pyridin-3-amine |
| J-49 | 3,4-dimethoxybenzenamine |
| J-50 | 3H-benzo[d]imidazol-5-amine |
| J-51 | 3-aminobenzonitrile |
| J-52 | 6-chloropyridin-3-amine |
| J-53 | o-toluidine |
| J-54 | 1H-indol-5-amine |
| J-55 | [1,2,4]triazolo[1,5-a]pyridin-8-amine |
| J-56 | 2-methoxypyridin-3-amine |
| J-57 | 2-butoxybenzenamine |
| J-58 | 2,6-dimethylbenzenamine |
| J-59 | 2-(methylthio)benzenamine |
| J-60 | 2-(5-methylfuran-2-yl)benzenamine |
| J-61 | 3-(4-aminophenyl)-3-ethylpiperidine-2,6-dione |
| J-62 | 2,4-dimethylbenzenamine |
| J-63 | 5-fluoropyridin-2-amine |
| J-64 | 4-cyclohexylbenzenamine |
| J-65 | 4-Amino-benzenesulfonamide |
| J-66 | 2-ethylbenzenamine |
| J-67 | 4-fluoro-3-methylbenzenamine |
| J-68 | 2,6-dimethoxypyridin-3-amine |
| J-69 | 4-tert-butylbenzenamine |
| J-70 | 4-sec-butylbenzenamine |
| J-71 | 5,6,7,8-tetrahydronaphthalen-2-amine |
| J-72 | 3-(Pyrrolidine-1-sulfonyl)-phenylamine |
| J-73 | 4-Adamantan-1-yl-phenylamine |
| J-74 | 3-amino-5,6,7,8-tetrahydronaphthalen-2-ol |
| J-75 | benzo[d][1,3]dioxol-5-amine |
| J-76 | 5-chloro-2-phenoxybenzenamine |
| J-77 | N1-tosylbenzene-1,2-diamine |
| J-78 | 3,4-dimethylbenzenamine |
| J-79 | 2-(trifluoromethylthio)benzenamine |
| J-80 | 1H-indol-7-amine |
| J-81 | 3-methoxybenzenamine |
| J-82 | quinolin-8-amine |
| J-83 | 2-(2,4-difluorophenoxy)pyridin-3-amine |
| J-84 | 2-(4-aminophenyl)acetonitrile |
| J-85 | 2,6-dichlorobenzenamine |
| J-86 | 2,3-dihydrobenzofuran-5-amine |
| J-87 | p-toluidine |
| J-88 | 2-methylquinolin-8-amine |
| J-89 | 2-tert-butylbenzenamine |
| J-90 | 3-chlorobenzenamine |
| J-91 | 4-tert-butyl-2-chlorobenzenamine |
| J-92 | 2-Amino-benzenesulfonamide |
| J-93 | 1-(2-aminophenyl)ethanone |
| J-94 | m-toluidine |
| J-95 | 2-(3-chloro-5-(trifluoromethyl)pyridin-2-yloxy)benzenamine |
| J-96 | 2-amino-6-methylbenzonitrile |
| J-97 | 2-(prop-1-en-2-yl)benzenamine |
| J-98 | 4-Amino-N-pyridin-2-yl-benzenesulfonamide |
| J-99 | 2-ethoxybenzenamine |
| J-100 | naphthalen-1-amine |
| J-101 | Biphenyl-2-ylamine |
| J-102 | 2-(trifluoromethyl)-4-isopropylbenzenamine |
| J-103 | 2,6-diethylbenzenamine |
| J-104 | 5-(trifluoromethyl)pyridin-2-amine |
| J-105 | 2-aminobenzamide |
| J-106 | 3-(trifluoromethoxy)benzenamine |
| J-107 | 3,5-bis(trifluoromethyl)benzenamine |
| J-108 | 4-vinylbenzenamine |
| J-109 | 4-(trifluoromethyl)benzenamine |
| J-110 | 2-morpholinobenzenamine |
| J-111 | 5-amino-1H-benzo[d]imidazol-2(3H)-one |
| J-112 | quinolin-2-amine |
| J-113 | 3-methyl-1H-indol-4-amine |
| J-114 | pyrazin-2-amine |
| J-115 | 1-(3-aminophenyl)ethanone |
| J-116 | 2-ethyl-6-isopropylbenzenamine |
| J-117 | 2-(3-(4-chlorophenyl)-1,2,4-oxadiazol-5-yl)benzenamine |
| J-118 | N-(4-amino-2,5-diethoxyphenyl)benzamide |
| J-119 | 5,6,7,8-tetrahydronaphthalen-1-amine |
| J-120 | 2-(1H-benzo[d]imidazol-2-yl)benzenamine |
| J-121 | 1,1-Dioxo-1H-1lambda*6*-benzo[b]thiophen-6-ylamine |
| J-122 | 2,5-diethoxybenzenamine |
| J-123 | 2-isopropyl-6-methylbenzenamine |
| J-124 | tert-butyl 5-amino-3,4-dihydroisoquinoline-2(1H)-carboxylate |
| J-125 | 2-(2-aminophenyl)ethanol |
| J-126 | (4-aminophenyl)methanol |
| J-127 | 5-methylpyridin-2-amine |
| J-128 | 2-(pyrrolidin-1-yl)benzenamine |
| J-129 | 4-propylbenzenamine |
| J-130 | 3,4-dichlorobenzenamine |
| J-131 | 2-phenoxybenzenamine |
| J-132 | Biphenyl-2-ylamine |
| J-133 | 2-chlorobenzenamine |
| J-134 | 2-amino-4-methylbenzonitrile |
| J-135 | (2-aminophenyl)(phenyl)methanone |
| J-136 | aniline |
| J-137 | 3-(trifluoromethylthio)benzenamine |
| J-138 | 2-(2,5-dimethyl-1H-pyrrol-1-yl)benzenamine |
| J-139 | 4-(Morpholine-4-sulfonyl)-phenylamine |
| J-140 | 2-methylbenzo[d]thiazol-5-amine |
| J-141 | 2-amino-3,5-dichlorobenzonitrile |
| J-142 | 2-fluoro-4-methylbenzenamine |
| J-143 | 6-ethylpyridin-2-amine |
| J-144 | 2-(1H-pyrrol-1-yl)benzenamine |
| J-145 | 2-methyl-1H-indol-5-amine |
| J-146 | quinolin-6-amine |
| J-147 | 1H-benzo[d]imidazol-2-amine |
| J-148 | 2-o-tolylbenzo[d]oxazol-5-amine |
| J-149 | 5-phenylpyridin-2-amine |
| J-150 | Biphenyl-2-ylamine |
| J-151 | 4-(difluoromethoxy)benzenamine |
| J-152 | 5-tert-butyl-2-methoxybenzenamine |

-continued

| Amine | Name |
|---|---|
| J-153 | 2-(2-tert-butylphenoxy)benzenamine |
| J-154 | 3-aminobenzamide |
| J-155 | 4-morpholinobenzenamine |
| J-156 | 6-aminobenzo[d]oxazol-2(3H)-one |
| J-157 | 2-phenyl-3H-benzo[d]imidazol-5-amine |
| J-158 | 2,5-dichloropyridin-3-amine |
| J-159 | 2,5-dimethylbenzenamine |
| J-160 | 4-(phenylthio)benzenamine |
| J-161 | 9H-fluoren-1-amine |
| J-162 | 2-(4-aminophenyl)-1,1,1,3,3,3-hexafluoropropan-2-ol |
| J-163 | 4-bromo-2-ethylbenzenamine |
| J-164 | 4-methoxybenzenamine |
| J-165 | 3-(Piperidine-1-sulfonyl)-phenylamine |
| J-166 | quinoxalin-6-amine |
| J-167 | 6-(trifluoromethyl)pyridin-3-amine |
| J-168 | 3-(trifluoromethyl)-2-methylbenzenamine |
| J-169 | (2-aminophenyl)(phenyl)methanol |
| J-170 | aniline |
| J-171 | 6-methoxypyridin-3-amine |
| J-172 | 4-butylbenzenamine |
| J-173 | 3-(Morpholine-4-sulfonyl)-phenylamine |
| J-174 | 2,3-dimethylbenzenamine |
| J-175 | aniline |
| J-176 | Biphenyl-2-ylamine |
| J-177 | 2-(2,4-dichlorophenoxy)benzenamine |
| J-178 | pyridin-4-amine |
| J-179 | 2-(4-methoxyphenoxy)-5-(trifluoromethyl)benzenamine |
| J-180 | 6-methylpyridin-2-amine |
| J-181 | 5-chloro-2-fluorobenzenamine |
| J-182 | 1H-indol-4-amine |
| J-183 | 6-morpholinopyridin-3-amine |
| J-184 | aniline |
| J-185 | 1H-indazol-5-amine |
| J-186 | 2-[(Cyclohexyl-methyl-amino)-methyl]-phenylamine |
| J-187 | 2-phenylbenzo[d]oxazol-5-amine |
| J-188 | naphthalen-2-amine |
| J-189 | 2-aminobenzonitrile |
| J-190 | N1,N1-diethyl-3-methylbenzene-1,4-diamine |
| J-191 | aniline |
| J-192 | 2-butylbenzenamine |
| J-193 | 1-(4-aminophenyl)ethanol |
| J-194 | 2-amino-4-methylbenzamide |
| J-195 | quinolin-3-amine |
| J-196 | 2-(piperidin-1-yl)benzenamine |
| J-197 | 3-Amino-benzenesulfonamide |
| J-198 | 2-ethyl-6-methylbenzenamine |
| J-199 | Biphenyl-4-ylamine |
| J-200 | 2-(o-tolyloxy)benzenamine |
| J-201 | 5-amino-3-methylbenzo[d]oxazol-2(3H)-one |
| J-202 | 4-ethylbenzenamine |
| J-203 | 2-isopropylbenzenamine |
| J-204 | 3-(trifluoromethyl)benzenamine |
| J-205 | 2-amino-6-fluorobenzonitrile |
| J-206 | 2-(2-aminophenyl)acetonitrile |
| J-207 | 2-(4-fluorophenoxy)pyridin-3-amine |
| J-208 | aniline |
| J-209 | 2-(4-methylpiperidin-1-yl)benzenamine |
| J-210 | 4-fluorobenzenamine |
| J-211 | 2-propylbenzenamine |
| J-212 | 4-(trifluoromethoxy)benzenamine |
| J-213 | 3-aminophenol |
| J-214 | 2,2-difluorobenzo[d][1,3]dioxol-5-amine |
| J-215 | 2,2,3,3-tetrafluoro-2,3-dihydrobenzo[b][1,4]dioxin-6-amine |
| J-216 | N-(3-aminophenyl)acetamide |
| J-217 | 1-(3-aminophenyl)-3-methyl-1H-pyrazol-5(4H)-one |
| J-218 | 5-(trifluoromethyl)benzene-1,3-diamine |
| J-219 | 5-tert-butyl-2-methoxybenzene-1,3-diamine |
| J-220 | N-(3-amino-4-ethoxyphenyl)acetamide |
| J-221 | N-(3-Amino-phenyl)-methanesulfonamide |
| J-222 | N-(3-aminophenyl)propionamide |
| J-223 | N1,N1-dimethylbenzene-1,3-diamine |
| J-224 | N-(3-amino-4-methoxyphenyl)acetamide |
| J-225 | benzene-1,3-diamine |
| J-226 | 4-methylbenzene-1,3-diamine |
| J-227 | 1H-indol-6-amine |
| J-228 | 6,7,8,9-tetrahydro-5H-carbazol-2-amine |
| J-229 | 1H-indol-6-amine |

-continued

| Amine | Name |
|---|---|
| J-230 | 1H-indol-6-amine |
| J-231 | 1H-indol-6-amine |
| J-232 | 1H-indol-6-amine |
| J-233 | 1H-indol-6-amine |
| J-234 | 1H-indol-6-amine |
| J-235 | 1H-indol-6-amine |
| J-236 | 1H-indol-6-amine |
| J-237 | 1H-indol-6-amine |
| J-238 | 1H-indol-6-amine |
| J-239 | 1-(6-Amino-2,3-dihydro-indol-1-yl)-ethanone |
| J-240 | 5-Chloro-benzene-1,3-diamine |

Amides (Compounds of Formula I)

General scheme:

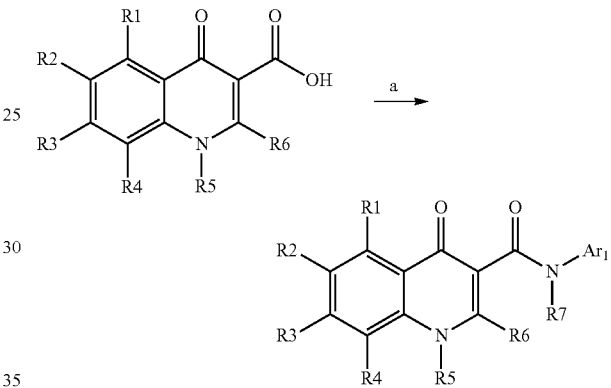

a) Ar$_1$R7NH, coupling reagent, base, solvent. Examples of conditions used:
HATU, DIEA, DMF; BOP, DIEA, DMF; HBTU, Et$_3$N, CH$_2$Cl$_2$; PFP-TFA, pyridine Specific Example

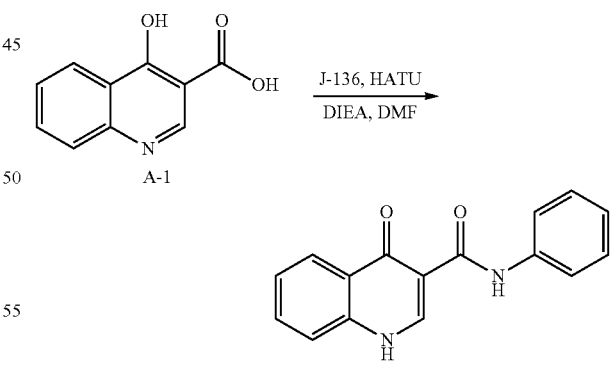

215; 4-Oxo-N-phenyl-1H-quinoline-3-carboxamide

To a solution of 4-hydroxy-quinoline-3-carboxylic acid (A-1) (19 mg, 0.1 mmol), HATU (38 mg, 0.1 mmol) and DIEA (34.9 μL, 0.2 mmol) in DMF (1 mL) was added aniline (18.2 μL, 0.2 mmol) and the reaction mixture was stirred at room temperature for 3 h. The resulting solution was filtered and purified by HPLC (10-99% CH$_3$CN/H$_2$O) to yield 4-oxo-N-phenyl-1H-quinoline-3-carboxamide (215) (12 mg, 45%). $^1$H NMR (400 MHz, DMSO-d$_6$) δ 12.97 (s, 1H), 12.50 (s, 1H), 8.89 (s, 1H), 8.34 (dd, J=8.1, 1.1 Hz, 1H), 7.83 (t, J=8.3 Hz, 1H), 7.75 (m, 3H), 7.55 (t, J=8.1 Hz, 1H), 7.37 (t, J=7.9 Hz, 2H), 7.10 (t, J=6.8 Hz, 1H); HPLC ret. time 3.02 min, 10-99% CH$_3$CN, 5 min run; ESI-MS 265.1 m/z (MH$^+$).

The table below lists other examples synthesized by the general scheme above.

| Compound of formula I | Acid | Amine |
| --- | --- | --- |
| 2 | A-1 | C-2 |
| 3 | A-1 | J-17 |
| 4 | A-1 | J-110 |
| 5 | A-1 | G-2 |
| 6 | A-1 | E-8 |
| 7 | A-1 | J-118 |
| 8 | A-1 | D-7 |
| 9 | A-1 | J-197 |
| 11 | A-1 | F-7 |
| 12 | A-1 | F-6 |
| 13 | A-1 | E-2 |
| 15 | A-1 | J-56 |
| 16 | A-1 | J-211 |
| 18 | A-1 | J-161 |
| 19 | A-1 | J-112 |
| 20 | A-1 | J-200 |
| 21 | A-1 | J-98 |
| 23 | A-1 | C-15 |
| 24 | A-1 | J-72 |
| 25 | A-1 | F-57 |
| 26 | A-1 | J-196 |
| 29 | A-21 | J-208 |
| 31 | A-1 | J-87 |
| 32 | A-1 | B-21 |
| 33 | A-1 | J-227 |
| 34 | A-1 | C-19 |
| 36 | A-1 | J-203 |
| 37 | A-1 | J-80 |
| 38 | A-1 | J-46 |
| 39 | A-17 | D-10 |
| 40 | A-1 | J-125 |
| 42 | A-1 | J-95 |
| 43 | A-1 | C-16 |
| 44 | A-1 | J-140 |
| 45 | A-1 | J-205 |
| 47 | A-1 | J-102 |
| 48 | A-1 | J-181 |
| 49 | A-1 | F-25 |
| 50 | A-1 | J-19 |
| 51 | A-7 | B-24 |
| 52 | A-1 | F-2 |
| 53 | A-1 | J-178 |
| 54 | A-1 | J-26 |
| 55 | A-1 | J-219 |
| 56 | A-1 | J-74 |
| 57 | A-1 | J-61 |
| 58 | A-1 | D-4 |
| 59 | A-1 | F-35 |
| 60 | A-1 | D-11 |
| 61 | A-1 | J-174 |
| 62 | A-1 | J-106 |
| 63 | A-1 | F-47 |
| 64 | A-1 | J-111 |
| 66 | A-1 | J-214 |
| 67 | A-10 | J-236 |
| 68 | A-1 | F-55 |
| 69 | A-1 | D-8 |
| 70 | A-1 | F-11 |
| 71 | A-1 | F-61 |
| 72 | A-1 | J-66 |
| 73 | A-1 | J-157 |
| 74 | A-1 | J-104 |
| 75 | A-1 | J-195 |
| 76 | A-1 | F-46 |
| 77 | A-1 | B-20 |
| 78 | A-1 | J-92 |
| 79 | A-1 | F-41 |
| 80 | A-1 | J-30 |
| 81 | A-1 | J-222 |
| 82 | A-1 | J-190 |
| 83 | A-1 | F-40 |
| 84 | A-1 | J-32 |
| 85 | A-1 | F-53 |
| 86 | A-1 | J-15 |
| 87 | A-1 | J-39 |
| 88 | A-1 | G-3 |
| 89 | A-1 | J-134 |
| 90 | A-1 | J-18 |
| 91 | A-1 | J-38 |
| 92 | A-1 | C-13 |
| 93 | A-1 | F-68 |
| 95 | A-1 | J-189 |
| 96 | A-1 | B-9 |
| 97 | A-1 | F-34 |
| 99 | A-1 | J-4 |
| 100 | A-1 | J-182 |
| 102 | A-1 | J-117 |
| 103 | A-2 | C-9 |
| 104 | A-1 | B-4 |
| 106 | A-1 | J-11 |
| 107 | A-1 | DC-6 |
| 108 | A-1 | DC-3 |
| 109 | A-1 | DC-4 |
| 110 | A-1 | J-84 |
| 111 | A-1 | J-43 |
| 112 | A-11 | J-235 |
| 113 | A-1 | B-7 |
| 114 | A-1 | D-18 |
| 115 | A-1 | F-62 |
| 116 | A-3 | J-229 |
| 118 | A-1 | F-12 |
| 120 | A-1 | J-1 |
| 121 | A-1 | J-130 |
| 122 | A-1 | J-49 |
| 123 | A-1 | F-66 |
| 124 | A-2 | B-24 |
| 125 | A-1 | J-143 |
| 126 | A-1 | C-25 |
| 128 | A-22 | J-176 |
| 130 | A-14 | J-233 |
| 131 | A-1 | J-240 |
| 132 | A-1 | J-220 |
| 134 | A-1 | F-58 |
| 135 | A-1 | F-19 |
| 136 | A-1 | C-8 |
| 137 | A-6 | C-9 |
| 138 | A-1 | F-44 |
| 139 | A-1 | F-59 |
| 140 | A-1 | J-64 |
| 142 | A-1 | J-10 |
| 143 | A-1 | C-7 |
| 144 | A-1 | J-213 |
| 145 | A-1 | B-18 |
| 146 | A-1 | J-55 |
| 147 | A-1 | J-207 |
| 150 | A-1 | J-162 |
| 151 | A-1 | F-67 |
| 152 | A-1 | J-156 |
| 153 | A-1 | C-23 |
| 154 | A-1 | J-107 |
| 155 | A-1 | J-3 |
| 156 | A-1 | F-36 |
| 160 | A-1 | D-6 |
| 161 | A-1 | C-3 |
| 162 | A-1 | J-171 |
| 164 | A-1 | J-204 |
| 165 | A-1 | J-65 |
| 166 | A-1 | F-54 |
| 167 | A-1 | J-226 |
| 168 | A-1 | J-48 |
| 169 | A-1 | B-1 |
| 170 | A-1 | J-42 |
| 171 | A-1 | F-52 |

-continued

| Compound of formula I | Acid | Amine |
|---|---|---|
| 172 | A-1 | F-64 |
| 173 | A-1 | J-180 |
| 174 | A-1 | F-63 |
| 175 | A-1 | DC-2 |
| 176 | A-1 | J-212 |
| 177 | A-1 | J-57 |
| 178 | A-1 | J-153 |
| 179 | A-1 | J-154 |
| 180 | A-1 | J-198 |
| 181 | A-1 | F-1 |
| 182 | A-1 | F-37 |
| 183 | A-1 | DC-1 |
| 184 | A-15 | J-231 |
| 185 | A-1 | J-173 |
| 186 | A-1 | B-15 |
| 187 | A-1 | B-3 |
| 188 | A-1 | B-25 |
| 189 | A-1 | J-24 |
| 190 | A-1 | F-49 |
| 191 | A-1 | J-23 |
| 192 | A-1 | J-36 |
| 193 | A-1 | J-68 |
| 194 | A-1 | J-37 |
| 195 | A-1 | J-127 |
| 197 | A-1 | J-167 |
| 198 | A-1 | J-210 |
| 199 | A-1 | F-3 |
| 200 | A-1 | H-1 |
| 201 | A-1 | J-96 |
| 245 | A-1 | J-177 |
| 246 | A-1 | J-78 |
| 247 | A-1 | F-33 |
| 250 | A-1 | J-224 |
| 252 | A-1 | J-135 |
| 253 | A-1 | F-30 |
| 254 | A-2 | B-20 |
| 255 | A-8 | C-9 |
| 256 | A-1 | J-45 |
| 257 | A-1 | J-67 |
| 259 | A-1 | B-14 |
| 261 | A-1 | F-13 |
| 262 | A-1 | DC-7 |
| 263 | A-1 | J-163 |
| 264 | A-1 | J-122 |
| 265 | A-1 | J-40 |
| 266 | A-1 | C-14 |
| 267 | A-1 | J-7 |
| 268 | A-1 | E-7 |
| 270 | A-1 | B-5 |
| 271 | A-1 | D-9 |
| 273 | A-1 | H-2 |
| 274 | A-8 | B-24 |
| 276 | A-1 | J-139 |
| 277 | A-1 | F-38 |
| 278 | A-1 | F-10 |
| 279 | A-1 | F-56 |
| 280 | A-1 | J-146 |
| 281 | A-1 | J-62 |
| 283 | A-1 | F-18 |
| 284 | A-1 | J-16 |
| 285 | A-1 | F-45 |
| 286 | A-1 | J-119 |
| 287 | A-3 | C-13 |
| 288 | A-1 | C-6 |
| 289 | A-1 | J-142 |
| 290 | A-1 | F-15 |
| 291 | A-1 | C-10 |
| 292 | A-1 | J-76 |
| 293 | A-1 | J-144 |
| 294 | A-1 | J-54 |
| 295 | A-1 | J-128 |
| 296 | A-17 | J-12 |
| 297 | A-1 | J-138 |
| 301 | A-1 | J-14 |
| 302 | A-1 | F-5 |
| 303 | A-1 | J-13 |
| 304 | A-1 | E-1 |

-continued

| Compound of formula I | Acid | Amine |
|---|---|---|
| 305 | A-1 | F-17 |
| 306 | A-1 | F-20 |
| 307 | A-1 | F-43 |
| 308 | A-1 | J-206 |
| 309 | A-1 | J-5 |
| 310 | A-1 | J-70 |
| 311 | A-1 | J-60 |
| 312 | A-1 | F-27 |
| 313 | A-1 | F-39 |
| 314 | A-1 | J-116 |
| 315 | A-1 | J-58 |
| 317 | A-1 | J-85 |
| 319 | A-2 | C-7 |
| 320 | A-1 | B-6 |
| 321 | A-1 | J-44 |
| 322 | A-1 | J-22 |
| 324 | A-1 | J-172 |
| 325 | A-1 | J-103 |
| 326 | A-1 | F-60 |
| 328 | A-1 | J-115 |
| 329 | A-1 | J-148 |
| 330 | A-1 | J-133 |
| 331 | A-1 | J-105 |
| 332 | A-1 | J-9 |
| 333 | A-1 | F-8 |
| 334 | A-1 | DC-5 |
| 335 | A-1 | J-194 |
| 336 | A-1 | J-192 |
| 337 | A-1 | C-24 |
| 338 | A-1 | J-113 |
| 339 | A-1 | B-8 |
| 344 | A-1 | F-22 |
| 345 | A-2 | J-234 |
| 346 | A-12 | J-6 |
| 348 | A-1 | F-21 |
| 349 | A-1 | J-29 |
| 350 | A-1 | J-100 |
| 351 | A-1 | B-23 |
| 352 | A-1 | B-10 |
| 353 | A-1 | D-10 |
| 354 | A-1 | J-186 |
| 355 | A-1 | J-25 |
| 357 | A-1 | B-13 |
| 358 | A-24 | J-232 |
| 360 | A-1 | J-151 |
| 361 | A-1 | F-26 |
| 362 | A-1 | J-91 |
| 363 | A-1 | F-32 |
| 364 | A-1 | J-88 |
| 365 | A-1 | J-93 |
| 366 | A-1 | F-16 |
| 367 | A-1 | F-50 |
| 368 | A-1 | D-5 |
| 369 | A-1 | J-141 |
| 370 | A-1 | J-90 |
| 371 | A-1 | J-79 |
| 372 | A-1 | J-209 |
| 373 | A-1 | J-21 |
| 374 | A-16 | J-238 |
| 375 | A-1 | J-71 |
| 376 | A-1 | J-187 |
| 377 | A-5 | J-237 |
| 378 | A-1 | D-3 |
| 380 | A-1 | J-99 |
| 381 | A-1 | B-24 |
| 383 | A-1 | B-12 |
| 384 | A-1 | F-48 |
| 385 | A-1 | J-83 |
| 387 | A-1 | J-168 |
| 388 | A-1 | F-29 |
| 389 | A-1 | J-27 |
| 391 | A-1 | F-9 |
| 392 | A-1 | J-52 |
| 394 | A-22 | J-170 |
| 395 | A-1 | C-20 |
| 397 | A-1 | J-199 |
| 398 | A-1 | J-77 |

| Compound of formula I | Acid | Amine |
|---|---|---|
| 400 | A-1 | J-183 |
| 401 | A-1 | F-4 |
| 402 | A-1 | J-149 |
| 403 | A-1 | C-22 |
| 405 | A-1 | J-33 |
| 406 | A-6 | B-24 |
| 407 | A-3 | C-7 |
| 408 | A-1 | J-81 |
| 410 | A-1 | F-31 |
| 411 | A-13 | J-191 |
| 412 | A-1 | B-19 |
| 413 | A-1 | J-131 |
| 414 | A-1 | J-50 |
| 417 | A-1 | F-65 |
| 418 | A-1 | J-223 |
| 419 | A-1 | J-216 |
| 420 | A-1 | G-1 |
| 421 | A-1 | C-18 |
| 422 | A-1 | J-20 |
| 423 | A-1 | B-16 |
| 424 | A-1 | F-42 |
| 425 | A-1 | J-28 |
| 426 | A-1 | C-11 |
| 427 | A-1 | J-124 |
| 428 | A-1 | C-1 |
| 429 | A-1 | J-218 |
| 430 | A-1 | J-123 |
| 431 | A-1 | J-225 |
| 432 | A-1 | F-14 |
| 433 | A-1 | C-9 |
| 434 | A-1 | J-159 |
| 435 | A-1 | J-41 |
| 436 | A-1 | F-24 |
| 437 | A-1 | J-75 |
| 438 | A-1 | E-10 |
| 439 | A-1 | J-164 |
| 440 | A-1 | J-215 |
| 441 | A-1 | D-19 |
| 442 | A-1 | J-165 |
| 443 | A-1 | J-166 |
| 444 | A-1 | E-6 |
| 445 | A-1 | J-97 |
| 446 | A-1 | J-121 |
| 447 | A-1 | J-51 |
| 448 | A-1 | J-69 |
| 449 | A-1 | J-94 |
| 450 | A-1 | J-193 |
| 451 | A-1 | J-31 |
| 452 | A-1 | J-108 |
| 453 | A-1 | D-1 |
| 454 | A-1 | J-47 |
| 455 | A-1 | J-73 |
| 456 | A-1 | J-137 |
| 457 | A-1 | J-155 |
| 458 | A-1 | C-4 |
| 459 | A-1 | J-53 |
| 461 | A-1 | J-150 |
| 463 | A-1 | J-202 |
| 464 | A-3 | C-9 |
| 465 | A-1 | E-4 |
| 466 | A-1 | J-2 |
| 467 | A-1 | J-86 |
| 468 | A-20 | J-184 |
| 469 | A-12 | J-132 |
| 470 | A-1 | J-160 |
| 473 | A-21 | J-89 |
| 474 | A-1 | J-201 |
| 475 | A-1 | J-158 |
| 477 | A-1 | J-63 |
| 478 | A-1 | B-11 |
| 479 | A-4 | J-230 |
| 480 | A-23 | J-175 |
| 481 | A-1 | J-188 |
| 483 | A-1 | C-21 |
| 484 | A-1 | D-14 |
| B-26-I | A-1 | B-26 |
| B-27-I | A-1 | B-27 |
| C-27-I | A-1 | C-27 |
| D-12-I | A-1 | D-12 |
| D-13-I | A-1 | D-13 |
| D-15-I | A-1 | D-15 |
| D-16-I | A-1 | D-16 |
| D-17-I | A-1 | D-17 |
| DC-10-I | A-1 | DC-10 |
| DC-8-I | A-1 | DC-8 |
| DC-9-I | A-1 | DC-9 |
Indoles
Example 1
General Scheme:
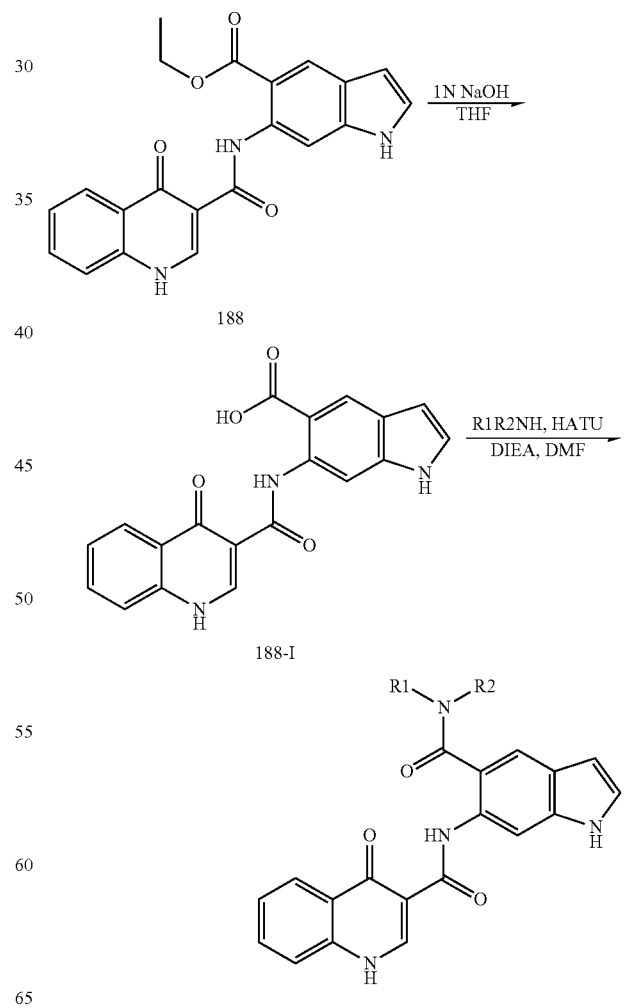

Specific Example

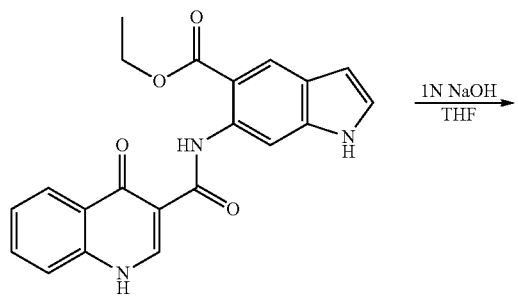

188

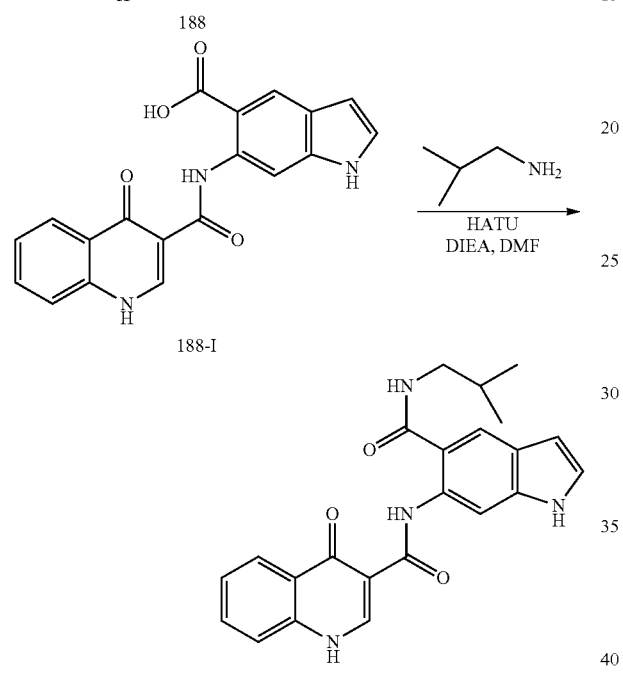

188-I; 6-[(4-oxo-1H-quinolin-3-yl)carbonylamino]-1H-indole-5-carboxylic acid

A mixture of 6-[(4-oxo-1H-quinolin-3-yl)carbonylamino]-1H-indole-5-carboxylic acid ethyl ester (188) (450 mg, 1.2 mmol) and 1N NaOH solution (5 mL) in THF (10 mL) was heated at 85° C. overnight. The reaction mixture was partitioned between EtOAc and water. The aqueous layer was acidified with 1N HCl solution to pH 5, and the precipitate was filtered, washed with water and air dried to yield 6-[(4-oxo-1H-quinolin-3-yl)carbonylamino]-1H-indole-5-carboxylic acid (188-I) (386 mg, 93%). $^1$H-NMR (400 MHz, DMSO-d$_6$) δ 12.92-12.75 (m, 2H), 11.33 (s, 1H), 8.84 (s, 1H), 8.71 (s, 1H), 8.30 (dd, J=8.1, 0.9 Hz, 1H), 8.22 (s, 1H), 7.80-7.72 (m, 2H), 7.49 (t, J=8.0 Hz, 1H), 7.41 (t, J=2.7 Hz, 1H), 6.51 (m, 1H); HPLC ret. time 2.95 min, 10-99% CH$_3$CN, 5 min run; ESI-MS 376.2 m/z (MH$^+$).

343; N-[5-(Isobutylcarbamoyl)-1H-indol-6-yl]-4-oxo-1H-quinoline-3-carboxamide

To a solution of 6-[(4-oxo-1H-quinolin-3-yl)carbonylamino]-1H-indole-5-carboxylic acid (188-I) (26 mg, 0.08 mmol), HATU (38 mg, 0.1 mmol) and DIEA (35 μL, 0.2 mmol) in DMF (1 mL) was added isobutylamine (7 mg, 0.1 mmol) and the reaction mixture was stirred at 65° C. overnight. The resulting solution was filtered and purified by HPLC (10-99% CH$_3$CN/H$_2$O) to yield the product, N-[5-(isobutylcarbamoyl)-1H-indol-6-yl]-4-oxo-1H-quinoline-3-carboxamide (343) (20 mg, 66%). $^1$H-NMR (400 MHz, DMSO-d$_6$) δ 12.66 (d, J=7.4 Hz, 1H), 12.42 (s, 1H), 11.21 (s, 1H), 8.81 (d, J=6.6 Hz, 1H), 8.47 (s, 1H), 8.36 (t, J=5.6 Hz, 1H), 8.30 (d, J=8.4 Hz, 1H), 7.79 (t, J=7.9 Hz, 1H), 7.72-7.71 (m, 2H), 7.51 (t, J=7.2 Hz, 1H), 7.38 (m, 1H), 6.48 (m, 1H), 3.10 (t, J=6.2 Hz, 2H), 1.88 (m, 1H), 0.92 (d, J=6.7 Hz, 6H); HPLC ret. time 2.73 min, 10-99% CH$_3$CN, 5 min run; ESI-MS 403.3 m/z (MH$^+$).

Another Example

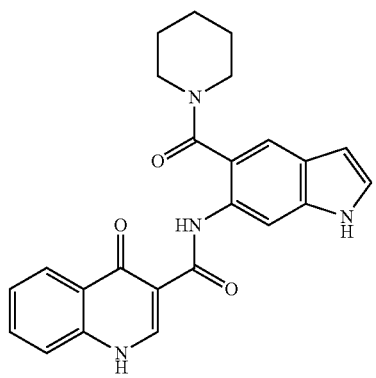 [SMILES: O=C(Nc1cc2[nH]ccc2cc1C(=O)N1CCCCC1)c1c[nH]c2ccccc2c1=O]

148; 4-oxo-N-[5-(1-piperidylcarbonyl)-1H-indol-6-yl]-1H-quinoline-3-carboxamide 4-oxo-N-[5-(1-piperidylcarbonyl)-1H-indol-6-yl]-1H-quinoline-3-carboxamide (148) was synthesized following the general scheme above, coupling the acid (188-I) with piperidine. Overall yield (12%). HPLC ret. time 2.79 min, 10-99% CH$_3$CN, 5 min run; ESI-MS 415.5 m/z (MH$^+$).

Example 2

General scheme:

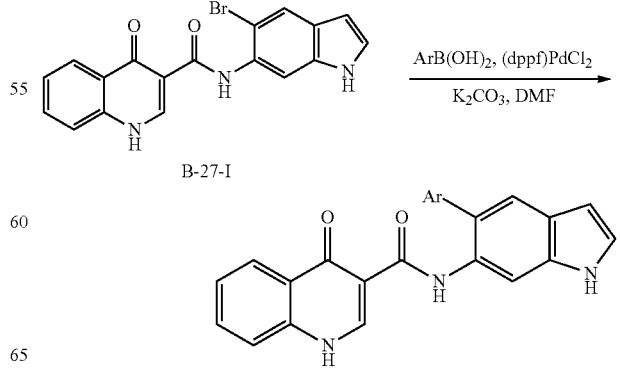

B-27-I

Specific Example

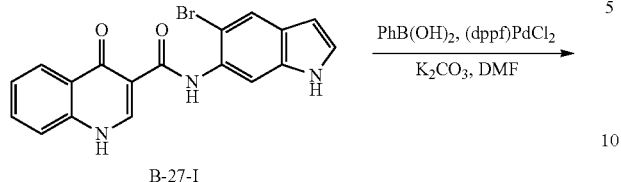

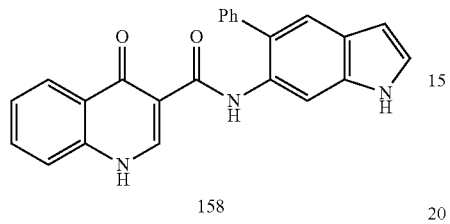

158; 4-Oxo-N-(5-phenyl-1H-indol-6-yl)-1H-quinoline-3-carboxamide

A mixture of N-(5-bromo-1H-indol-6-yl)-4-oxo-1H-quinoline-3-carboxamide (B-27-I) (38 mg, 0.1 mol), phenyl boronic acid (18 mg, 0.15 mmol), (dppf)PdCl$_2$ (cat.), and K$_2$CO$_3$ (100 μL, 2M solution) in DMF (1 mL) was heated in the microwave at 180° C. for 10 min. The reaction was filtered and purified by HPLC (10-99% CH$_3$CN/H$_2$O) to yield the product, 4-oxo-N-(5-phenyl-1H-indol-6-yl)-1H-quinoline-3-carboxamide (158) (5 mg, 13%). HPLC ret. time 3.05 min, 10-99% CH$_3$CN, 5 min run; ESI-MS 380.2 m/z (MH$^+$).

The table below lists other examples synthesized following the general scheme above.

| Compound of formula I | Boronic acid |
|---|---|
| 237 | 2-methoxyphenylboronic acid |
| 327 | 2-ethoxyphenylboronic acid |
| 404 | 2,6-dimethoxyphenylboronic acid |
| 1 | 5-chloro-2-methoxy-phenylboronic acid |
| 342 | 4-isopropylphenylboronic acid |
| 347 | 4-(2-Dimethylaminoethylcarbamoyl)phenylboronic acid |
| 65 | 3-pyridinylboronic acid |

Example 3

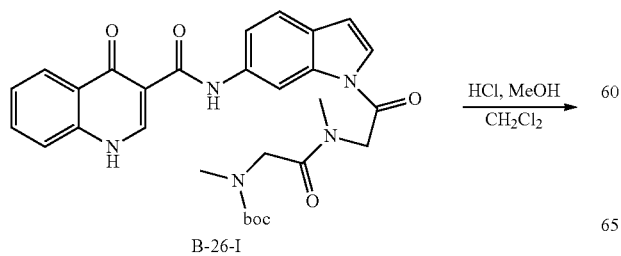

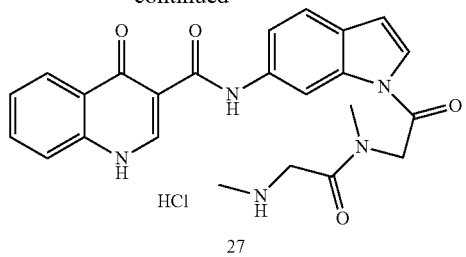

27; N-[1-[2-[Methyl-(2-methylaminoacetyl)-amino]acetyl]-1H-indol-6-yl]-4-oxo-1H-quinoline-3-carboxamide To a solution of methyl-{[methyl-(2-oxo-2-{6-[(4-oxo-1,4-dihydro-quinoline-3-carbonyl)-amino]-indol-1-yl}-ethyl)-carbamoyl]-methyl}-carbamic acid tert-butyl ester (B-264) (2.0 g, 3.7 mmol) dissolved in a mixture of CH$_2$Cl$_2$ (50 mL) and methanol (15 mL) was added HCl solution (60 mL, 1.25 M in methanol). The reaction was stirred at room temperature for 64 h. The precipitated product was collected via filtration, washed with diethyl ether and dried under high vacuum to provide the HCl salt of the product, N-[1-[2-[methyl-(2-methylaminoacetyl)-amino]acetyl]-1H-indol-6-yl]-4-oxo-1H-quinoline-3-carboxamide (27) as a greyish white solid (1.25 g, 70%). $^1$H-NMR (400 MHz, DMSO-d$_6$) δ 13.20 (d, J=6.7 Hz, 1H), 12.68 (s, 1H), 8.96-8.85 (m, 1H), 8.35 (d, J=7.9 Hz, 1H), 7.91-7.77 (m, 3H), 7.64-7.54 (m, 3H), 6.82 (m, 1H), 5.05 (s, 0.7H), 4.96 (s, 1.3H), 4.25 (t, J=5.6 Hz, 1.3H), 4.00 (t, J=5.7 Hz, 0.7H), 3.14 (s, 2H), 3.02 (s, 1H), 2.62 (t, J=5.2 Hz, 2H), 2.54 (t, J=5.4 Hz, 1H); HPLC ret. time 2.36 min, 10-99% CH$_3$CN, 5 min run; ESI-MS 446.5 m/z (MH$^+$).

Phenols

Example 1

General scheme:

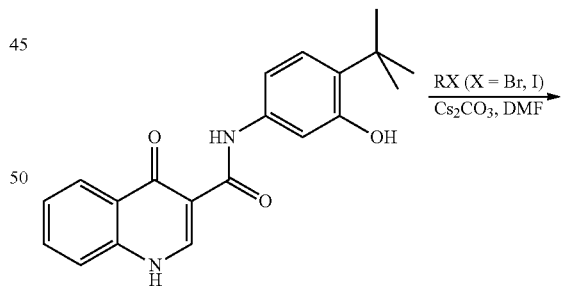

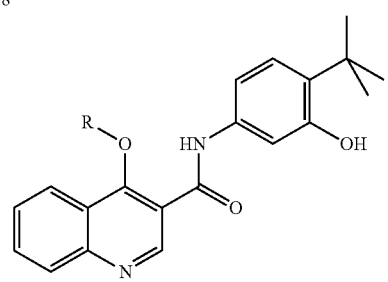

Specific Example

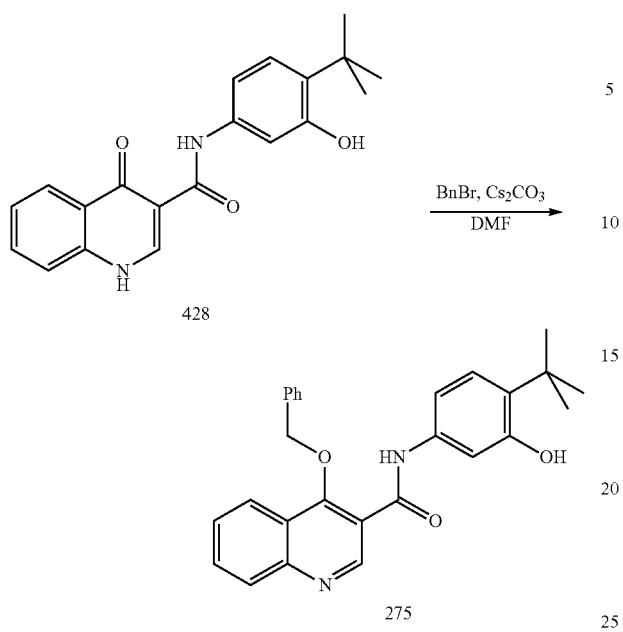

275; 4-Benzyloxy-N-(3-hydroxy-4-tert-butyl-phenyl)-quinoline-3-carboxamide

To a mixture of N-(3-hydroxy-4-tert-butyl-phenyl)-4-oxo-1H-quinoline-3-carboxamide (428) (6.7 mg, 0.02 mmol) and $Cs_2CO_3$ (13 mg, 0.04 mmol) in DMF (0.2 mL) was added BnBr (10 uL, 0.08 mmol). The reaction mixture was stirred at room temperature for 3 h. The reaction mixture was filtered and purified using HPLC to give 4-benzyloxy-N-(3-hydroxy-4-tert-butyl-phenyl)-quinoline-3-carboxamide (275). $^1$H NMR (400 MHz, DMSO-$d_6$) δ 12.23 (s, 1H), 9.47 (s, 1H), 9.20 (s, 1H), 8.43 (d, J=7.9 Hz, 1H), 7.79 (t, J=2.0 Hz, 2H), 7.56 (m, 1H), 7.38-7.26 (m, 6H), 7.11 (d, J=8.4 Hz, 1H), 6.99 (dd, J=8.4, 2.1 Hz, 1H), 5.85 (s, 2H), 1.35 (s, 9H).

HPLC ret. time 3.93 min, 10-99% $CH_3CN$, 5 min run; ESI-MS 427.1 m/z (MH$^+$).

Another Example

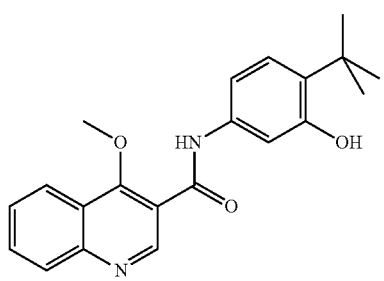 [SMILES: COc1c(C(=O)Nc2ccc(C(C)(C)C)c(O)c2)cnc2ccccc12]

415; N-(3-Hydroxy-4-tert-butyl-phenyl)-4-methoxy-quinoline-3-carboxamide

N-(3-Hydroxy-4-tert-butyl-phenyl)-4-methoxy-quinoline-3-carboxamide (415) was synthesized following the general scheme above reacting N-(3-hydroxy-4-tert-butyl-phenyl)-4-oxo-1H-quinoline-3-carboxamide (428) with methyl iodide. $^1$H NMR (400 MHz, DMSO-$d_6$) δ 12.26 (s, 1H), 9.46 (s, 1H), 8.99 (s, 1H), 8.42 (t, J=4.2 Hz, 1H), 7.95-7.88 (m, 2H), 7.61-7.69 (m, 1H), 7.38 (d, J=2.1 Hz, 1H), 7.10 (d, J=8.4 Hz, 1H), 6.96 (dd, J=8.4, 2.1 Hz, 1H), 4.08 (s, 3H), 1.35 (s, 9H); HPLC ret. time 3.46 min, 10-99% $CH_3CN$, 5 min run; ESI-MS 351.5 m/z (MH$^+$).

Example 2

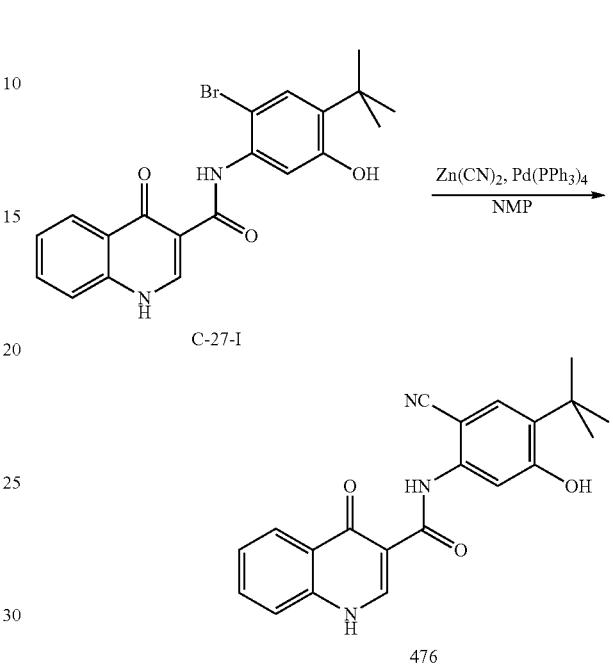

476; N-(4-tert-Butyl-2-cyano-5-hydroxyphenyl)-1,4-dihydro-4-oxoquinoline-3-carboxamide To a suspension of N-(4-tert-butyl-2-bromo-5-hydroxyphenyl)-1,4-dihydro-4-oxoquinoline-3-carboxamide (C-27-I) (84 mg, 0.2 mmol), $Zn(CN)_2$ (14 mg, 0.12 mmol) in NMP (1 mL) was added $Pd(PPh_3)_4$ (16 mg, 0.014 mmol) under nitrogen. The mixture was heated in a microwave oven at 200° C. for 1 h, filtered and purified using preparative HPLC to give N-(4-tert-butyl-2-cyano-5-hydroxyphenyl)-1,4-dihydro-4-oxoquinoline-3-carboxamide (476). $^1$H NMR (400 MHz, DMSO-$d_6$) δ 13.00 (d, J=6.4 Hz, 1H), 12.91 (s, 1H), 10.72 (s, 1H), 8.89 (d, J=6.8 Hz, 1H), 8.34 (d, J=8.2 Hz, 1H), 8.16 (s, 1H), 7.85-7.75 (m, 2H), 7.56-7.54 (m, 1H), 7.44 (s, 1H), 1.35 (s, 9H); HPLC ret. time 3.42 min, 10-100% $CH_3CN$, 5 min gradient; ESI-MS 362.1 m/z (MH$^+$).

Anilines

Example 1

General scheme:

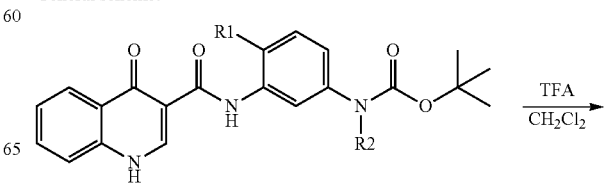

Example 2

General Scheme:

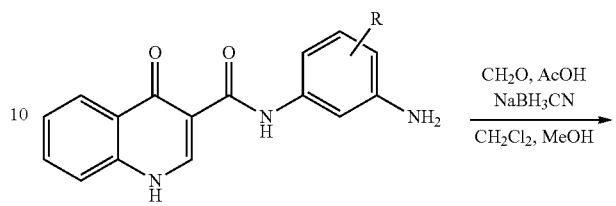

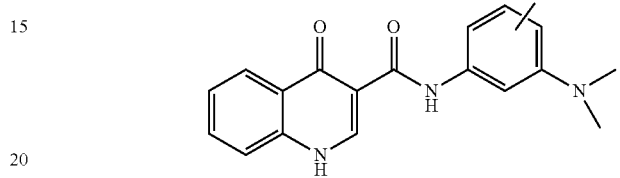

Specific Example

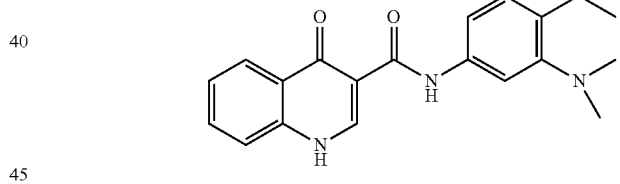

-continued

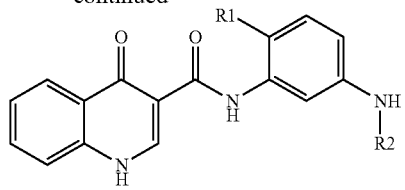

Specific Example

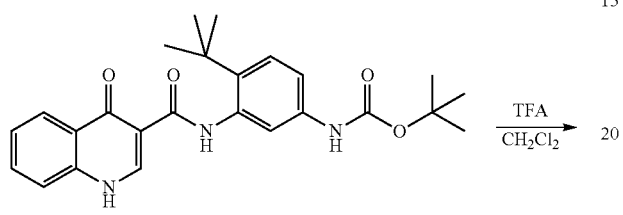

260; N-(5-Amino-2-tert-butyl-phenyl)-4-oxo-1H-quinoline-3-carboxamide

A mixture of [3-[(4-oxo-1H-quinolin-3-yl)carbonylamino]-4-tert-butyl-phenyl]aminoformic acid tert-butyl ester (353) (33 mg, 0.08 mmol), TFA (1 mL) and CH$_2$Cl$_2$ (1 mL) was stirred at room temperature overnight. The solution was concentrated and the residue was dissolved in DMSO (1 mL) and purified by HPLC (10-99% CH$_3$CN/H$_2$O) to yield the product, N-(5-amino-2-tert-butyl-phenyl)-4-oxo-1H-quinoline-3-carboxamide (260) (15 mg, 56%). $^1$H NMR (400 MHz, DMSO-d$_6$) δ 13.23 (d, J=6.6 Hz, 1H), 12.20 (s, 1H), 10.22 (br s, 2H), 8.88 (d, J=6.8 Hz, 1H), 8.34 (d, J=7.8 Hz, 1H), 7.86-7.80 (m, 3H), 7.56-7.52 (m, 2H), 7.15 (dd, J=8.5, 2.4 Hz, 1H), 1.46 (s, 9H); HPLC ret. time 2.33 min, 10-99% CH$_3$CN, 5 min run; ESI-MS 336.3 m/z (MH$^+$).

The table below lists other examples synthesized following the general scheme above.

| Starting Intermediate | Product |
|---|---|
| 60 | 101 |
| D-12-I | 282 |
| D-13-I | 41 |
| 114 | 393 |
| D-16-I | 157 |
| D-15-I | 356 |
| D-17-I | 399 |

485; N-(3-Dimethylamino-4-tert-butyl-phenyl)-4-oxo-1H-quinoline-3-carboxamide

To a suspension of N-(3-amino-4-tert-butyl-phenyl)-4-oxo-1H-quinoline-3-carboxamide (271) (600 mg, 1.8 mmol) in CH$_2$Cl$_2$ (15 mL) and methanol (5 mL) were added acetic acid (250 µL) and formaldehyde (268 µL, 3.6 mmol, 37 wt % in water). After 10 min, sodium cyanoborohydride (407 mg, 6.5 mmol) was added in one portion. Additional formaldehyde (135 µL, 1.8 mmol, 37 wt % in water) was added at 1.5 and 4.2 h. After 4.7 h, the mixture was diluted with ether (40 mL), washed with water (25 mL) and brine (25 mL), dried (Na$_2$SO$_4$), filtered, and concentrated. The resulting red-brown foam was purified by preparative HPLC to afford N-(3-dimethylamino-4-tert-butyl-phenyl)-4-oxo-1H-quinoline-3-carboxamide (485) (108 mg, 17%).

$^1$H NMR (300 MHz, CDCl$_3$) δ 13.13 (br s, 1H), 12.78 (s, 1H), 8.91 (br s, 1H), 8.42 (br s, 1H), 8.37 (d, J=8.1 Hz, 1H), 7.72-7.58 (m, 2H), 7.47-7.31 (m, 3H), 3.34 (s, 6H), 1.46 (s, 9H); HPLC ret. time 2.15 min, 10-100% CH$_3$CN, 5 min run; ESI-MS 364.3 m/z (MH$^+$).

The table below lists other examples synthesized following the general scheme above.

| Starting Intermediate | Product |
| --- | --- |
| 69 | 117 |
| 160 | 462 |
| 282 | 409 |
| 41 | 98 |

Example 3

General Scheme:

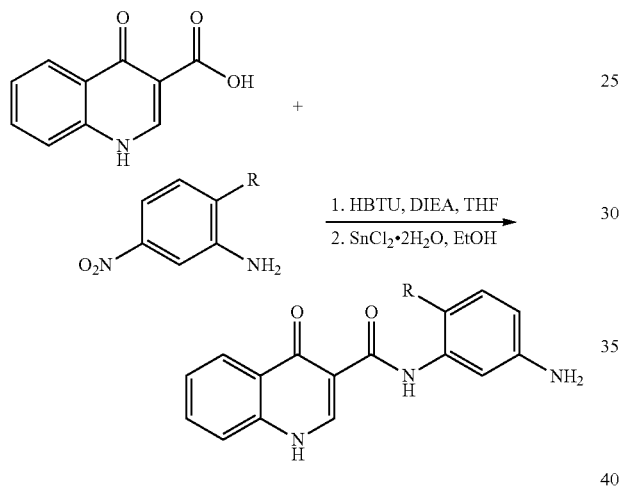

Specific Example

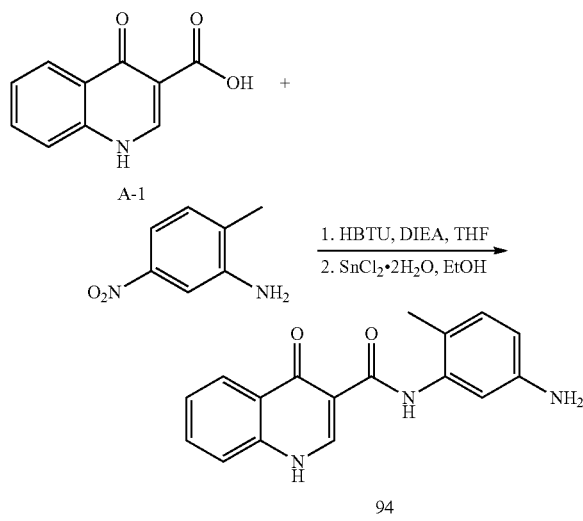

94; N-(5-Amino-2-methyl-phenyl)-4-oxo-1H-quinoline-3-carboxamide

To a solution of 4-hydroxy-quinoline-3-carboxylic acid (A-1) (50 mg, 0.26 mmol), HBTU (99 mg, 0.26 mmol) and DIEA (138 µL, 0.79 mmol) in THF (2.6 mL) was added 2-methyl-5-nitro-phenylamine (40 mg, 0.26 mmol). The mixture was heated at 150° C. in the microwave for 20 min and the resulting solution was concentrated. The residue was dissolved in EtOH (2 mL) and SnCl$_2$.2H$_2$O (293 mg, 1.3 mmol) was added. The reaction was stirred at room temperature overnight. The reaction mixture was basified with sat. NaHCO$_3$ solution to pH 7-8 and extracted with ethyl acetate. The combined organic layers were washed with brine, dried over Na$_2$SO$_4$, filtered and concentrated. The residue was dissolved in DMSO and purified by HPLC (10-99% CH$_3$CN/H$_2$O) to yield the product, N-(5-amino-2-methyl-phenyl)-4-oxo-1H-quinoline-3-carboxamide (94) (6 mg, 8%). HPLC ret. time 2.06 min, 10-99% CH$_3$CN, 5 min run; ESI-MS 294.2 m/z (MH$^+$).

Another Example

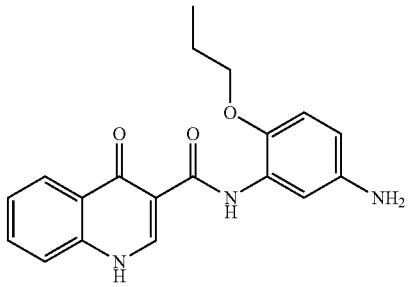 [SMILES: CCCOc1ccc(N)cc1NC(=O)c1c[nH]c2ccccc2c1=O]

17; N-(5-Amino-2-propoxy-phenyl)-4-oxo-1H-quinoline-3-carboxamide

N-(5-Amino-2-propoxy-phenyl)-4-oxo-1H-quinoline-3-carboxamide (17) was made following the general scheme above starting from 4-hydroxy-quinoline-3-carboxylic acid (A-1) and 5-nitro-2-propoxy-phenylamine. Yield (9%). HPLC ret. time 3.74 min, 10-99% CH$_3$CN, 5 min run; ESI-MS 338.3 m/z (MH$^+$).

Example 4

General Scheme:

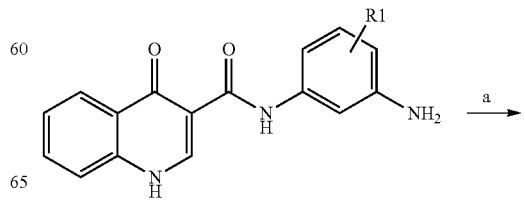

-continued

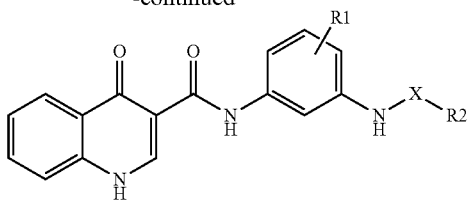

X = CO, CO₂, SO₂; a) R2XCl, DIEA, THF or R2XCl, NMM, 1,4-dioxane or R2XCl, Et₃N, CH₂Cl₂, DMF.

Specific Example

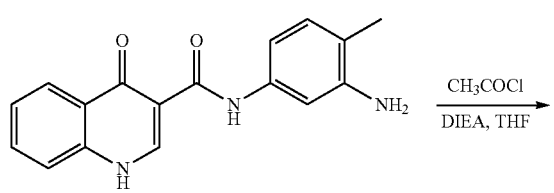

248; N-(3-Acetylamino-4-methyl-phenyl)-4-oxo-1H-quinoline-3-carboxamide

To a solution of N-(3-amino-4-methyl-phenyl)-4-oxo-1H-quinoline-3-carboxamide (167) (33 mg, 0.11 mmol) and DIEA (49 µL, 0.28 mmol) in THF (1 mL) was added acetyl chloride (16 µL, 0.22 mmol). The reaction was stirred at room temperature for 30 min. LCMS analysis indicated that diacylation had occurred. A solution of piperidine (81 µL, 0.82 mmol) in CH₂Cl₂ (2 mL) was added and the reaction stirred for a further 30 min at which time only the desired product was detected by LCMS. The reaction solution was concentrated and the residue was dissolved in DMSO and purified by HPLC (10-99% CH₃CN/H₂O) to yield the product, N-(3-acetylamino-4-methyl-phenyl)-4-oxo-1H-quinoline-3-carboxamide (248) (4 mg, 11%). $^1$H NMR (400 MHz, DMSO-d₆) δ 12.95 (d, J=6.6 Hz, 1H), 12.42 (s, 1H), 9.30 (s, 1H), 8.86 (d, J=6.8 Hz, 1H), 8.33 (dd, J=8.1, 1.3 Hz, 1H), 7.85-7.81 (m, 2H), 7.76 (d, J=7.8 Hz, 1H), 7.55 (t, J=8.1 Hz, 1H), 7.49 (dd, J=8.2, 2.2 Hz, 1H), 7.18 (d, J=8.3 Hz, 1H), 2.18 (s, 3H), 2.08 (s, 3H); HPLC ret. time 2.46 min, 10-99% CH₃CN, 5 min run; ESI-MS 336.3 m/z (MH⁺).

The table below lists other examples synthesized following the general scheme above.

| Starting from | X | R² | Product |
|---|---|---|---|
| 260 | CO | Me | 316 |
| 260 | CO | neopentyl | 196 |
| 429 | CO | Me | 379 |
| 41 | CO | Me | 232 |

-continued

| Starting from | X | R² | Product |
|---|---|---|---|
| 101 | CO | Me | 243 |
| 8 | CO | Me | 149 |
| 271 | CO₂ | Et | 127 |
| 271 | CO₂ | Me | 14 |
| 167 | CO₂ | Et | 141 |
| 69 | CO₂ | Me | 30 |
| 160 | CO₂ | Me | 221 |
| 160 | CO₂ | Et | 382 |
| 69 | CO₂ | Et | 225 |
| 282 | CO₂ | Me | 249 |
| 282 | CO₂ | Et | 472 |
| 41 | CO₂ | Me | 471 |
| 101 | CO₂ | Me | 239 |
| 101 | CO₂ | Et | 269 |
| 8 | CO₂ | Me | 129 |
| 8 | CO₂ | Et | 298 |
| 160 | SO₂ | Me | 340 |

Example 5

General Scheme:

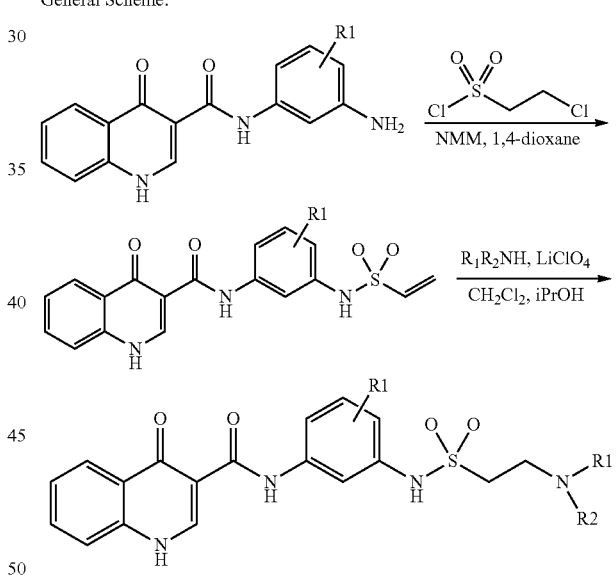

Specific Example

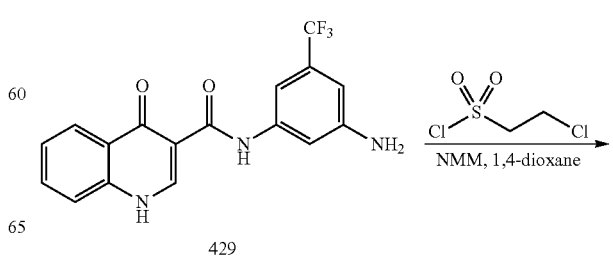

-continued

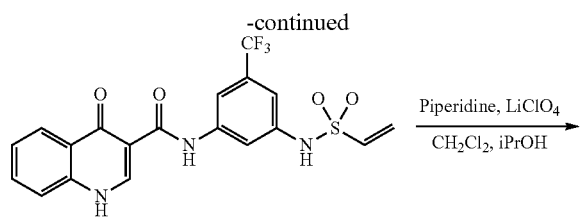

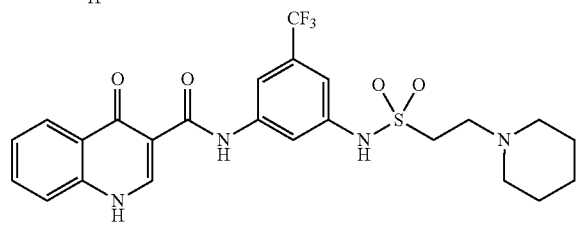

318

4-oxo-N-[3-(trifluoromethyl)-5-(vinylsulfonamido)phenyl]-1,4-dihydroquinoline-3-carboxamide To a suspension of N-[3-amino-5-(trifluoromethyl)phenyl]-4-oxo-1H-quinoline-3-carboxamide (429) (500 mg 1.4 mmol) in 1,4-dioxane (4 mL) was added NMM (0.4 mL, 3.6 mmol). 13-Chloroethylsulfonyl chloride (0.16 mL, 1.51 mmol) was added under an argon atmosphere. The mixture was stirred at room temperature for 6½h, after which TLC (CH$_2$Cl$_2$-EtOAc, 8:2) showed a new spot with a very similar R$_f$ to the starting material. Another 0.5 eq. of NMM was added, and the mixture was stirred at room temperature overnight. LCMS analysis of the crude mixture showed >85% conversion to the desired product. The mixture was concentrated, treated with 1M HCl (5 mL), and extracted with EtOAc (3×10 mL) and CH$_2$Cl$_2$ (3×10 mL). The combined organic extracts were dried over Na$_2$SO$_4$, filtered, and concentrated to yield 4-oxo-N-[3-(trifluoromethyl)-5-(vinylsulfonamido)phenyl]-1,4-dihydroquinoline-3-carboxamide as an orange foam (0.495 g, 79%), which was used in the next step without further purification. $^1$H-NMR (d$_6$-Acetone, 300 MHz) δ 8.92 (s, 1H), 8.41-8.38 (m, 1H), 7.94 (m, 2H), 7.78 (br s, 2H), 7.53-7.47 (m, 1H), 7.30 (s, 1H), 6.87-6.79 (dd, J=9.9 Hz, 1H), 6.28 (d, J=16.5 Hz, 1H), 6.09 (d, J=9.9 Hz, 1H); ESI-MS 436.4 m/z (MH$^-$)

318; 4-oxo-N-[3-[2-(1-piperidyl)ethylsulfonylamino]-5-(trifluoromethyl)phenyl]-1H-quinoline-3-carboxamide A mixture of 4-oxo-N-[3-(trifluoromethyl)-5-(vinylsulfonamido)phenyl]-1,4-dihydroquinoline-3-carboxamide (50 mg, 0.11 mmol), piperidine (18 µL, 1.6 eq) and LiClO$_4$ (20 mg, 1.7 eq) was suspended in a 1:1 solution of CH$_2$Cl$_2$:isopropanol (1.5 mL). The mixture was refluxed at 75° C. for 18 h. After this time, LCMS analysis showed >95% conversion to the desired product. The crude mixture was purified by reverse-phase HPLC to provide 4-oxo-N-[3-[2-(1-piperidyl)ethylsulfonylamino]-5-(trifluoromethyl)phenyl]-1H-quinoline-3-carboxamide (318) as a yellowish solid (15 mg, 25%). $^1$H-NMR (d$_6$-Acetone, 300 MHz) δ 8.92 (br s, 1H), 8.4 (d, J=8.1 Hz, 1H), 8.05 (br s, 1H), 7.94 (br s, 1H), 7.78 (br s, 2H), 7.53-751 (m, 1H), 7.36 (br s, 1H), 3.97 (t, J=7.2 Hz, 2H), 3.66 (t, J=8 Hz, 2H), 3.31-3.24 (m, 6H), 1.36-1.31 (m, 4H); ESI-MS 489.1 m/z (MH$^+$).

The table below lists other examples synthesized following the general scheme above.

| Starting Intermediate | Amine | Product |
|---|---|---|
| 429 | morpholine | 272 |
| 429 | dimethylamine | 359 |
| 131 | piperidine | 133 |
| 131 | morpholine | 46 |

Example 6

General Scheme:

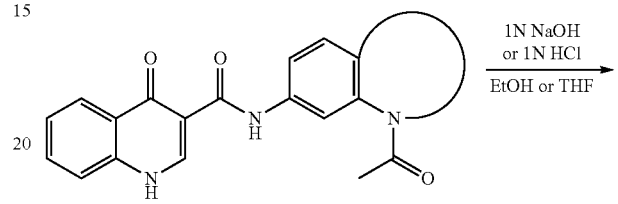

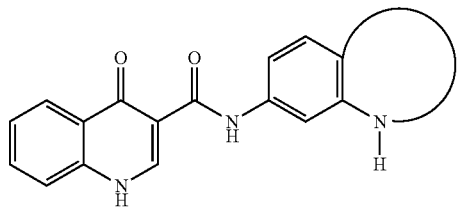

Specific Example

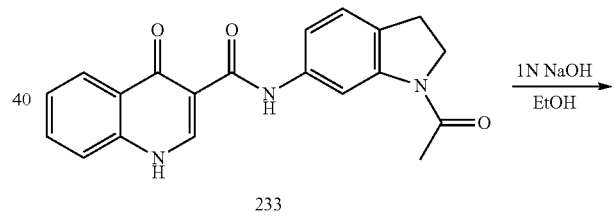

233

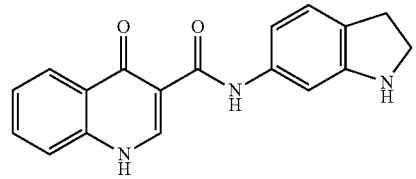

258;
N-Indolin-6-yl-4-oxo-1H-quinoline-3-carboxamide

A mixture of N-(1-acetylindolin-6-yl)-4-oxo-1H-quinoline-3-carboxamide (233) (43 mg, 0.12 mmol), 1N NaOH solution (0.5 mL) and ethanol (0.5 mL) was heated to reflux for 48 h. The solution was concentrated and the residue was dissolved in DMSO (1 mL) and purified by HPLC (10-99% CH$_3$CN—H$_2$O) to yield the product, N-indolin-6-yl-4-oxo-1H-quinoline-3-carboxamide (258) (10 mg, 20%). HPLC ret. time 2.05 min, 10-99% CH$_3$CN, 5 min run; ESI-MS 306.3 m/z (MH$^+$).

The table below lists other examples synthesized following the general scheme above.

| Starting from | Product | Conditions | Solvent |
|---|---|---|---|
| DC-8-I | 386 | NaOH | EtOH |
| DC-9-I | 10 | HCl | EtOH |
| 175 | 22 | HCl | EtOH |
| 109 | 35 | HCl | EtOH |
| 334 | 238 | NaOH | EtOH |
| DC-10-I | 105 | NaOH | THF |

Example 2

General Scheme:

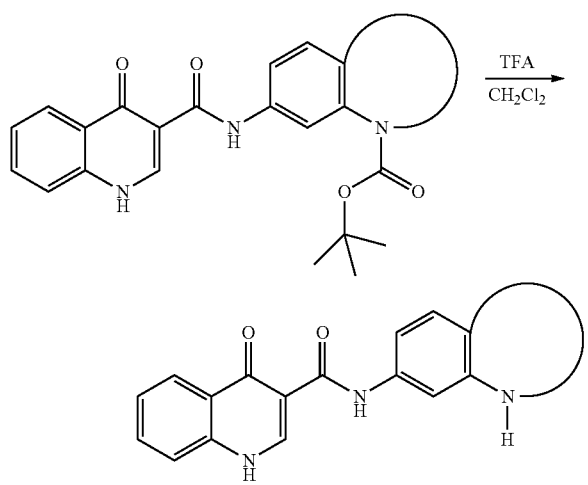

Specific Example

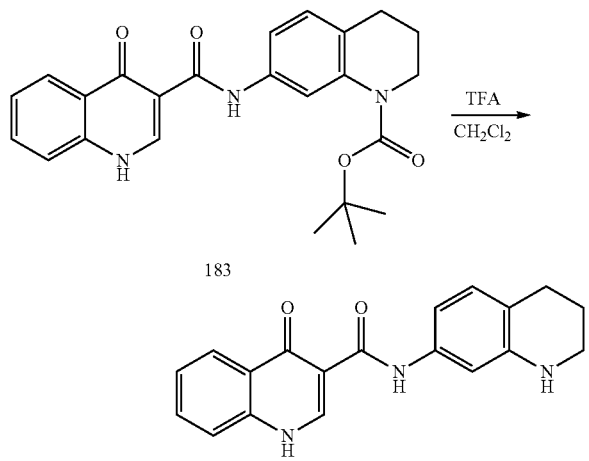

299; 4-oxo-N-(1,2,3,4-tetrahydroquinolin-7-yl)-1H-quinoline-3-carboxamide

A mixture of 7-[(4-oxo-1H-quinolin-3-yl)carbonylamino]-1,2,3,4-tetrahydroquinoline-1-carboxylic acid tert-butyl ester (183) (23 mg, 0.05 mmol), TFA (1 mL) and CH$_2$Cl$_2$ (1 mL) was stirred at room temperature overnight. The solution was concentrated and the residue was dissolved in DMSO (1 mL) and purified by HPLC (10-99% CH$_3$CN—H$_2$O) to yield the product, 4-oxo-N-(1,2,3,4-tetrahydroquinolin-7-yl)-1H-quinoline-3-carboxamide (299) (7 mg, 32%).

HPLC ret. time 2.18 min, 10-99% CH$_3$CN, 5 min run; ESI-MS 320.3 m/z (MH$^+$).

Another Example

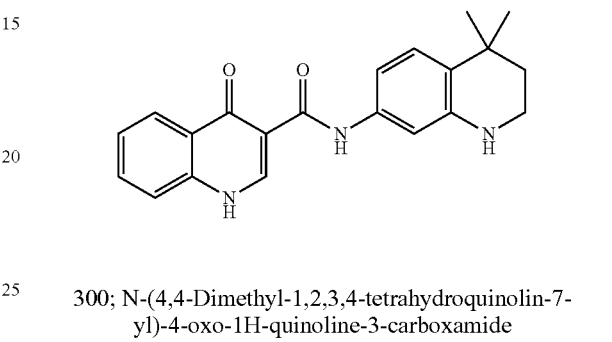

300; N-(4,4-Dimethyl-1,2,3,4-tetrahydroquinolin-7-yl)-4-oxo-1H-quinoline-3-carboxamide N-(4,4-Dimethyl-1,2,3,4-tetrahydroquinolin-7-yl)-4-oxo-1H-quinoline-3-carboxamide (300) was synthesized following the general scheme above starting from 4,4-dimethyl-74 [4-oxo-1H-quinolin-3-yl)carbonylamino]-1,2,3,4-tetrahydroquinoline-1-carboxylic acid tert-butyl ester (108). Yield (33%). $^1$H NMR (400 MHz, DMSO-d$_6$) δ 13.23 (d, J=6.6 Hz, 1H), 12.59 (s, 1H), 8.87 (d, J=6.8 Hz, 1H), 8.33 (d, J=7.7 Hz, 1H), 7.86-7.79 (m, 3H), 7.58-7.42 (m, 3H), 3.38 (m, 2H), 1.88 (m, 2H), 1.30 (s, 6H); HPLC ret. time 2.40 min, 10-99% CH$_3$CN, 5 min run; ESI-MS 348.2 m/z (MH$^+$).

Other

Example 1

General scheme:

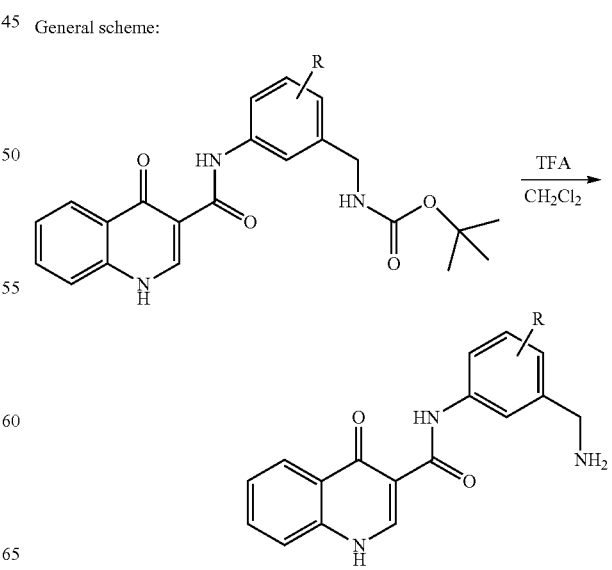

235

Specific Example

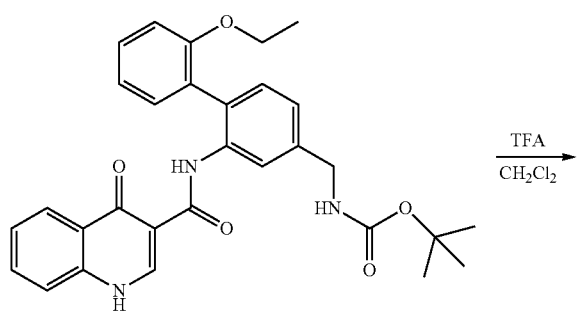

304

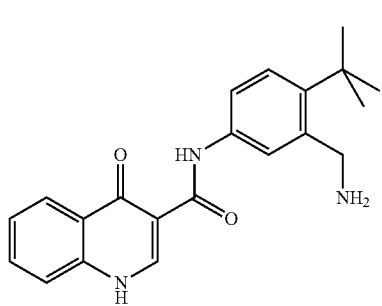 [SMILES: CC(C)(C)c1ccc(NC(=O)c2c[nH]c3ccccc3c2=O)cc1CN]

163

163; 4-Oxo-1,4-dihydro-quinoline-3-carboxylic acid (4-aminomethyl-2'-ethoxy-biphenyl-2-yl)-amide {2'-Ethoxy-2-[(4-oxo-1,4-dihydroquinoline-3-carbonyl)-amino]-biphenyl-4-ylmethyl}-carbamic acid tert-butyl ester (304) (40 mg, 0.078 mmol) was stirred in a $CH_2Cl_2$/TFA mixture (3:1, 20 mL) at room temperature for 1 h. The volatiles were removed on a rotary evaporator. The crude product was purified by preparative HPLC to afford 4-oxo-1,4-dihydroquinoline-3-carboxylix acid (4-aminomethyl-2'-ethoxy-biphenyl-2-yl)amine (163) as a tan solid (14 mg. 43%). $^1$H NMR (300 MHz, DMSO-$d_6$) δ 12.87 (d, J=6.3 Hz, 1H), 11.83 (s, 1H), 8.76 (d, J=6.3 Hz, 1H), 8.40 (s, 1H), 8.26 (br s, 2H), 8.01 (dd, J=8.4 Hz, J=1.5 Hz, 1H), 7.75 (dt, J=8.1 Hz, J=1.2 Hz, 1H), 7.67 (d, J=7.8 Hz, 1H), 7.47-7.37 (m, 2H), 7.24 (s, 2H), 7.15 (dd, J=7.5 Hz, J=1.8 Hz, 1H), 7.10 (d, J=8.1 Hz, 1H), 7.02 (dt, J=7.5 Hz, J=0.9 Hz, 1H), 4.09 (m, 2H), 4.04 (q, J=6.9 Hz, 2H), 1.09 (t, J=6.9 Hz, 3H); HPLC ret. time 1.71 min, 10-100% $CH_3CN$, 5 min gradient; ESI-MS 414.1 m/z ($MH^+$).

Another Example

236

390; N-[3-(Aminomethyl)-4-tert-butyl-phenyl]-4-oxo-1H-quinoline-3-carboxamide

N-[3-(Aminomethyl)-4-tert-butyl-phenyl]-4-oxo-1H-quinoline-3-carboxamide (390) was synthesized following the general scheme above starting from [5-[(4-oxo-1H-quinolin-3-yl)carbonylamino]-2-tert-butyl-phenyl]methylaminoformic acid tert-butyl ester (465). HPLC ret. time 2.44 min, 10-99% $CH_3CN$, 5 min gradient; ESI-MS m/z 350.3 (M+H)'.

Example 2

General scheme:

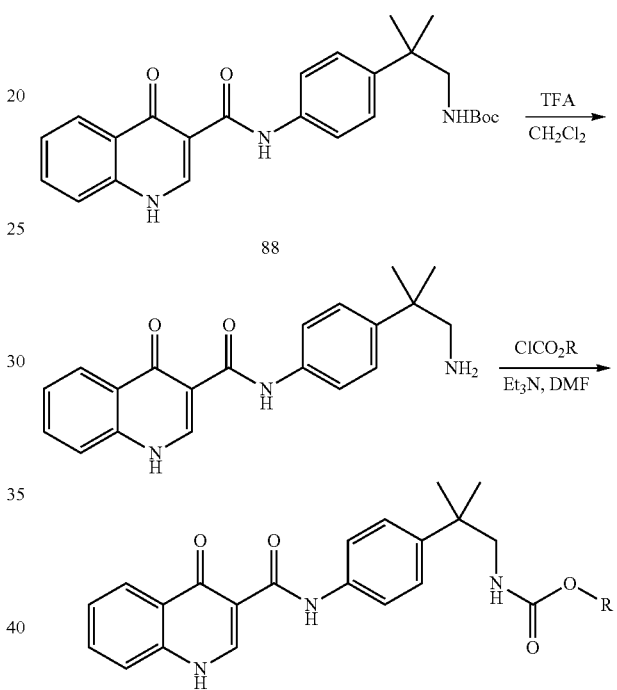

Specific Example

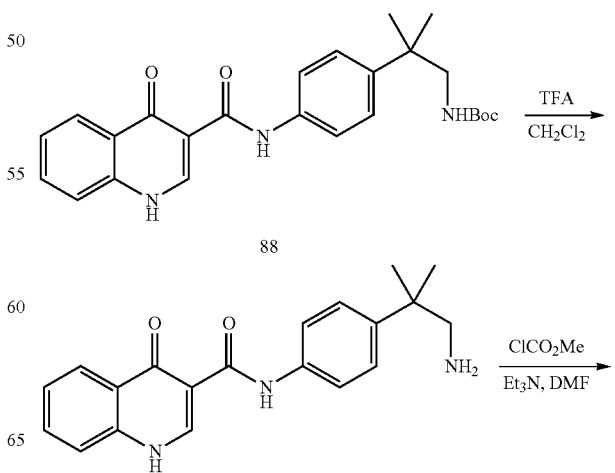

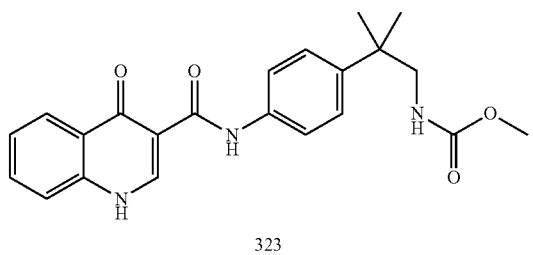

323

3-(2-(4-(1-Amino-2-methylpropan-2-yl)phenyl)
acetyl)quinolin-4(1H)-one (2-Methyl-2-{4-[2-oxo-2-(4-oxo-1,4-dihydro-quinolin-3-yl)-ethyl]-phenyl}-propyl)-carbamic acid tert-butyl ester (88) (0.50 g, 1.15 mmol), TFA (5 mL) and CH$_2$Cl$_2$ (5 mL) were combined and stirred at room temperature overnight. The reaction mixture was then neutralized with 1N NaOH. The precipitate was collected via filtration to yield the product 3-(2-(4-(1-amino-2-methylpropan-2-yl)phenyl)acetyl) quinolin-4(1H)-one as a brown solid (651 mg, 91%). HPLC ret. time 2.26 min, 10-99% CH$_3$CN, 5 min run; ESI-MS 336.5 m/z (MH$^+$).

323; [2-Methyl-2-[4-[(4-oxo-1H-quinolin-3-yl)carbonylamino]phenyl]-propyl]aminoformic acid methyl ester Methyl chloroformate (0.012 g, 0.150 mmol) was added to a solution of 3-(2-(4-(1-amino-2-methylpropan-2-yl)phenyl) acetyl)quinolin-4(1H)-one (0.025 g, 0.075 mmol), TEA (0.150 mmol, 0.021 mL) and DMF (1 mL) and stirred at room temperature for 1 h. Then piperidine (0.074 ml, 0.750 mmol) was added and the reaction was stirred for another 30 min. The reaction mixture was filtered and purified by preparative HPLC (10-99% CH$_3$CN—H$_2$O) to yield the product [2-methyl-2-[4-[(4-oxo-1H-quinolin-3-yl)carbonylamino]phenyl]-propyl]aminoformic acid methyl ester (323). $^1$H NMR (400 MHz, DMSO-d6) δ12.94 (br s, 1H), 12.44 (s, 1H), 8.89 (s, 1H), 8.33 (dd, J=8.2, 1.1 Hz, 1H), 7.82 (t, J=8.3 Hz, 1H), 7.76 (d, J=7.7 Hz, 1H), 7.67 (d, J=8.8 Hz, 2H), 7.54 (t, J=8.1 Hz, 1H), 7.35 (d, J=8.7 Hz, 2H), 7.02 (t, J=6.3 Hz, 1H), 3.50 (s, 3H), 3.17 (d, J=6.2 Hz, 2H), 1.23 (s, 6H); HPLC ret. time 2.93 min, 10-99% CH$_3$CN, 5 min run; ESI-MS 394.0 m/z (MH$^+$).

The table below lists other examples synthesized following the general scheme above.

| Product | Chloroformate |
| --- | --- |
| 119 | Ethyl chloroformate |
| 416 | Propyl chloroformate |
| 460 | Butyl chloroformate |
| 251 | Isobutyl chloroformate |
| 341 | Neopentyl chloroformate |
| 28 | 2-methoxyethyl chloroformate |
| 396 | (tetrahydrofuran-3-yl)methyl chloroformate |

Example 3

General Scheme:

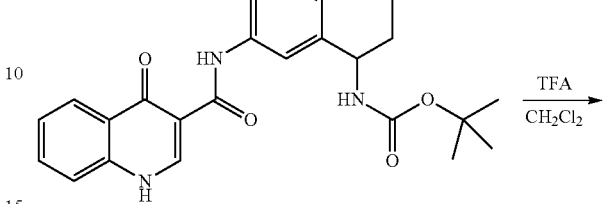

273

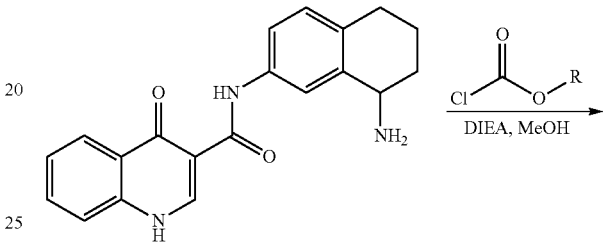

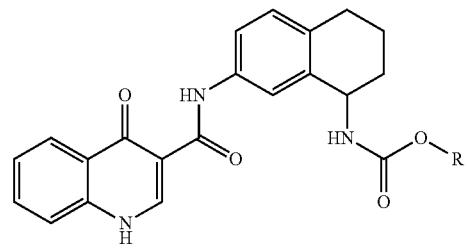

Specific Example

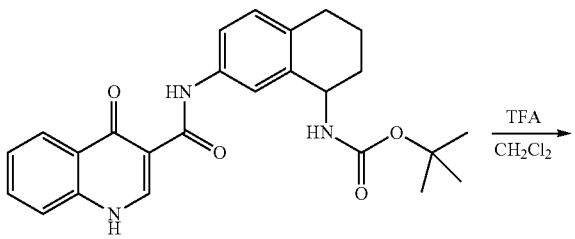

273

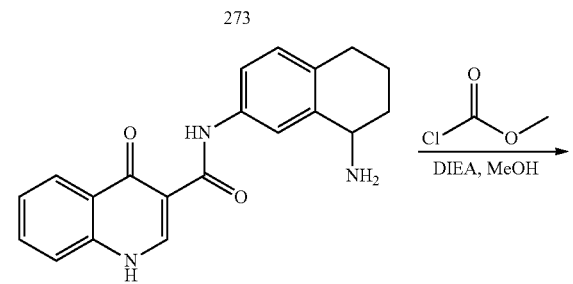

273-I

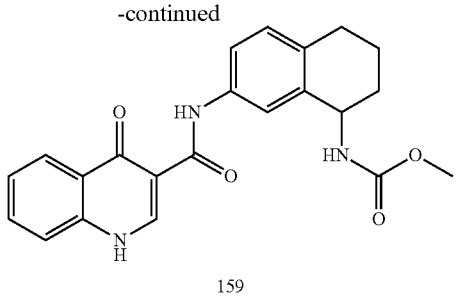

159

273-I; N-(1-Aminotetralin-7-yl)-4-oxo-1H-quino-line-3-carboxamide

To a solution of [7-[(4-oxo-1H-quinolin-3-yl)carbonylamino]tetralin-1-yl]aminoformic acid tert-butyl ester (273) (250 mg, 0.6 mmol) in dichloromethane (2 mL) was added TFA (2 mL). The reaction was stirred at room temperature for 30 min. More dichloromethane (10 mL) was added to the reaction mixture and the solution was washed with sat. NaHCO₃ solution (5 mL). A precipitate began to form in the organic layer so the combined organic layers were concentrated to yield N-(1-aminotetralin-7-yl)-4-oxo-1H-quinoline-3-carboxamide (273-I) (185 mg, 93%).

HPLC ret. time 1.94 min, 10-99% $CH_3CN$, 5 min run; ESI-MS 334.5 m/z ($MH^+$).

159; [7-[(4-oxo-1H-quinolin-3-yl)carbonylamino] tetralin-1-yl]aminoformic acid methyl ester To a solution of N-(1-aminotetralin-7-yl)-4-oxo-1H-quinoline-3-carboxamide (273-I) (65 mg, 0.20 mmol) and DIEA (52 µL, 0.29 mmol) in methanol (1 mL) was added methyl chloroformate (22 µL, 0.29 mmol). The reaction was stirred at room temperature for 1 h. LCMS analysis of the reaction mixture showed peaks corresponding to both the single and bis addition products. Piperidine (2 mL) was added and the reaction was stirred overnight after which only the single addition product was observed. The resulting solution was filtered and purified by HPLC (10-99% $CH_3CN$—$H_2O$) to yield the product, [7-[(4-oxo-1H-quinolin-3-yl)carbonylamino]tetralin-1-yl]aminoformic acid methyl ester (159) (27 mg, 35%). HPLC ret. time 2.68 min, 10-99% $CH_3CN$, 5 min run; ESI-MS 392.3 m/z ($MH^+$).

Another Example

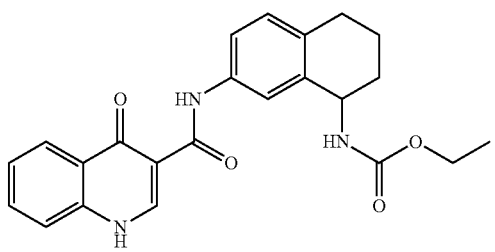 [SMILES: CCOC(=O)NC1CCCc2ccc(NC(=O)c3c[nH]c4ccccc4c3=O)cc21]

482; [7-[(4-oxo-1H-quinolin-3-yl)carbonylamino] tetralin-1-yl]aminoformic acid ethyl ester

[7-[(4-oxo-1H-quinolin-3-yl)carbonylamino]tetralin-1-yl]aminoformic acid ethyl ester (482) was synthesized following the general scheme above, from amine (273-I) and ethyl chloroformate. Overall yield (18%). HPLC ret. time 2.84 min, 10-99% $CH_3CN$, 5 min run; ESI-MS 406.5 m/z ($MH^+$).

Set forth below is the characterizing data for compounds of the present invention prepared according to the above Examples.

TABLE 2

| Cmd No. | LC-MS M + 1 | LC-RT min |
|---|---|---|
| 1 | 444.3 | 3.19 |
| 2 | 350.1 | 3.8 |
| 3 | 455.3 | 3.75 |
| 4 | 350.3 | 2.81 |
| 5 | 337.3 | 2.76 |
| 6 | 351.4 | 3 |
| 7 | 472.3 | 3.6 |
| 8 | 307.1 | 1.21 |
| 9 | 344.1 | 2.43 |
| 10 | 334.2 | 2.2 |
| 11 | 408.1 | 2.91 |
| 12 | 383.1 | 2.63 |
| 13 | 346.3 | 3.48 |
| 14 | 394.3 | 3.07 |
| 15 | 296.3 | 2.68 |
| 16 | 307.3 | 3.38 |
| 17 | 338.3 | 3.74 |
| 18 | 352.9 | 3.62 |
| 19 | 316.3 | 2.71 |
| 20 | 371.3 | 3.53 |
| 21 | 421.1 | 2.66 |
| 22 | 332.2 | 2.21 |
| 23 | 457.5 | 3.56 |
| 24 | 398.3 | 3.13 |
| 25 | 397.1 | 2.38 |
| 26 | 348.1 | 2.51 |
| 27 | 446.2 | 2.33 |
| 28 | 438.4 | 2.9 |
| 29 | 307.1 | 3.32 |
| 30 | 379.1 | 2.62 |
| 31 | 278.9 | 3.03 |
| 32 | 338.2 | 3 |
| 33 | 303.9 | 2.83 |
| 34 | 397.1 | 4.19 |
| 35 | 362.2 | 2.53 |
| 36 | 307.3 | 3.25 |
| 37 | 303.9 | 2.98 |
| 38 | 380.3 | 3.33 |
| 39 | 480.5 | 3.82 |
| 40 | 309.1 | 2.46 |
| 41 | 321.1 | 1.88 |
| 42 | 460.0 | 3.71 |
| 43 | 457.5 | 3.6 |
| 44 | 336.1 | 2.95 |
| 45 | 308.1 | 3.18 |
| 46 | 490.1 | 1.89 |
| 47 | 375.3 | 3.33 |
| 48 | 317.1 | 3.06 |
| 49 | 400.1 | 2.88 |
| 50 | 307.3 | 3.08 |
| 51 | 521.5 | 3.79 |
| 52 | 354.1 | 3.02 |
| 53 | 266.1 | 1.99 |
| 54 | 323.3 | 2.97 |
| 55 | 366.3 | 2.6 |
| 56 | 335.4 | 3.18 |
| 57 | 403.1 | 2.86 |
| 58 | 364.3 | 3.02 |
| 59 | 412.1 | 3.31 |
| 60 | 422.2 | 3.53 |
| 61 | 293.1 | 3.05 |
| 62 | 349.1 | 3.4 |
| 63 | 376.1 | 2.89 |
| 64 | 321.1 | 2.31 |
| 65 | 381.5 | 1.85 |
| 66 | 345.1 | 3.32 |
| 67 | 332.3 | 3.17 |

TABLE 2-continued

| Cmd No. | LC-MS M + 1 | LC-RT min |
|---|---|---|
| 68 | 398.1 | 2.85 |
| 69 | 322.5 | 2.37 |
| 70 | 341.1 | 2.15 |
| 71 | 426.1 | 2.6 |
| 72 | 293.1 | 3.27 |
| 73 | 380.9 | 2.4 |
| 74 | 334.1 | 3.32 |
| 75 | 316.3 | 2.43 |
| 76 | 376.1 | 2.97 |
| 77 | 322.5 | 2.93 |
| 78 | 344.1 | 2.38 |
| 79 | 372.1 | 3.07 |
| 80 | 295.3 | 2.78 |
| 81 | 336.3 | 2.73 |
| 82 | 350.3 | 2.11 |
| 83 | 365.1 | 2.76 |
| 84 | 280.3 | 2.11 |
| 85 | 408.0 | 3.25 |
| 86 | 370.3 | 2.08 |
| 87 | 357.1 | 3.5 |
| 88 | 436.3 | 3.37 |
| 89 | 303.9 | 3.1 |
| 90 | 321.1 | 3.43 |
| 91 | 355.2 | 3.47 |
| 92 | 295.2 | 3.84 |
| 93 | 371.0 | 2.75 |
| 94 | 294.2 | 2.06 |
| 95 | 290.1 | 2.78 |
| 96 | 343.0 | 2.75 |
| 97 | 402.1 | 2.59 |
| 98 | 349.1 | 1.96 |
| 99 | 334.1 | 3.13 |
| 100 | 303.9 | 2.63 |
| 101 | 322.5 | 2.35 |
| 102 | 443.1 | 3.97 |
| 103 | 411.2 | 3.85 |
| 104 | 318.0 | 2.94 |
| 105 | 322.2 | 2.4 |
| 106 | 350.3 | 2.86 |
| 107 | 420.2 | 3.37 |
| 108 | 448.2 | 3.77 |
| 109 | 404.5 | 3.17 |
| 110 | 303.9 | 2.75 |
| 111 | 333.1 | 3 |
| 112 | 348.5 | 3.07 |
| 113 | 318.3 | 3.02 |
| 114 | 499.2 | 3.74 |
| 115 | 330.1 | 2.67 |
| 116 | 320.2 | 3.18 |
| 117 | 349.1 | 1.32 |
| 118 | 379.1 | 2.61 |
| 119 | 408.4 | 3.07 |
| 120 | 309.1 | 2.93 |
| 121 | 333.1 | 3.69 |
| 122 | 325.1 | 2.66 |
| 123 | 330.1 | 2.64 |
| 124 | 378.3 | 3.4 |
| 125 | 294.3 | 2.21 |
| 126 | 411.1 | 3.06 |
| 127 | 408.5 | 3.22 |
| 128 | 369.1 | 3.53 |
| 129 | 365.1 | 1.74 |
| 130 | 440.2 | 3.57 |
| 131 | 313.0 | 2.4 |
| 132 | 365.9 | 2.73 |
| 133 | 488.1 | 1.97 |
| 134 | 402.1 | 2.25 |
| 135 | 384.1 | 2.94 |
| 136 | 393.1 | 4.33 |
| 137 | 580.5 | 4.1 |
| 138 | 376.1 | 2.98 |
| 139 | 408.0 | 3.17 |
| 140 | 346.1 | 4 |
| 141 | 366.3 | 2.89 |
| 142 | 321.3 | 3.58 |
| 143 | 355.2 | 3.45 |
| 144 | 281.3 | 2.49 |
| 145 | 376.2 | 2.98 |
| 146 | 306.3 | 2.51 |
| 147 | 376.3 | 3.27 |
| 148 | 415.5 | 2.79 |
| 149 | 349.1 | 1.45 |
| 150 | 430.0 | 3.29 |
| 151 | 360.0 | 3 |
| 152 | 322.3 | 2.31 |
| 153 | 425.1 | 4.52 |
| 154 | 401.3 | 3.77 |
| 155 | 266.1 | 2.11 |
| 156 | 424.1 | 3.12 |
| 157 | 321.0 | 2.13 |
| 158 | 380.2 | 3.05 |
| 159 | 392.3 | 2.68 |
| 160 | 321.1 | 1.34 |
| 161 | 409.2 | 3.82 |
| 162 | 296.3 | 2.61 |
| 163 | 413.1 | 1.71 |
| 164 | 333.1 | 3.33 |
| 165 | 344.1 | 2.41 |
| 166 | 398.1 | 2.83 |
| 167 | 294.3 | 2.12 |
| 168 | 265.9 | 1.96 |
| 169 | 318 | 2.98 |
| 170 | 300.3 | 3.08 |
| 171 | 408.0 | 3.08 |
| 172 | 396.0 | 3.14 |
| 173 | 280.3 | 2.14 |
| 174 | 388.0 | 2.58 |
| 175 | 374.2 | 2.85 |
| 176 | 349.1 | 3.38 |
| 177 | 337.1 | 3.5 |
| 178 | 413.3 | 4 |
| 179 | 308.5 | 2.33 |
| 180 | 307.3 | 3.08 |
| 181 | 354.1 | 2.97 |
| 182 | 358.1 | 2.89 |
| 183 | 420.3 | 3.47 |
| 184 | 372.3 | 2.66 |
| 185 | 414.1 | 2.96 |
| 186 | 372.3 | 3.59 |
| 187 | 346.3 | 2.9 |
| 188 | 376.2 | 2.95 |
| 189 | 370.9 | 3.38 |
| 190 | 392.0 | 3.09 |
| 191 | 316.3 | 2.1 |
| 192 | 280.3 | 2.13 |
| 193 | 326.3 | 3.02 |
| 194 | 290.1 | 2.98 |
| 195 | 280.3 | 2.14 |
| 196 | 434.5 | 3.38 |
| 197 | 334.1 | 3.15 |
| 198 | 283.1 | 3 |
| 199 | 354.1 | 2.96 |
| 200 | 335.5 | 2.49 |
| 201 | 303.9 | 3.08 |
| 202 | 404.0 | 3.19 |
| 203 | 394.3 | 3.42 |
| 204 | 349.3 | 3.32 |
| 205 | 455.5 | 3.74 |
| 206 | 386.1 | 3.5 |
| 207 | 390.3 | 2.71 |
| 208 | 429.7 | 3.89 |
| 209 | 294.1 | 2.39 |
| 210 | 385.2 | 3.72 |
| 211 | 351.3 | 3.53 |
| 212 | 360.9 | 2.45 |
| 213 | 408.0 | 3.3 |
| 214 | 358.1 | 2.7 |
| 215 | 265.3 | 3.07 |
| 216 | 305.3 | 2.27 |
| 217 | 305.3 | 2.41 |
| 218 | 413.2 | 3.98 |
| 219 | 266.9 | 2.48 |
| 220 | 409.0 | 3.35 |
| 221 | 379.1 | 2.68 |

TABLE 2-continued

| Cmd No. | LC-MS M + 1 | LC-RT min |
|---|---|---|
| 222 | 324.3 | 3.27 |
| 223 | 386.1 | 3.14 |
| 224 | 466.3 | 3.08 |
| 225 | 393.1 | 2.75 |
| 226 | 306.1 | 3.6 |
| 227 | 381.1 | 2.24 |
| 228 | 371.1 | 2.84 |
| 229 | 311.1 | 2.93 |
| 230 | 318.1 | 2.81 |
| 231 | 471.3 | 3.41 |
| 232 | 363.1 | 2.57 |
| 233 | 348.5 | 2.75 |
| 234 | 372.3 | 3.2 |
| 235 | 308.4 | 2.12 |
| 236 | 333.1 | 3.35 |
| 237 | 410.3 | 2.96 |
| 238 | 489.4 | 2.78 |
| 239 | 379.0 | 2.62 |
| 240 | 370.9 | 3.65 |
| 241 | 316.3 | 2.61 |
| 242 | 348.3 | 3.08 |
| 243 | 363.0 | 2.44 |
| 244 | 358.1 | 3.48 |
| 245 | 425.1 | 3.69 |
| 246 | 292.9 | 3.2 |
| 247 | 432.1 | 3.23 |
| 248 | 336.3 | 2.46 |
| 249 | 365.0 | 2.54 |
| 250 | 352.3 | 2.53 |
| 251 | 436.2 | 3.38 |
| 252 | 368.9 | 3.17 |
| 253 | 424.1 | 3.25 |
| 254 | 340.1 | 3.08 |
| 255 | 526.5 | 3.89 |
| 256 | 306.1 | 2.4 |
| 257 | 297.3 | 3.28 |
| 258 | 306.3 | 2.05 |
| 259 | 360.3 | 3.46 |
| 260 | 336.3 | 2.33 |
| 261 | 368.1 | 3.08 |
| 262 | 352.3 | 2.7 |
| 263 | 372.9 | 3.69 |
| 264 | 353.1 | 3.42 |
| 265 | 354.9 | 3.4 |
| 266 | 405.3 | 4.05 |
| 267 | 357.1 | 3.43 |
| 268 | 400.3 | 6.01 |
| 269 | 393.0 | 2.75 |
| 270 | 329.3 | 3.02 |
| 271 | 336.5 | 2.75 |
| 272 | 524.1 | 1.87 |
| 273 | 434.5 | 3.17 |
| 274 | 493.5 | 3.46 |
| 275 | 427.1 | 3.93 |
| 276 | 414.3 | 2.81 |
| 277 | 358.1 | 2.89 |
| 278 | 408.1 | 3.09 |
| 279 | 386.1 | 2.88 |
| 280 | 316.3 | 2.06 |
| 281 | 293.1 | 3.22 |
| 282 | 307.1 | 1.22 |
| 283 | 370.1 | 3 |
| 284 | 305.3 | 2.57 |
| 285 | 376.1 | 2.88 |
| 286 | 319.1 | 3.35 |
| 287 | 411.2 | 4.15 |
| 288 | 413.3 | 3.8 |
| 289 | 297.3 | 3.25 |
| 290 | 382.1 | 3.19 |
| 291 | 371.0 | 3.57 |
| 292 | 391.1 | 3.69 |
| 293 | 330.3 | 3.05 |
| 294 | 303.9 | 2.67 |
| 295 | 334.3 | 2.26 |
| 296 | 365.3 | 3.6 |
| 297 | 358.3 | 3.26 |
| 298 | 379.1 | 1.91 |
| 299 | 320.3 | 2.18 |
| 300 | 348.2 | 2.4 |
| 301 | 346.3 | 2.26 |
| 302 | 370.1 | 2.28 |
| 303 | 362.2 | 2.51 |
| 304 | 513.2 | 3.66 |
| 305 | 370.1 | 2.98 |
| 306 | 384.1 | 3.11 |
| 307 | 374.0 | 3.05 |
| 308 | 304.1 | 2.71 |
| 309 | 316.3 | 2.83 |
| 310 | 320.1 | 3.73 |
| 311 | 344.9 | 3.43 |
| 312 | 400.1 | 2.86 |
| 313 | 358.1 | 2.8 |
| 314 | 335.1 | 3.52 |
| 315 | 293.1 | 2.9 |
| 316 | 378.5 | 2.84 |
| 317 | 333.2 | 2.91 |
| 318 | 522.1 | 1.8 |
| 319 | 373.3 | 3.59 |
| 320 | 360.1 | 3.5 |
| 321 | 453.5 | 3.12 |
| 322 | 349.3 | 3.7 |
| 323 | 394.0 | 2.93 |
| 324 | 320.1 | 3.81 |
| 325 | 321.3 | 3.22 |
| 326 | 418.0 | 2.5 |
| 327 | 424.2 | 3.2 |
| 328 | 307.1 | 2.76 |
| 329 | 396.3 | 3.72 |
| 330 | 299.3 | 3.02 |
| 331 | 308.3 | 2.25 |
| 332 | 288.0 | 2.5 |
| 333 | 379.1 | 2.61 |
| 334 | 531.3 | 3.26 |
| 335 | 322.3 | 2.41 |
| 336 | 321.5 | 3.52 |
| 337 | 407.5 | 3.37 |
| 338 | 318.3 | 2.73 |
| 339 | 329.0 | 2.75 |
| 340 | 399.1 | 2.6 |
| 341 | 450.4 | 3.56 |
| 342 | 422.3 | 3.41 |
| 343 | 403.3 | 2.73 |
| 344 | 384.1 | 3.07 |
| 345 | 322.2 | 2.96 |
| 346 | 333.1 | 3.38 |
| 347 | 494.5 | 1.97 |
| 348 | 384.1 | 3.12 |
| 349 | 405.3 | 2.85 |
| 350 | 315.1 | 3.23 |
| 351 | 332.3 | 3.18 |
| 352 | 447.5 | 3.17 |
| 353 | 436.3 | 3.53 |
| 354 | 390.3 | 2.36 |
| 355 | 370.9 | 3.37 |
| 356 | 335.0 | 1.81 |
| 357 | 346.3 | 3.08 |
| 358 | 338.2 | 3.15 |
| 359 | 482.1 | 1.74 |
| 360 | 331.3 | 3.07 |
| 361 | 400.1 | 2.91 |
| 362 | 355.5 | 3.46 |
| 363 | 388.1 | 2.92 |
| 364 | 330.3 | 2.68 |
| 365 | 307.1 | 2.6 |
| 366 | 408.1 | 3.09 |
| 367 | 408.0 | 3.14 |
| 368 | 338.2 | 2.33 |
| 369 | 358.1 | 3.29 |
| 370 | 299.1 | 3.03 |
| 371 | 365.0 | 3.27 |
| 372 | 362.1 | 2.66 |
| 373 | 305.3 | 3.38 |
| 374 | 350.3 | 3.01 |
| 375 | 319.3 | 3.4 |

TABLE 2-continued

| Cmd No. | LC-MS M + 1 | LC-RT min |
|---|---|---|
| 376 | 382.3 | 3.48 |
| 377 | 340.2 | 3.08 |
| 378 | 310.3 | 2.07 |
| 379 | 389.0 | 2.53 |
| 380 | 309.3 | 3.02 |
| 381 | 360.2 | 3.18 |
| 382 | 393.1 | 2.84 |
| 383 | 332.3 | 3.2 |
| 384 | 376.1 | 2.87 |
| 385 | 393.9 | 3.32 |
| 386 | 334.3 | 2.3 |
| 387 | 347.1 | 3.22 |
| 388 | 424.1 | 3.3 |
| 389 | 355.3 | 3.65 |
| 390 | 350.3 | 2.44 |
| 391 | 396.1 | 3.43 |
| 392 | 300.3 | 2.86 |
| 393 | 399.4 | 2.12 |
| 394 | 293.1 | 3.17 |
| 395 | 433.5 | 4.21 |
| 396 | 464.4 | 2.97 |
| 397 | 341.3 | 3.45 |
| 398 | 434.3 | 3.1 |
| 399 | 335.0 | 1.75 |
| 400 | 351.3 | 2.11 |
| 401 | 368.1 | 3.09 |
| 402 | 342.1 | 2.96 |
| 403 | 423.1 | 4.45 |
| 404 | 440.3 | 2.87 |
| 405 | 299.3 | 3.16 |
| 406 | 547.3 | 3.74 |
| 407 | 371.3 | 3.8 |
| 408 | 295.3 | 2.9 |
| 409 | 335.1 | 1.82 |
| 410 | 432.1 | 3.41 |
| 411 | 299.1 | 3.17 |
| 412 | 376.2 | 2.93 |
| 413 | 357.1 | 3.37 |
| 414 | 305.3 | 2.11 |
| 415 | 351.5 | 3.44 |
| 416 | 422.4 | 3.23 |
| 417 | 396.0 | 2.67 |
| 418 | 308.3 | 2.23 |
| 419 | 322.3 | 2.48 |
| 420 | 379.1 | 3.2 |
| 421 | 419.2 | 3.82 |
| 422 | 333.1 | 2.48 |
| 423 | 376.3 | 3.02 |
| 424 | 374.0 | 3.06 |
| 425 | 306.1 | 3.53 |
| 426 | 371.3 | 2.95 |
| 427 | 420.3 | 3.3 |
| 428 | 337.2 | 3.32 |
| 429 | 348.3 | 2.98 |
| 430 | 321.3 | 3.22 |
| 431 | 280.3 | 2.09 |
| 432 | 382.1 | 3.22 |
| 433 | 393.2 | 3.71 |
| 434 | 293.1 | 3.12 |
| 435 | 376.3 | 3.22 |
| 436 | 400.1 | 2.88 |
| 437 | 309.3 | 2.82 |
| 438 | 427.5 | 3.87 |
| 439 | 295.3 | 2.8 |
| 440 | 395.3 | 3.61 |
| 441 | 425.0 | 2.67 |
| 442 | 412.3 | 3.35 |
| 443 | 317.3 | 2.45 |
| 444 | 379.2 | 3.42 |
| 445 | 305.5 | 3.08 |
| 446 | 353.1 | 2.85 |
| 447 | 290.1 | 2.88 |
| 448 | 321.3 | 3.5 |
| 449 | 279.1 | 3.22 |
| 450 | 308.1 | 1.97 |
| 451 | 318.1 | 3.28 |
| 452 | 290.1 | 3.32 |
| 453 | 314.1 | 2.75 |
| 454 | 355.1 | 3.58 |
| 455 | 398.1 | 3.6 |
| 456 | 365.1 | 3.65 |
| 457 | 350.3 | 2.26 |
| 458 | 381.2 | 3.19 |
| 459 | 279.3 | 2.9 |
| 460 | 436.2 | 3.38 |
| 461 | 341.3 | 3.23 |
| 462 | 349.1 | 1.9 |
| 463 | 292.1 | 3.35 |
| 464 | 409.4 | 4.03 |
| 465 | 450.5 | 3.65 |
| 466 | 349.3 | 3.5 |
| 467 | 307.3 | 2.98 |
| 468 | 279.1 | 2.98 |
| 469 | 409.1 | 3.69 |
| 470 | 373.3 | 3.64 |
| 471 | 379.0 | 2.73 |
| 472 | 379.0 | 2.67 |
| 473 | 363.3 | 3.64 |
| 474 | 336.3 | 2.8 |
| 475 | 334.3 | 3.23 |
| 476 | 362.1 | 3.42 |
| 477 | 283.9 | 2.8 |
| 478 | 360.3 | 3.44 |
| 479 | 334.3 | 2.59 |
| 480 | 323.5 | 3.22 |
| 481 | 315.3 | 3.25 |
| 482 | 406.5 | 2.84 |
| 483 | 409.5 | 4.35 |
| 484 | 349.1 | 2.16 |
| 485 | 363.1 | 2.15 |

NMR data for selected compounds is shown below in Table 2-A:

| Cmpd No. | NMR Data |
|---|---|
| 2 | 1H NMR (300 MHz, CDCl$_3$) δ 12.53 (s, 1H), 11.44 (br d, J = 6.0 Hz, 1H), 9.04 (d, J = 6.7 Hz, 1H), 8.43 (d, J = 7.8 Hz, 1H), 7.51 (t, J = 7.3 Hz, 1H), 7.43 (t, J = 7.5 Hz, 1H), 7.33-7.21 (m, 3H), 7.10 (d, J = 8.2 Hz, 1H), 3.79 (s, 3H), 1.36 (s, 9H) |
| 5 | H NMR (400 MHz, DMSO-d6) δ 12.94 (bs, 1H), 12.41 (s, 1H), 8.88 (s, 1H), 8.34 (dd, J = 8, 1 Hz, 1H), 7.82 (ddd, J = 8, 8, 1 Hz, 1H), 7.75 (d, J = 8 Hz, 1H), 7.64 (dd, J = 7, 2 HZ, 2H), 7.54 (ddd, J = 8, 8, 1 Hz, 1H), 7.35 (dd, J = 7, 2 HZ, 2H), 4.66 (t, J = 5 Hz, 1H), 3.41 (d, J = 5 Hz, 2H), 1.23 (s, 6H). |
| 8 | 1H NMR (CD3OD, 300 MHz) δ 8.86 (s, 1H), 8.42 (d, J = 8.5 Hz, 1H), 7.94 (s, 1H), 7.81 (t, J = 8.3 Hz, 1H), 7.67 (d, J = 8.3 Hz, 1H), 7.54-7.47 (m, 2H), 7.38 (d, J = 8.5 Hz, 1H), 2.71 (q, J = 7.7 Hz, 2H), 1.30 (t, J = 7.4 Hz, 3H). |

| Cmpd No. | NMR Data |
|---|---|
| 10 | H NMR (400 MHz, DMSO-d6) δ 13.02 (d, J = 6.4 Hz, 1H), 12.58 (s, 1H), 8.87 (d, J = 6.8 Hz, 1H), 8.33 (dd, J = 8.1, 1.2 Hz, 1H), 7.89-7.77 (m, 3H), 7.56 (t, J = 8.1 Hz, 1H), 7.39 (d, J = 7.8 Hz, 1H), 7.26 (d, J = 8.4 Hz, 1H), 3.23 (m, 2H), 2.81 (m, 2H), 1.94 (m, 2H), 1.65 (m, 2H) |
| 13 | H NMR (400 MHz, DMSO-d6) δ 13.05 (bs, 1H), 12.68 (s, 1H), 8.89 (s, 1H), 8.35 (t, J = 2.5 Hz, 1H), 8.32 (d, J = 1.1 Hz, 1H), 7.85-7.76 (m, 3H), 7.58-7.54 (m, 2H), 1.47 (s, 9H) |
| 14 | H NMR (400 MHz, DMSO-d6) δ 1.32 (s, 9H), 3.64 (s, 3H), 7.36 (d, J = 8.4 Hz, 1H), 7.55 (m, 3H), 7.76 (d, J = 8.0 Hz, 1H), 7.83 (m, 1H), 8.33 (d, J = 7.0 Hz, 1H), 8.69 (s, 1H), 8.87 (d, J = 6.7 Hz, 1H), 12.45 (s, 1H), 12.97 (s, 1H) |
| 27 | H NMR (400 MHz, DMSO-d6) δ 13.20 (d, J = 6.7 Hz, 1H), 12.68 (s, 1H), 8.96-8.85 (m, 4H), 8.35 (d, J = 7.9 Hz, 1H), 7.91-7.77 (m, 3H), 7.64-7.54 (m, 3H), 6.82 (m, 1H), 5.05 (s, 0.7H), 4.96 (s, 1.3H), 4.25 (t, J = 5.6 Hz, 1.3H), 4.00 (t, J = 5.7 Hz, 0.7H), 3.14 (s, 2H), 3.02 (s, 1H), 2.62 (t, J = 5.2 Hz, 2H), 2.54 (t, J = 5.4 Hz, 1H) |
| 29 | H NMR (400 MHz, CDCl3) δ 9.09 (s, 1H), 8.62 (dd, J = 8.1 and 1.5 Hz, 1H), 7.83-7.79 (m, 3H), 7.57 (d, J = 7.2 Hz, 1H), 7.38 (t, J = 7.6 Hz, 2H), 7.14 (t, J = 7.4 Hz, 2H), 5.05 (m, 1H), 1.69 (d, J = 6.6 Hz, 6H) |
| 32 | H NMR (400 MHz, DMSO-d6) δ 12.93 (d, J = 6.6 Hz, 1H), 12.74 (s, 1H), 11.27 (s, 1H), 8.91 (d, J = 6.7 Hz, 1H), 8.76 (s, 1H), 8.37 (d, J = 8.1 Hz, 1H), 7.83 (t, J = 8.3 Hz, 1H), 7.77 (d, J = 7.6 Hz, 1H), 7.70 (s, 1H), 7.54 (t, J = 8.1 Hz, 1H), 7.38 (m, 1H), 6.40 (m, 1H) |
| 33 | H NMR (400 MHz, DMSO-d6) δ 12.92 (s, 1H), 12.47 (s, 1H), 11.08 (s, 1H), 8.90 (s, 1H), 8.35 (dd, J = 8.1, 1.1 Hz, 1H), 8.20 (t, J = 0.8 Hz, 1H), 7.83 (t, J = 8.3 Hz, 1H), 7.76 (d, J = 7.7 Hz, 1H), 7.55 (t, J = 8.1 Hz, 1H), 7.50 (d, J = 8.4 Hz, 1H), 7.30 (t, J = 2.7 Hz, 1H), 7.06 (dd, J = 8.4, 1.8 Hz, 1H), 6.39 (m, 1H) |
| 35 | H NMR (400 MHz, DMSO-d6) δ 13.01 (d, J = 6.7 Hz, 1H), 12.37 (s, 1H), 8.86 (d, J = 6.8 Hz, 1H), 8.33 (dd, J = 8.1, 1.3 Hz, 1H), 7.82 (t, J = 8.3 Hz, 1H), 7.76 (d, J = 8.2 Hz, 1H), 7.54 (t, J = 8.1 Hz, 1H), 7.36 (s, 1H),, 7.19 (d, J = 8.4 Hz, 1H), 7.08 (d, J = 8.2 Hz, 1H), 3.29 (m, 2H), 1.85 (m, 1H), 1.73-1.53 (m, 3H), 1.21 (s, 3H), 0.76 (t, J = 7.4 Hz, 3H) |
| 43 | H NMR (400 MHz, DMSO-d6) δ 12.77 (s, 1H), 11.94 (s, 1H), 9.56 (s, 1H), 8.81 (s, 1H), 8.11 (dd, J = 8.2, 1.1 Hz, 1H), 7.89 (s, 1H), 7.79-7.75 (m, 1H), 7.70 (d, J = 7.7 Hz, 1H), 7.49-7.45 (m, 1H), 7.31 (t, J = 8.1 Hz, 1H), 7.00 (s, 1H), 6.93-6.87 (m, 3H), 4.07 (q, J = 7.0 Hz, 2H), 1.38 (s, 9H), 1.28 (t, J = 7.0 Hz, 3H) |
| 47 | H NMR (400 MHz, DMSO-d6) δ 1.24 (d, J = 6.9 Hz, 6H), 3.00 (m, 1H), 7.55 (m, 3H), 7.76 (d, J = 7.7 Hz, 1H), 7.83 (m, 1H), 8.26 (d, J = 8.2 Hz, 1H), 8.33 (d, J = 9.2 Hz, 1H), 8.89 (s, 1H), 12.65 (s, 1H), 12.95 (s, 1H) |
| 56 | H NMR (400 MHz, DMSO-d6) δ 12.81 (d, J = 6.7 Hz, 1H), 12.27 (s, 1H), 9.62 (s, 1H), 8.82 (d, J = 6.7 Hz, 1H), 8.32 (dd, J = 8.2, 1.3 Hz, 1H), 8.07 (s, 1H), 7.80 (t, J = 8.4 Hz, 1H), 7.73 (d, J = 7.8 Hz, 1H), 7.52 (t, J = 8.1 Hz, 1H), 6.58 (s, 1H), 2.62 (m, 4H), 1.71 (m, 4H) |
| 58 | H NMR (400 MHz, DMSO-d6) δ 12.95 (d, J = 6.6 Hz, 1H), 12.39 (s, 1H), 8.86 (d, J = 6.8 Hz, 1H), 8.33 (d, J = 7.3 Hz, 1H), 7.82 (t, J = 8.3 Hz, 1H), 7.75 (d, J = 7.8 Hz, 1H), 7.54 (t, J = 8.1 Hz, 1H), 7.29 (d, J = 2.5 Hz, 1H), 7.07 (dd, J = 8.7, 1.3 Hz, 1H), 6.91 (dd, J = 8.8, 2.5 Hz, 1H), 5.44 (br s, 2H) |
| 64 | H NMR (400 MHz, DMSO-d6) δ 12.92 (s, 1H), 12.41 (s, 1H), 10.63 (s, 1H), 10.54 (s, 1H), 8.86 (s, 1H), 8.33 (d, J = 8.1 Hz, 1H), 7.82 (t, J = 8.3 Hz, 1H), 7.76 (d, J = 7.7 Hz, 1H), 7.69 (s, 1H), 7.54 (t, J = 8.1 Hz, 1H), 7.04 (d, J = 8.3 Hz, 1H), 6.90 (d, J = 8.3 Hz, 1H) |
| 69 | H NMR (400 MHz, DMSO-d6) δ 13.06 (d, J = 6.5 Hz, 1H), 12.51 (s, 1H), 8.88 (d, J = 6.6 Hz, 1H), 8.33 (dd, J = 8.1, 1.0 Hz, 1H), 7.85-7.74 (m, 3H), 7.55 (t, J = 8.1 Hz, 1H), 7.38 (dd, J = 8.4, 1.9 Hz, 1H), 7.32 (d, J = 8.5 Hz, 1H), 3.03 (septet, J = 6.8 Hz, 1H), 1.20 (d, J = 6.7 Hz, 6H) |
| 76 | 1H-NMR (CDCl3, 300 MHz) δ 8.84 (d, J = 6.6 Hz, 1H), 8.31 (d, J = 6.2 Hz, 1H), 8.01 (d, J = 7.9 Hz, 1H), 7.44-7.13 (m, 8H), 6.78 (d, J = 7.5 Hz, 1H). |
| 77 | H NMR (400 MHz, DMSO-d6) δ 6.40 (m, 1H), 7.36 (t, J = 2.7 Hz, 1H), 7.43 (d, J = 11.8 Hz, 1H), 7.55 (t, J = 8.1 Hz, 1H), 7.80 (m, 2H), 8.36 (d, J = 9.2 Hz, 1H), 8.65 (d, J = 6.8 Hz, 1H), 8.91 (s, 1H), 11.19 (s, 1H), 12.72 (s, 1H), 12.95 (s, 1H) |
| 88 | H NMR (400 MHz, DMSO-d6) δ 12.96 (d, J = 6.6 Hz, 1H), 12.42 (s, 1H), 8.89 (d, J = 6.7 Hz, 1H), 8.33 (dd, J = 8.1, 1.2 Hz, 1H), 7.82 (t, J = 8.3 Hz, 1H), 7.76 (d, J = 7.8 Hz, 1H), 7.66 (d, J = 8.7 Hz, 2H), 7.54 (t, J = 8.1 Hz, 1H), 7.34 (d, J = 8.7 Hz, 2H), 6.67 (t, J = 6.3 Hz, 1H), 3.12 (d, J = 6.3 Hz, 2H), 1.35 (s, 9H), 1.22 (s, 6H) |
| 90 | 1H NMR (400 MHz, DMSO-d6) δ 11.98 (s, 1H), 8.89 (s, 1H), 8.34 (dd, J = 8.2, 1.1 Hz, 1H), 7.84-7.75 (m, 2H), 7.59 (dd, J = 7.8, 1.5 Hz, 1H), 7.55-7.51 (m, 1H), 7.42 (dd, J = 7.9, 1.5 Hz, 1H), 7.26-7.21 (m, 1H), 7.19-7.14 (m, 1H), 1.43 (s, 9H) |

| Cmpd No. | NMR Data |
|---|---|
| 96 | 1H NMR (400 MHz, DMSO-d6) δ 12.58 (s, 1H), 11.11 (s, 1H), 8.89 (s, 1H), 8.35 (dd, J = 8.1, 1.1 Hz, 1H), 8.22 (d, J = 1.5 Hz, 1H), 7.83-7.74 (m, 2H), 7.56-7.51 (m, 2H), 7.30 (d, J = 2.3 Hz, 1H), 7.13 (dd, J = 8.5, 1.8 Hz, 1H), 4.03 (d, J = 0.5 Hz, 2H) |
| 103 | H NMR (400 MHz, DMSO-d6) δ 1.37 (s, 9H), 1.38 (s, 9H), 7.08 (s, 1H), 7.17 (s, 1H), 7.74 (m, 1H), 7.86 (m, 1H), 7.98 (dd, J = 9.2, 2.9 Hz, 1H), 8.90 (d, J = 6.7 Hz, 1H), 9.21 (s, 1H), 11.71 (s, 1H), 13.02 (d, J = 6.7 Hz, 1H) |
| 104 | 1H NMR (400 MHz, DMSO-d6) δ 12.93 (d, J = 6.6 Hz, 1H), 12.41 (s, 1H), 10.88 (s, 1H), 8.88 (d, J = 6.7 Hz, 1H), 8.36-8.34 (m, 1H), 8.05 (d, J = 0.8 Hz, 1H), 7.84-7.75 (m, 2H), 7.56-7.52 (m, 1H), 7.35 (d, J = 8.3 Hz, 1H), 7.01 (dd, J = 8.4, 1.9 Hz, 1H), 6.07-6.07 (m, 1H), 2.37 (s, 3H) |
| 107 | H NMR (400 MHz, DMSO-d6) δ 12.52 (s, 1H), 8.87 (s, 1H), 8.33 (dd, J = 8.2, 1.1 Hz, 1H), 7.81 (t, J = 8.3 Hz, 1H), 7.75 (d, J = 7.7 Hz, 1H), 7.57-7.51 (m, 3H), 7.15 (d, J = 8.3 Hz, 1H), 4.51 (s, 2H), 3.56 (t, J = 5.7 Hz, 2H), 2.75 (t, J = 5.5 Hz, 2H), 1.44 (s, 9H) |
| 109 | H NMR (400 MHz, DMSO-d6) δ 12.97 (br s, 1H), 12.45 (s, 1H), 8.89 (s, 1H), 8.33 (dd, J = 8.2, 1.1 Hz, 1H), 7.88 (s, 1H), 7.82 (t, J = 8.4 Hz, 1H), 7.75 (d, J = 7.7 Hz, 1H), 7.54 (t, J = 8.1 Hz, 1H), 7.43 (m, 1H), 7.31 (d, J = 8.5 Hz, 1H), 4.01 (m, 1H), 3.41 (m, 1H), 2.21 (s, 3H), 1.85 (m, 1H), 1.68-1.51 (m, 3H), 1.23 (s, 3H), 0.71 (t, J = 7.4 Hz, 3H) |
| 113 | 1H NMR (400 MHz, DMSO-d6) δ 12.92 (d, J = 6.6 Hz, 1H), 12.46 (s, 1H), 10.72 (d, J = 1.5 Hz, 1H), 8.89 (d, J = 6.7 Hz, 1H), 8.35 (dd, J = 8.1, 1.2 Hz, 1H), 8.13 (d, J = 1.5 Hz, 1H), 7.84-7.75 (m, 2H), 7.56-7.52 (m, 1H), 7.44 (d, J = 8.4 Hz, 1H), 7.07-7.04 (m, 2H), 2.25 (d, J = 0.9 Hz, 3H) |
| 114 | 1H NMR (300 MHz, DMSO-d6): δ 12.65 (d, J = 6.9 Hz, 1H), 11.60 (s, 1H), 9.33 (s, 1H), 8.71 (d, J = 6.6 Hz, 1H), 8.36 (d, J = 1.8 Hz, 1H), 8.03 (d, J = 7.8 Hz, 1H), 7.66 (t, J = 7.2 Hz, 1H), 7.60 (d, J = 8.1 Hz, 1H), 7.38 (t, J = 7.8 Hz, 1H), 7.29 (t, J = 7.5 Hz, 1H), 7.12 (m, 2H), 6.97 (m, 3H), 3.97 (m, 2H), 1.45 (s, 9H), 1.06 (t, J = 6.6 Hz, 3H). |
| 126 | H NMR (400 MHz, DMSO-d6) δ 12.94 (s, 1H), 12.33 (s, 1H), 9.49 (s, 1H), 8.88 (s, 1H), 8.35 (dd, J = 8.7, 0.5 Hz, 1H), 7.86-7.82 (m, 1H), 7.77 (d, J = 7.8 Hz,, 7.58-7.54 (m, 1H), 7.40 (d, J = 2.2 Hz, 1H), 7.11 (d, J = 8.5 Hz, 1H), 6.98 (dd, J = 8.4, 2.2 Hz, 1H), 3.67 (s, 2H), 3.51-3.47 (m, 2H), 3.44-3.41 (m, 2H), 3.36 (s, 3H), 1.33 (s, 6H) |
| 127 | H NMR (400 MHz, DMSO-d6) δ 1.23 (t, J = 7.0 Hz, 3H), 1.32 (s, 9H), 4.10 (q, J = 7.0 Hz, 2H), 7.36 (d, J = 8.5 Hz, 1H), 7.54 (m, 3H), 7.76 (d, J = 7.9 Hz, 1H), 7.82 (m, 1H) 8.33 (d, J = 9.2 Hz, 1H), 8.64 (s, 1H), 8.87 (s, 1H), 12.45 (s, 1H), 12.99 (s, 1H) |
| 129 | 1H-NMR (CD3OD, 300 MHz) δ 8.83 (s, 1H), 8.41 (d, J = 8.1 Hz, 1H), 7.80 (m, 1H), 7.65 (d, J = 8.1 Hz, 1H), 7.55 (m, 2H), 7.22 (d, J = 8.1 Hz, 1H), 3.76 (s, 3H, OMe), 2.62 (q, J = 7.5 Hz, 2H), 1.21 (t, J = 7.5 Hz, 3H). |
| 131 | 1H NMR (300 MHz, DMSO-d6) δ 12.37 (s, 1H), 8.81 (s, 1H), 8.30 (d, J = 8.1 Hz, 1H), 7.77 (m, 2H), 7.52 (t, J = 7.2 Hz, 1H), 7.09 (s, 1H), 6.74 (s, 1H), 6.32 (s, 1H), 5.47 (s, 2H). |
| 135 | 1H-NMR (CDCl3, 300 MHz) δ 8.86 (d, J = 6.6 Hz, 1H), 8.32 (d, J = 6.2 Hz, 1H), 8.07 (d, J = 7.9 Hz, 1H), 7.47-7.24 (m, 6H), 6.95-6.83 (m, 3H), 5.95 (s, 2H). |
| 136 | H NMR (400 MHz, DMSO-d6) δ 1.29 (s, 9H), 1.41 (s, 9H), 7.09 (d, J = 2.4 Hz, 1H), 7.47 (d, J = 2.3 Hz, 1H), 7.57 (t, J = 8.1 Hz, 1H), 7.77 (d, J = 7.8 Hz, 1H), 7.85 (t, J = 8.4 Hz, 1H), 8.36 (d, J = 9.5 Hz, 1H), 8.93 (d, J = 6.8 Hz, 1H), 9.26 (s, 1H), 12.66 (s, 1H), 13.04 (d, J = 6.6 Hz, 1H) |
| 141 | H NMR (400 MHz, DMSO-d6) δ 12.96 (d, J = 6.6 Hz, 1H), 12.42 (s, 1H), 8.87 (d, J = 6.8 Hz, 1H), 8.33 (dd, J = 8.1, 1.2 Hz, 1H), 7.85-7.75 (m, 3H), 7.55 (t, J = 8.1 Hz, 1H), 7.46 (dd, J = 8.2, 2.2 Hz, 1H), 7.16 (d, J = 8.5 Hz, 1H), 4.14 (q, J = 7.1 Hz, 2H), 2.18 (s, 3H), 1.27 (t, J = 7.1 Hz, 3H) |
| 143 | H NMR (400 MHz, DMSO-d6) δ 12.96 (d, J = 6.8 Hz, 1H), 12.56 (s, 1H), 9.44 (s, 1H), 8.87 (d, J = 6.8 Hz, 1H), 8.34 (dd, J = 8.2, 1.3 Hz, 1H), 8.08 (d, J = 7.4 Hz, 1H), 7.83 (t, J = 8.3 Hz, 1H), 7.76 (d, J = 7.7 Hz, 1H), 7.55 (t, J = 8.1 Hz, 1H), 7.00 (d, J = 13.3 Hz, 1H), 1.34 (s, 9H) |
| 150 | 1H-NMR (DMSO d6, 300 MHz) δ 8.86 (d, J = 6.9 Hz, 1H), 8.63 (s, 1H), 8.30 (d, J = 8.1 Hz, 1H), 7.86 (d, J = 8.7 Hz, 2H), 7.82-7.71 (m, 2H), 7.64 (d, J = 8.4 Hz, 2H), 7.52 (td, J = 1.2 Hz, 1H). |
| 157 | 1H-NMR (CD3OD, 300 MHz) δ 8.91 (s, 1H), 8.57 (s, 1H), 8.45 (d, J = 8.3 Hz, 1H), 7.83 (t, J = 7.2 Hz, 1H), 7.69 (d, J = 9.0 Hz, 1H), 7.57 (t, J = 7.9 Hz, 1H), 7.46 (d, J = 8.5 Hz, 1H), 7.16 (d, J = 6.0 Hz, 1H), 3.08 (s, 3H, NMe), 2.94 (q, J = 7.4 Hz, 2H), 1.36 (t, J = 7.4 Hz, 3H). |
| 161 | H NMR (400 MHz, DMSO-d6) δ 12.96 (s, 1H), 12.41 (s, 1H), 8.88 (s, 1H),, 8.33 (dd, J = 8.2, 1.2 Hz, 1H), 7.84-7.80 (m, 1H), 7.75 (d, J = 7.9 Hz, 1H), 7.55 (t, J = 8.1 Hz, 1H),, 7.44 (s, 1H), 7.19 (s, 2H), 4.13 (t, J = 4.6 Hz, 2H), 3.79 (t, J = 4.6 Hz, 2H), 3.54 (q, J = 7.0 Hz, 2H), 1.36 (s, 9H), 1.15 (t, J = 7.0 Hz, 3H) |

-continued

| Cmpd No. | NMR Data |
|---|---|
| 163 | 1H-NMR (300 MHz, DMSO-d6) δ 12.87 (d, J = 6.3 Hz, 1H), 11.83 (s, 1H), 8.76 (d, J = 6.3 Hz, 1H), 8.40 (s, 1H), 8.26 (br s, 2H), 8.08 (dd, J = 8.4 Hz, J = 1.5 Hz, 1H), 7.75 (m, 1H), 7.67 (d, J = 7.8 Hz, 1H), 7.47-7.37 (m, 2H), 7.24 (d, J = 0.9 Hz, 1H), 7.15 (dd, J = 7.5 Hz, J = 1.8 Hz, 1H), 7.10 (d, J = 8.1 Hz, 1H), 7.02 (dt, J = 7.5 Hz, J = 0.9 Hz, 1H), 4.07 (m, 4H), 1.094 (t, J = 6.9 Hz, 3H). |
| 167 | H NMR (400 MHz, DMSO-d6) δ 2.03 (s, 3H), 4.91 (s, 2H), 6.95 (m, 3H), 7.53 (m, 1H), 7.75 (d, J = 8.2 Hz, 1H), 7.81 (m, 1H), 8.33 (d, J = 8.0 Hz, 1H), 8.84 (s, 1H), 12.20 (s, 1H), 12.90 (s, 1H) |
| 169 | 1H NMR (400 MHz, DMSO-d6) δ 12.94 (d, J = 5.3 Hz, 1H), 12.51 (s, 1H), 8.89 (d, J = 6.3 Hz, 1H), 8.36 (dd, J = 8.1, 1.1 Hz, 1H), 8.06 (t, J = 0.7 Hz, 1H), 7.85-7.75 (m, 2H), 7.57-7.51 (m, 2H), 7.28 (d, J = 3.1 Hz, 1H), 7.24 (dd, J = 8.4, 1.8 Hz, 1H), 6.39 (dd, J = 3.1, 0.8 Hz, 1H), 3.78 (s, 3H) |
| 178 | 1H NMR (400 MHz, DMSO-d6) δ 12.86 (s, 1H), 8.89 (d, J = 6.8 Hz, 1H), 8.65 (dd, J = 8.1, 1.6 Hz, 1H), 8.19 (dd, J = 8.2, 1.3 Hz, 1H), 7.80-7.71 (m, 2H), 7.48-7.44 (m, 2H), 7.24-7.20 (m, 1H), 7.16-7.09 (m, 2H), 7.04-7.00 (m, 1H), 6.80 (dd, J = 8.0, 1.3 Hz, 1H), 6.69 (dd, J = 8.1, 1.4 Hz, 1H), 1.45 (s, 9H) |
| 183 | 1H NMR (400 MHz, DMSO-d6) δ 12.42 (s, 1H), 8.88 (s, 1H), 8.33 (dd, J = 8.2, 1.1 Hz, 1H), 8.06 (d, J = 2.1 Hz, 1H), 7.84-7.75 (m, 2H), 7.56-7.52 (m, 1H), 7.38 (dd, J = 8.2, 2.1 Hz, 1H), 7.08 (d, J = 8.3 Hz, 1H), 3.66-3.63 (m, 2H), 2.70 (t, J = 6.5 Hz, 2H), 1.86-1.80 (m, 2H), 1.51 (s, 9H) |
| 186 | H NMR (400 MHz, DMSO-d6) δ 12.93 (s, 1H), 12.47 (s, 1H), 10.72 (s, 1H), 8.89 (s, 1H), 8.35 (dd, J = 8.2, 1.1 Hz, 1H), 8.13 (d, J = 1.6 Hz, 1H), 7.82 (t, J = 8.2 Hz, 1H), 7.76 (d, J = 7.8 Hz, 1H), 7.54 (t, J = 7.5 Hz, 1H), 7.50 (d, J = 8.4 Hz, 1H), 7.05-7.02 (m, 2H), 3.19 (quintet, J = 8.2 Hz, 1H), 2.08 (m, 2H), 1.82-1.60 (m, 6H) |
| 187 | 1H NMR (400 MHz, DMSO-d6) δ 12.63 (s, 1H), 8.91 (s, 1H), 8.87-8.87 (m, 1H), 8.36 (dd, J = 8.2, 1.2 Hz, 1H), 7.85-7.75 (m, 3H), 7.64-7.53 (m, 3H), 6.71 (dd, J = 3.7, 0.5 Hz, 1H), 2.67 (s, 3H) |
| 188 | H NMR (400 MHz, DMSO-d6) δ 12.84 (s, 1H), 12.73 (d, J = 6.6 Hz, 1H), 11.39 (s, 1H), 8.85 (d, J = 6.7 Hz, 1H), 8.61 (s, 1H), 8.33 (d, J = 6.8 Hz, 1H), 8.23 (s, 1H), 7.80 (t, J = 8.4 Hz, 1H), 7.73 (d, J = 7.8 Hz, 1H), 7.52 (t, J = 8.1 Hz, 1H), 7.43 (m, 1H), 6.54 (m, 1H), 4.38 (q, J = 7.1 Hz, 2H), 1.36 (t, J = 7.1 Hz, 3H) |
| 204 | H NMR (400 MHz, DMSO-d6) δ 12.97 (s, 1H), 12.37 (s, 1H), 8.87 (d, J = 1.2 Hz, 1H), 8.32 (d, J = 8.2 Hz, 1H), 7.82 (dd, J = 8.2, 7.0 Hz, 1H), 7.75 (d, J = 8.3 Hz, 1H), 7.54 (t, J = 7.5 Hz, 1H), 7.32-7.28 (m, 2H), 7.05 (d, J = 8.4 Hz, 1H), 4.16 (t, J = 4.9 Hz, 2H), 1.78 (t, J = 4.9 Hz, 2H), 1.29 (s, 6H), |
| 207 | H NMR (400 MHz, DMSO-d6) δ 12.92 (br s, 1H), 12.50 (s, 1H), 10.95 (s, 1H), 8.89 (s, 1H), 8.35 (dd, J = 8.2, 1.1 Hz, 1H), 8.17 (d, J = 1.5 Hz, 1H), 7.82 (t, J = 8.3 Hz, 1H), 7.76 (d, J = 7.7 Hz, 1H), 7.55 (t, J = 8.1 Hz, 1H), 7.46 (d, J = 8.4 Hz, 1H), 7.21 (d, J = 2.3 Hz, 1H), 7.06 (dd, J = 8.5, 1.8 Hz, 1H), 4.09 (q, J = 7.1 Hz, 2H), 3.72 (s, 2H), 1.20 (t, J = 7.1 Hz, 3H) |
| 215 | H NMR (400 MHz, DMSO-d6) δ 12.97 (s, 1H), 12.50 (s, 1H), 8.89 (s, 1H), 8.34 (dd, J = 8.1, 1.1 Hz, 1H), 7.83 (t, J = 8.3 Hz, 1H), 7.75 (m, 3H), 7.55 (t, J = 8.1 Hz, 1H), 7.37 (t, J = 7.9 Hz, 2H), 7.10 (t, J = 6.8 Hz, 1H) |
| 220 | H NMR (400 MHz, DMSO-d6) δ 12.99 (d, J = 6.6 Hz, 1H), 12.07 (s, 1H), 8.93 (d, J = 6.8 Hz, 1H), 8.35 (d, J = 7.1 Hz, 1H), 8.27 (s, 1H), 8.12 (s, 1H), 7.85-7.77 (m, 2H), 7.54 (td, J = 7.5, 1.2 Hz, 1H), 6.81 (s, 1H), 1.37 (d, J = 3.9 Hz, 9H), 1.32 (d, J = 17.1 Hz, 9H) |
| 225 | 1H NMR (CD3OD, 300 MHz) δ 8.79 (s, 1H), 8.37 (d, J = 7.9 Hz, 1H), 7.75 (m, 2H), 7.61 (d, J = 8.3 Hz, 1H), 7.5 (m, 2H), 7.29 (d, J = 8.3 Hz, 1H), 4.21 (q, J = 7.2, 2H), 3.17 (m, 1H), 1.32 (t, J = 7.2 Hz, 3H), 1.24 (d, J = 6.9 Hz, 6H). |
| 232 | 1H-NMR (CD3OD, 300 MHz) δ 8.87 (s, 1H), 8.45 (d, J = 8.25, 1H), 8.27 (m, 1H), 7.83 (t, J = 6.88, 1H), 7.67 (d, J = 8.25, 1H), 7.54 (t, J = 7.15, 1H), 7.39 (d, J = 6.05, 1H), 7.18 (d, J = 8.5, 1H), 2.77 (t, J = 6.87, 2H), 2.03 (s, 3H), 1.7 (q, 2H), 1.04 (t, J = 7.42, 3H) |
| 233 | 1H NMR (400 MHz, DMSO-d6) δ 12.75 (d, J = 13.6 Hz, 1H), 8.87 (s, 1H), 8.32-8.28 (m, 2H), 7.76-7.70 (m, 2H), 7.60 (d, J = 7.8 Hz, 1H), 7.49-7.45 (m, 1H), 7.18 (d, J = 8.4 Hz, 1H), 4.11 (t, J = 8.3 Hz, 2H), 3.10 (t, J = 7.7 Hz, 2H), 2.18 (s, 3H) |
| 234 | 1H NMR (400 MHz, DMSO-d6) δ 12.49 (s, 1H), 11.50 (s, 1H), 8.90 (s, 1H), 8.36-8.34 (m, 2H), 7.97 (s, 1H), 7.85-7.81 (m, 1H), 7.77-7.75 (m, 1H), 7.56-7.50 (m, 2H), 6.59-6.58 (m, 1H) |
| 235 | H NMR (400 MHz, DMSO-d6) δ 13.09 (d, J = 6.5 Hz, 1H), 12.75 (s, 1H), 9.04 (s, 1H), 8.92 (d, J = 6.8 Hz, 1H), 8.42 (d, J = 7.1 Hz, 1H), 8.34 (d, J = 6.9 Hz, 1H), 7.85 (t, J = 8.4 Hz, 1H), 7.78 (d, J = 7.7 Hz, 1H), 7.63-7.56 (m, 2H), 3.15 (m, 1H), 1.29 (d, J = 6.9 Hz, 6H) |
| 238 | H NMR (400 MHz, DMSO-d6) δ 12.93 (d, J = 6.4 Hz, 1H), 12.29 (s, 1H), 8.85 (d, J = 6.7 Hz, 1H), 8.32 (d, J = 8.1 Hz, 1H), 7.82 (t, J = 8.3 Hz, 1H), 7.75 (d, J = 7.9 Hz, 1H), 7.54 (t, J = 8.1 Hz, 1H), 7.17 (m, 2H), 6.94 (m, 1H), 3.79 (m, 2H), 3.21-2.96 (m, 4H), 1.91-1.76 (m, 4H), 1.52 (m, 2H), 1.43 (s, 9H) |

| Cmpd No. | NMR Data |
|---|---|
| 242 | H NMR (400 MHz, DMSO-d6) δ 12.95 (d, J = 6.6 Hz, 1H), 12.65 (s, 1H), 8.87 (d, J = 6.8 Hz, 1H), 8.34 (dd, J = 8.1, 1.1 Hz, 1H), 8.17 (s, 1H), 7.83 (t, J = 8.3 Hz, 1H), 7.76 (d, J = 7.8 Hz, 1H), 7.54 (t, J = 8.1 Hz, 1H), 7.37 (s, 1H), 5.60 (s, 2H) |
| 243 | 1H-NMR (CD3OD, 300 MHz) δ 8.87 (s, 1H), 8.45 (d, J = 8.25, 1H), 8.27 (m, 1H), 7.83 (t, J = 6.88, 1H), 7.67 (d, J = 8.25, 1H), 7.54 (t, J = 7.15, 1H), 7.39 (d, J = 6.05, 1H), 7.18 (d, J = 8.5, 1H), 2.77 (t, J = 6.87, 2H), 2.03 (s, 3H), 1.7 (q, 2H), 1.04 (t, J = 7.42, 3H) NMR Shows regio isomer |
| 244 | H NMR (400 MHz, DMSO-d6) δ 12.89 (s, 1H), 12.42 (s, 1H), 10.63 (s, 1H), 8.88 (d, J = 6.7 Hz, 1H), 8.35 (d, J = 8.2 Hz, 1H), 8.03 (d, J = 1.6 Hz, 1H), 7.82 (t, J = 8.3 Hz, 1H), 7.76 (d, J = 7.7 Hz, 1H), 7.54 (t, J = 8.1 Hz, 1H), 7.29 (d, J = 8.3 Hz, 1H), 7.02 (dd, J = 8.4, 1.8 Hz, 1H), 2.69 (t, J = 5.3 Hz, 2H), 2.61 (t, J = 5.0 Hz, 2H), 1.82 (m, 4H) |
| 248 | H NMR (400 MHz, DMSO-d6) δ 12.95 (d, J = 6.6 Hz, 1H), 12.42 (s, 1H), 9.30 (s, 1H), 8.86 (d, J = 6.8 Hz, 1H), 8.33 (dd, J = 8.1, 1.3 Hz, 1H), 7.85-7.81 (m, 2H), 7.76 (d, J = 7.8 Hz, 1H), 7.55 (t, J = 8.1 Hz, 1H), 7.49 (dd, J = 8.2, 2.2 Hz, 1H), 7.18 (d, J = 8.3 Hz, 1H), 2.18 (s, 3H), 2.08 (s, 3H) |
| 259 | H NMR (400 MHz, DMSO-d6) δ 0.86 (t, J = 7.4 Hz, 3H), 1.29 (d, J = 6.9 Hz, 3H), 1.67 (m, 2H), 2.88 (m, 1H), 7.03 (m, 2H), 7.53 (m, 2H), 7.80 (m, 2H), 8.13 (s, 1H), 8.35 (d, J = 8.2 Hz, 1H), 8.89 (s, 1H), 10.75 (s, 1H), 12.45 (s, 1H), 12.84 (s, 1H) |
| 260 | H NMR (400 MHz, DMSO-d6) δ 13.23 (d, J = 6.6 Hz, 1H), 12.20 (s, 1H), 10.22 (br s, 2H), 8.88 (d, J = 6.8 Hz, 1H), 8.34 (d, J = 7.8 Hz, 1H), 7.86-7.80 (m, 3H), 7.56-7.52 (m, 2H), 7.15 (dd, J = 8.5, 2.4 Hz, 1H), 1.46 (s, 9H) |
| 261 | 1H-NMR (d6-DMSO, 300 MHz) δ 11.99 (s, 1H, NH), 8.76 (s, J = 6.6 Hz, 1H), 8.26 (d, J = 6.2 Hz, 1H), 8.09 (d, J = 7.9 Hz, 1H), 7.72-7.63 (m, 2H), 7.44-7.09 (m, 7H), 2.46 (s, 3H), 2.25 (s, 3H). |
| 262 | 1H NMR (400 MHz, DMSO-d6) δ 13.00 (s, 1H), 12.53 (s, 1H), 10.62 (s, 1H), 8.88 (s, 1H), 8.33 (dd, J = 8.2, 1.2 Hz, 1H), 7.85-7.75 (m, 2H), 7.57-7.50 (m, 2H), 7.34-7.28 (m, 2H), 3.46 (s, 2H) |
| 266 | H NMR (400 MHz, DMSO-d6) δ 12.94 (d, J = 6.6 Hz, 1H), 12.57 (s, 1H), 10.37 (s, 1H), 8.88 (d, J = 6.8 Hz, 1H), 8.34-8.32 (m, 1H), 7.99 (s, 1H), 7.85-7.81 (m, 1H), 7.76 (d, J = 7.8 Hz, 1H), 7.56-7.52 (m, 1H), 7.38 (s, 1H), 1.37 (s, 9H) |
| 268 | H NMR (400 MHz, DMSO-d6) δ 13.02 (s, 1H), 12.62 (s, 1H), 8.91 (s, 1H), 8.34 (dd, J = 8.1, 1.1 Hz, 1H), 8.22 (d, J = 2.4 Hz, 1H), 8.14 (dd, J = 8.8, 2.4 Hz, 1H), 7.84 (t, J = 8.3 Hz, 1H), 7.77 (d, J = 7.8 Hz, 1H), 7.65-7.54 (m, 4H), 1.52 (s, 9H) |
| 271 | H NMR (400 MHz, DMSO-d6) δ 1.38 (s, 9H), 4.01 (s, 2H), 7.35 (s, 2H), 7.55 (m, 1H), 7.65 (s, 1H), 7.79 (d, J = 8.2 Hz, 1H), 7.83 (m, 1H), 8.33 (d, J = 7.6 Hz, 1H), 8.86 (d, J = 6.8 Hz, 1H), 12.49 (s, 1H), 13.13 (s, 1H) |
| 272 | 1H-NMR (d6-Acetone, 300 MHz) δ 8.92 (d, J = 6.6 Hz, 1H), 8.39 (d, J = 7.8 Hz, 1H), 7.94 (s, 1H), 7.79 (s, 1H), 7.77 (s, 2H), 7.53 (m, 1H), 7.36 (s, 1H), 3.94-3.88 (m, 5H), 3.64-3.59 (m, 3H), 3.30 (m, 4H). |
| 274 | H NMR (400 MHz, DMSO-d6) δ 13.21 (d, J = 6.6 Hz, 1H), 11.66 (s, 1H), 10.95 (s, 1H), 9.00 (d, J = 6.5 Hz, 1H), 8.65 (d, J = 2.1 Hz, 1H), 8.18 (dd, J = 8.7, 2.2 Hz, 1H), 7.97 (d, J = 8.8 Hz, 1H), 7.57 (m, 2H), 7.31 (t, J = 2.7 Hz, 1H), 6.40 (t, J = 2.0 Hz, 1H), 3.19 (m, 4H), 1.67 (m, 4H), 1.46 (s, 9H) |
| 275 | H NMR (400 MHz, DMSO-d6) δ 12.23 (s, 1H), 9.47 (s, 1H), 9.20 (s, 1H), 8.43 (d, J = 7.9 Hz, 1H), 7.79 (t, J = 2.0 Hz, 2H), 7.56 (m, 1H), 7.38-7.26 (m, 6H), 7.11 (d, J = 8.4 Hz, 1H), 6.99 (dd, J = 8.4, 2.1 Hz, 1H), 5.85 (s, 2H), 1.35 (s, 9H) |
| 282 | 1H NMR (CD3OD, 300 MHz) δ 8.90 (s, 1H), 8.51 (s, 1H), 8.44 (d, J = 7.9 Hz, 1H), 7.82 (t, J = 8.3 Hz, 1H), 7.69 (d, J = 8.5 Hz, 1H), 7.56 (t, J = 7.7 Hz, 2H), 7.42 (d, J = 7.9 Hz, 1H), 7.07 (d, J = 5.8 Hz, 1H), 2.93 (q, J = 7.4 Hz, 2H), 1.36 (t, J = 7.5 Hz, 3H). |
| 283 | 1H-NMR (CDCl3, 300 MHz) δ 8.82 (d, J = 6.6 Hz, 1H), 8.29 (d, J = 6.2 Hz, 1H), 8.06 (d, J = 7.9 Hz, 1H), 7.43-7.24 (m, 6H), 7.02 (m, 2H), 6.87-6.81 (dd, 2H), 3.76 (s, 3H). |
| 287 | H NMR (400 MHz, DMSO-d6) δ 13.51 (s, 1H), 13.28 (d, J = 6.6 Hz, 1H), 11.72 (d, J = 2.2 Hz, 1H), 9.42 (s, 1H), 8.87 (d, J = 6.9 Hz, 1H), 8.04 (d, J = 7.4 Hz, 1H), 7.67 (t, J = 8.2 Hz, 1H), 7.17 (dd, J = 8.3, 0.8 Hz, 1H), 7.01 (d, J = 13.7 Hz, 1H), 6.81 (dd, J = 8.1, 0.8 Hz, 1H), 2.10 (m, 2H), 1.63-1.34 (m, 8H), 1.26 (s, 3H) |
| 288 | H NMR (400 MHz, DMSO-d6) δ 13.16 (s, 1H), 12.85 (s, 1H), 8.98 (s, 1H), 8.43 (dd, J = 8.1, 1.1 Hz, 1H), 8.34 (dd, J = 10.3, 3.1 Hz, 1H), 7.93 (t, J = 8.4 Hz, 1H), 7.86 (d, J = 7.7 Hz, 1H), 7.66 (t, J = 8.1 Hz, 1H), 7.03 (dd, J = 10.7, 3.2 Hz, 1H), 4.06 (s, 3H), 1.42 (s, 9H) |
| 295 | H NMR (400 MHz, DMSO-d6) δ 1.98 (m, 4H), 3.15 (m, 4H), 7.04 (m, 2H), 7.17 (d, J = 7.8 Hz, 1H), 7.52 (m, 1H), 7.74 (d, J = 7.8 Hz, 1H), 7.81 (m, 1H), 8.19 (dd, J = 7.9, 1.4 Hz, 1H), 8.33 (d, J = 8.1 Hz, 1H), 8.88 (d, J = 6.7 Hz, 1H), 12.19 (s, 1H), 12.87 (s, 1H) |

| Cmpd No. | NMR Data |
|---|---|
| 299 | 1H NMR (400 MHz, DMSO-d6) δ 12.93-12.88 (m, 1H), 12.18 (s, 1H), 8.83 (d, J = 6.8 Hz, 1H), 8.38-8.31 (m, 1H), 7.85-7.67 (m, 2H), 7.57-7.51 (m, 1H), 6.94 (s, 1H), 6.81-6.74 (m, 2H), 3.19-3.16 (m, 2H), 2.68-2.61 (m, 2H), 1.80-1.79 (m, 2H) |
| 300 | H NMR (400 MHz, DMSO-d6) δ 13.23 (d, J = 6.6 Hz, 1H), 12.59 (s, 1H), 8.87 (d, J = 6.8 Hz, 1H), 8.33 (d, J = 7.7 Hz, 1H), 7.86-7.79 (m, 3H), 7.58-7.42 (m, 3H), 3.38 (m, 2H), 1.88 (m, 2H), 1.30 (s, 6H) |
| 303 | H NMR (400 MHz, DMSO-d6) δ 12.96 (d, J = 6.5 Hz, 1H), 12.47 (s, 0.4H), 12.43 (s, 0.6H), 8.87 (dd, J = 6.7, 2.3 Hz, 1H), 8.33 (d, J = 8.1 Hz, 1H), 7.82 (t, J = 8.2 Hz, 1H), 7.75 (d, J = 8.3 Hz, 1H), 7.62-7.52 (m, 3H), 7.17 (d, J = 8.3 Hz, 1H), 4.66 (s, 0.8H), 4.60 (s, 1.2H), 3.66 (t, J = 5.9 Hz, 2H), 2.83 (t, J = 5.8 Hz, 1.2H), 2.72 (t, J = 5.9 Hz, 0.8H), 2.09 (m, 3H) |
| 304 | 1H NMR (300 MHz, DMSO-d6) δ 11.70 (s, 1H), 8.74 (s, 1H), 8.15 (s, 1H), 8.07 (m, 1H), 7.72 (m, 1H), 7.63 (d, J = 8.4 Hz, 1H), 7.45-7.31 (m, 3H), 7.15-6.95 (m, 5H), 4.17 (d, J = 6.0 Hz, 2H), 4.02 (q, J = 6.9 Hz, 2H), 1.40 (s, 9H), 1.09 (t, J = 6.9 Hz, 3H). |
| 307 | 1H-NMR (CDCl3, 300 MHz) δ 8.81 (d, J = 6.6 Hz, 1H), 8.30 (d, J = 6.2 Hz, 1H), 8.02 (d, J = 7.9 Hz, 1H), 7.44-7.26 (m, 9H), 6.79 (d, J = 7.5 Hz, 1H). |
| 318 | 1H-NMR (d6-Acetone, 300 MHz) δ 8.92 (bs, 1H), 8.40 (d, J = 8.1 Hz, 1H), 8.05 (bs, 1H), 7.94 (bs, 1H), 7.78 (bs, 2H), 7.52 (m, 1H), 7.36 (bs, 1H), 3.97 (t, J = 7.2 Hz, 2H), 3.66 (t, J = 8 Hz, 2H), 3.31-3.24 (m, 6H), 1.36-1.31 (m, 4H). |
| 320 | $^1$H NMR (400 MHz, DMSO-d6) δ 12.90 (s, 1H), 12.44 (s, 1H), 10.86 (s, 1H), 8.90 (s, 1H), 8.35 (dd, J = 8.2, 1.0 Hz, 1H), 8.12 (t, J = 0.8 Hz, 1H), 7.84-7.75 (m, 2H), 7.56-7.52 (m, 1H), 7.37 (d, J = 8.3 Hz, 1H), 6.99 (dd, J = 8.4, 1.9 Hz, 1H), 6.08-6.07 (m, 1H), 1.35 (s, 9H) |
| 321 | H NMR (400 MHz, DMSO-d6) δ 2.93 (m, 4H), 3.72 (m, 4H), 7.10 (m, 2H), 7.27 (d, J = 7.8 Hz, 1H), 7.51 (m, 6H), 7.74 (d, J = 8.2 Hz, 1H), 7.81 (m, 1H), 8.40 (d, J = 8.1 Hz, 1H), 8.58 (d, J = 8.0 Hz, 1H), 8.88 (d, J = 6.7 Hz, 1H), 12.69 (s, 1H), 12.86 (s, 1H) |
| 323 | H NMR (400 MHz, DMSO-d6) δ 12.94 (br s, 1H), 12.44 (s, 1H), 8.89 (s, 1H), 8.33 (dd, J = 8.2, 1.1 Hz, 1H), 7.82 (t, J = 8.3 Hz, 1H), 7.76 (d, J = 7.7 Hz, 1H), 7.67 (d, J = 8.8 Hz, 2H), 7.54 (t, J = 8.1 Hz, 1H), 7.35 (d, J = 8.7 Hz, 2H), 7.02 (t, J = 6.3 Hz, 1H), 3.50 (s, 3H), 3.17 (d, J = 6.2 Hz, 2H), 1.23 (s, 6H) |
| 334 | H NMR (400 MHz, DMSO-d6) δ 13.02 (br s, 1H), 12.46 (s, 1H), 8.89 (s, 1H), 8.33 (dd, J = 8.2, 1.1 Hz, 1H), 7.89 (s, 1H), 7.82 (t, J = 8.3 Hz, 1H), 7.76 (d, J = 7.8 Hz, 1H), 7.55 (t, J = 8.1 Hz, 1H), 7.44 (m, 1H), 7.37 (d, J = 8.6 Hz, 1H), 3.85 (m, 2H), 3.72 (t, J = 6.0 Hz, 2H), 3.18-3.14 (m, 2H), 2.23 (s, 3H), 1.93 (t, J = 5.7 Hz, 2H), 1.79 (m, 2H), 1.53 (m, 2H), 1.43 (s, 9H) |
| 337 | H NMR (400 MHz, DMSO-d6) δ 12.19 (s, 1H), 9.35 (s, 1H), 8.22 (dd, J = 8.1, 1.1 Hz, 1H), 8.08 (s, 1H), 7.74-7.70 (m, 1H), 7.65 (d, J = 7.8 Hz, 1H), 7.44-7.40 (m, 1H), 7.23 (s, 1H), 3.31 (s, 3H), 1.37 (s, 9H), 1.36 (s, 9H) |
| 351 | 1H NMR (400 MHz, DMSO-d6) δ 12.92 (s, 1H), 12.34 (s, 1H), 10.96 (s, 1H), 8.91 (s, 1H), 8.48 (s, 1H), 8.37 (d, J = 8.1 Hz, 1H), 7.84-7.76 (m, 2H), 7.53 (t, J = 7.4 Hz, 1H), 7.39 (s, 1H), 7.26 (t, J = 2.6 Hz, 1H), 6.34 (s, 1H), 2.89-2.84 (m, 2H), 1.29 (t, J = 7.4 Hz, 3H) |
| 353 | 1H NMR (400 MHz, DMSO-d6) δ 11.90 (s, 1H), 9.30 (s, 1H), 8.88 (s, 1H), 8.34 (dd, J = 8.2, 1.1 Hz, 1H), 7.84-7.71 (m, 3H), 7.55-7.50 (m, 1H), 7.28-7.26 (m, 1H), 7.20-7.17 (m, 1H), 1.47 (s, 9H), 1.38 (s, 9H) |
| 356 | 1H-NMR (CD3OD, 300 MHz) δ 8.89 (s, 1H), 8.59 (s, 1H), 8.45 (d, J = 8.3 Hz, 1H), 7.83 (t, J = 7.2 Hz, 1H), 7.69 (d, J = 9.0 Hz, 1H), 7.57 (t, J = 7.9 Hz, 1H), 7.42 (d, J = 8.5 Hz, 1H), 7.17 (d, J = 6.0 Hz, 1H), 3.09 (s, 3H, NMe), 2.91 (t, J = 7.4 Hz, 2H), 1.76 (m, 2H), 1.09 (t, J = 7.4 Hz, 3H). |
| 357 | H NMR (400 MHz, DMSO-d6) δ 12.91 (d, J = 6.6 Hz, 1H), 12.45 (s, 1H), 10.73 (d, J = 1.9 Hz, 1H), 8.89 (d, J = 6.7 Hz, 1H), 8.35 (dd, J = 8.1, 1.3 Hz, 1H), 8.13 (d, J = 1.6 Hz, 1H), 7.83 (t, J = 8.3 Hz, 1H), 7.76 (d, J = 7.7 Hz, 1H), 7.57-7.51 (m, 2H), 7.06-7.02 (m, 2H), 3.12 (septet, J = 6.6 Hz, 1H), 1.31 (d, J = 6.9 Hz, 6H) |
| 363 | 1H-NMR (CDCl3, 300 MHz) δ 8.86 (d, J = 6.6 Hz, 1H), 8.24 (d, J = 6.2 Hz, 1H), 8.14 (d, J = 7.9 Hz, 1H), 7.43-7.16 (m, 5H), 7.02-6.92 (m, 2H), 6.83 (d, J = 7.9 Hz, 2H), 3.87 (s, 3H). |
| 368 | H NMR (400 MHz, DMSO-d6) δ 12.97 (d, J = 6.6 Hz, 1H), 12.36 (s, 1H), 8.86 (d, J = 6.7 Hz, 1H), 8.33 (dd, J = 8.1, 1.0 Hz, 1H), 7.83 (t, J = 8.3 Hz, 1H), 7.76 (d, J = 7.8 Hz, 1H), 7.62 (s, 1H), 7.55 (t, J = 8.1 Hz, 1H), 7.25 (dd, J = 8.7, 2.2 Hz, 1H), 7.01 (d, J = 8.8 Hz, 1H), 3.98 (t, J = 6.5 Hz, 2H), 1.78 (sextet, J = 6.9 Hz, 2H), 1.02 (t, J = 7.4 Hz, 3H) |
| 375 | H NMR (400 MHz, DMSO-d6) δ 12.93 (d, J = 6.2 Hz, 1H), 12.35 (s, 1H), 8.86 (d, J = 6.7 Hz, 1H), 8.33 (d, J = 6.9 Hz, 1H), 7.82 (t, J = 8.3 Hz, 1H), 7.75 (d, J = 7.8 Hz, 1H), 7.54 (t, J = 8.1 Hz, 1H), 7.47-7.43 (m, 2H), 7.04 (d, J = 8.2 Hz, 1H), 2.71 (m, 4H), 1.75 (m, 4H) |

| Cmpd No. | NMR Data |
|---|---|
| 378 | H NMR (400 MHz, DMSO-d6) δ 12.98 (d, J = 6.6 Hz, 1H), 12.39 (s, 1H), 8.86 (d, J = 6.7 Hz, 1H), 8.33 (dd, J = 8.1, 1.2 Hz, 1H), 7.83 (t, J = 8.3 Hz, 1H), 7.77 (d, J = 7.7 Hz, 1H), 7.69 (s, 1H), 7.55 (t, J = 8.1 Hz, 1H), 7.31 (dd, J = 8.8, 2.4 Hz, 1H), 7.06 (d, J = 8.8 Hz, 1H), 3.85 (s, 3H). |
| 379 | 1H NMR (300 MHz, DMSO-d6) δ 12.79 (s, 1H), 10.30 (s, 1H), 8.85 (s, 1H), 8.32 (d, J = 7.8 Hz, 1H), 8.06 (s, 1H), 7.93 (s, 1H), 7.81 (t, J = 7.8 Hz, 1H), 7.74 (d, J = 6.9 Hz, 1H), 7.73 (s, 1H), 7.53 (t, J = 6.9 Hz, 1H), 2.09 (s, 3H). |
| 381 | H NMR (400 MHz, DMSO-d6) δ 12.78 (br s, 1H), 11.82 (s, 1H), 10.86 (s, 1H), 8.83 (s, 1H), 8.28 (dd, J = 8.1, 1.0 Hz, 1H), 7.75 (t, J = 8.3 Hz, 1H), 7.69 (d, J = 7.7 Hz, 1H),, 7.49-7.43 (m, 3H), 7.23 (m, 1H), 6.32 (m, 1H), 1.39 (s, 9H) |
| 382 | 1H NMR (CD3OD, 300 MHz) δ 8.83 (s, 1H), 8.40 (d, J = 7.4 Hz, 1H), 7.81-7.25 (m, 2H), 7.65 (d, J = 8.3 Hz, 1H), 7.51 (d, J = 8.2, 1H), 7.24 (d, J = 8.3 Hz, 1H), 2.58 (t, J = 7.7 Hz, 2H), 2.17 (s, 3H), 1.60 (m, 2H), 0.97 (t, J = 7.4 Hz, 3H). |
| 383 | H NMR (400 MHz, DMSO-d6) δ 1.27 (t, J = 7.5 Hz, 3H), 2.70 (q, J = 7.7 Hz, 2H), 7.05 (m, 2H), 7.47 (d, J = 8.4 Hz, 1H), 7.55 (t, J = 8.1 Hz, 1H), 7.76 (d, J = 7.7 Hz, 1H), 7.83 (t, J = 8.3 Hz, 1H), 8.13 (s, 1H), 8.35 (d, J = 6.9 Hz, 1H), 8.89 (d, J = 6.7 Hz, 1H), 10.73 (s, 1H), 12.46 (s, 1H), 12.91 (s, 1H) |
| 386 | H NMR (400 MHz, DMSO-d6) δ 13.18 (d, J = 6.8 Hz, 1H), 12.72 (s, 1H), 8.88 (d, J = 6.8 Hz, 1H), 8.34 (d, J = 8.1 Hz, 1H), 8.09 (s, 1H), 7.86-7.79 (m, 2H), 7.58-7.50 (m, 2H), 7.43 (d, J = 8.2 Hz, 1H), 3.51 (s, 2H), 1.36 (s, 6H) |
| 393 | 1H NMR (300 MHz, MeOH) δ 8.78 (s, 1H), 8.45 (d, J = 2.1 Hz, 1H), 8.16 (d, J = 8.1 Hz, 1H), 7.71 (t, J = 6.9 Hz, 1H), 7.56 (d, J = 8.7 Hz, 1H), 7.39 (m, 3H), 7.18 (m, 2H), 7.06 (m, 2H), 4.02 (m, 2H), 1.13 (t, J = 6.9, Hz, 3H); |
| 399 | 1H-NMR (CD3OD, 300 MHz) δ 8.91 (s, 1H), 8.51 (s, 1H), 8.42 (d, J = 8.3 Hz, 1H), 7.84 (t, J = 7.2 Hz, 1H), 7.67 (d, J = 9.0 Hz, 1H), 7.56 (t, J = 7.9 Hz, 1H), 7.46 (d, J = 8.5 Hz, 1H), 7.24 (d, J = 6.0 Hz, 1H), 3.48 (m, 1H), 3.09 (s, 3H, NMe), 1.39 (d, J = 6.8 Hz, 6H). |
| 412 | H NMR (400 MHz, DMSO-d6) δ 12.81-12.79 (m, 2H), 10.96 (s, 1H), 8.87 (d, J = 6.7 Hz, 1H), 8.35 (d, J = 8.1 Hz, 1H), 7.99 (d, J = 8.6 Hz, 1H), 7.83-7.73 (m, 3H), 7.53 (t, J = 8.1 Hz, 1H), 7.36 (m, 1H), 6.52 (m, 1H), 4.51 (q, J = 7.1 Hz, 2H), 1.37 (t, J = 7.1 Hz, 3H) |
| 415 | H NMR (400 MHz, DMSO-d6) δ 12.26 (s, 1H), 9.46 (s, 1H), 8.99 (s, 1H), 8.43-8.41 (m, 1H), 7.94-7.88 (m, 2H),, 7.65-7.61 (m, 1H), 7.38 (d, J = 2.1 Hz, 1H), 7.10 (d, J = 8.4 Hz, 1H), 6.96 (dd, 1H), 4.08 (s, 3H), 1.35 (s, 9H) |
| 420 | H NMR (400 MHz, DMSO-d6) δ 12.91 (bs, 1H), 12.51 (s, 1H), 8.89 (s, 1H), 8.33 (dd, J = 8, 1 Hz, 2H), 7.82 (ddd, J = 8, 8, 1 Hz, 1H), 7.75 (dd, J = 8, 1 Hz, 1H), 7.70 (d, J = 9 Hz, 2H), 7.54 (ddd, J = 8, 8, 1 Hz, 1H), 4.09 (q, J = 7 Hz, 2H), 1.51 (s, 6H), 1.13 (t, J = 7 Hz, 3H). |
| 423 | H NMR (400 MHz, DMSO-d6) δ 12.91 (br s, 1H), 12.48 (s, 1H), 10.81 (d, J = 1.8 Hz, 1H), 8.89 (s, 1H), 8.35 (dd, J = 8.2, 1.1 Hz, 1H), 8.14 (d, J = 1.6 Hz, 1H), 7.82 (t, J = 7.6 Hz, 1H), 7.76 (d, J = 7.8 Hz, 1H), 7.56-7.48 (m, 2H), 7.11 (d, J = 2.2 Hz, 1H), 7.05 (dd, J = 8.5, 1.8 Hz, 1H), 3.62 (t, J = 7.3 Hz, 2H), 3.48 (q, J = 7.0 Hz, 2H), 2.91 (t, J = 7.3 Hz, 2H), 1.14 (t, J = 7.0 Hz, 3H) |
| 425 | 1H-NMR (DMSO d6, 300 MHz) δ 8.84 (s, 1H), 8.29 (d, J = 8.1 Hz, 1H), 7.78-7.70 (m, 2H), 7.61 (d, J = 8.4 Hz, 2H), 7.50 (t, J = 7.8 Hz, 1H), 7.20 (d, J = 8.7 Hz, 2H), 2.85 (h, J = 6.9 Hz, 1H), 1.19 (d, J = 6.9 Hz, 6H). |
| 427 | H NMR (400 MHz, DMSO-d6) δ 1.45 (s, 9H), 2.84 (t, J = 5.9 Hz, 2H), 3.69 (m, 2H), 4.54 (s, 1H), 6.94 (d, J = 7.5 Hz, 1H), 7.22 (t, J = 7.9 Hz, 1H), 7.55 (m, 1H), 7.77 (d, J = 7.7 Hz, 1H), 7.83 (m, 1H), 8.24 (d, J = 8.0 Hz, 1H), 8.37 (d, J = 9.2 Hz, 1H), 8.91 (s, 1H), 12.36 (s, 1H), 12.99 (s, 1H) |
| 428 | 1H NMR (300 MHz, CD3OD) δ 12.30 (s, 1H), 8.83 (s, 1H), 8.38 (d, J = 7.4 Hz, 1H), 7.78 (app dt, J = 1.1, 7.1 Hz, 1H), 7.64 (d, J = 8..3 Hz, 1H), 7.53 (app t, J = 7.5 Hz, 1H), 7.21 (br d, J = 0.9 Hz, 1H), 7.15 (d, J = 8.4 Hz, 1H), 6.98 (dd, J = 2.1, 8.4 Hz, 1H), 1.38 (s, 9H) |
| 429 | H NMR (400 MHz, DMSO-d6) δ 13.13 (d, J = 6.8 Hz, 1H), 12.63 (s, 1H), 8.86 (d, J = 6.8 Hz, 1H), 8.33 (d, J = 7.0 Hz, 1H), 7.84 (t, J = 8.3 Hz, 1H), 7.78 (d, J = 7.6 Hz, 1H), 7.56 (t, J = 8.1 Hz, 1H), 7.51 (s, 1H), 7.30 (s, 1H), 6.77 (s, 1H) |
| 433 | H NMR (400 MHz, DMSO-d6) δ 12.87 (br s, 1H), 11.82 (s, 1H), 9.20 (s, 1H), 8.87 (s, 1H), 8.33 (dd, J = 8.2, 1.1 Hz, 1H), 7.81 (t, J = 8.3 Hz, 1H), 7.75 (d, J = 7.7 Hz, 1H), 7.52 (t, J = 8.1 Hz, 1H), 7.17 (s, 1H), 7.10 (s, 1H), 1.38 (s, 9H), 1.36 (s, 9H) |
| 438 | H NMR (400 MHz, DMSO-d6) δ 12.97 (d, J = 6.6 Hz, 1H), 12.08 (s, 1H), 8.90 (d, J = 6.8 Hz, 1H), 8.35-8.34 (m, 1H), 8.03 (s, 1H), 7.85-7.81 (m, 1H), 7.77-7.71 (m, 1H), 7.58-7.44 (m, 2H), 1.46 (s, 9H), 1.42 (s, 9H) |
| 441 | 1H-NMR (d6-Acetone, 300 MHz) δ 11.90 (br s, 1H), 8.93 (br s, 1H), 8.42 (d, J = 8.1 Hz, 1H), 8.08 (s, 1H), 7.92 (s, 1H), 7.79 (m, 2H), 7.57 (m, 1H), 7.36 (s, 1H), 3.13 (s, 3H). |

-continued

| Cmpd No. | NMR Data |
|---|---|
| 444 | H NMR (400 MHz, DMSO-d6) δ 12.56 (s, 1H), 12.17 (br d, J = 6 Hz, 1H), 8.89 (d, J = 6 Hz, 1H), 8.42 (dd, J = 9, 2 Hz, 1H), 7.77 (d, J = 2 Hz, 1H), 7.68 (dd, J = 9, 2 Hz, 1H), 7.60 (ddd, J = 9, 9, 2 Hz, 1H), 7.46-7.40 (m, 3H), 3.47 (s, 3H), 1.35 (s, 9H). |
| 448 | H NMR (400 MHz, DMSO-d6) δ 12.96 (br s, 1H), 12.42 (s, 1H), 8.88 (s, 1H), 8.33 (dd, J = 8.2, 1.1 Hz, 1H), 7.82 (t, J = 8.3 Hz, 1H), 7.75 (d, J = 7.7 Hz, 1H), 7.66 (d, J = 8.7 Hz, 2H), 7.54 (t, J = 8.1 Hz, 1H), 7.39 (d, J = 8.7 Hz, 2H), 1.29 (s, 9H) |
| 453 | H NMR (400 MHz, DMSO-d6) δ 12.95 (d, J = 6.5 Hz, 1H), 12.38 (s, 1H), 8.86 (d, J = 6.8 Hz, 1H), 8.33 (d, J = 8.1 Hz, 1H), 7.83 (t, J = 8.3 Hz, 1H), 7.76 (d, J = 7.8 Hz, 1H), 7.54 (t, J = 8.1 Hz, 1H), 7.28 (d, J = 2.4 Hz, 1H), 7.15 (d, J = 8.6 Hz, 1H), 6.94 (dd, J = 8.6, 2.4 Hz, 1H) |
| 458 | H NMR (400 MHz, DMSO-d6) δ 12.97 (d, J = 7.1 Hz, 1H), 12.39 (s, 1H), 8.88 (d, J = 6.8 Hz, 1H), 8.33 (d, J = 7.9 Hz, 1H), 7.83 (t, J = 7.6 Hz, 1H), 7.75 (d, J = 8.2 Hz, 1H), 7.55 (t, J = 7.6 Hz, 1H), 7.47 (s, 1H), 7.17 (s, 2H), 4.04 (t, J = 5.0 Hz, 2H), 3.82 (t, J = 5.0 Hz, 2H), 1.36 (s, 9H) |
| 461 | 1H-NMR (d6-DMSO, 300 MHz) δ 11.97 (s, 1H), 8.7 (s, 1H), 8.30 (d, J = 7.7 Hz, 1H), 8.07 (d, J = 7.7 Hz, 1H), 7.726-7.699 (m, 2H), 7.446-7.357 (m, 6H), 7.236-7.178 (m, 2H). 13C-NMR (d6-DMSO, 75 MHz) d 176.3, 163.7, 144.6, 139.6, 138.9, 136.3, 134.0, 133.4, 131.0, 129.8, 129.2, 128.4, 128.1, 126.4, 126.0, 125.6, 124.7, 123.6, 119.6, 111.2. |
| 463 | 1H-NMR (DMSO d6, 300 MHz) δ 8.83 (s, 1H), 8.29 (d, J = 7.8 Hz, 1H), 7.78-7.70 (m, 2H), 7.61 (d, J = 7.8 Hz, 2H), 7.51 (t, 1H), 7.17 (d, J = 8.1 Hz, 2H), 2.57 (q, J = 7.5 Hz, 2H), 1.17 (t, J = 7.5 Hz, 1H), 0.92 (t, J = 7.8 Hz, 3H). |
| 464 | H NMR (400 MHz, DMSO-d6) δ 1.37 (s, 9H), 1.38 (s, 9H), 6.80 (dd, J = 8.1, 0.9 Hz, 1H), 7.15 (m, 3H), 7.66 (t, J = 8.2 Hz, 1H), 8.87 (d, J = 6.9 Hz, 1H), 9.24 (s, 1H), 11.07 (s, 1H), 13.23 (d, J = 6.5 Hz, 1H), 13.65 (s, 1H) |
| 465 | H NMR (400 MHz, DMSO-d6) δ 12.94 (d, J = 6.0 Hz, 1H), 12.40 (s, 1H), 8.87 (d, J = 6.8 Hz, 1H), 8.33 (d, J = 8.2 Hz, 1H), 7.84-7.75 (m, 3H), 7.57-7.43 (m, 2H), 7.31 (d, J = 8.6 Hz, 1H), 4.40 (d, J = 5.8 Hz, 2H), 1.44 (s, 9H), 1.38 (s, 9H) |
| 471 | 1H-NMR (CD3OD, 300 MHz) δ 8.87 (s, 1H), 8.44 (d, J = 8.25, 1H), 8.18 (m, 1H), 7.79 (t, J = 6.88, 1H), 7.67 (d, J = 8.25, 1H), 7.54 (t, J = 7.15, 1H), 7.23 (d, J = 6.05, 1H), 7.16 (d, J = 8.5, 1H), 3.73 (s, 3H), 2.75 (t, J = 6.87, 2H), 1.7 (q, 2H), 1.03 (t, J = 7.42, 3H) |
| 476 | H NMR (400 MHz, DMSO-d6) δ 13.00 (d, J = 6.4 Hz, 1H), 12.91 (s, 1H), 10.72 (s, 1H), 8.89 (d, J = 6.8 Hz, 1H), 8.34 (d, J = 8.2 Hz, 1H), 8.16 (s, 1H), 7.85-7.75 (m, 2H), 7.56-7.54 (m, 1H), 7.44 (s, 1H), 1.35 (s, 9H) |
| 478 | H NMR (400 MHz, DMSO-d6) δ 1.40 (s, 9H), 6.98 (d, J = 2.4 Hz, 1H), 7.04 (dd, J = 8.6, 1.9 Hz, 1H), 7.55 (t, J = 8.1 Hz, 1H), 7.66 (d, J = 8.6 Hz, 1H), 7.76 (d, J = 7.7 Hz, 1H), 7.83 (t, J = 8.3 Hz, 1H), 8.13 (d, J = 1.7 Hz, 1H), 8.35 (d, J = 8.1 Hz, 1H), 8.89 (d, J = 6.7 Hz, 1H), 10.74 (s, 1H), 12.44 (s, 1H), 12.91 (s, 1H) |
| 484 | 1H NMR (300 MHz, DMSO-d6) δ 12.90 (d, J = 6.3 Hz, 1H), 12.21 (s, 1H), 8.85 (d, J = 6.8 Hz, 1H), 8.31 (d, J = 8.0 Hz, 1H), 7.79 (app dt, J = 12, 8.0 Hz, 1H), 7.72 (d, J = 8.3 Hz, 1H), 7.52 (dd, J = 6.9, 8.1 Hz, 1H), 7.05 (d, J = 8.3 Hz, 1H), 6.94 (s with fine str, 1H), 6.90 (d with fine str, J = 8.4 Hz, 1H), 2.81 (s, 3H), 1.34 (s, 9H) |
| 485 | 1H NMR (300 MHz, CDCl$_3$) δ 13.13 (br s, 1H), 12.78 (s, 1H), 8.91 (br s, 1H), 8.42 (br s, 1H), 8.37 (d, J = 8.1 Hz, 1H), 7.72-7.58 (m, 2H), 7.47-7.31 (m, 3H), 3.34 (s, 6H), 1.46 (s, 9H) |

B) Assays for Detecting and Measuring ΔF508-CFTR Correction Properties of Compounds I) Membrane Potential Optical Methods for Assaying ΔF508-CFTR Modulation Properties of Compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a Cl⁻-free medium with or without test compound was added to each well. After 22 sec, a second addition of CF-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hoursB) Electrophysiological Assays for assaying ΔF508-CFTR modulation properties of compounds 1. Using Chamber Assay Using chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Using chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 ΩK/cm$^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

Solutions

Basolateral solution (in mM): NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing ΔF508-CFTR (FRT$^{\Delta F508\text{-}CFTR}$) were used for Using chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), MgCl$_2$ (1), HEPES (10), and 240 µg/ml amphotericin-B (pH adjusted to 7.35 with CsOH).

Extracellular solution (in mM): N-methyl-D-glucamine (NMDG)-Cl (150), MgCl$_2$ (2), CaCl$_2$ (2), HEPES (10) (pH adjusted to 7.35 with HCl).

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F (10 mM NaF) was added to the bath solution. Under these recording conditions, channel activity remained constant throughout the duration of the patch recording (up to 60 min). Currents produced by positive charge moving from the intra-to extracellular solutions (anions moving in the opposite direction) are shown as positive currents. The pipette potential ($V_p$) was maintained at 80 mV.

Channel activity was analyzed from membrane patches containing 2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

Solutions

Extracellular solution (in mM): NMDG (150), aspartic acid (150), CaCl$_2$ (5), MgCl$_2$ (2), and HEPES (10) (pH adjusted to 7.35 with Tris base).

Intracellular solution (in mM): NMDG-Cl (150), MgCl$_2$ (2), EGTA (5), TES (10), and Tris base (14) (pH adjusted to 7.35 with HCl).

Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For single channel recordings, 2,500-5,000 cells were seeded on poly-L-lysine-coated glass coverslips and cultured for 24-48 hrs at 27° C. before use.

Compounds of the invention are useful as modulators of ATP binding cassette transporters. Table 3 below illustrates the EC50 and relative efficacy of certain embodiments in Table 1.

In Table 3 below, the following meanings apply:
EC50: "+++" means <10 uM; "++" means between 10 uM to 25 uM; "+" means between 25 uM to 60 uM.
% Efficacy: "+" means <25%; "++" means between 25% to 100%; "+++" means >100%.

TABLE 3

| Cmpd # | EC50 (uM) | % Activity |
|---|---|---|
| 1 | +++ | ++ |
| 2 | +++ | ++ |
| 3 | +++ | ++ |
| 4 | +++ | ++ |
| 5 | ++ | ++ |
| 6 | +++ | +++ |

TABLE 3-continued

| Cmpd # | EC50 (uM) | % Activity |
|---|---|---|
| 7 | + | + |
| 8 | +++ | ++ |
| 9 | + | + |
| 10 | +++ | ++ |
| 11 | +++ | ++ |
| 12 | +++ | ++ |
| 13 | +++ | ++ |
| 14 | +++ | ++ |
| 15 | ++ | ++ |
| 16 | +++ | ++ |
| 17 | +++ | ++ |
| 18 | +++ | ++ |
| 19 | ++ | + |
| 20 | +++ | ++ |
| 21 | + | + |
| 22 | ++ | ++ |
| 23 | +++ | ++ |
| 24 | + | + |
| 25 | ++ | ++ |
| 26 | +++ | ++ |
| 28 | ++ | ++ |
| 29 | ++ | ++ |
| 30 | +++ | ++ |
| 31 | +++ | ++ |
| 32 | +++ | ++ |
| 33 | +++ | ++ |
| 34 | +++ | ++ |
| 35 | +++ | ++ |
| 36 | +++ | ++ |
| 37 | +++ | ++ |
| 38 | +++ | ++ |
| 39 | ++ | ++ |
| 40 | + | + |
| 41 | +++ | ++ |
| 42 | +++ | ++ |
| 43 | +++ | ++ |
| 44 | ++ | ++ |
| 46 | ++ | ++ |
| 47 | +++ | ++ |
| 48 | +++ | ++ |
| 49 | +++ | ++ |
| 50 | +++ | ++ |
| 51 | +++ | ++ |
| 52 | +++ | ++ |
| 53 | + | + |
| 54 | + | + |
| 55 | + | + |
| 56 | +++ | ++ |
| 57 | ++ | +++ |
| 58 | +++ | ++ |
| 59 | +++ | +++ |
| 60 | +++ | ++ |
| 61 | +++ | ++ |
| 62 | +++ | ++ |
| 63 | +++ | ++ |
| 64 | + | + |
| 65 | +++ | ++ |
| 66 | ++ | ++ |
| 67 | +++ | ++ |
| 68 | +++ | ++ |
| 69 | +++ | ++ |
| 70 | ++ | ++ |
| 71 | +++ | ++ |
| 72 | +++ | ++ |
| 73 | + | + |
| 74 | + | + |
| 75 | + | + |
| 76 | +++ | ++ |
| 77 | +++ | ++ |
| 78 | + | + |
| 79 | +++ | ++ |
| 80 | +++ | ++ |
| 81 | + | + |
| 82 | +++ | ++ |
| 83 | +++ | ++ |
| 84 | + | + |
| 85 | +++ | ++ |
| 86 | ++ | ++ |
| 87 | +++ | ++ |
| 88 | +++ | ++ |
| 89 | + | + |
| 90 | +++ | ++ |
| 91 | +++ | ++ |
| 92 | +++ | ++ |
| 93 | +++ | ++ |
| 94 | +++ | ++ |
| 95 | ++ | ++ |
| 96 | +++ | ++ |
| 97 | +++ | ++ |
| 98 | +++ | ++ |
| 99 | +++ | ++ |
| 100 | + | + |
| 101 | +++ | ++ |
| 102 | ++ | ++ |
| 103 | +++ | +++ |
| 104 | +++ | ++ |
| 105 | ++ | ++ |
| 106 | + | + |
| 107 | ++ | ++ |
| 108 | +++ | ++ |
| 109 | ++ | ++ |
| 110 | + | + |
| 111 | +++ | ++ |
| 112 | +++ | ++ |
| 113 | +++ | ++ |
| 114 | +++ | ++ |
| 115 | +++ | ++ |
| 116 | +++ | ++ |
| 117 | +++ | ++ |
| 118 | +++ | ++ |
| 119 | +++ | ++ |
| 120 | ++ | ++ |
| 122 | + | + |
| 123 | +++ | ++ |
| 124 | +++ | +++ |
| 125 | ++ | ++ |
| 126 | +++ | ++ |
| 127 | +++ | ++ |
| 128 | + | + |
| 129 | ++ | ++ |
| 130 | +++ | ++ |
| 131 | +++ | ++ |
| 132 | + | + |
| 133 | ++ | ++ |
| 134 | +++ | ++ |
| 135 | +++ | +++ |
| 136 | +++ | ++ |
| 137 | +++ | ++ |
| 138 | +++ | ++ |
| 139 | +++ | ++ |
| 140 | +++ | ++ |
| 141 | ++ | ++ |
| 142 | +++ | ++ |
| 143 | +++ | ++ |
| 144 | +++ | ++ |
| 145 | +++ | ++ |
| 146 | + | + |
| 147 | +++ | ++ |
| 148 | +++ | ++ |
| 149 | ++ | ++ |
| 150 | +++ | ++ |
| 151 | +++ | ++ |
| 152 | + | + |
| 153 | +++ | ++ |
| 154 | + | + |
| 155 | + | + |
| 156 | +++ | ++ |
| 157 | +++ | ++ |
| 158 | +++ | ++ |
| 159 | ++ | ++ |
| 160 | +++ | ++ |
| 161 | +++ | ++ |
| 162 | + | + |
| 163 | ++ | ++ |

TABLE 3-continued

| Cmpd # | EC50 (uM) | % Activity |
|---|---|---|
| 164 | +++ | ++ |
| 165 | + | + |
| 166 | +++ | ++ |
| 167 | ++ | ++ |
| 168 | + | + |
| 169 | ++ | ++ |
| 170 | + | + |
| 171 | +++ | ++ |
| 172 | +++ | ++ |
| 173 | + | + |
| 174 | +++ | ++ |
| 175 | ++ | ++ |
| 176 | +++ | ++ |
| 177 | +++ | +++ |
| 178 | +++ | ++ |
| 179 | + | + |
| 180 | +++ | ++ |
| 181 | +++ | ++ |
| 182 | +++ | ++ |
| 183 | +++ | ++ |
| 184 | + | + |
| 185 | + | + |
| 186 | +++ | ++ |
| 187 | +++ | ++ |
| 188 | +++ | ++ |
| 189 | +++ | ++ |
| 190 | +++ | ++ |
| 191 | + | + |
| 192 | + | + |
| 193 | ++ | ++ |
| 194 | + | + |
| 195 | + | + |
| 196 | +++ | ++ |
| 197 | + | + |
| 198 | +++ | ++ |
| 199 | +++ | ++ |
| 200 | ++ | ++ |
| 201 | ++ | + |
| 202 | +++ | ++ |
| 203 | +++ | ++ |
| 204 | +++ | ++ |
| 205 | +++ | ++ |
| 206 | +++ | ++ |
| 207 | +++ | ++ |
| 208 | +++ | ++ |
| 209 | ++ | ++ |
| 210 | ++ | ++ |
| 211 | +++ | ++ |
| 212 | + | + |
| 213 | +++ | ++ |
| 214 | ++ | ++ |
| 215 | +++ | ++ |
| 216 | + | + |
| 217 | ++ | ++ |
| 218 | +++ | ++ |
| 219 | + | + |
| 220 | +++ | ++ |
| 221 | +++ | ++ |
| 222 | ++ | ++ |
| 223 | +++ | ++ |
| 224 | +++ | ++ |
| 225 | +++ | ++ |
| 226 | +++ | ++ |
| 227 | + | + |
| 228 | +++ | ++ |
| 229 | +++ | ++ |
| 230 | ++ | ++ |
| 231 | +++ | ++ |
| 232 | ++ | ++ |
| 233 | ++ | + |
| 234 | +++ | ++ |
| 235 | +++ | ++ |
| 236 | +++ | ++ |
| 237 | +++ | ++ |
| 238 | +++ | ++ |
| 239 | +++ | ++ |
| 240 | +++ | ++ |

TABLE 3-continued

| Cmpd # | EC50 (uM) | % Activity |
|---|---|---|
| 241 | ++ | ++ |
| 242 | +++ | ++ |
| 243 | ++ | ++ |
| 244 | +++ | ++ |
| 245 | +++ | ++ |
| 246 | +++ | ++ |
| 247 | +++ | ++ |
| 248 | ++ | ++ |
| 249 | ++ | ++ |
| 250 | + | + |
| 251 | +++ | ++ |
| 252 | ++ | ++ |
| 253 | +++ | ++ |
| 254 | +++ | ++ |
| 255 | +++ | ++ |
| 256 | + | + |
| 257 | +++ | ++ |
| 258 | +++ | ++ |
| 259 | +++ | ++ |
| 260 | +++ | ++ |
| 261 | +++ | ++ |
| 262 | +++ | ++ |
| 263 | +++ | ++ |
| 264 | ++ | ++ |
| 265 | +++ | ++ |
| 266 | +++ | ++ |
| 267 | +++ | ++ |
| 268 | ++ | ++ |
| 269 | +++ | ++ |
| 270 | +++ | ++ |
| 271 | +++ | ++ |
| 272 | ++ | ++ |
| 273 | +++ | +++ |
| 274 | +++ | ++ |
| 275 | ++ | ++ |
| 276 | ++ | ++ |
| 277 | +++ | +++ |
| 278 | +++ | ++ |
| 279 | +++ | ++ |
| 280 | + | + |
| 281 | +++ | ++ |
| 282 | +++ | ++ |
| 283 | +++ | +++ |
| 284 | ++ | ++ |
| 285 | +++ | ++ |
| 286 | +++ | +++ |
| 287 | +++ | ++ |
| 288 | +++ | ++ |
| 289 | +++ | ++ |
| 290 | +++ | ++ |
| 291 | +++ | ++ |
| 292 | +++ | ++ |
| 293 | ++ | +++ |
| 294 | ++ | ++ |
| 295 | +++ | ++ |
| 296 | ++ | ++ |
| 297 | +++ | ++ |
| 298 | +++ | ++ |
| 299 | +++ | ++ |
| 300 | +++ | ++ |
| 301 | + | + |
| 302 | ++ | ++ |
| 303 | ++ | ++ |
| 304 | +++ | ++ |
| 305 | +++ | +++ |
| 306 | +++ | +++ |
| 307 | +++ | ++ |
| 308 | ++ | ++ |
| 309 | + | + |
| 310 | +++ | ++ |
| 311 | +++ | ++ |
| 312 | +++ | ++ |
| 313 | +++ | ++ |
| 314 | +++ | ++ |
| 315 | +++ | ++ |
| 316 | ++ | ++ |
| 317 | +++ | ++ |

TABLE 3-continued

| Cmpd # | EC50 (uM) | % Activity |
|---|---|---|
| 318 | ++ | ++ |
| 319 | +++ | ++ |
| 320 | +++ | ++ |
| 321 | +++ | ++ |
| 322 | +++ | ++ |
| 323 | +++ | ++ |
| 324 | +++ | ++ |
| 325 | +++ | ++ |
| 326 | ++ | ++ |
| 327 | +++ | ++ |
| 328 | + | + |
| 329 | ++ | ++ |
| 330 | +++ | ++ |
| 331 | + | + |
| 332 | +++ | ++ |
| 333 | +++ | ++ |
| 334 | ++ | ++ |
| 335 | + | + |
| 336 | +++ | ++ |
| 337 | +++ | ++ |
| 338 | ++ | ++ |
| 339 | +++ | ++ |
| 340 | +++ | ++ |
| 341 | +++ | ++ |
| 342 | +++ | ++ |
| 343 | ++ | ++ |
| 344 | +++ | ++ |
| 345 | +++ | ++ |
| 346 | +++ | ++ |
| 347 | ++ | ++ |
| 348 | +++ | ++ |
| 350 | +++ | ++ |
| 351 | +++ | ++ |
| 352 | +++ | ++ |
| 353 | +++ | ++ |
| 354 | +++ | ++ |
| 355 | +++ | ++ |
| 356 | +++ | ++ |
| 357 | +++ | ++ |
| 358 | +++ | ++ |
| 359 | ++ | ++ |
| 360 | +++ | ++ |
| 361 | +++ | +++ |
| 362 | +++ | ++ |
| 363 | +++ | +++ |
| 364 | +++ | ++ |
| 365 | ++ | ++ |
| 366 | +++ | ++ |
| 367 | +++ | ++ |
| 368 | +++ | ++ |
| 369 | ++ | + |
| 370 | +++ | ++ |
| 371 | +++ | ++ |
| 372 | +++ | ++ |
| 373 | +++ | ++ |
| 374 | + | + |
| 375 | +++ | ++ |
| 376 | + | + |
| 377 | ++ | ++ |
| 378 | ++ | ++ |
| 379 | ++ | ++ |
| 380 | +++ | ++ |
| 381 | +++ | ++ |
| 382 | +++ | ++ |
| 383 | +++ | ++ |
| 384 | +++ | ++ |
| 385 | +++ | ++ |
| 386 | +++ | ++ |
| 387 | +++ | ++ |
| 388 | +++ | ++ |
| 389 | +++ | ++ |
| 390 | + | + |
| 391 | +++ | ++ |
| 392 | + | + |
| 393 | +++ | ++ |
| 394 | + | + |
| 395 | +++ | ++ |

TABLE 3-continued

| Cmpd # | EC50 (uM) | % Activity |
|---|---|---|
| 396 | ++ | ++ |
| 397 | +++ | ++ |
| 398 | ++ | ++ |
| 399 | +++ | ++ |
| 400 | + | + |
| 401 | +++ | ++ |
| 402 | +++ | + |
| 403 | +++ | ++ |
| 404 | +++ | ++ |
| 405 | +++ | ++ |
| 406 | +++ | ++ |
| 407 | +++ | ++ |
| 408 | +++ | ++ |
| 409 | +++ | ++ |
| 410 | +++ | +++ |
| 411 | +++ | ++ |
| 412 | +++ | ++ |
| 413 | +++ | ++ |
| 414 | + | + |
| 415 | +++ | ++ |
| 416 | +++ | ++ |
| 417 | +++ | ++ |
| 418 | ++ | ++ |
| 419 | + | + |
| 420 | +++ | ++ |
| 421 | +++ | ++ |
| 423 | +++ | ++ |
| 424 | +++ | ++ |
| 425 | +++ | ++ |
| 426 | +++ | ++ |
| 427 | +++ | ++ |
| 428 | +++ | ++ |
| 429 | +++ | ++ |
| 430 | +++ | ++ |
| 431 | ++ | ++ |
| 432 | +++ | ++ |
| 433 | +++ | ++ |
| 434 | +++ | ++ |
| 435 | +++ | ++ |
| 436 | +++ | ++ |
| 437 | + | + |
| 438 | +++ | ++ |
| 439 | +++ | ++ |
| 440 | +++ | ++ |
| 441 | +++ | ++ |
| 442 | + | + |
| 443 | + | + |
| 444 | +++ | ++ |
| 445 | +++ | +++ |
| 446 | + | + |
| 447 | ++ | ++ |
| 448 | +++ | ++ |
| 449 | +++ | ++ |
| 450 | ++ | ++ |
| 451 | +++ | ++ |
| 452 | +++ | ++ |
| 453 | +++ | ++ |
| 454 | + | + |
| 455 | +++ | ++ |
| 456 | +++ | ++ |
| 457 | + | + |
| 458 | +++ | ++ |
| 459 | +++ | ++ |
| 460 | +++ | ++ |
| 461 | +++ | ++ |
| 462 | +++ | ++ |
| 463 | +++ | ++ |
| 464 | +++ | ++ |
| 465 | +++ | ++ |
| 466 | +++ | ++ |
| 467 | + | + |
| 468 | + | + |
| 469 | +++ | ++ |
| 470 | +++ | ++ |
| 471 | +++ | ++ |
| 472 | +++ | ++ |
| 473 | ++ | ++ |

TABLE 3-continued

| Cmpd # | EC50 (uM) | % Activity |
|---|---|---|
| 474 | + | + |
| 476 | +++ | ++ |
| 477 | + | + |
| 478 | +++ | ++ |
| 479 | +++ | ++ |
| 480 | + | + |
| 481 | +++ | ++ |
| 482 | ++ | ++ |
| 483 | +++ | ++ |
| 484 | +++ | ++ |
| 485 | +++ | ++ |

What is claimed is:

1. A compound having formula A-I:

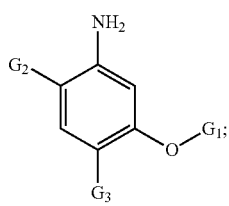

or a salt thereof;
wherein:
G$_1$ is hydrogen, R', C(O)R', C(S)R', S(O)R', S(O)$_2$R', Si(CH$_3$)$_2$R', P(O)(OR')$_3$, P(S)(OR')$_3$, or B(OR')$_2$;
G$_2$ is halo, CN, CF$_3$, isopropyl, or phenyl wherein said isopropyl or phenyl is optionally substituted with up to 3 substituents independently selected from WR$^W$;
G$_3$ is an isopropyl or a C3-C10 cycloaliphatic ring, wherein said G$_3$ is optionally substituted with up to 3 substituents independently selected from WR$^W$;
provided that when G$_1$ is methyl, G$_3$ is tert-butyl, then G$_2$ is not 2-amino-4-methoxy-5-tert-butyl-phenyl;
W is a bond or is an optionally substituted C$_1$-C$_6$ alkylidene chain, wherein up to two methylene units of W are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;
R$^W$ is independently R', halo, NO$_2$, CN, CF$_3$, or OCF$_3$; and
R' is independently selected from hydrogen or an optionally substituted group selected from a C$_1$-C$_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

2. The compound according to claim 1, wherein:
G$_1$ is hydrogen;
G$_2$ is halo or isopropyl, wherein said isopropyl is optionally substituted with up to 3 substituents independently selected from R'; and
G$_3$ is an isopropyl or a C3-C10 cycloaliphatic ring, wherein said G$_3$ is optionally substituted with up to 3 substituents independently selected from R'.

3. The compound according to claim 2, wherein:
G$_1$ is hydrogen;
G$_2$ is halo; and
G$_3$ is a C3-C10 cycloaliphatic ring, wherein said G$_3$ is optionally substituted with up to 3 substituents independently selected from methyl, ethyl, propyl, or butyl.

4. The compound according to claim 1, wherein:
G$_1$ is hydrogen;
G$_2$ is CN, halo, or CF$_3$; and
G$_3$ is an isopropyl or a C3-C10 cycloaliphatic ring, wherein said G$_3$ is optionally substituted with up to 3 substituents independently selected from R'.

5. The compound according to claim 1, wherein:
G$_1$ is hydrogen;
G$_2$ is phenyl, wherein said phenyl is optionally substituted with up to 3 substituents independently selected from —OC1-C4 alkyl, CF$_3$, halo, or CN; and
G$_3$ is an isopropyl or a C3-C10 cycloaliphatic ring, wherein said G$_3$ is optionally substituted with up to 3 substituents independently selected from R'.

6. The compound according to claim 1, wherein G$_3$ is selected from optionally substituted cyclopentyl, cyclohexyl, cycloheptyl, or adamantyl.

7. The compound according to claim 1, wherein G$_3$ is C3-C8 branched aliphatic chain.

8. The compound according to claim 1, wherein the compound is C-9

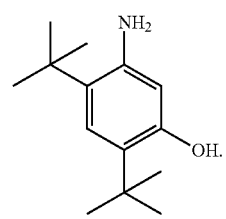

9. A process for the preparation of a compound having the formula FF

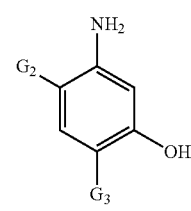

comprising hydrogenating a compound having the formula EE

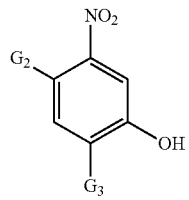

in the presence of a Palladium catalyst
wherein
$G_2$ is halo, CN, $CF_3$, isopropyl, or phenyl wherein said isopropyl or phenyl is optionally substituted with up to 3 substituents independently selected from $WR^W$;
$G_3$ is an isopropyl or a $C_3$-$C_{10}$ cycloaliphatic ring, wherein said $G_3$ is optionally substituted with up to 3 substituents independently selected from $WR^W$;
W is a bond or is a $C_1$-$C_6$ alkylidene chain wherein up to two methylene units of W are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR'—, —NR'NR'CO—, —NR'CO—, —S—, —SO, —$SO_2$—, —NR'—, —$SO_2$NR'—, NR'$SO_2$—, or —NR'$SO_2$NR'—;
$R^W$ is independently R', halo, $NO_2$, CN, $CF_3$, or $OCF_3$; and
R' is independently selected from hydrogen or a group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form a 3-12 membered saturated, partially unsaturated, or fully unsaturated monocyclic or bicyclic ring having 0-4 heteroatoms independently selected from nitrogen, oxygen, or sulfur.

10. A process for preparing the compound C-9

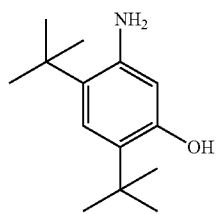

comprising the steps of:
contacting 2,4-di-tert-butylphenol with methyl chloroformate to produce 2,4-di-tert-butylphenyl methyl carbonate

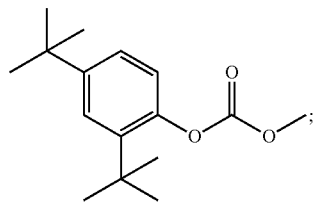 [SMILES: COC(=O)Oc1ccc(C(C)(C)C)cc1C(C)(C)C]

2,4-di-tert-butylphenyl methyl carbonate
contacting 2,4-di-tert-butylphenyl methyl carbonate with a mixture of nitric acid and sulfuric acid to produce 2,4-di-tert-butyl-5-nitrophenyl methyl carbonate

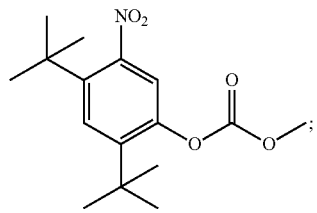 [SMILES: COC(=O)Oc1cc([N+](=O)[O-])c(C(C)(C)C)cc1C(C)(C)C]

2,4-di-tert-butyl-5-nitrophenyl methyl carbonate
contacting 2,4-di-tert-butyl-5-nitrophenyl methyl carbonate with a mixture of methanol and KOH to produce 2,4-di-tert-butyl-5-nitrophenol

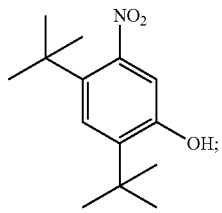 [SMILES: CC(C)(C)c1cc(C(C)(C)C)c([N+](=O)[O-])cc1O]

and
2,4-di-tert-butyl-5-nitrophenol
hydrogenating 2,4-di-tert-butyl-5-nitrophenol in the presence of a palladium catalyst.

* * * * *